(12) United States Patent
Richter et al.

(10) Patent No.: US 9,657,006 B2
(45) Date of Patent: May 23, 2017

(54) MACROCYCLIC FACTOR VIIA INHIBITORS

(71) Applicant: BRISTOL-MYERS SQUIBB COMPANY, Princeton, NJ (US)

(72) Inventors: Jeremy Richter, Ewing, NJ (US); J. Alex Bates, Hillsborough, NJ (US); Daniel L. Cheney, Ringoes, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 14/897,764

(22) PCT Filed: Jun. 11, 2014

(86) PCT No.: PCT/US2014/041823
§ 371 (c)(1),
(2) Date: Dec. 11, 2015

(87) PCT Pub. No.: WO2014/201073
PCT Pub. Date: Dec. 18, 2014

(65) Prior Publication Data
US 2016/0115159 A1    Apr. 28, 2016

Related U.S. Application Data

(60) Provisional application No. 61/834,457, filed on Jun. 13, 2013.

(51) Int. Cl.
*C07D 401/12* (2006.01)
*A61K 31/4709* (2006.01)
*C07D 413/12* (2006.01)
*C07D 245/04* (2006.01)
*C07D 255/04* (2006.01)

(52) U.S. Cl.
CPC ......... *C07D 413/12* (2013.01); *C07D 245/04* (2013.01); *C07D 255/04* (2013.01); *C07D 401/12* (2013.01)

(58) Field of Classification Search
None
See application file for complete search history.

(56) References Cited

U.S. PATENT DOCUMENTS 7,592,331 B2    9/2009    Priestley et al.

FOREIGN PATENT DOCUMENTS

WO    WO 2007/076431 A1    7/2007
WO    WO 2008/079836 A2    7/2008

OTHER PUBLICATIONS

Arnold, C.S. et al., "The antithrombotic and anti-inflammatory effects of BCX-3607, a small molecule tissue factor/factor VIIa inhibitor", Thrombosis Research, vol. 117, pp. 343-349 (2006).

Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).
Bundgaard, H., ed., Design of Prodrugs, Elsevier Science Publishers B.V., publ. (1985).
Bundgaard, H., "Prodrugs as a means to improve the delivery of peptide drugs", Advanced Drug Delivery Reviews, vol. 8, pp. 1-38 (1992).
Carson, S.D. et al., "The role of tissue factor in the production of thrombin", Blood Coagulation and Fibrinolysis, vol. 4, pp. 281-292 (1993).
Frédérick, R. et al., "Modulators of the Coagulation Cascade: Focus and Recent Advances in Inhibitors of Tissue Factor, Factor VIIa and Their Complex", Current Medicinal Chemistry, vol. 12, No. 4, pp. 397-417 (2005).
Gennaro, A.R., ed., Remington's Pharmaceutical Sciences, 18th Edition, pp. xv-xvi, Mack Publishing Company, publ. (1990).
Giesen, P.L.A. et al., "Blood-borne tissue factor: Another view of thrombosis", Proc. Natl. Acad. Sci. USA, vol. 96, pp. 2311-2315 (1999).
Girard, T.J. et al., "The role of tissue factor/factor VIIa in the pathophysiology of acute thrombotic formation", Current Opinion in Pharmacology, vol. 1, pp. 159-163 (2001).
Greene, T.W. et al., Protective Groups in Organic Synthesis, Third Edition, pp. xi-xii, John Wiley & Sons, Inc., publ. (1999).
Himber, J. et al., "Inhibition of tissue factor limits the growth of venous thrombus in the rabbit", Journal of Thrombosis and Haemostasis, vol. 1, pp. 889-895 (2003).
Hirsh, J. et al., "New anticoagulants", Blood, vol. 105, No. 2, pp. 453-463 (2005).
Hoffman, M., "A cell-based model of coagulation and the role of factor VIIa", Blood Reviews, vol. 17, pp. S1-S5 (2003).
Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).
Lazarus, R.A. et al., "Inhibitors of Tissue Factor•Factor VIIa for Anticoagulant Therapy", Current Medicinal Chemistry, vol. 11, No. 17, pp. 2275-2290 (2004).

(Continued)

Primary Examiner — Zinna Northington Davis
(74) Attorney, Agent, or Firm — Hong Liu

(57) ABSTRACT

The present invention provides compounds of Formula (I) as defined in the specification and compositions comprising any of such novel compounds. These compounds are Factor VIIa inhibitors which may be used as medicaments.

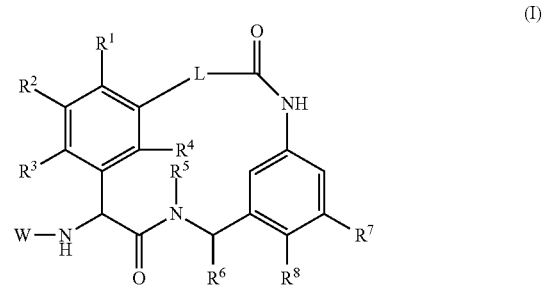

7 Claims, No Drawings

(56) References Cited

OTHER PUBLICATIONS

Lee, A. et al., "Dose-Response Study of Recombinant Factor VIIa/Tissue Factor Inhibitor Recombinant Nematode Anticoagulant Protein c2 in Prevention of Postoperative Venous Thromboembolism in Patients Undergoing Total Knee Replacement", Circulation, vol. 104, pp. 74-78 (2001).

Miyaura, N. et al., "Palladium-Catalyzed Cross-Coupling Reactions of Organoboron Compounds", Chemical Reviews, vol. 95, No. 7, pp. 2457-2483 (1995).

Montalbetti, C.A.G.N. et al., "Amide bond formation and peptide coupling", Tetrahedron, vol. 61, pp. 10827-10852 (2005).

Moons, A.H.M. et al., "Recombinant Nematode Anticoagulant Protein c2, an Inhibitor of the Tissue Factor/Factor VIIa Complex, in Patients Undergoing Elective Coronary Angioplasty", Journal of the American College of Cardiology, vol. 41, No. 12, pp. 2147-2153i (2003).

Morrissey, J.H., "Tissue factor: in at the start . . . and the finish?", Journal of Thrombosis and Haemostasis, vol. 1, pp. 878-880 (2003).

Morrissey, J.H. et al., "Quantitation of Activated Factor VII Levels in Plasma Using a Tissue Factor Mutant Selectively Deficient in Promoting Factor VII Activation", Blood, vol. 81, No. 3, pp. 734-744 (1993).

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Olivero, A.G. et al., "A Selective, Slow Binding Inhibitor of Factor VIIa Binds to a Nonstandard Active Site Conformation and Attenuates Thrombus Formation in Vivo", The Journal of Biological Chemistry, vol. 280, No. 10, pp. 9160-9169 (2005).

Petasis, N.A. et al., "A New and Practical Synthesis of α-Amino Acids from Alkenyl Boronic Acids", J. Am. Chem. Soc., vol. 119, No. 2, pp. 445-446 (1997).

Petasis, N.A. et al., "A New Synthesis of α-Arylglycines from Aryl Boronic Acids", Tetrahedron, vol. 53, No. 48, pp. 16463-16470 (1997).

Suleymanov, O.D. et al., "Pharmacological Interruption of Acute Thrombus Formation with Minimal Hemorrhagic Complications by a Small Molecule Tissue Factor/Factor VIIa Inhibitor: Comparison to Factor Xa and Thrombin Inhibition in a Nonhuman Primate Thrombosis Model", The Journal of Pharmacology and Experimental Therapeutics, vol. 306, No. 3, pp. 1115-1121 (2003).

Szalony, J.A. et al., "Administration of a small molecule tissue factor/Factor VIIa inhibitor in a non-human primate thrombosis model of venous thrombosis: effects on thrombus formation and bleeding time", Thrombosis Research, vol. 112, pp. 167-174 (2003).

Szalony, J.A. et al., "Pharmacological Intervention at Disparate Sites in the Coagulation Cascade: Comparison of Anti-thrombotic Efficacy vs. Bleeding Propensity in a Rat Model of Acute Arterial Thrombosis", Journal of Thrombosis and Thrombolysis, vol. 14, No. 2, pp. 113-121 (2002).

Testa, B. et al., Hydrolysis in Drug and Prodrug Metabolism: Chemistry, Biochemistry, and Enzymology, pp. xi-xx, Wiley-VCH GmbH & Co., publ. (2003).

Widder, K.J. et al., eds., Section III: "Prodrugs", Methods in Enzymology, vol. 112, pp. 309-396, Academic Press, Inc., publ. (1985).

Wong, P.C. et al., "Nonpeptide Factor Xa Inhibitors: I. Studies with SF303 and SK549, a New Class of Potent Antithrombotics", The Journal of Pharmacology and Experimental Therapeutics, vol. 292, No. 1, pp. 351-357 (2000).

Wong, P.C. et al., "Nonpeptide Factor Xa Inhibitors II. Antithrombotic Evaluation in a Rabbit Model of Electrically Induced Carotid Artery Thrombosis", The Journal of Pharmacology and Experimental Therapeutics, vol. 295, No. 1, pp. 212-218 (2000).

Young, W.B. et al., "Factor VIIa inhibitors: Chemical optimization, preclinical pharmacokinetics, pharmacodynamics, and efficacy in an arterial baboon thrombosis model", Bioorganic & Medicinal Chemistry Letters, vol. 16, pp. 2037-2041 (2006).

Zbinden, K.G. et al., "Dose-dependent antithrombotic activity of an orally active tissue factor/factor VIIa inhibitor without concomitant enhancement of bleeding propensity", Bioorganic & Medicinal Chemistry, vol. 14, pp. 5357-5369 (2006).

Driggers, et al., The exploration of macrocycles for drug discovery—an underexploited structural class, Nat. Rev. Drug Dis, vol. 7, pp. 608-624, (2008).

You, et al., Macrocyclic Compounds: Emerging Opportunities for Current Drug Discovery, Curr. Pharm Design, vol. 22, pp. 4086-4093, (2016).

Mallison et al., Macrocycles in new drug discovery, Future Med. Chem., vol. 4(11), pp. 1409-1438 (2012).

Marsault, et al., Macrocycles are great cycles: Applications, Opportunities, and Challenges of Synthetic Macrocycles in Drug Discovery, J. Med. Chem., vol. 54, pp. 1961-2004, (2011).

MACROCYCLIC FACTOR VIIA INHIBITORS

CROSS-REFERENCE TO RELATED APPLICATIONS

The present application is a 371 of International Application No. PCT/US2014/041823 filed on Jun. 11, 2014, which claims priority benefit of U.S. provisional application Ser. No. 61/834,457, filed Jun. 13, 2013 each of which is fully incorporated by reference herein.

FIELD OF THE INVENTION

The present invention relates to novel macrocyclic factor VIIa inhibitors and pharmaceutical compositions thereof.

BACKGROUND OF THE INVENTION

Factor VII is a plasma serine protease involved in the initiation of the coagulation cascade. It is present in human blood at a concentration of approximately 500 ng/mL, with about 1% of the total amount in the proteolytically active form factor VIIa (Morrissey, J. H. et al., Blood, 81:734-744 (1993)). Factor VIIa binds with high affinity to its cofactor, tissue factor, in the presence of calcium ions to form a complex with enhanced proteolytic activity (Carson, S. D. et al., Blood Coag. Fibrinol., 4:281-292 (1993)). Tissue factor is normally expressed in cells surrounding the vasculature, and is exposed to factor VIIa in blood by vessel injury or atherosclerotic plaque rupture. Once formed, the tissue factor/factor VIIa complex initiates blood coagulation by proteolytic cleavage of factor X to factor Xa, factor IX to factor IXa and autoactivation of additional factor VII to VIIa. Factor Xa, generated either directly by tissue factor/factor VIIa or indirectly through action of factor IXa, catalyzes the conversion of prothrombin to thrombin. Thrombin converts fibrinogen to fibrin, which polymerizes to form the structural framework of a blood clot, and activates platelets, which are a key cellular component of coagulation (Hoffman, M., Blood Reviews, 17:S1-S5 (2003)). In addition, there is evidence that tissue factor is present in blood, likely in an encrypted form that is de-encrypted during clot formation. (Giesen, P. L. A. et al., Proc. Natl. Acad. Sci., 96:2311-2315 (1999); Himber, J. et al., J. Thromb. Haemost., 1:889-895 (2003)). The tissue factor/factor VIIa complex derived from blood borne tissue factor may play an important role in propagation of the coagulation cascade (clot growth) and in thrombus formation in the absence of vessel wall injury (i.e., stasis induced deep vein thrombosis or sepsis). The source of blood borne tissue factor is an area of active research (Morrissey, J. H., J. Thromb. Haemost., 1:878-880 (2003)).

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thrombotic or thromboembolic disorders and include acute coronary syndrome, unstable angina, myocardial infarction, ischemic stroke, deep vein thrombosis, peripheral occlusive arterial disease, transient ischemic attack, and pulmonary embolism. In addition, thrombosis occurs on artificial surfaces in contact with blood, including catheters and artificial heart valves. Therefore, drugs that inhibit blood coagulation, or anticoagulants, are "pivotal agents for prevention and treatment of thromboembolic disorders" (Hirsh, J. et al., Blood, 105:453-463 (2005)).

Because of its key role in the coagulation cascade, researchers have postulated that inhibition of factor VIIa could be used to treat or prevent thrombotic or thromboembolic disease. (Girard, T. J. et al., Curr. Opin. Pharmacol., 1:159-163 (2001); Lazarus, R. A. et al., Curr. Med. Chem., 11:2275-2290 (2004); Frederick, R. et al., Curr. Med. Chem., 12:397-417 (2005).) Several studies have confirmed that various biological and small molecule inhibitors of factor VIIa have in vivo antithrombotic efficacy with a low bleeding liability. For instance, it has been demonstrated that a biological factor VIIa inhibitor XK1, comprising a hybrid of Factor X light chain and tissue factor pathway inhibitor first kunitz domain, prevents thrombus formation in a rat model of arterial thrombosis, with no change in bleeding time or total blood loss (Szalony, J. A. et al., J. Thrombosis and Thrombolysis, 14:113-121 (2002)). In addition, small molecule active site directed factor VIIa inhibitors have demonstrated antithrombotic efficacy in animal models of arterial thrombosis (Suleymanov, O. et al., J. Pharmacology and Experimental Therapeutics, 306:1115-1121 (2003); Olivero, A. G. et al., J. Biol. Chem., 280:9160-9169 (2005); Young, W. B. et al., Bioorg. Med. Chem. Leu., 16:2037-2041 (2006); Zbinden, K. G. et al., Bioorg. Med. Chem., 14:5357-5369 (2006)) and venous thrombosis (Szalony, J. A. et al., Thrombosis Research, 112:167-174 (2003); Arnold, C. S. et al., Thrombosis Research, 117:343-349 (2006)), with little impact on bleeding time or blood loss. Moreover, the biological factor VIIa inhibitor recombinant nematode anticoagulant protein c2 (rNAPc2) is currently under clinical investigation for treatment of acute coronary syndromes. Results of initial clinical trials demonstrate that rNAPc2 prevents deep vein thrombosis in patients undergoing total knee replacement (Lee, A. et al., Circulation, 104:74-78 (2001)), reduces systemic thrombin generation in patients undergoing coronary angioplasty (Moons, A. H. M., J. Am. Coll. Cardiol., 41:2147-2153 (2003)), and reduces magnitude and duration of ischemic events in patients with acute coronary syndromes (Giugliano, R. P. et al., World Congress of Cardiology, Barcelona, Poster #3897 (2006)).

U.S. Patent Publication No. 2007/0208054 A1, published Sep. 7, 2007, discloses a series of macrocyclic factor VIIa inhibitors of the following formula:

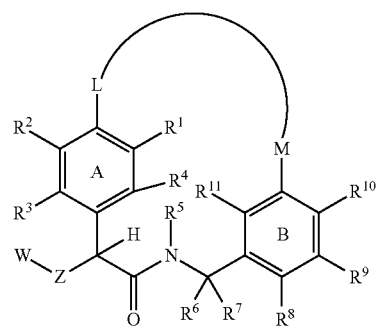

wherein ring A is phenyl or a pyridyl isomer defined by replacing one of $CR^1$, $CR^2$, $CR^3$, or $CR^4$ in ring A of the above formula with N;

ring B is phenyl or a pyridyl isomer defined by replacing one of $CR^8$, $CR^9$, $CR^{10}$, or $CR^{11}$ in ring B of the above formula with N;

M is —CONH—, —SO₂NH—, —NHCO—, or —NHSO₂—;
X is O, S(O)$_p$, or NR$^{16}$;
Y is O or NR$^{16}$ $^a$;
Z is NH, O or S;
W is substituted with 0-2 R$^{14}$ and is selected from:

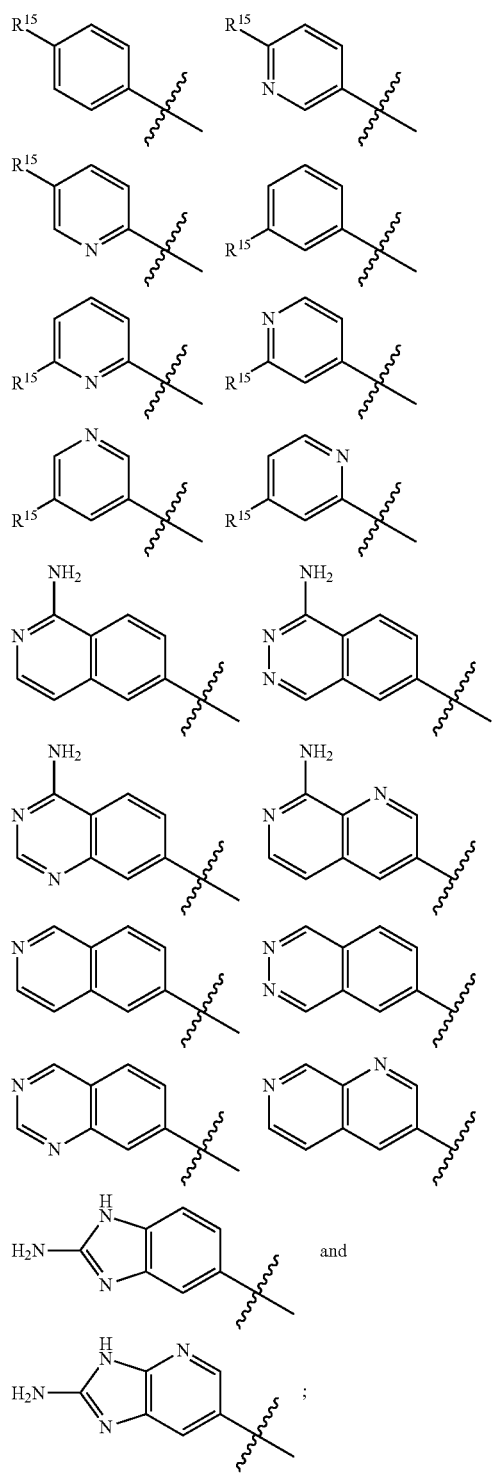

and L and other variables are defined therein.

SUMMARY OF THE INVENTION

The present disclosure provides novel macrocyclic compounds and their analogues, including stereoisomers, tautomers, pharmaceutically acceptable salts, or solvates thereof, which are useful as selective inhibitors of the factor VIIa.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in therapy.

The compounds of the invention may be used for the manufacture of a medicament for the treatment and/or prophylaxis of thromboembolic disorders.

The compounds of the invention can be used alone, in combination with other compounds of the present invention, or in combination with one or more, preferably one to two, and other agent.

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

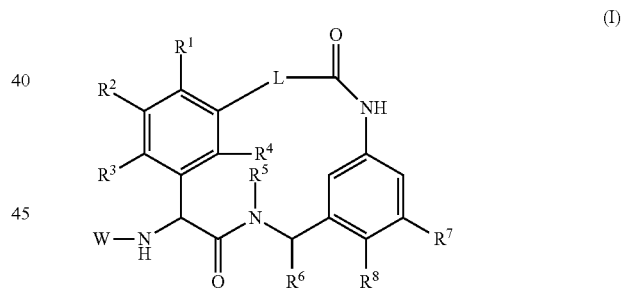

(I)

or a stereoisomer, a tautomer, a pharmaceutically acceptable salt, or a solvate thereof, wherein:
W is independently selected from:
W is independently selected from:

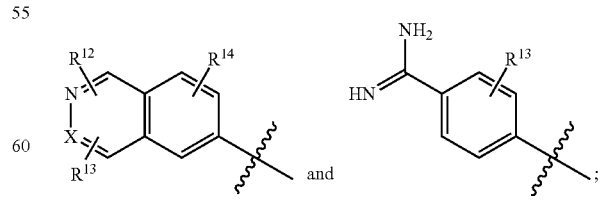

X is independently selected from: CR$^{13}$ and N;
L is independently C$_{1-5}$ alkylene substituted with 0-2 R$^9$ or C$_{2-5}$ alkenylene substituted with 0-2 R$^9$; optionally one of the carbon atoms of said alkylene and alkenylene may be replaced by O, S, SO$_2$, NH, N(C$_{1-4}$ alkyl), N(C$_{1-4}$ fluoroalkyl), and N(—CH$_2$—C$_{3-6}$ carboycle);

R$^9$ is independently selected from: halogen, C$_{1-4}$ alkyl, C$_{1-4}$ haloalkyl, hydroxy, C$_{1-4}$ alkoxy, and C$_{1-4}$ haloalkoxy; optionally when two R$^9$ groups are substituted on the same carbon atom of L, they may combine, with the carbon atom to which they are attached, to form a C$_{3-6}$ cycloalkyl ring;

R$^1$ and R$^2$ are independently selected from: H, OH, halogen, C$_{1-4}$ alkyl, C$_{1-4}$ haloalkyl, C$_{1-4}$ alkoxy, C$_{1-4}$ haloalkoxy, C$_{2-4}$ alkenyl, C$_{2-4}$ alkynyl, —(CH$_2$)$_{0-1}$—C$_{3-6}$ carboycle and —O—(CH$_2$)$_{0-1}$—C$_{3-6}$ carboycle;

R$^3$, R$^4$ and R$^7$ are independently selected from H, halogen, C$_{1-2}$ alkyl, C$_{1-2}$ alkoxy, and C$_{1-2}$ haloalkoxy;

R$^5$ is independently selected from: H C$_{1-2}$ alkyl, and C$_{1-2}$ haloalkyl;

R$^6$ is independently selected from: H, CN, C$_{1-4}$ alkyl, —CO$_2$H, CO$_2$(C$_{1-4}$ alkyl), —CH$_2$CO$_2$H, and —CH$_2$CO$_2$(C$_{1-4}$ alkyl);

R$^8$ is independently selected from: H, halogen, CN, OH, SH, C$_{1-4}$ alkyl, C$_{1-4}$ haloalkyl, C$_{1-4}$ alkoxy, C$_{1-4}$ haloalkoxy, C$_{1-4}$ alkylthio, C$_{1-4}$ haloalkylthio, —SO$_2$(C$_{1-4}$ alkyl), —SO$_2$(C$_{1-4}$ haloalkyl), —SO$_2$(C$_{3-6}$ cycloalkyl), —SO$_2$NH$_2$, —SO$_2$NH(C$_{1-4}$ alkyl), —SO$_2$N(C$_{1-4}$ alkyl)$_2$, and —SO$_2$(C$_{3-6}$ cycloalkyl);

R$^{12}$ is independently selected from H, halogen, CN, —C(=NH)NH$_2$, NH$_2$, NH(C$_{1-4}$ alkyl), N(C$_{1-4}$ alkyl)$_2$, CH$_2$NH$_2$, CH$_2$NH(C$_{1-4}$ alkyl), CH$_2$N(C$_{1-4}$ alkyl)$_2$, C(O)NH$_2$, C(O)NH(C$_{1-4}$ alkyl), and C(O)N(C$_{1-4}$ alkyl)$_2$; and R$^{13}$ and R$^{14}$ are independently selected from: H, F, Cl, C$_{1-2}$ alkyl, and C$_{1-2}$ alkoxy.

In a second aspect, the present disclosure provides a compound of Formula (I), or a stereoisomer, a tautomer, a pharmaceutically acceptable salt, or a solvate thereof, within the scope of the first aspect, wherein:

W is independently selected from:

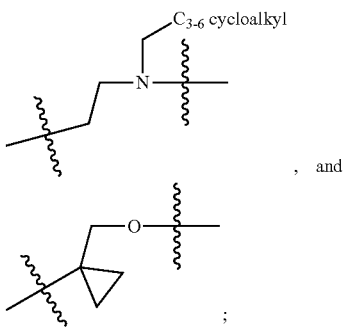

L is independently selected from: —CH$_2$CH$_2$—, —CH(C$_{1-2}$ alkyl)CH$_2$—, —CH$_2$O—, —OCH$_2$—, —CH$_2$CH$_2$O—, —CH$_2$OCH$_2$—, —C(C$_{1-2}$ alkyl)$_2$CH$_2$O—, —CH$_2$CH$_2$N(C$_{1-2}$ alkyl)-, —CH(C$_{1-2}$ alkyl)CH$_2$N(C$_{1-2}$ alkyl)-, —CH$_2$CH$_2$N(Bn)-,

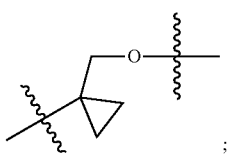 [SMILES: *OCC1(*)CC1]

, and

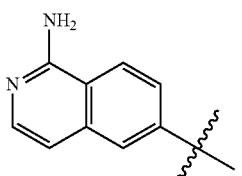

;

R$^1$ is independently selected from: H, F, Cl, OH, C$_{1-4}$ alkoxy, C$_{1-4}$ fluoroalkoxy, OBn, C$_{3-6}$ cycloalkyl, and —O—C$_{3-6}$ cycloalkyl;

R$^2$ is independently selected from: H, F, Cl and C$_{1-4}$ alkoxy;

R$^3$, R$^4$ and R$^9$ are independently selected from: H and F;

R$^5$ is independently selected from: H and CH$_3$;

R$^6$ is independently selected from: H and —CH$_2$CO$_2$H; and

R$^8$ is independently selected from: H, C$_{1-4}$ fluoroalkoxy, —SO$_2$(C$_{1-4}$ fluoroalkyl), and —SO$_2$(C$_{3-6}$ cycloalkyl).

In a third aspect, the present invention includes a compound of Formula (I), or a stereoisomer, a tautomer, a pharmaceutically acceptable salt, or a solvate thereof, within the scope of the first or second aspect, wherein:

L is independently selected from: —CH$_2$CH$_2$—, —CH(CH$_3$)CH$_2$—, —CH$_2$O—, —OCH$_2$—, —CH$_2$CH$_2$O—, —CH$_2$OCH$_2$—, —C(CH$_3$)$_2$CH$_2$O—, —CH$_2$CH$_2$N(CH$_3$)—, —CH(CH$_3$)CH$_2$N(CH$_3$)—, —CH$_2$CH$_2$N(cyclopropylmethyl)-, —CH$_2$CH$_2$N(cyclobutylmethyl)-, —CH$_2$CH$_2$N(Bn)-, and

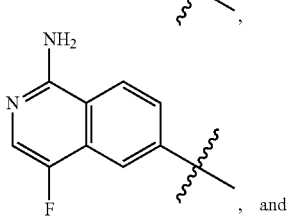

;

W is independently selected from:

-continued

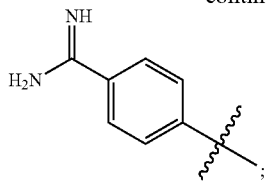

$R^6$ is independently selected from: H and —CH$_2$CO$_2$H; and $R^8$ is independently selected from: H, —OCHF$_2$, —OCH$_2$CHF$_2$, —OCH(CH$_2$F)$_2$, —SO$_2$CHF$_2$, —SO$_2$CF$_3$, and —SO$_2$(cyclopropyl).

In a fourth aspect, the present invention includes a compound of Formula (I), or a stereoisomer, a tautomer, a pharmaceutically acceptable salt, or a solvate thereof, within the scope of any of the above aspects, wherein:

L is independently selected from: —CH$_2$CH$_2$—, —CH(CH$_3$)CH$_2$—, —CH$_2$CH$_2$O—, —CH$_2$OCH$_2$—, —CH$_2$CH$_2$N(CH$_3$)—, —CH(CH$_3$)CH$_2$N(CH$_3$)—, —CH$_2$CH$_2$N(cyclopropylmethyl)-, and —CH$_2$CH$_2$N(Bn)-;

$R^1$ is independently selected from: H, F, OH, OCH$_3$, —OCH(CH$_3$)$_2$, —O(CH$_2$)$_3$CH$_3$, —OCH$_2$CH(CH$_3$)$_2$, —OCH$_2$CHF$_2$, OBn, cyclopropyl,

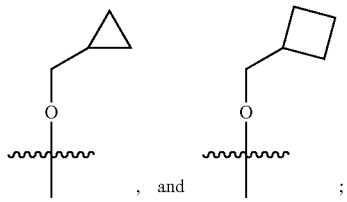 [SMILES: *OCC1CC1 ; *OCC1CCC1]

, and $R^2$ is independently selected from: H, F, and OCH$_3$;
$R^5$ is CH$_3$;
$R^6$ is H; and
$R^8$ is independently selected from: —OCHF$_2$, —OCH$_2$CHF$_2$, —OCH(CH$_2$F)$_2$, —SO$_2$CF$_3$, and —SO$_2$(cyclopropyl).

In another embodiment, W is

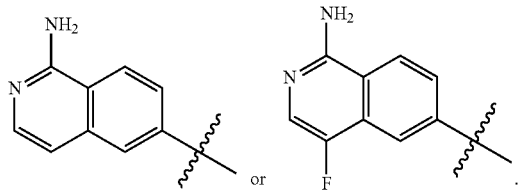 [SMILES: *c1ccc2c(N)nccc2c1 ; *c1ccc2c(N)ncc(F)c2c1]

In another embodiment, W is

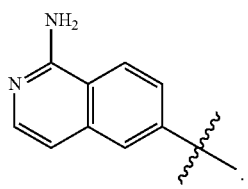 [SMILES: *c1ccc2c(N)nccc2c1]

In another embodiment, W is

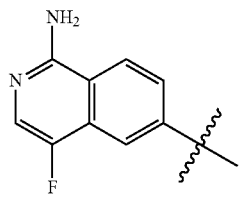

In another embodiment, W is

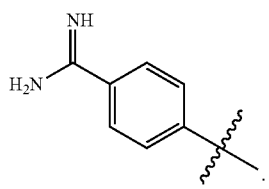

In a fifth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of any of the above aspects.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the modulation of platelet reactivity comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In one embodiment, the present invention provides a method for the treatment and/or prophylaxis of thromboembolic disorders, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another embodiment, the thromboembolic disorder is selected from the group consisting of unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a compound of the present invention for use in therapy.

In another embodiment, the present invention provides a compound of the present invention for use in therapy for the treatment and/or prophylaxis of thromboembolic disorders.

In another embodiment, the present invention also provides the use of a compound of the present invention for the manufacture of a medicament for the treatment and/or prophylaxis of thromboembolic disorders.

In another embodiment, the present invention provides a method for the treatment and/or prophylaxis of thromboembolic disorders, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of thromboembolic disorders.

The compounds of the present invention may be employed in combination with additional therapeutic agent(s) selected from one or more, preferably one to three, of the following therapeutic agents: potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning.

In another embodiment, additional therapeutic agent(s) used in combined pharmaceutical compositions or combined methods or combined uses, are selected from one or more, preferably one to three, of the following therapeutic agents in treating a thromboembolic disorder: an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a cholesterol/lipid lowering agent.

In another embodiment, additional therapeutic agent(s) used in combined pharmaceutical compositions or combined methods or combined uses, are selected from one or more, preferably one to three, of the following therapeutic agents in treating a thromboembolic disorder: warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase.

In another embodiment, additional therapeutic agent(s) used in combined pharmaceutical compositions or combined methods or combined uses, are selected from one or more, preferably one to three, of the following therapeutic agents in treating a thromboembolic disorder: an antihypertensive agent selected from ACE inhibitors, AT-1 receptor antagonists, ET receptor antagonists, dual ET/AII receptor antagonists, and vasopepsidase inhibitors, or an antithrombotic agent selected from an antiplatelet agent selected from GPIIb/IIIa blockers, $P2Y_1$ and $P2Y_{12}$ antagonists, thromboxane receptor antagonists, and aspirin.

In another embodiment, the additional therapeutic agent(s) are an anti-platelet agent or a combination thereof.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" (or alkylene), is intended to include $C_1$, $C_2$, $C_3$, $C_4$, $C_5$, and $C_6$ alkyl groups. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo.

The term "counter ion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of Formula (I) may have prodrug forms. Any compound that will be converted in vivo to provide the bioactive agent (i.e., a compound of Formula (I)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);
d) Bundgaard, H. et al., *J. Pharm. Sci.*, 77:285 (1988); and
e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield Formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
MeOH methanol
EtOH ethanol
i-PrOH or IPA isopropanol
AcOH or HOAc acetic acid
DCM dichloromethane
DIEA or DIPEA diethylpropyl amine
DMF dimethyl formamide
DMSO dimethyl sulfoxide
EtOAc ethyl acetate
Et$_2$O diethyl ether
BINAP 2,2'-bis(diphenylphosphino)-1,1'-binaphthyl
Boc tert-butyloxycarbonyl
CH$_2$Cl$_2$ dichloromethane
CH$_3$CN or ACN acetonitrile
Cs$_2$CO$_3$ cesium carbonate
Cu(OAc)$_2$ copper (II) acetate
DCM dichloromethane
DEAD diethyl azodicarboxylate
DIAD diisopropyl azodicarboxylate
DIBAL diisobutylaluminum hydride
HATU (O-(7-azabenzotriazol-1-yl)-N,N,N',N'-tetramethyl-uronium hexafluorophosphate)
HCl hydrochloric acid
H$_2$SO$_4$ sulfuric acid
HEPES 4-(2-hydroxyethyl)piperaxine-1-ethanesulfonic acid
Hex hexane
Hunig's base N, N-diisopropylethyl amine
K$_2$CO$_3$ potassium carbonate
K—O-t-Bu/t-BuOK potassium tert-butoxide
LAH/LiAlH$_4$ lithium aluminum hydride LiBH$_4$ lithium borohydride
mCPBA or m-CPBA meta-chloroperbenzoic acid
NBS N-bromosuccinimide
NCS N-chlorosuccinimide
PCy$_3$ tricyclohexylphosphine
Pd/C palladium on carbon
Pd$_2$(dba)$_3$ tris(dibenzylideneacetone)dipalladium(0)
Pd(OAc)$_2$ palladium acetate
PMB p-methoxybenzyl
P(t-Bu)$_3$ tri-tert-butylphosphine
SiO$_2$ silica oxide
SnCl$_2$ tin(II) chloride
TBAF tetra-n-butylammonium fluoride
TBAI tetra-n-butylammonium iodide
TBS tert-butyldimethylsilyl
TMSCN trimethylsilyl cyanide
TEA triethylamine
Teoc (trimethylsilyl)ethoxycarbonyloxy
TFA trifluoroacetic acid
THF tetrahydrofuran
TRIS tris(hydroxymethyl)aminomethane
KOAc potassium acetate
K$_3$PO$_4$ potassium phosphate
MgSO$_4$ magnesium sulfate
MsOH or MSA methylsulfonic acid
NaCl sodium chloride
NaHCO$_3$ sodium bicarbonate
NaOH sodium hydroxide
Na$_2$SO$_4$ sodium sulfate
Na$_2$S$_2$O$_4$ sodium dithionite
NaBH$_4$ sodium borohydride
NaO-t-Bu/t-BuONa sodium tert-butoxide
NH$_4$Cl ammonium chloride
OTs tosylate, para-toluenesulfonate
Xantphos 4,5-bis(diphenylphosphino)-9,9-dimethylxanthene
Zn zinc
ZnCl$_2$ zinc chloride
Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, 3rd Edition, Wiley-Interscience (1999)).

Compounds having the general Formula (I) can be prepared according to the general methods shown in the Schemes below. Compounds of formula (I) can be prepared using the general method shown in Scheme 1. Using the Petasis boronic acid Mannich reaction (Petasis, N. A. et al., *J. Am. Chem. Soc.*, 119:445-446 (1997); Petasis, N. A. et al., *Tetrahedron*, 53:16463-16470 (1997)), amines 1 are reacted with glyoxylic acid and phenyl boronic acids 2 to afford arylglycines 3. Arylglycines 3 in turn are coupled with amines 4 to afford amino alcohol amides 5. Treatment of amides 5 with phosgene (or a phosgene equivalent such as triphosgene) to generate the carbamic chloride intermediate in situ, followed by slow addition of this intermediate into a basic reaction mixture, such as triethylamine or Hunig's base in DCM or acetonitrile, effects macrocyclization to yield compounds 6 of formula (I) after protecting group manipulation if necessary.

Petasis boronic acid Mannich reaction is typically conducted in a solvent such as, but not limited to, toluene, dichloromethane, 1,2-dichloroethane, methanol, ethanol, dimethylformamide, or acetonitrile, or appropriate mixtures thereof. In some cases, mixtures of acetonitrile and dimethylformamide are preferred. Fluorinated alcohols such as hexafluoroisopropanol are useful additives that may improve the rate and or yield of the reaction. If necessary, the reaction is heated conventionally or in a microwave reactor to achieve a practical reaction rate.

The preparation of amines 1 is described in the experimental procedures for Intermediates 1-4. Preparation of phenylboronic acids 2 is described in the synthesis of Intermediate 5 and in examples. Additionally, preparation of phenylboronic acids 2 can be achieved through methods known to one skilled in the art of organic synthesis. The preparation of amines 4 is described in the experimental procedures for Intermediates 6, 8 and in the examples. Additionally, preparation of N-methylated benzylamines 4 can be achieved through methods known to one skilled in the art of organic synthesis.

Coupling reagents and conditions can be found in Bodanszky, *Principles of Peptide Synthesis*, Second Edition, Springer Verlag Ed, Berlin (1993) and in a recent review (Montalbetti, C. A. G. N. et al., *Tetrahedron*, 61:10819-11046 (2005)). Coupling reagents include, but not limited to, CDI, DIC, and EDCI. Optionally, an intermediate activated ester can be prepared by adding one equivalent of 1-hydroxybenzotriazole or 1-hydroxy-7-azabenzotriazole. Other coupling reagents include, but not limited to, BOP or HATU, which are usually reacted in the presence of a tertiary base such as DIEA or TEA. BOP is a preferred reagent for preparation of compounds of Formula (I). Addition of catalytic or stoichiometric DMAP may improve the reaction rate or yield. The reaction may be conducted in solvents such as, but not limited to, DCE, DCM, DMF, or mixtures thereof. Finally, it may be necessary to run the macrocyclization reaction under dilute conditions (initial concentration of 4<0.1 M) to favor macrocyclization over dimerization. Depending on the particular substituent groups present in the final compounds, deprotection steps may be required before or after the macrocyclization step to afford compounds of Formula (I).

Scheme 1

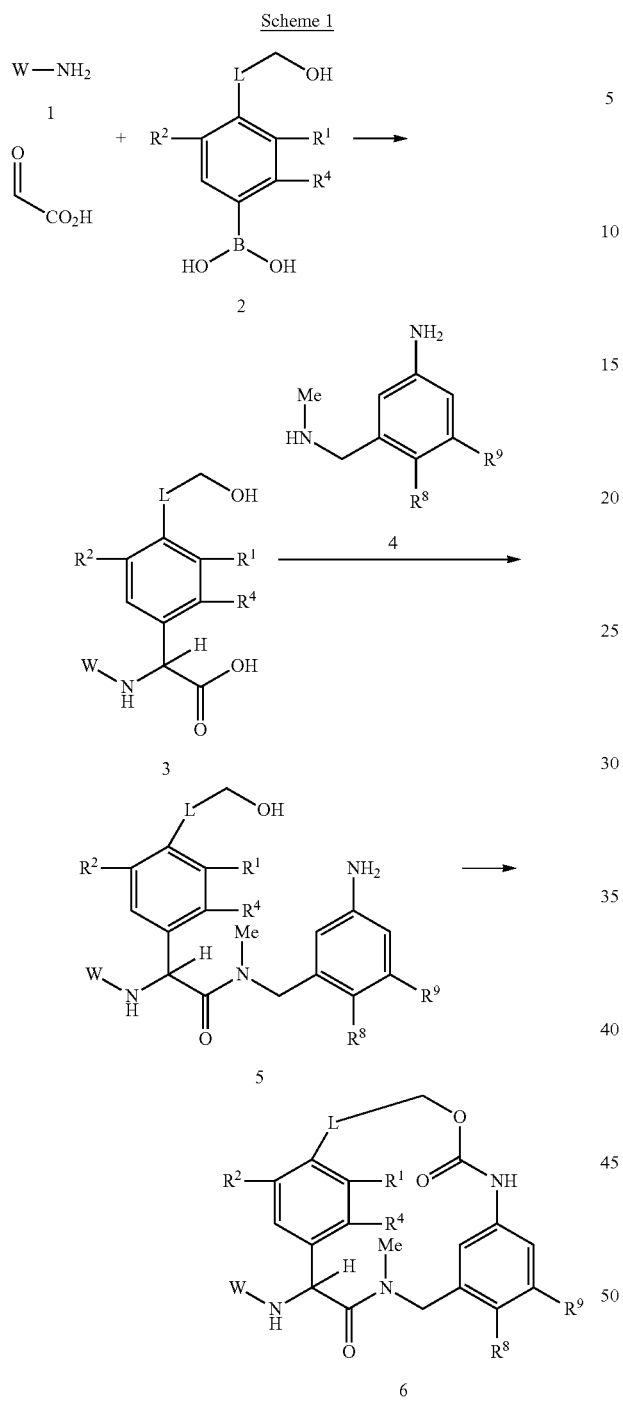

Scheme 2

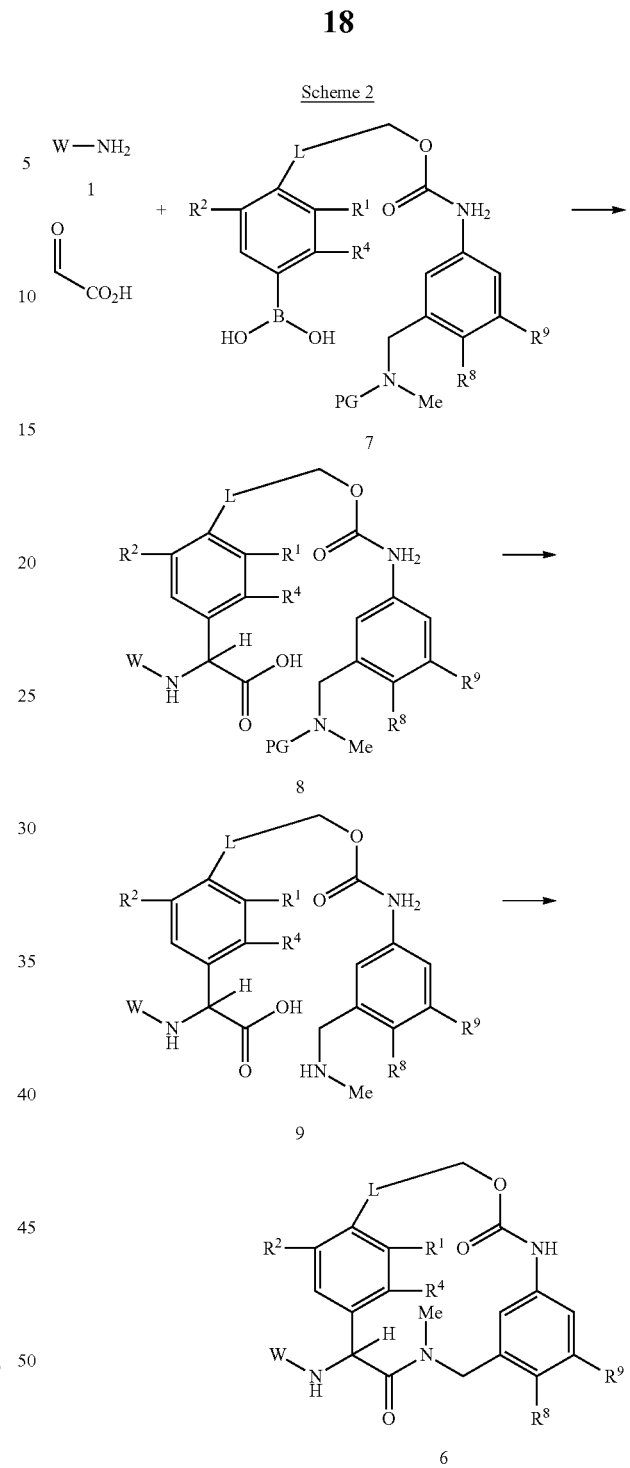

Compounds of formula (I) can also be prepared using the general method shown in Scheme 2. Using the Petasis boronic acid Mannich reaction, amines 1 are reacted with glyoxylic acid and elaborated phenyl boronic acids 7 to afford arylglycines 8. The protecting group PG in 8, for instance, a carbamate such as Cbz, may be deprotected by catalytic hydrogenation to an N-methylated benzylamine 9. Amino acids 9 can be cyclized to macrocycles 6 by slow addition of this intermediate into a mixture of base such as triethylamine or Hunig's base and coupling reagent such as BOP in DCM or acetonitrile. After a final protecting group manipulation, compounds of formula (I) are obtained.

Preparation of the elaborated phenyl boronic acids 7 is described in Scheme 3. Treatment of amines 11 with phosgene (or a phosgene equivalent such as triphosgene) to generate the carbamic chloride intermediate in situ, followed by addition of this intermediate into a reaction mixture of aryl bromides 10 and base, such as triethylamine or Hunig's base in DCM or acetonitrile, affords carbamates 12. The bromide in carbamates 12 is converted to the boronic acids 7 by the Suzuki-Miyara coupling (Miyaura, N. et al., *Chem. Rev.*, 95:2457 (1995)).

Scheme 3

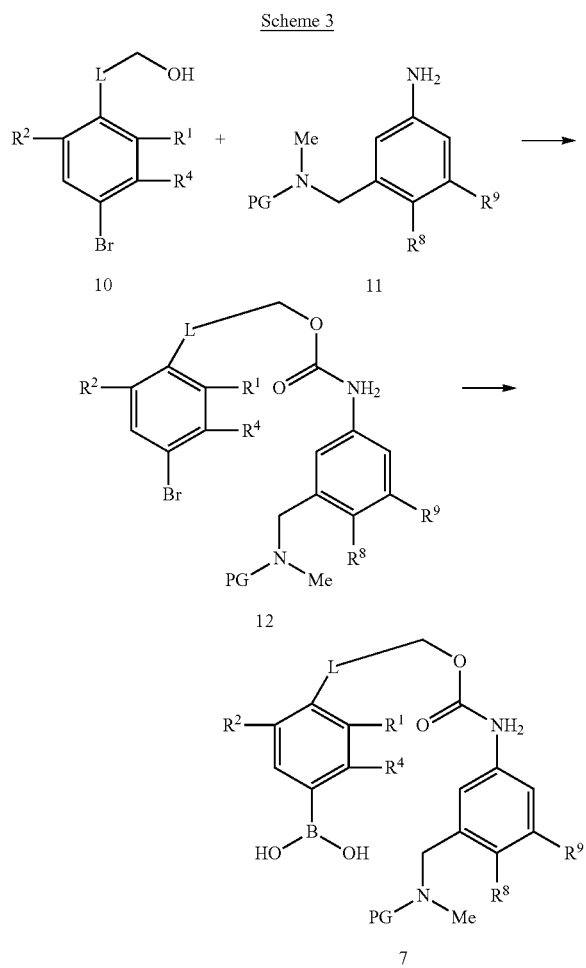

General Methods

The following methods were used in the exemplified Examples, except where noted otherwise.

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm). Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Axia Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). LCMS chromatograms were obtained on a Shimadzu HPLC system running Discovery VP software, coupled with a Waters ZQ mass spectrometer running MassLynx version 3.5 software using:

Method A: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5μ C18 (4.5×30 mm) Flow rate was 4 ml/min. and UV detection was set to 220 nm. The LC column was maintained at room temperature.

Method B: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (2.0×30 mm) Flow rate was 1 ml/min. and UV detection was set to 220 nm. The LC column was maintained at room temperature.

Method C: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (4.5×30 mm) Flow rate was 5 mL/min. and UV detection was set to 220 nm. The LC column was maintained at room temperature.

Method D: 30-95% acetonitrile in $H_2O$ with 0.1% TFA in 8 min run, Waters Xbridge 4.6×50 mm 5 um C18, flow rate 1.2 mL/min and UV detection was set to 220 nm. The LC column was maintained at room temperature.

Method E: 10-95% methanol in water, 0.1% TFA in a 10 min run, PHENOMENEX® Onyx Monolithic 4.6×100 mm 5 um C18, flow rate 2.0 mL/mL and UV detection was set to 220 nm. The LC column was maintained at room temperature.

Method F: 5-95% acetonitrile in water, 10 mM of modifier in 6 min run, Waters Xbridge 2.1×50 mm 5 um C18, flow rate 1.0 mL/min and UV detection was set to 220 nm. The LC column was maintained at room temperature.

In addition, the following orthogonal HPLC conditions were used to check the purity of the compounds:

Method A: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 μm (4.6×150 mm) Flow rate was 2 ml/min. and UV detection was set to 220 nm. The LC column was maintained at room temperature.

Method B: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 μm (4.6×150 mm) Flow rate was 2 ml/min. and UV detection was set to 220 nm. The LC column was maintained at room temperature.

III. Biology

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders (or conditions)" as used herein includes arterial or venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but are not limited to: cardiopulmonary bypass, percutaneous coronary intervention, and hemodialysis.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant or antithrombotic effect of compounds of the present invention is believed to be due to inhibition of coagulation factor VIIa.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel. The term "stroke", as used herein, refers to embolic stroke or atherothrombotic stroke arising from occlusive thrombosis in the carotid communis, carotid interna, or intracerebral arteries.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

A. In Vitro Assays

The effectiveness of compounds of the present invention as inhibitors of the coagulation Factors, VIIa, IXa, Xa, XIa, XIIa, plasma kallikrein or thrombin, tissue kallikrein and activated protein C, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

a. FVIIa Ki (25° C.): FVIIa Peptide Substrate Assay

S2288 (range of concentrations) and FVIIa inhibitor were incubated for 15 minutes (min) at 25° C. Reactions were initiated by addition of a solution of full-length human TF (6 nM), FVIIa (0.75 nM), and PCPS (25 µM). FVIIa hydrolyses S2288, which was monitored for up to 60 min at 405 nm. Steady-state reaction velocity data (vs) was globally fit to Equation 1 for competitive inhibition.

$$vs = V\max[S]/([S]+Km(1+[I]/Ki)) \quad \text{(Eq. 1)}$$

where Vmax is maximum velocity, [S] is substrate concentration, Km is the Michaelis-Menten constant, [I] is the inhibitor concentration, and Ki is the inhibitor dissociation constant (GraFit, version 5, Erithacus Software Ltd, West Sussex, UK).

FVIIa-Xase Ki (37° C.): 52765 (0.5 mM), PCPS (25 µM), calcium chloride (5 mM), full-length human TF (3 nM), human FVIIa (5 pM), and FVIIa inhibitor were incubated for 15 min at 37° C. Reactions were initiated by the addition of human FX (range of concentrations). Preliminary experiments revealed that the plasma purified FX contains a residual amount of human FVIIa which could not be removed by affinity chromatography. The residual FVIIa is sufficient, when combined with PCPS, calcium and TF to catalyze the conversion of FX to Xa, and was increased by the addition of 5 pM human FVIIa. FXa in turn hydrolyses S2765, which was monitored for 60 min at 405 nm. FXase activity was derived from the parabolic change in absorbance over time according to Equation 2:

$$\text{Absorbance} = \tfrac{1}{2} \text{ at } 2+bt+c \quad \text{(Eq. 2)}$$

where a is proportional to the rate of FX activation=product=vs; b is proportional to the hydrolysis of S2765 in the absence of FXa; c is the absorbance at t=0. Steady-state reaction velocity data (vs) was globally fit to Equation 3 for non-competitive inhibition modified for contaminating enzyme (FVIIa) in the substrate (FX) as $$vs = (kcat(E+f[S])/((Km+[S])(1+[I]/Ki)) \quad \text{(Eq. 3)}$$

where kcat is the enzyme turnover rate, E is the concentration of enzyme added, f is the molar fraction of enzyme contained in the substrate, and the rest as defined above.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; CHROMOGENIX) at a concentration of 0.00008-0.0004 M. The $K_m$ value used for calculation of $K_i$ was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

Tissue kallikrein-1 activity was determined in reactions containing 0.05 nM enzyme and 90 µM substrate (H-D-Val-Leu-Arg-AFC) in buffer (0.1M sodium phosphate pH 7.4, 0.2 M NaCl, 0.5% PEG 8000, and 1% DMSO). Assays were performed using 96-well microtiter plates (COSTAR® 3600, CORNING®, NY, USA) and a thermostatic temperature controlled plate reader (SPECTRAMAX® Gemini, Molecular Devices, Sunnyvale, Calif., USA). Fluorescence was monitored using 400 nm excitation and 505 nm emission wavelengths.

APC activity was determined in reactions containing 0.05 nM enzyme and 90 nM substrate (pyroGlu-Pro-Arg-pNA) in buffer (0.1M sodium phosphate pH 7.4, 0.2 M NaCl, 0.5% PEG 8000, and 1% DMSO). Assays were performed using 96-well microtiter plates (COSTAR® 3600, CORNING®, NY, USA) and a thermostatic temperature controlled plate reader (SPECTRAMAX® Gemini, Molecular Devices, Sunnyvale, Calif., USA). Fluorescence was monitored using 400 nm excitation and 505 nm emission wavelengths.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o-v_s)/v_s=I/(K_i(1+S/K_m)) \text{ for a competitive inhibitor with one binding site; or}$$

$$v_s/v_o=A+((B-A)/1+((IC_{50}/(I)_n))); \text{ and}$$

$$K_i=IC_{50}/(1+S/K_m) \text{ for a competitive inhibitor}$$

where:
 $v_o$ is the velocity of the control in the absence of inhibitor;
 $v_s$ is the velocity in the presence of inhibitor;
 I is the concentration of inhibitor;
 A is the minimum activity remaining (usually locked at zero);
 B is the maximum activity remaining (usually locked at 1.0);
 n is the Hill coefficient, a measure of the number and cooperativity of potential inhibitor binding sites;
 $IC_{50}$ is the concentration of inhibitor that produces 50% inhibition under the assay conditions;
 $K_i$ is the dissociation constant of the enzyme:inhibitor complex;
 S is the concentration of substrate; and
 $K_m$ is the Michaelis constant for the substrate.

The selectivity of a compound may be evaluated by taking the ratio of the $K_i$ value for a given protease with the $K_i$ value for the protease of interest (i.e., selectivity for FVIIa versus protease P=$K_i$ for protease P/$K_i$ for FVIIa). Compounds with selectivity ratios>20 are considered selective. Compounds with selectivity ratios>100 are preferred, and compounds with selectivity ratios>500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Prothrombin Time (PT) is determined using thromboplastin (Thromboplastin C Plus, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

Deficient FVII-PT (FVII-def PT) was performed by mixing human FVII immunodepleted plasma with normal pooled plasma from different species to produce a clotting time of about 40 seconds (s). For PT and FVII-def PT, plasma (50 µl) was warmed to 37° C. for 3 min before adding PT reagent (100 µl). Determinations were performed in duplicate and expressed as a mean ratio of treated vs. baseline control. The concentrations required to prolong clotting time by two-fold (EC2×) were calculated by linear interpolation (Microsoft Excel, Redmond, Wash., USA) and are expressed as total plasma concentrations, not final assay concentrations after addition of clotting assay reagents.

Activated Partial Thromboplastin Time (aPTT) is determined using ALEXIN® (Trinity Biotech, Ireland) or ACTIN® (Dade-Behring, Illinois) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-venous (AV) Shunt Thrombosis Model

The rabbit AV shunt model, described by Wong et al. (Wong, P. C. et al., *J. Pharmacol. Exp. Ther.*, 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm) The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, IL.).

TABLE 1

Representative In Vitro Biological Data for Exemplified Compounds

| Example No. in this application | FVIIa Ki, nM |
|---|---|
| Example 1 | 188 |
| Example 2 | 265 |
| Example 3 | 560 |
| Example 4 | 1476 |
| Example 5 | 950 |
| Example 6 | 44 |
| Example 7 | 115 |
| Example 8 | 5 |
| Example 9 | 23 |
| Example 10 | 714 |
| Example 11 | 5 |
| Example 12 | 47 |
| Example 13 | 6 (37° C.) |
| Example 14 | 5 |
| Example 15 | 6 |
| Example 16 | 92 (37° C.) |
| Example 17 | 7 |
| Example 18 | 6 |
| Example 19 | 115 |
| Example 20 | 59 |
| Example 21 | 5 |
| Example 22 | 5 |
| Example 23 | 5 |
| Example 24 | 5 |
| Example 25 | 6 |
| Example 26 | 5 |
| Example 27 | 148 |
| Example 28 | 14 |
| Example 29 | 80 |
| Example 30 | 10 |
| Example 31 | 5 |
| Example 32 | 31 |
| Example 33 | 21 |
| Example 34 | 5 |
| Example 35 | 6 |
| Example 36 | 5 |
| Example 37 | 11 |
| Example 38 | 5 |
| Example 39 | 120 |
| Example 40 | 5 |
| Example 41 | 17 |
| Example 42 | 5 |
| Example 43 | 5 |
| Example 44 | 5 |

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., other anti-platelet agents or other pharmaceutically active material. Additionally, the present compounds may be used in combination with one or more of various other therapeutic agents, including: anti-arrhythmic agents; anti-hypertensive agents; anti-thrombotic and/or anti-thrombolytic agents; calcium channel blockers (L-type and T-type); cardiac glycosides; diuretics, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; antianxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving $P2Y_1$ or anti-platelet activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Intermediate 1

3-(2-Hydroxyethyl)phenylboronic acid

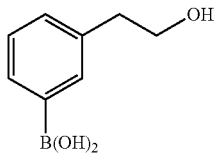 [SMILES: OCCc1cccc(B(O)O)c1]

Intermediate 1A (3-Bromophenethoxy)(tert-butyl)dimethylsilane

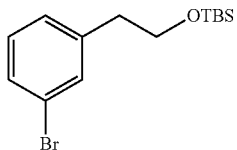 [SMILES: CC(C)(C)[Si](C)(C)OCCc1cccc(Br)c1]

2-(3-Bromophenyl)ethanol (1.89 g, 9.40 mmol) was dissolved in DCM (47.0 mL). Imidazole (2.56 g, 37.6 mmol) then TBS-Cl (2.83 g, 18.80 mmol) were added at ambient temperature. The reaction was stirred for 2 h. The reaction was diluted with DCM and washed with saturated NaHCO$_3$, then water, then brine, dried (Na$_2$SO$_4$), filtered, and concentrated in vacuo to yield Intermediate 1A (2.93 g, 99%). 1H NMR (400 MHz, CHLOROFORM-d) δ ppm 7.38 (1 H, s), 7.34 (1 H, ddd, J=6.40, 2.38, 2.26 Hz), 7.08-7.20 (2 H, m), 3.80 (2 H, t, J=6.78 Hz), 2.79 (2 H, t, J=6.78 Hz), 0.87 (9 H, s), −0.02 (6 H, s). MS (ESI) m/z: 315.0 (M+H)$^+$.

Intermediate 1

Intermediate 1A (0.500 g, 1.586 mmol) was dissolved in THF (7.93 mL) and cooled to −78° C. BuLi (1.374 mL, 2.061 mmol) was added. Stirring was continued for 60 min. After this time, triisopropyl borate (0.736 mL, 3.17 mmol) was added and stirring continued for 10 min, then the reaction was warmed to ambient temperature and allowed to stir for 2 h. The reaction was diluted with EtOAc and washed with water, brine, dried (Na$_2$SO$_4$), filtered, and concentrated in vacuo. The crude material was then dissolved in 90:10:0.1 MeCN:H$_2$O:TFA and allowed to stir at ambient temperature and stirred for 2 h. The crude material was purified by reversed phase HPLC to yield Intermediate 1 (0.105 g, 40%) as a 2:1 mixture of ester isomers. 1H NMR (400 MHz, MeOD) δ ppm 7.46 (2 H, br. s.), 7.18-7.37 (2 H, m), 3.74 (2 H, t, J=7.03 Hz), 2.82 (2 H, t, J=7.03 Hz).

Intermediate 2

2-(Trimethylsilyl)ethyl 5-amino-2-(cyclopropylsulfonyl)benzyl(methyl)carbamate

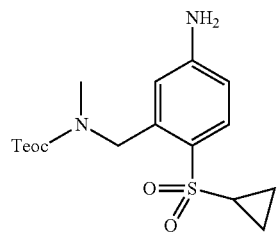

To a mixture of 4-(cyclopropylsulfonyl)-3-((methylamino)methyl)aniline dihydrochloride (1.09 g, 4.54 mmol) and 2,5-dioxopyrrolidin-1-yl 2-(trimethylsilyl)ethyl carbonate (1.176 g, 4.54 mmol) in MeOH (25 mL) was added DIPEA (2.376 mL, 13.61 mmol) and stirred at rt for 5 min. The reaction mixture was concentrated under reduced pressure, diluted with EtOAc, and washed with brine. The crude product was subjected to silica gel column chromatography (0-100% EtOAc/Hex gradient) to yield Intermediate 2 (1.744 g, 80%). 1H NMR 78017-063-02 (500 MHz, CD$_3$OD) δ ppm 8.25 (d, J=8.80 Hz, 1 H) 7.30 (d, J=8.25 Hz, 1 H) 7.22 (s, 1 H) 6.95 (s, 2 H) 5.54 (s, 2 H) 4.91 (d, J=17.60 Hz, 2 H) 3.68 (s, 3 H) 3.55-3.63 (m, 1 H) 1.66-1.85 (m, 6 H) 0.81 (d, J=43.44 Hz, 9 H).

Intermediate 3

(6-Amino-4-fluoro-isoquinolin-1-yl)-bis(carbamic acid tert-butyl ester)

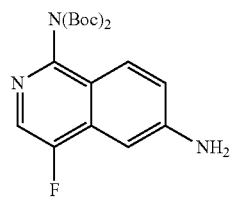

Intermediate 3A

2-Methyl-4-nitro-benzoic acid methyl ester

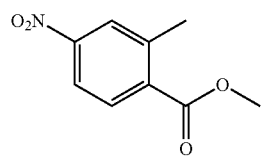

To 2-methyl-4-nitrobenzoic acid (6.5 g, 35.9 mmol) in DCM (40 mL) was added 2.0 M oxalyl chloride in DCM (24.67 mL, 49.3 mmol), followed by DMF (0.139 mL, 1.794 mmol). The mixture was stirred at 40° C. for 1.5 h and then at rt for 0.5 h. The solvent was removed and the residue was stored under high vacuum for 0.5 h. The intermediate acid chloride was then dissolved in DCM (40 mL) and cooled to 0° C., MeOH (40 mL) was then added and the mixture was stirred at 0° C. for 0.5 h. Solvent was removed, the crude reaction mixture was diluted with EtOAc, washed with saturated NaHCO₃ and brine. The organic layer was dried over sodium sulfate and concentrated to give Intermediate 3A (7.0 g, 35.9 mmol, 100% yield) as a white solid. ¹H NMR (400 MHz, CHLOROFORM-d) δ ppm 7.98-8.11 (m, 3 H) 3.93 (s, 3 H) 2.67 (s, 3 H).

Intermediate 3B 2-((E)-2-Dimethylamino-vinyl)-4-nitro-benzoic acid methyl ester

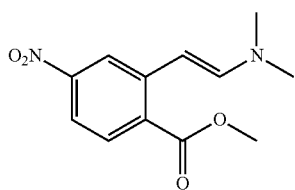 [SMILES: COC(=O)c1ccc([N+](=O)[O-])cc1/C=C/N(C)C]

To Intermediate 3A (6.6 g, 33.8 mmol) in DMF (9.0 mL) was added 1-tert-butoxy-N,N,N',N'-tetramethylmethanediamine (23.04 mL, 112 mmol). The mixture was heated at 143° C. for 3 h. The crude reaction mixture was vacuum distilled at 70° C. to leave a semi-solid. The semi-solid was triturated with EtOAc/Hexanes (1:4) and stored at 4° C. overnight. The precipitate was collected by filtration to give Intermediate 3B (5.9 g, 23.58 mmol, 69.7% yield) as a dark solid. ¹H NMR (400 MHz, CHLOROFORM-d) δ ppm 8.21 (d, J=2.20 Hz, 1 H) 7.87 (d, J=8.79 Hz, 1 H) 7.66 (dd, J=8.79, 2.20 Hz, 1 H) 7.02 (d, J=13.19 Hz, 1 H) 6.12 (d, J=13.74 Hz, 1 H) 3.91 (s, 3 H) 2.94 (s, 6 H).

Intermediate 3C

6-Nitro-2H-isoquinolin-1-one

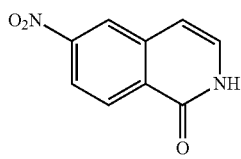 [SMILES: O=c1[nH]ccc2cc([N+](=O)[O-])ccc12]

To Intermediate 3B (980 mg, 3.92 mmol) in a microwave tube was added 7.0 N ammonia in ethyleneglycol (5.69 mL, 39.2 mmol). The tube was placed in microwave and heated at 140° C. for 30 min. The crude reaction mixture was triturated with EtOAc, and the precipitate was centrifuged and collected to yield Intermediate 3C (0.514 g, 69%). ¹H NMR (400 MHz, DMSO-d₆) δ ppm 11.22 (br. s., 1 H) 8.62 (d, J=2.20 Hz, 1 H) 8.37 (d, J=8.79 Hz, 1 H) 8.17 (dd, J=8.79, 2.20 Hz, 1 H) 7.35 (d, J=7.47 Hz, 1 H) 6.81 (d, 1 H). MS (ESI) m/z: 191.1 (M+H)⁺.

Intermediate 3D

4-Fluoro-3-methoxy-6-nitro-3,4-dihydro-2H-isoquinolin-1-one

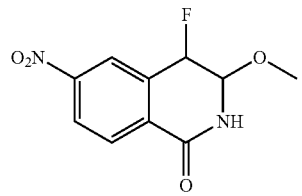 [SMILES: COC1NC(=O)c2ccc([N+](=O)[O-])cc2C1F]

To Intermediate 3C (1.15 g, 6.05 mmol) in MeCN (40 mL) and MeOH (40.0 mL) was added Selectorfluor (2.357 g, 6.65 mmol). The mixture was heated at 82° C. for 1.0 h. Additional SelectorFluor (750 mg, 2.1 mmol) was added and refluxed for additional 1.5 h. The solvent was removed under reduced pressure, and the residue was suspended in EtOAc, stirred with 60 mL 0.5 N HCl, and the organic layer separated. The aqueous layer was further extracted with EtOAc, and the combined organic layers were washed with brine and dried over Na₂SO₄ to yield Intermediate 3D (1.453 g, 96%). ¹H NMR (400 MHz, CHLOROFORM-d) δ ppm 8.56 (br, 1 H) 8.11-8.38 (m, 3 H) 5.83-5.99 (dd, J=47.8, 3.85 Hz) and 5.38-5.54 (dd, J=48.37, 2.2 Hz, 1 H) 4.89-4.97 (m, 2 H) 3.39 and 3.38 (s, 3 H).

Intermediate 3E

4-Fluoro-6-nitro-isoquinolin-1-ol

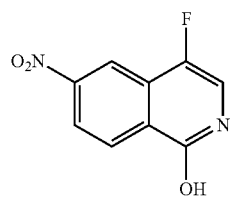 [SMILES: O=[N+]([O-])c1ccc2c(O)ncc(F)c2c1]

To a solution of Intermediate 3D (85 mg, 0.354 mmol) in MeCN (1.0 mL) was added 4.0 N HCl in dioxane (0.265 mL, 1.062 mmol). The mixture was stirred at 65° C. for 40 min. A yellow precipitate formed. The solvent was removed under reduced pressure to yield Intermediate 3E (74 mg, 95%). ¹H NMR (400 MHz, DMSO-d₆) δ ppm 8.38-8.46 (m, 2 H) 8.31 (dd, J=8.79, 2.20 Hz, 1 H) 7.61 (d, 1 H); ¹⁹F NMR (376 MHz, DMSO-d₆) δ ppm −160.17 (s., 1 F). MS (ESI) m/z: 209.2 (M+H)⁺.

Intermediate 3F

4-Fluoro-6-nitro-isoquinolin-1-ylamine

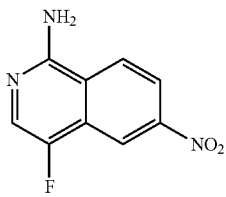 [SMILES: Nc1ncc(F)c2cc([N+](=O)[O-])ccc12]

To Intermediate 3E (1.2 g, 4.91 mmol) was added phosphoryl trichloride (11.23 mL, 123 mmol). The suspension was heated to 115° C. for 1 h. The reaction was concentrated under reduced pressure. The residue was diluted with EtOAc, washed with saturated NaHCO$_3$, washed with brine, and dried over Na$_2$SO$_4$ to yield 1-chloro-4-fluoro-6-nitro-isoquinoline (0.95 g, 4.19 mmol, 85% yield) which was used immediately in the next step without further purification.

A mixture of 1-chloro-4-fluoro-6-nitro-isoquinoline (580 mg, 2.56 mmol), BINAP (159 mg, 0.256 mmol) and tris(dibenzylideneacetone)dipalladium (0) (117 mg, 0.128 mmol) in toluene (12 mL) was degassed with argon for 10 min. To this mixture was added diphenylmethanimine (0.471 mL, 2.82 mmol) and sodium t-butoxide (312 mg, 3.25 mmol). The reaction mixture was heated to 90° C. for 4 h. The reaction was diluted with EtOAc and brine and filtered through a pad of wet Celite. The organic layer was collected and washed with brine, dried over Na$_2$SO$_4$, and concentrated. The resultant residue was dissolved in THF (15 mL) and was treated with 4.0 N HCl (9.60 mL, 38.4 mmol) for 30 min. The reaction mixture was diluted with EtOAc. The layers were separated and the organic layer was back extracted with 4.0 N HCl (2×10 mL). The aqueous layers were combined and treated at 0° C. with 5.0 N NaOH to adjust the pH to 12-13. The precipitate that formed was then collected by filtration, dried under the vacuum to yield Intermediate 3F (300 mg, 1.448 mmol, 56.6% yield) as a brown solid. $^1$H NMR (400 MHz, DMSO-d$_6$) δ ppm 8.59 (d, J=2.20 Hz, 1 H) 8.51 (dd, J=9.34, 2.20 Hz, 1 H) 8.29 (dd, J=9.34, 2.20 Hz, 1 H) 7.99 (d, J=2.20 Hz, 1 H) 7.16 (s, 2 H).

Intermediate 3G (4-Fluoro-6-nitro-isoquinolin-1-yl)-bis(carbamic acid tert-butyl ester)

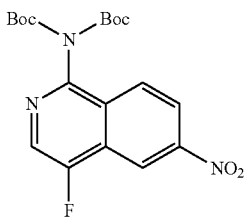 [SMILES: CC(C)(C)OC(=O)N(C(=O)OC(C)(C)C)c1ncc(F)c2cc([N+](=O)[O-])ccc12]

To Intermediate 3F (205 mg, 0.990 mmol) suspended in MeCN (8.0 mL) was added TEA (0.552 mL, 3.96 mmol) and DMAP (30.2 mg, 0.247 mmol). The reaction was stirred at rt for 6 h. The reaction was diluted with EtOAc, washed with 0.5 N HCl, washed with saturated Na$_2$CO$_3$, washed with brine, and dried over Na$_2$SO$_4$. The compound was purified by silica gel column chromatography (0-30% EtOAc/Hex gradient to yield Intermediate 3G (0.403 g, 66%). $^1$H NMR (400 MHz, METHANOL-d$_3$) δ ppm 9.06 (d, J=2.20 Hz, 1 H) 8.58 (dd, J=9.23, 2.20 Hz, 1 H) 8.51 (s, 1 H) 8.27 (d, J=9.23 Hz, 1 H) 1.30 (s, 18 H); $^{19}$F NMR (376 MHz, METHANOL-d$_3$) δ ppm −136.64 (s, 1 F).

Intermediate 3

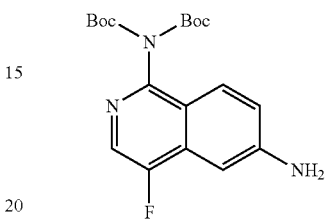

To Intermediate 3G (20 mg, 0.049 mmol) and 1.0 N HCl (5.89 μL, 5.89 μmol) dissolved in MeOH (3 mL) was added 10% Pd/C (8.0 mg, 0.049 mmol). The mixture was hydrogenated with a hydrogen balloon for 30 min. The reaction was filtered, and the filtrate was concentrated to yield Intermediate 3 (0.017 g, 92%). $^1$H NMR (400 MHz, ACETONITRILE-d$_3$) δ ppm 7.96 (d, J=3.08 Hz, 1 H) 7.65 (dd, J=9.23, 2.20 Hz, 1 H) 7.13 (dd, J=9.23, 2.20 Hz, 1 H) 6.95 (d, J=2.20 Hz, 1 H) 1.27 (s, 18 H). $^{19}$F NMR (376 MHz, ACETONITRILE-d$_3$) δ ppm −142.33 (s., 41 F). MS (ESI) m/z: 378.3 (M+H)$^+$.

Intermediate 4

(S)-3-(2-(Benzyloxy)-5-bromophenyl)butanoic acid

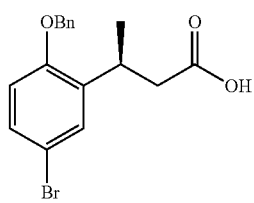 [SMILES: C[C@@H](CC(=O)O)c1cc(Br)ccc1OCc1ccccc1]

Intermediate 4A 1-(2-(Benzyloxy)-5-bromophenyl)ethanone

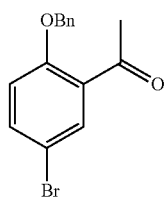 [SMILES: CC(=O)c1cc(Br)ccc1OCc1ccccc1]

1-(5-Bromo-2-hydroxyphenyl)ethanone (0.5 g, 2.325 mmol) and K$_2$CO$_3$ (0.321 g, 2.325 mmol) were dissolved in EtOH (11.63 mL). Benzyl bromide (0.277 mL, 2.325 mmol)

was added and the reaction was heated to reflux for 4 h. The reaction was cooled to ambient temperature and concentrated in vacuo. The residue was dissolved in water and extracted with EtOAc. The organic layer was further washed with brine, dried (Na$_2$SO$_4$), filtered, and concentrated in vacuo. The crude reaction mixture was purified by silica gel column chromatography (0 to 100% Et$_2$O in hexanes) to yield Intermediate 4A (0.596 g, 84%). 1H NMR (400 MHz, CHLOROFORM-d) δ ppm 7.85 (1 H, d, J=2.76 Hz), 7.52 (1 H, dd, J=8.78, 2.51 Hz), 7.39-7.45 (4 H, m), 7.32-7.39 (1 H, m), 6.91 (1 H, d, J=8.78 Hz), 5.15 (2 H, s), 2.58 (3 H, s). MS (ESI) m/z: 305.1 (M+H)$^+$.

Intermediate 4B 1-(2-(Benzyloxy)-5-bromophenyl)ethanol

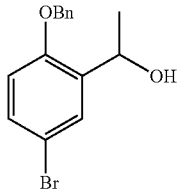

Intermediate 4A (590 mg, 1.933 mmol) was dissolved in MeOH (7.73 mL) and cooled to 0° C. NaBH$_4$ (110 mg, 2.90 mmol) was added, and the reaction was stirred for 1 h. The reaction was quenched with saturated NH$_4$Cl and diluted with water, then extracted with EtOAc. The organic layer was further washed with brine, dried (Na$_2$SO$_4$), filtered, and concentrated in vacuo to yield Intermediate 4B (0.599 g, 100%). 1H NMR (400 MHz, CHLOROFORM-d) δ ppm 7.52 (1 H, d, J=2.51 Hz), 7.33-7.44 (5 H, m), 7.31 (1 H, dd, J=8.78, 2.51 Hz), 6.80 (1 H, d, J=8.53 Hz), 5.13 (1 H, td, J=5.77, 2.76 Hz), 5.08 (2 H, s), 2.40 (1 H, d, J=3.26 Hz), 1.49 (3 H, d, J=6.53 Hz).

Intermediate 4C

Dimethyl 2-(1-(2-(benzyloxy)-5-bromophenyl)ethyl)malonate

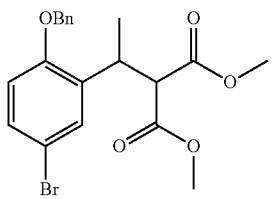 [SMILES: COC(=O)C(C(=O)OC)C(C)c1cc(Br)ccc1OCc1ccccc1]

Intermediate 4B (0.55 g, 1.790 mmol) was dissolved in MeCN (17.90 mL) at ambient temperature. TMS-Cl (0.252 mL, 1.970 mmol) then sodium iodide (0.537 g, 3.58 mmol) was added, and the reaction was stirred for 3 h. The reaction was quenched with dilute Na$_2$SO$_3$ solution, extracted with EtOAc. The organic layer was further washed with water, then brine, dried (Na$_2$SO$_4$), filtered, and concentrated in vacuo as to yield 1-(benzyloxy)-4-bromo-2-(1-iodoethyl)benzene which was utilized immediately. Dimethyl malonate (0.826 mL, 7.19 mmol) was dissolved in DMPU (7.19 mL). NaH (0.288 g, 7.19 mmol) was added at ambient temperature and stirred for 10 min. After this time, a solution of 1-(benzyloxy)-4-bromo-2-(1-iodoethyl)benzene (0.75 g, 1.798 mmol) in DMPU (4.80 mL) was added and the reaction was heated to 85° C. for 4 h. The reaction was diluted with EtOAc and saturated NH$_4$Cl. The organic layer was washed with water, brine, dried (Na$_2$SO$_4$), filtered, and concentrated in vacuo to yield Intermediate 4C (0.535 g, 71%). 1H NMR (400 MHz, CHLOROFORM-d) δ ppm 7.37-7.47 (4 H, m), 7.30-7.36 (1 H, m), 7.23-7.29 (2 H, m), 6.77 (1 H, d, J=8.53 Hz), 5.05-5.15 (2 H, m), 3.94-3.99 (1 H, m), 3.80-3.92 (1 H, m), 3.72 (3 H, s), 3.54 (3 H, s), 1.32 (3 H, d, J=7.03 Hz).

Intermediate 4D

Methyl 3-(2-(benzyloxy)-5-bromophenyl)butanoate

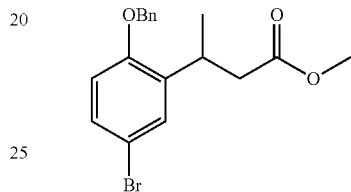

Intermediate 4C (0.535 g, 1.270 mmol), lithium chloride (0.162 g, 3.81 mmol), and H$_2$O (23 µL, 1.270 mmol) were dissolved in DMSO (12.70 mL). The reaction was heated for 2.5 h in the microwave at 150° C. The reaction was diluted with EtOAc and washed with brine (twice), dried (Na$_2$SO$_4$), filtered, and concentrated in vacuo to yield Intermediate 4D (0.340 g, 74%). 1H NMR (400 MHz, CHLOROFORM-d) δ ppm 7.36-7.47 (4 H, m), 7.29-7.36 (1 H, m), 7.21-7.29 (3 H, m), 6.78 (1 H, d, J=8.53 Hz), 5.08 (2 H, s), 3.64-3.76 (1 H, m), 3.62 (3 H, s), 2.70 (1 H, dd, J=15.31, 6.02 Hz), 2.49 (1 H, dd, J=15.18, 8.66 Hz), 1.28 (3 H, d, J=7.03 Hz).

Intermediate 4E (S)-Methyl 3-(2-(benzyloxy)-5-bromophenyl)butanoate

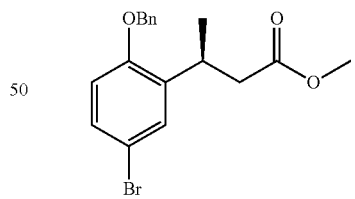

Intermediate 4D (1.84 g, 5.07 mmol) was separated by Chiral Prep LC (Chiralcel AD-H 21×150 mm column, 15% isocratic CO$_2$ in heptane/IPA (3:1)). The two enantiomers were separated and Peak 1 was collected to yield Intermediate 4E (0.7 g, 38%).

Intermediate 4

Intermediate 4E (700 mg, 1.927 mmol) was dissolved in THF (8.76 mL) and MeOH (876 µL). NaOH (2.89 mL, 2.89 mmol) was added at ambient temperature, and the reaction was allowed to stir o/n. The reaction was diluted with 1 N NaOH and washed with DCM. The aqueous layer was acidified with HCl and extracted with EtOAc. The EtOAc layer was washed with brine, dried (Na$_2$SO$_4$), filtered, and concentrated in vacuo to yield Intermediate 4 (0.668 g, 99%). 1H NMR (400 MHz, CHLOROFORM-d) δ ppm 7.34-7.45 (4 H, m), 7.16-7.34 (4 H, m), 6.78 (1 H, d, J=8.53 Hz), 5.08 (2 H, s), 3.56-3.75 (1 H, m), 2.75 (1 H, dd, J=15.69, 6.15 Hz), 2.52 (1 H, dd, J=15.56, 8.53 Hz), 1.31 (3 H, d, J=7.03 Hz).

Intermediate 5

(R)-3-(2-(Benzyloxy)-5-bromophenyl)butanoic acid

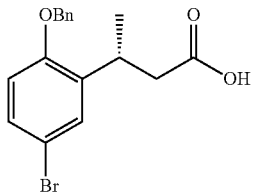 [SMILES: C[C@H](CC(=O)O)c1cc(Br)ccc1OCc1ccccc1]

Intermediate 5A (R)-methyl 3-(2-(benzyloxy)-5-bromophenyl)butanoate

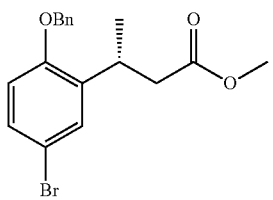 [SMILES: COC(=O)C[C@@H](C)c1cc(Br)ccc1OCc1ccccc1]

Intermediate 4D (1.84 g, 5.07 mmol) was separated by Chiral Prep LC (Chiralcel AD-H 21×150 mm column, 15% isocratic CO$_2$ in heptane/IPA (3:1)). The two enantiomers were separated and Peak 2 was collected to yield Intermediate 5A (0.7 g, 38%).

Intermediate 5

Using a procedure analogous to the one used to prepare Intermediate 4, Intermediate 5A (0.700 g, 1.93 mmol) was reacted with NaOH (2.89 mL, 2.89 mmol) to yield Intermediate 5 (0.457 g, 68%). 1H NMR (400 MHz, CHLOROFORM-d) δ ppm 7.35-7.51 (4 H, m), 7.17-7.34 (4 H, m), 6.78 (1 H, d, J=8.78 Hz), 5.08 (2 H, s), 3.55-3.78 (1 H, m), 2.75 (1 H, dd, J=15.69, 5.90 Hz), 2.53 (1 H, dd, J=15.56, 8.53 Hz), 1.31 (3 H, d, J=7.03 Hz).

Intermediate 6

3-(5-Bromo-2-(2,2-difluoroethoxy)phenyl)propanoic acid

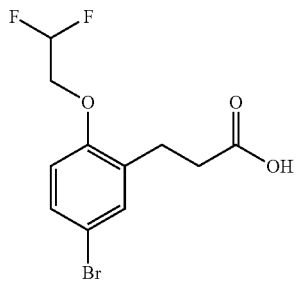 [SMILES: O=C(O)CCc1cc(Br)ccc1OCC(F)F]

Intermediate 6A

5-Bromo-2-(2,2-difluoroethoxy)benzaldehyde

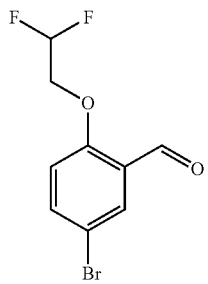

5-Bromo-2-hydroxybenzaldehyde (0.5 g, 2.487 mmol) and 2-Bromo-1,1-difluoroethane (0.239 mL, 2.98 mmol) were dissolved in DMF (24.87 mL). Cs$_2$CO$_3$ (1.216 g, 3.73 mmol) was added, and the reaction allowed to stir for 2 days at 50° C. The reaction was quenched with 1 N HCl and extracted thrice with EtOAc. The combined organic extracts were washed with water, brine, dried (Na$_2$SO$_4$), filtered, and concentrated in vacuo. The crude reaction mixture was purified by silica gel column chromatography (0 to 100% EtOAc in hexanes) to yield Intermediate 6A (0.492 g, 75%). 1H NMR (400 MHz, CHLOROFORM-d) δ ppm 10.41 (1 H, s), 7.97 (1 H, d, J=2.51 Hz), 7.67 (1 H, dd, J=8.91, 2.64 Hz), 6.88 (1 H, d, J=8.78 Hz), 5.95-6.38 (1 H, m), 4.30 (2 H, td, J=12.80, 4.02 Hz).

Intermediate 6B

Dimethyl 2-(5-bromo-2-(2,2-difluoroethoxy)benzyl)malonate

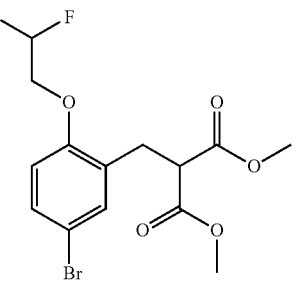

Intermediate 6A (0.490 g, 1.85 mmol) was dissolved in MeCN (17.90 mL) at ambient temperature. TMS-Cl (0.252 mL, 1.970 mmol) then sodium iodide (0.537 g, 3.58 mmol)

was added, and the reaction was stirred for 3 h. The reaction was quenched with dilute Na$_2$SO$_3$ solution, then extracted with EtOAc. The organic layer was further washed with water, then brine, dried (Na$_2$SO$_4$), filtered, and concentrated in vacuo as to yield 4-bromo-1-(2,2-difluoroethoxy)-2-(iodomethyl)benzene which was utilized immediately. Dimethyl malonate (0.850 mL, 7.40 mmol) was dissolved in DMPU (2.8 mL). NaH (0.296 g, 7.40 mmol) was added at ambient temperature and stirred for 10 min. After this time, a solution of 4-bromo-1-(2,2-difluoroethoxy)-2-(iodomethyl)benzene (0.697 g, 1.85 mmol) in DMPU (1.8 mL) was added and the reaction was heated to 85° C. for 4 h. The reaction was diluted with EtOAc and saturated NH$_4$Cl. The organic layer was washed with water, brine, dried (Na$_2$SO$_4$), filtered, and concentrated in vacuo to yield Intermediate 6B (0.333 g, 47%). MS (ESI) m/z: 381.0 (M+H)$^+$.

Intermediate 6C

Methyl 3-(5-bromo-2-(2,2-difluoroethoxy)phenyl)propanoate

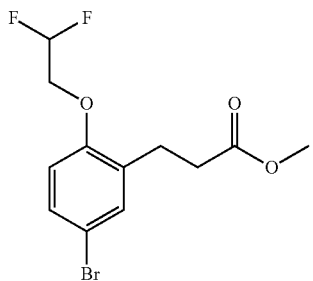 [SMILES: COC(=O)CCc1cc(Br)ccc1OCC(F)F]

Intermediate 6B (0.333 g, 0.874 mmol), lithium chloride (0.111 g, 2.62 mmol), and H$_2$O (16 μL, 0.874 mmol) were dissolved in DMSO (8.7 mL). The reaction was heated for 2.5 h in the microwave at 150° C. The reaction was diluted with EtOAc and washed with brine (twice), dried (Na$_2$SO$_4$), filtered, and concentrated in vacuo to yield Intermediate 6C (0.197 g, 70%). 1H NMR (400 MHz, CHLOROFORM-d) δ ppm 7.28-7.34 (2 H, m, J=4.52, 2.48, 2.48, 2.32 Hz), 6.68 (1 H, d, J=9.29 Hz), 5.92-6.29 (1 H, m), 4.17 (3 H, td, J=12.99, 4.14 Hz), 3.67 (3 H, s), 2.92 (2 H, t, J=7.65 Hz), 2.60 (2 H, t, J=7.65 Hz).

Intermediate 6

Intermediate 6C (197 mg, 0.610 mmol) was dissolved in THF (5.5 mL) and MeOH (0.554 mL). NaOH (0.915 μL, 0.915 mmol) was added at ambient temperature, and the reaction was allowed to stir overnight. The reaction was diluted with 1 N NaOH and washed with DCM. The aqueous layer was acidified with HCl and extracted with EtOAc. The EtOAc layer was washed with brine, dried (Na$_2$SO$_4$), filtered, and concentrated in vacuo to yield Intermediate 6 (0.120, 64%). 1H NMR (400 MHz, CHLOROFORM-d) δ ppm 7.32 (2 H, dt, J=5.84, 2.98 Hz), 6.69 (1 H, d, J=9.29 Hz), 5.91-6.29 (1 H, m), 4.07-4.27 (2 H, m), 2.93 (2 H, t, J=7.53 Hz), 2.65 (2 H, t, J=7.65 Hz).

Intermediate 7

4-(Difluoromethoxy)-3-fluoro-5-((methylamino)methyl)aniline dihydrochloride

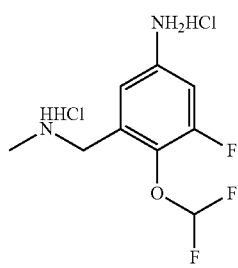

Intermediate 7A (3-Fluoro-2-hydroxy-5-nitro-benzyl)-methyl-carbamic acid tert-butyl ester

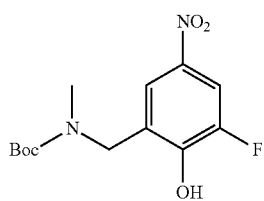

To 3-fluoro-2-hydroxy-5-nitro-benzaldehyde (2.2 g, 11.88 mmol) in MeOH (80 mL) was added aminomethane, 2 M (0.443 g, 14.26 mmol) dropwise, and the reaction was stirred at rt for 1 h. The reaction was cooled to 0° C. and sodium borohydride (0.540 g, 14.26 mmol) was added, and the reaction was stirred at rt for 1 h. The reaction was concentrated under reduced pressure. The residue was dissolved in NaHCO$_3$ (3.00 g, 35.7 mmol) in water (15 mL) and THF (15 mL). Di-tert-butyl dicarbonate (3.11 g, 14.26 mmol) was added, and the mixture was stirred at rt for 1 h. The reaction mixture was diluted with EtOAc. The layers were separated, and the organic layer was washed with water, washed with brine, and dried with Na$_2$SO$_4$. The crude reaction mixture was purified by silica gel column chromatography (0-50% EtOAc/Hex gradient) to yield Intermediate 7A (2.52 g, 70.6% yield). 1H NMR (400 MHz, CHLOROFORM-d) δ ppm 11.11 (1 H, br. s.), 7.70-8.02 (2 H, m), 4.35 (2 H, s), 2.91 (3 H, s), 1.37 (9 H, s).

Intermediate 7B tert-Butyl 2-(difluoromethoxy)-3-fluoro-5-nitrobenzyl(methyl)carbamate

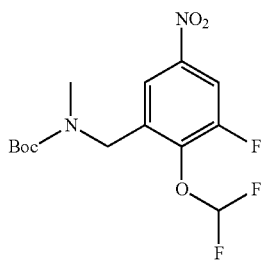

Intermediate 7A (5 g, 16.65 mmol), K$_2$CO$_3$ (4.60 g, 33.3 mmol), and sodium chlorodifluoroacetate (5.08 g, 33.3 mmol) were dissolved in DMF (76 mL) and water (7.57 mL). The reaction was heated to 130° C. for 20 min. The reaction was diluted with EtOAc and washed with 1 N HCl, washed with brine, dried (Na$_2$SO$_4$), filtered, and concentrated in vacuo to yield Intermediate 7B (5.9 g, 100%). 1H NMR (400 MHz, CHLOROFORM-d) δ ppm 7.99 (2 H, d, J=9.54 Hz), 6.39-7.01 (1 H, m), 4.58 (2 H, s), 2.92 (3 H, s), 1.53 (9 H, s).

Intermediate 7

Intermediate 7B (5.9 g, 16.84 mmol), was dissolved in MeOH (42 mL). 10% Pd/C (1.792 g, 1.684 mmol) was added, and the reaction was flushed with hydrogen then sealed under two hydrogen balloons and allowed to stir overnight. The reaction was filtered through Celite and the filtrate was concentrated. The crude reaction mixture was dissolved in dichloromethane and 4 M HCl in dioxanes (14.74 mL, 59 mmol) and allowed to stir for 3 h. The reaction was filtered and the solid was collected to yield Intermediate 7 (4.45 g, 90%). 1H NMR (400 MHz, MeOD) δ ppm 7.13-7.27 (2 H, m), 6.64-7.14 (1 H, m), 4.29 (2 H, s), 2.78 (3 H, s).

Intermediate 8

3-(5-bromo-2-(2,2-difluoroethoxy)phenyl)propanoic acid

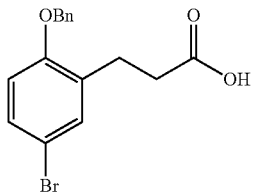 [SMILES: O=C(O)CCc1cc(Br)ccc1OCc1ccccc1]

Intermediate 8A 3-(2-(Benzyloxy)-5-bromophenyl)propanoic acid

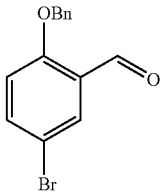 [SMILES: O=Cc1cc(Br)ccc1OCc1ccccc1]

Using a procedure analogous to the one used to prepare Intermediate 6A, 5-bromo-2-hydroxybenzaldehyde (2.0 g, 9.95 mmol) was reacted with benzyl bromide (1.70 g, 9.95 mmol) to yield Intermediate 8A (2.90 g, 92%). 1H NMR (400 MHz, CHLOROFORM-d) δ ppm 10.46 (1 H, s), 7.95 (1 H, d, J=2.76 Hz), 7.61 (1 H, dd, J=8.78, 2.51 Hz), 7.33-7.47 (5 H, m), 6.95 (1 H, d, J=8.78 Hz), 5.19 (2 H, s).

Intermediate 8B 1-(Benzyloxy)-4-bromo-2-(iodomethyl)benzene

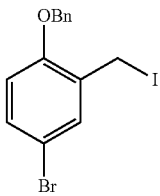 [SMILES: Brc1ccc(OCc2ccccc2)c(CI)c1]

Using a procedure analogous to the one used to prepare Intermediate 6B, Intermediate 8A (0.5 g, 1.72 mmol) was reacted with 1,1,3,3-tetramethyldisiloxane (0.231 g, 1.72 mmol), TMS-Cl (0.220 mL, 1.72 mmol), and sodium iodide (0.257 g, 1.72) to yield Intermediate 8B (0.692 g, 100%). Used immediately upon isolation.

Intermediate 8C

Dimethyl 2-(2-(benzyloxy)-5-bromobenzyl)malonate

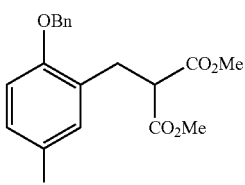

Using a procedure analogous to the one used to prepare Intermediate 6C, Intermediate 8B (0.692 g, 1.72 mmol) was reacted with dimethyl malonate (0.907 g, 6.87 mmol) to yield Intermediate 8C (0.382 g, 55%). 1H NMR (400 MHz, CHLOROFORM-d) δ ppm 7.36-7.46 (4 H, m), 7.31-7.36 (1 H, m), 7.22-7.31 (2 H, m), 6.76 (1 H, dd, J=9.29, 1.76 Hz), 5.09 (2 H, d, J=1.25 Hz), 3.86 (1 H, td, J=7.65, 2.01 Hz), 3.68 (6 H, d, J=2.26 Hz), 3.22 (2 H, dd, J=7.65, 1.63 Hz).

Intermediate 8D

Methyl 3-(2-(benzyloxy)-5-bromophenyl)propanoate

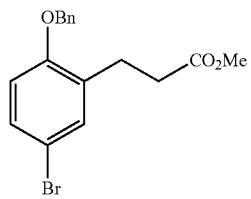 [SMILES: COC(=O)CCc1cc(Br)ccc1OCc1ccccc1]

Using a procedure analogous to the one used to prepare Intermediate 6, Intermediate 8C (0.380 g, 0.933 mmol) was reacted with lithium chloride (0.119 g, 2.80 mmol) to yield Intermediate 8D (0.234 g, 72%). 1H NMR (400 MHz, CHLOROFORM-d) δ ppm 7.36-7.42 (4 H, m), 7.31-7.35 (1 H, m), 7.24-7.30 (2 H, m), 6.76 (1 H, d, J=8.78 Hz), 5.07 (2 H, s), 3.66 (3 H, s), 2.96 (2 H, t, J=7.65 Hz), 2.63 (2 H, t, J=7.65 Hz).

Intermediate 8

Intermediate 8D (0.2459 g, 0.704 mmol) was dissolved in THF (6.40 mL) and MeOH (0.640 mL). 1 M NaOH (0.775 mL, 0.775 mmol) was added at ambient temperature and allowed to stir overnight. The reaction was concentrated in vacuo, diluted with 1 N NaOH and extracted twice with DCM. The aqueous layer was acidified with HCl and extracted twice with EtOAc. The combined EtOAc layers were washed with brine, dried (Na$_2$SO$_4$), filtered, and concentrated in vacuo to yield Intermediate 8 (0.179 g, 76%). 1H NMR (400 MHz, CHLOROFORM-d) δ ppm 7.29-7.42 (6 H, m), 7.25-7.29 (1 H, m), 6.77 (1 H, d, J=8.53 Hz), 5.07 (2 H, s), 2.96 (2 H, t, J=7.65 Hz), 2.68 (2 H, t, J=7.65 Hz).

Intermediate 9

3-(5-Bromo-3-fluoro-2-methoxyphenyl)propanoic acid

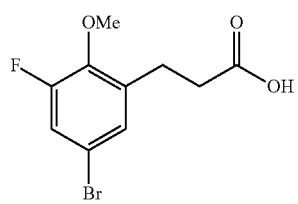 [SMILES: COc1c(F)cc(Br)cc1CCC(=O)O]

Intermediate 9A

5-Bromo-3-fluoro-2-methoxybenzaldehyde

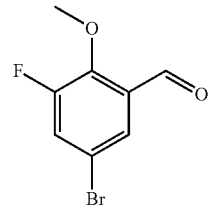

5-Bromo-3-fluoro-2-hydroxybenzaldehyde (1 g, 4.57 mmol) was dissolved in DMF (18.26 mL) and cooled to 0° C. NaH (0.365 g, 9.13 mmol) was added in three portions. MeI (1.142 mL, 18.26 mmol) was added, and the reaction was allowed warm ambient temperature and stir overnight. The reaction was quenched with water and extracted twice with DCM. The combined organic layers were washed with water, brine, dried (Na$_2$SO$_4$), filtered, and concentrated in vacuo. The crude reaction mixture was purified by silica gel column chromatography (0 to 100% EtOAc in hexanes) to yield Intermediate 9A (1.1 g, 100%). 1H NMR (400 MHz, CHLOROFORM-d) δ ppm 10.33 (1 H, s), 7.73 (1 H, s), 7.38-7.53 (2 H, m), 3.92 (3 H, d, J=1.25 Hz).

Intermediate 9B (E)-3-(5-Bromo-3-fluoro-2-methoxy-phenyl)-acrylic acid

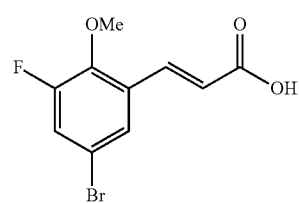 [SMILES: COc1c(F)cc(Br)cc1/C=C/C(=O)O]

Intermediate 9A (1.1 g, 4.72 mmol) was dissolved in toluene (56.2 mL). Methyl (triphenylphosphoranylidine)acetate (1.578 g, 4.72 mmol) was added, and the reaction heated to reflux overnight. The reaction was cooled to ambient temperature and concentrated in vacuo. The crude material (1.17 g, 4.05) was dissolved in THF (18.4 mL) and MeOH (1.84 mL) and treated with 1 M NaOH (4.45 mL, 4.45 mmol). The reaction was allowed to stir at ambient temperature for 3 h, and then partially concentrated in vacuo. The reaction was diluted with 1N NaOH and water. The mixture was washed twice with DCM. The aqueous layer was then acidified with HCl and extracted with EtOAc. The EtOAc layer was washed with brine, dried (Na$_2$SO$_4$), filtered, and concentrated in vacuo to yield Intermediate 9B (0.634 g, 56%). MS (ESI) m/z: 275.0 (M+H)$^+$.

Intermediate 9

Intermediate 9B (0.600 g, 2.181 mmol) was dissolved in MeOH (10.91 mL). Magnesium (0.106 g, 4.36 mmol) was added at ambient temperature and stirred for 5 h. The reaction was quenched with 1 N HCl and allowed to stir until the Mg was gone. The reaction was then extracted with EtOAc. The organic layer was washed with brine, dried (Na$_2$SO$_4$), filtered, and concentrated in vacuo to yield Intermediate 9 (0.557 g, 92%). MS (ESI) m/z: 277.1 (M+H)$^+$.

Intermediate 10

3-(5-Bromo-2-methoxyphenyl)propanoic acid

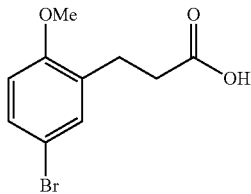 [SMILES: COc1ccc(Br)cc1CCC(=O)O]

Intermediate 10A (E)-Methyl 3-(5-bromo-2-methoxyphenyl)acrylate

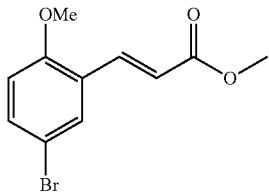

5-Bromo-2-methoxybenzaldehyde (0.5 g, 2.325 mmol) was dissolved in toluene (27.7 mL). Methyl (triphenylphosphoranylidene)acetate (0.777 g, 2.325 mmol) was added, and the reaction heated to reflux and stirred overnight. The reaction was cooled to ambient temperature concentrated in vacuo. The crude material was purified by silica gel column chromatography (0 to 100% EtOAc in hexanes) to yield Intermediate 10A (0.600 g, 95%). 1H NMR (400 MHz, CHLOROFORM-d) δ ppm 7.90 (1 H, d, J=16.31 Hz), 7.60 (1 H, d, J=2.51 Hz), 7.43 (1 H, dd, J=8.78, 2.51 Hz), 6.79 (1 H, d, J=8.78 Hz), 6.49 (1 H, d, J=16.06 Hz), 3.87 (3 H, s), 3.80 (3 H, s).

Intermediate 10B

Methyl 3-(5-bromo-2-methoxyphenyl)propanoate

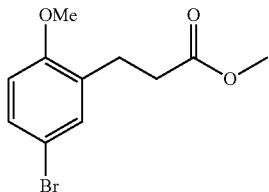

Intermediate 10A (60 mg, 0.221 mmol) was dissolved in MeOH (1.1 mL). Magnesium (10.76 mg, 0.443 mmol) was added at ambient temperature and was stirred for 30 min. After this time, the reaction was cooled to 0° C. and stirred for 1 h. The reaction was quenched with 1 N HCl and allowed to stir until the Mg was gone. The crude reaction was basified with NH$_4$OH, diluted with saturated NH$_4$Cl, then extracted with EtOAc. The organic layer was further washed with brine, dried (Na$_2$SO$_4$), filtered, and concentrated in vacuo to yield Intermediate 10B (0.061 g, 100%) 1H NMR (400 MHz, CHLOROFORM-d) δ ppm 7.29 (1 H, dd, J=8.53, 2.51 Hz), 7.25 (1 H, d, J=2.51 Hz), 6.71 (1 H, d, J=8.78 Hz), 3.80 (3 H, s), 3.68 (3 H, s), 2.89 (2 H, t, J=7.91 Hz), 2.59 (2 H, t, J=7.78 Hz).

Intermediate 10

Intermediate 10B (0.375 g, 1.373 mmol) was dissolved in THF (12.48 mL) and MeOH (1.248 mL). 1 M NaOH (1.510 mL, 1.510 mmol) was added at ambient temperature and stirred at −20° C. for 3 days. The reaction was concentrated in vacuo and diluted with 1 N NaOH. The material was washed twice with DCM. The aqueous layer was then acidified with 1 N HCl and extracted thrice with EtOAc. The combined organic layers were washed with brine, dried (Na$_2$SO$_4$), filtered, and concentrated in vacuo to yield Intermediate 10 (0.323 g, 91%). 1H NMR (400 MHz, MeOD) δ ppm 7.24-7.34 (2 H, m), 6.85 (1 H, d, J=8.53 Hz), 3.82 (3 H, s), 2.85 (2 H, t, J=7.65 Hz), 2.53 (2 H, t, J=7.53 Hz).

Intermediate 11

3-((Methylamino)methyl)-4-(trifluoromethylsulfonyl)aniline dihydrochloride

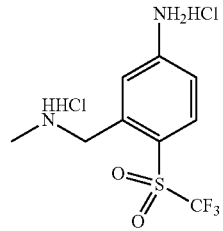

Intermediate 11A

5-Nitro-2-(trifluoromethylthio)benzaldehyde

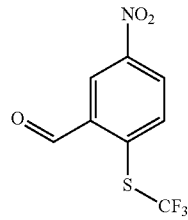 [SMILES: O=Cc1cc([N+](=O)[O-])ccc1SC(F)(F)F]

2-(Trifluoromethylthio)benzaldehyde (5.0 g, 24.5 mmol) was dissolved in H$_2$SO$_4$ (25 mL) and cooled to 0° C. Potassium nitroperoxous acid (3.15 g, 32 mmol) was added portion-wise over 15 min. while maintaining 0° C. Reaction was stirred at rt for 18 h. Reaction was poured onto ice and extracted with EtOAc (3×50 mL) and dried with MgSO$_4$. The crude product was purified by silica gel chromatography (0-100% Hexane/EtOAc) to yield Intermediate 11A (1.9 g, 31%). 1H NMR (400 MHz, CHLOROFORM-d) δ ppm 10.48 (1 H, s), 8.83 (1 H, d, J=2.64 Hz), 8.49 (1 H, dd, J=8.79, 2.64 Hz), 8.00 (1 H, d, J=8.79 Hz).

Intermediate 11B

5-Nitro-2-(trifluoromethylthio)benzaldehyde

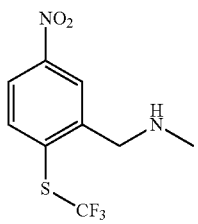 [SMILES: CNCc1cc([N+](=O)[O-])ccc1SC(F)(F)F]

Intermediate 11A (3 g, 11.94 mmol) was dissolved MeOH (50 mL). Methylamine 33% w/w ethanol (29.7 mL, 239 mmol) was added and the reaction was stirred at rt 30 min. The reaction was acidified with AcOH to pH 5 and stirred for 10 min. The reaction was cooled to 0° C. then solid sodium borohydride (0.904 g, 23.89 mmol) was added slowly. The reaction was concentrated. The residue was dissolved in DCM and washed with water, dried with $Na_2SO_4$, and concentrated under reduced pressure to yield Intermediate 11B (2.9 g, 91%). MS (ESI) m/z: 267.3 $(M+H)^+$.

Intermediate 11C tert-Butyl methyl(5-nitro-2-(trifluoromethylthio)benzyl)carbamate

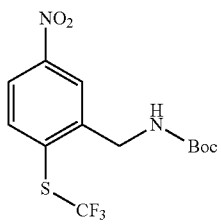 [SMILES: CC(C)(C)OC(=O)NCc1cc([N+](=O)[O-])ccc1SC(F)(F)F]

Intermediate 11B (500 mg, 1.878 mmol), di-tert-butyl dicarbonate (820 mg, 3.76 mmol) and TEA (1.309 mL, 9.39 mmol) were dissolved in DCM (50 mL). The reaction was stirred at rt for 18 h under argon. The reaction was diluted with DCM (25 mL) and water. The layers were separated, and the organic layer was washed with brine, dried ($MgSO_4$), and concentrated in vacuo. The crude product purified by silica gel column chromatography (0-30% EtOAc/Hex) to yield Intermediate 11C (0.523 g, 76%). MS (ESI) m/z: 365.4 $(M+H)^+$.

Intermediate 11D tert-Butyl methyl(5-nitro-2-(trifluoromethylsulfonyl)benzyl)carbamate

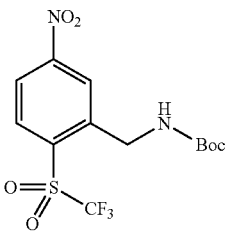 [SMILES: CC(C)(C)OC(=O)NCc1cc([N+](=O)[O-])ccc1S(=O)(=O)C(F)(F)F]

Ruthenium(III) chloride hydrate (62 mg, 0.275 mmol), sodium periodate (1.75 g, 8.19 mmol), and Intermediate 11C (1 g, 2.73 mmol) were stirred in MeCN (2 mL), $CCl_4$ (2 mL) and water (4 mL). The reaction was stirred at rt 72 h under argon. The reaction was filtered, diluted with $Et_2O$ (50 mL), washed with brine, dried ($MgSO_4$), and concentrated under reduced pressure to yield Intermediate 11D (1 g, 92%). MS (ESI) m/z: 399.1 (M+H)+.

Intermediate 11E tert-Butyl 5-amino-2-(trifluoromethylsulfonyl)benzyl(methyl)carbamate

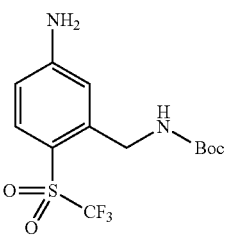 [SMILES: CC(C)(C)OC(=O)NCc1cc(N)ccc1S(=O)(=O)C(F)(F)F]

Intermediate 11D (1 g, 2.51 mmol), palladium on carbon (100 mg, 0.940 mmol), and 1 N HCl (2 mL, 2.0 mmol) were stirred in MeOH (50 mL). The reaction was stirred at room temperature 18 h under hydrogen pressure (50 psi). The reaction was filtered through a pad of Celite and the pH was adjusted to pH 9-10 with TEA. The solution was concentrated and redissolved in DCM (50 mL), washed with brine, dried ($MgSO_4$) and concentrated under reduced pressure to yield Intermediate 11E (0.800 g, 87% yield). MS (ESI) m/z: 369.0 (M+H)+. 1H NMR (400 MHz, CHLOROFORM-d) δ ppm 7.55 (1 H, d, J=8.79 Hz), 6.38-6.51 (1 H, m), 6.00-6.40 (1 H, m), 4.46-4.69 (2 H, m), 2.63-2.80 (3 H, m), 1.19-1.30 (9 H, m).

Intermediate 11

HCl (4 M in dioxane, 1 mL) was added to Intermediate 11E (65 mg, 0.176 mmol) and stirred at RT for 1 h. The reaction was concentrated to yield Intermediate 11 (60 mg, 100% yield). MS (ESI) m/z: 269.2 (M+H)+.

Intermediate 12

4-((Difluoromethyl)sulfonyl)-3-((methylamino)methyl)aniline dihydrochloride

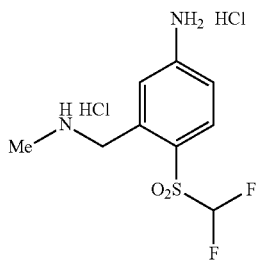 [SMILES: Cl ; CNCc1cc(N)ccc1S(=O)(=O)C(F)F ; Cl]

Intermediate 12A tert-Butyl 2-chloro-5-nitrobenzyl(methyl)carbamate

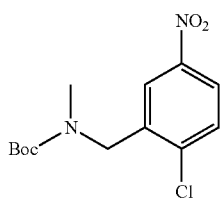 [SMILES: CN(Cc1cc([N+](=O)[O-])ccc1Cl)C(=O)OC(C)(C)C]

To a solution of 2-chloro-5-nitrobenzaldehyde (20 g, 108 mmol) in MeOH (400 mL) was added methylamine (33% in EtOH) (59.3 mL, 119 mmol). The mixture was stirred at RT for 3 h. The reaction was cooled to 0° C. and treated with NaBH$_4$ (4.89 g, 129 mmol). The mixture was stirred at RT for 15 h and then was concentrated. The residue was dissolved in THF (200 mL) and treated with H$_2$O (80 mL) and sat. NaHCO$_3$ (80 mL). After stirring for 10 min, Boc$_2$O (108 mL, 108 mmol) was added dropwise. The mixture was stirred at RT for 1.5 h and the THF was evaporated. The mixture was extracted with EtOAc×2. The combined organic phase was washed with brine, dried with Na$_2$SO$_4$ and concentrated. The crude product was purified by silica gel column chromatography (gradient from 0 to 50% EtOAc/hexanes) to yield Intermediate 12A (27 g, 90 mmol, 83% yield) as a yellow solid. MS (ESI) m/z: 323.0 (M+Na)$^+$. 1H NMR (400 MHz, CHLOROFORM-d) δ ppm 7.94-8.18 (m, 2 H), 7.54 (d, J=8.24 Hz, 1 H), 4.58 (d, J=12.64 Hz, 2 H), 2.96 (s, 3 H), 1.48 (d, J=36.28 Hz, 9 H).

Intermediate 12B tert-Butyl 2-mercapto-5-nitrobenzyl(methyl)carbamate

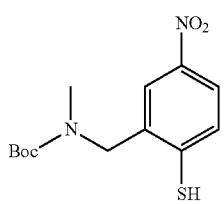 [SMILES: CN(Cc1cc([N+](=O)[O-])ccc1S)C(=O)OC(C)(C)C]

Sodium sulfide (0.837 mL, 19.95 mmol) was added in one portion to a solution of Intermediate 12A (3 g, 9.98 mmol) in DMSO (25 mL) and heated at 50° C. for 1 h. The reaction was poured onto ice and then acidified to pH 3 with citric acid. The mixture was extracted with EtOAc×2, dried over Na$_2$SO$_4$ and concentrated. The crude product was purified by silica gel column chromatography (gradient from 0% to 75% ethyl acetate in hexane) to yield Intermediate 12B (2.22 g, 7.44 mmol, 74.6% yield) as a yellow solid. 1H NMR (400 MHz, CHLOROFORM-d) δ ppm 8.02-8.13 (2 H, m), 7.68 (1 H, d, J=8.79 Hz), 4.67 (2 H, br. s.), 2.95 (3 H, s), 1.51 (9 H, br. s.)

Intermediate 12C tert-Butyl 2-((difluoromethyl)thio)-5-nitrobenzyl(methyl)carbamate

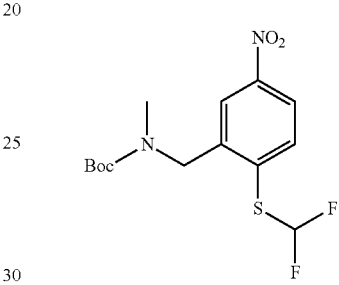

A mixture of Intermediate 12B (1.0 g, 3.35 mmol), K$_2$CO$_3$ (0.926 g, 6.70 mmol) and sodium chlorodifluoroacetate (1.022 g, 6.70 mmol) in DMF (8 mL) and Water (1.1 mL) was flushed with nitrogen. The reaction was heated in the microwave for 15 min at 130° C. The reaction was diluted with EtOAc and washed with 1 N citric acid, washed with brine, and dried with sodium sulfate. The crude product was purified by silica gel column chromatography (gradient from 0% to 100% EtOAc in hexane) to yield Intermediate 12C (0.52 g, 1.493 mmol, 44.5% yield) as a yellow oil. MS (ESI) m/z: 349.2 (M+H)$^+$. 1H NMR (400 MHz, CHLOROFORM-d) δ ppm 8.14 (2 H, d, J=8.79 Hz), 7.80 (1 H, d, J=8.79 Hz), 6.90 (1 H, t, J=55.81 Hz), 4.70 (2 H, br. s.), 2.93 (3 H, s), 1.52 (9 H, br. s.).

Intermediate 12D tert-Butyl 2-((difluoromethyl)sulfonyl)-5nitrobenzyl(methyl)carbamate

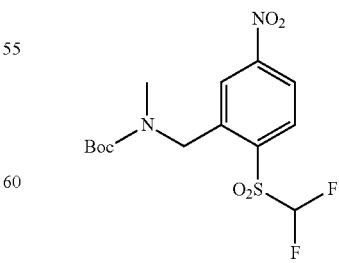

mCPBA (0.804 g, 3.59 mmol) was added to a solution of Intermediate 12C (0.5 g, 1.435 mmol) in DCM (14.35 mL) and stirred overnight at 45° C. in a sealed tube. Additional mCPBA (0.402 g, 1.79 mmol) was added and the reaction was stirred at 45° C. for overnight. The reaction was diluted with DCM and washed with saturated NaHCO$_3$×2, dried with Na$_2$SO$_4$ and concentrated under reduced pressure. The crude product was purified by silica gel column chromatography (gradient from 0% to 50% EtOAc in hexane) to yield Intermediate 12D (0.5 g, 92% yield). MS (ESI) m/z: 379.4 (M+H)$^+$. 1H NMR (400 MHz, CHLOROFORM-d) δ ppm 8.21-8.40 (3 H, m), 6.34 (1 H, t, J=53.69 Hz), 4.98 (2 H, s), 2.99 (3 H, s), 1.49 (9 H, br. s.).

Intermediate 12E tert-Butyl 5-amino-2-((difluoromethyl)sulfonyl)benzyl(methyl)carbamate

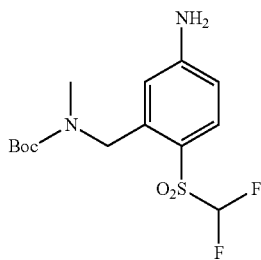

A solution of Intermediate 12D (400 mg, 1.052 mmol) in MeOH (25 mL) was stirred with Pd/C (30 mg) under H$_2$ (50 psi) overnight. The mixture was filtered and concentrated to yield Intermediate 12E (350 mg, 0.999 mmol, 95% yield) as an off-white solid. MS (ESI) m/z: 351.0 (M+H)$^+$. 1H NMR (400 MHz, DMSO-d$_6$) δ ppm 7.54 (1 H, d, J=8.79 Hz), 6.84-7.25 (1 H, m), 6.71 (1 H, s), 6.58 (1 H, dd, J=9.01, 1.98 Hz), 6.44 (1 H, br. s.), 4.61 (2 H, s), 2.84 (3 H, s), 1.23-1.50 (9 H, m).

Intermediate 12

HCl (4.0 M in dioxane, 0.25 mL) was added to Intermediate 12E (11 mg, 0.031 mmol) and stirred at rt for 2 h. The mixture was concentrated to yield Intermediate 12 as a brown solid. MS (ESI) m/z: 251.0 (M+H)+. 1H NMR (400 MHz, METHANOL-d$_3$) δ ppm 7.75 (1 H, d, J=8.79 Hz), 6.91 (1 H, d, J=2.64 Hz), 6.53-6.88 (2 H, m), 4.31 (2 H, s), 2.76 (3 H, s).

Intermediate 13

2-(Trimethylsilyl)ethyl 5-amino-2-(2,2-difluoroethoxy)-3-fluorobenzyl(methyl)carbamate

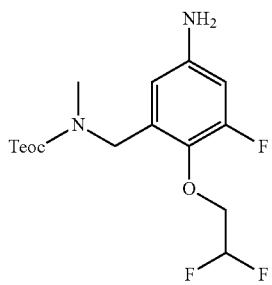

Intermediate 13A

3-Fluoro-2-hydroxy-5-nitrobenzaldehyde

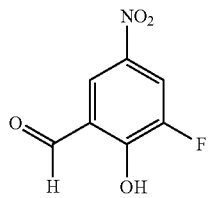 [SMILES: O=Cc1cc([N+](=O)[O-])cc(F)c1O]

To a solution of 3-fluorosalicylaldehyde (2 g, 14.27 mmol) in acetic Acid (10 ml) was added nitric acid (2.233 ml, 50.0 mmol) at 0° C. The mixture was stirred at 0° C. for 1 h. The reaction was quenched with ice and extracted with EtOAc (3×30 mL). The combined organic layer was washed with brine×3, dried with MgSO$_4$, and concentrated under reduced pressure to yield Intermediate 13A (2.5 g, 95% yield) as a brown solid. 1H NMR (400 MHz, CD3OD) δ ppm 11.65 (s, 1 H) 10.03 (d, J=1.76 Hz, 1 H) 8.43 (d, J=2.64 Hz, 1 H) 8.26 (dd, J=10.11, 2.64 Hz, 1 H).

Intermediate 13B

Benzyl 3-fluoro-2-hydroxy-5-nitrobenzyl(methyl)carbamate

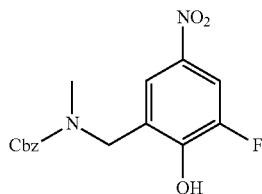 [SMILES: CN(Cc1cc([N+](=O)[O-])cc(F)c1O)C(=O)OCc1ccccc1]

To a solution of Intermediate 13A (1.00 g, 5.40 mmol) in MeOH (30 mL) was added methylamine (33% in EtOH) (1 mL, 8.03 mmol). The resultant yellow suspension, was stirred at rt for 1 h and then cooled to 0° C. To this suspension was added NaBH4 (0.409 g, 10.80 mmol), portion wise. After addition was complete, the mixture was stirred at rt for 3 h and concentrated. The resultant yellow solid was suspended in THF (30.0 mL) and water (10 mL). The mixture was treated with sat. aq. NaHCO$_3$ (6 mL) and cooled to 0° C. To this mixture, Cbz-Cl (1.003 mL, 7.02 mmol) was added dropwise. The reaction mixture was removed from the cooling bath and stirred at rt for 16 h. The reaction mixture was diluted with MeOH (10 mL) and treated with 1 N NaOH (7 mL). The mixture was stirred at 50° C. for 45 min. The reaction mixture was concentrated under reduced pressure and was acidified to pH 4 with 1 N HCl. The aqueous phase was extracted with EtOAc×3. The combined organic phase was washed with brine, dried with sodium sulfate, filtered through a 1" pad of SiO$_2$ and concentrated. The crude product was purified by silica gel column chromatography (gradient from 0 to 100% EtOAc/hexanes). The resultant solid was washed with 10% Et$_2$O/hexanes (10 mL) and dried under vacuum to yield Intermediate 13B (1.32 g, 73.1% yield) as a pale yellow solid. MS (ESI) m/z: 335.0 (M+H)+. 1H NMR (400 MHz, CHLORO- FORM-d) δ ppm 10.74 (1 H, br. s.) 7.99 (1 H, d, J=9.5 Hz) 7.91 (1 H, br. s.) 7.37 (5 H, br. s.) 5.21 (2 H, br. s.) 4.45 (2 H, br. s.) 3.02 (3 H, br. s.).

Intermediate 13C

Benzyl 2-(2,2-difluoroethoxy)-3-fluoro-5-nitrobenzyl(methyl)carbamate

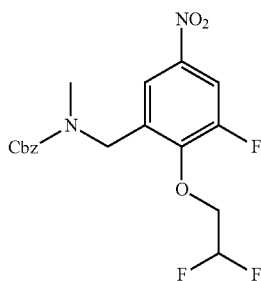 [SMILES: CN(Cc1cc([N+](=O)[O-])cc(F)c1OCC(F)F)C(=O)OCc1ccccc1]

Intermediate 13B (1 g, 2.99 mmol) and 2-bromo-1,1-difluoroethane (0.287 mL, 3.59 mmol) were dissolved in DMF (11.97 mL). $Cs_2CO_3$ (1.462 g, 4.49 mmol) was added and the reaction heated to 50° C. for 5 h. The reaction was heated to 100° C. and stirred overnight. The reaction was diluted with 1 N HCl and extracted thrice with EtOAc. The combined organic layers were washed with brine, dried ($Na_2SO_4$), filtered, and concentrated in vacuo. The crude material was purified by silica gel column chromatography (gradient from 0 to 100% EtOAc in hexanes) to yield Intermediate 13C (1.164 g, 98% yield). MS (ESI) m/z: 399.1 (M+H)+. 1H NMR (400 MHz, CHLOROFORM-d) δ ppm 7.78-8.05 (2 H, m), 7.27-7.49 (5 H, m), 5.77-6.28 (1 H, m), 5.19 (2 H, d, J=8.78 Hz), 4.60 (2 H, br. s.), 4.44 (2 H, br. s.), 3.00 (3 H, d, J=10.54 Hz).

Intermediate 13D

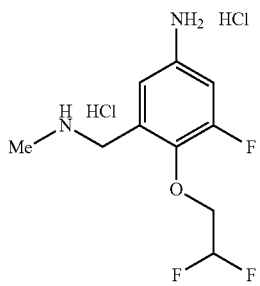 [SMILES: Cl ; CNCc1cc(N)cc(F)c1OCC(F)F ; Cl]

Intermediate 13D (4.65 g, 11.67 mmol) was dissolved in MeOH (46.7 mL). Pd/C (1.242 g, 1.167 mmol) was added and the reaction flushed with hydrogen then sealed with a hydrogen balloon and allowed to stir overnight. The reaction was filtered through celite, concentrated in vacuo. The crude residue was dissolved in DCM (25 mL) and 4 M HCl in Dioxanes (7.30 mL, 29.2 mmol) and allowed to stir overnight. The slurry was concentrated in vacuo and resuspended in DCM. The solids were collected and dried in vacuo to yield Intermediate 13D (3.11 g, 87% yield) as a tan solid. 1H NMR (400 MHz, MeOD) δ ppm 7.29-7.40 (2 H, m), 6.25 (1 H, tt, J=54.33, 3.26 Hz), 4.45-4.58 (2 H, m, J=14.62, 14.62, 1.63, 1.51 Hz), 4.31 (2 H, s), 2.76 (3 H, s).

Intermediate 13

Intermediate 13D (0.5 g, 1.628 mmol) and 2,5-dioxopyrrolidin-1-yl 2-(trimethylsilyl)ethyl carbonate (0.422 g, 1.628 mmol) were dissolved in MeOH (16.28 mL). DIPEA (0.853 mL, 4.88 mmol) was added, and the reaction was allowed to stir for 30 min. The reaction was concentrated in vacuo and diluted with EtOAc, washed with brine, dried ($Na_2SO_4$), filtered, and concentrated in vacuo. The crude material was purified by silica gel column chromatography (0 to 100% EtOAc in hexanes) to yield Intermediate 13 (0.583 g, 95%). 1H NMR (400 MHz, CHLOROFORM-d) δ ppm 5.80-6.45 (3 H, m), 4.46 (2 H, s), 4.05-4.27 (4 H, m), 3.61 (2 H, br. s.), 2.85 (3 H, br. s.), 1.02 (2 H, br. s.), 0.05 (9 H, br. s.).

Intermediate 14

2-(Trimethylsilyl)ethyl 5-amino-2-(1,3-difluoropropan-2-yloxy)-3-fluorobenzyl(methyl)carbamate

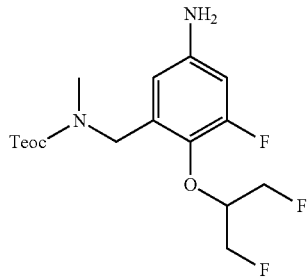

Intermediate 14A

Benzyl 2-(1,3-difluoropropan-2-yloxy)-3-fluoro-5-nitrobenzyl(methyl)carbamate

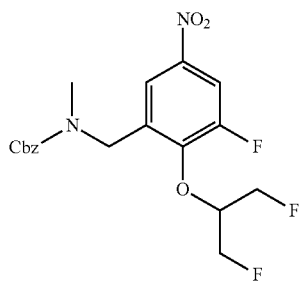 [SMILES: CN(Cc1cc([N+](=O)[O-])cc(F)c1OC(CF)CF)C(=O)OCc1ccccc1]

To a solution of triphenylphosphine (2.59 g, 9.87 mmol), benzyl 3-fluoro-2-hydroxy-5-nitrobenzyl(methyl)carbamate (3.00 g, 8.97 mmol), and 1,3-difluoropropan-2-ol (0.948 g, 9.87 mmol) dissolved in THF (90 mL) at 0° C., was added DIAD (1.919 mL, 9.87 mmol), dropwise. The reaction mixture was stirred at 0° C. for 30 min, then was removed from the cooling bath and allowed to stir at rt overnight. Reaction was concentrated. The crude product was purified

Intermediate 14B 4-(1,3-Difluoropropan-2-yloxy)-3-fluoro-5-((methylamino)methyl)aniline dihydrochloride

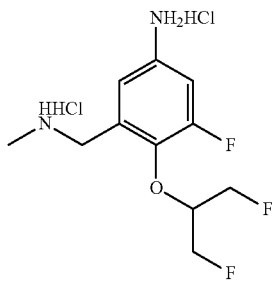

Intermediate 14A (4.14 g, 10.04 mmol) was dissolved in MeOH (40.2 mL). Pd/C (1.068 g, 1.004 mmol) was added and the reaction flushed with hydrogen then sealed with a hydrogen balloon and allowed to stir overnight. The reaction was filtered through Celite, concentrated in vacuo, filtered through a syringe filter, and concentrated in vacuo. The crude residue was dissolved in DCM and 4 M HCl in dioxanes (6.27 mL, 25.10 mmol) was added and the reaction was allowed to stir overnight. The slurry was concentrated in vacuo, slurried in DCM, and filtered through a Buchner funnel to yield Intermediate 14B (2.84 g, 88%). MS (ESI) m/z: 249.1 (M+H)+.

Intermediate 14

Intermediate 14B (0.250 g, 0.878 mmol) and 2-(trimethylsilyl)ethyl p-nitrophenyl carbonate (0.249 g, 0.878 mmol) were dissolved in MeOH (10 mL), and DIPEA (0.460 mL, 2.63 mmol) was added. The reaction was allowed to stir at rt for 3 h. The reaction was concentrated and purified through a plug of silica gel eluting with 20% EtOAc/Hex to yield Intermediate 14 (0.256 g, 0.652 mmol, 74.3% yield). MS (ESI) m/z: 365.3 (M-28)+ (M-28 is consistent with Teoc containing compounds). 1H NMR (400 MHz, CHLOROFORM-d) δ ppm 6.34 (2 H, dd, J=12.92, 2.64 Hz), 4.72 (2 H, dd, J=4.52, 1.25 Hz), 4.60 (2 H, dd, J=4.52, 1.25 Hz), 4.49 (2 H, s), 4.21 (2 H, t, J=8.28 Hz), 2.85 (2 H, br. s.), 1.21-1.37 (4 H, m), 1.01 (2 H, br. s.), −0.03-0.10 (9 H, m).

Intermediate 15

(R)-ethyl 3-(3-aminophenyl)-3-(tert-butoxycarbonylamino)propanoate

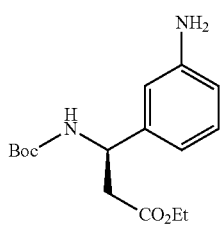 [SMILES: CCOC(=O)C[C@@H](NC(=O)OC(C)(C)C)c1cccc(N)c1]

Intermediate 15A (R)-ethyl 3-amino-3-(3-nitrophenyl)propanoate, HCl

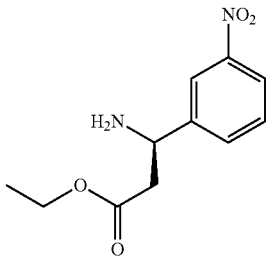 [SMILES: CCOC(=O)C[C@@H](N)c1cccc([N+](=O)[O-])c1]

(R)-3-Amino-3-(3-nitrophenyl)propanoic acid (0.500 g, 2.379 mmol) was suspended in acetonitrile (5 mL) and hydrochloric acid, 4 M in dioxane (5 mL) was added. The solution was concentrated under reduced pressure. In a separate flask, thionyl chloride (0.200 mL, 2.74 mmol) was added to EtOH (8 mL) at 0° C. This solution was allowed to stir for 30 min. This solution was added to the HCl salt and allowed to stir overnight at 40° C. The reaction was concentrated. The solid was triturated with Et₂O to yield Intermediate 15A (0.508 g, 1.849 mmol, 78% yield). MS (ESI) m/z: 239.1 (M+H)+.

Intermediate 15B (R)-ethyl 3-(tert-butoxycarbonylamino)-3-(3-nitrophenyl)propanoate

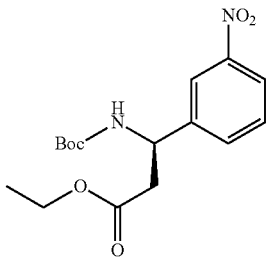 [SMILES: CCOC(=O)C[C@@H](NC(=O)OC(C)(C)C)c1cccc([N+](=O)[O-])c1]

Intermediate 15A (0.500 g, 2.099 mmol) was dissolved in MeOH (10 mL) and DIEA (1.100 mL, 6.30 mmol) was added. To the reaction was added Boc₂O (0.585 mL, 2.52 mmol). The reaction was allowed to stir at rt overnight. Reaction was concentrated and residue dissolved in EtOAc and water. The layers were separated, and the aqueous layer was back extracted with EtOAc×3. The combined organic layer was washed with brine, dried with Na₂SO₄, and concentrated under reduced pressure to yield Intermediate 15B (0.730 g, 2.157 mmol, 100% yield). MS (ESI) m/z: 339.0 (M+H)+.

Intermediate 15

Intermediate 15B (0.730 g, 2.157 mmol) was dissolved in MeOH (10 mL) and Pd/C (23 mg, 0.216 mmol) was added. The reaction was evacuated and back filled with argon×3. The reaction was then evacuated and back filled with hydrogen×3. The reaction was allowed to stir at rt for 2 h. The reaction was filtered through Celite and concentrated to yield Intermediate 15 (0.445 g, 1.443 mmol, 66.9% yield). MS (ESI) m/z: 309.1.1 (M+H)⁺.

Intermediate 16

Benzyl 5-amino-2-(cyclopropylsulfonyl)benzyl(methyl)carbamate

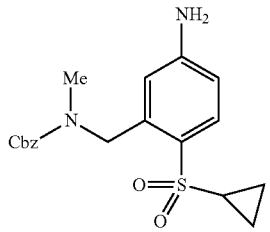 [SMILES: CN(Cc1cc(N)ccc1S(=O)(=O)C1CC1)C(=O)OCc1ccccc1]

To the solution of 4-(cyclopropylsulfonyl)-3-((methylaminomethyl)aniline dihydrochloride (3.13 g, 10 mmol) in THF (15 ml) was added sodium cabonate (3.18 g, 30.0 mmol) dissolved in water (15.00 ml). The mixture was stirred and cooled to 0° C. To this solution was added benzyl chloroformate (1.570 ml, 11.00 mmol) in THF (1.0 mL) and allowed to stir for 20 min. The mixture was diluted with EtOAc/H₂O, the organic layer was separated, washed with brine, and dried over Na₂SO₄. The crude product in small amount of CHCl₃ was charged to a 120 g silica gel column and eluted with a 0-100% EtOAc/Hex gradient over 40 min to yield Intermediate 16 (3.1 g, 8.28 mmol, 83% yield) as a solid. MS (ESI) m/z: 375.0 (M+H)⁺. 1H NMR (400 MHz, DMSO-d6) d ppm 7.08-7.56 (m, 6 H) 6.37-6.58 (m, 2 H) 6.17 (s, 2 H) 5.10 (d, J=30.32 Hz, 2 H) 4.77 (s, 2 H) 2.95 (s, 3 H) 2.60-2.88 (m, 1 H) 0.77-1.03 (m, 4 H).

Intermediate 17

(S)-2-(5-Bromo-2-methoxyphenyl)-N-methylpropan-1-amine

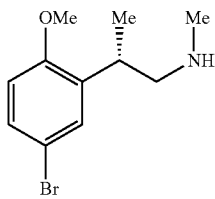 [SMILES: CNC[C@@H](C)c1cc(Br)ccc1OC]

Intermediate 17A (S)-4-Benzyl-3-(5-bromo-2-methoxyphenyl)acetyl)oxazolidin-2-one

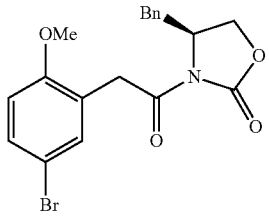 [SMILES: COc1ccc(Br)cc1CC(=O)N1C(=O)OC[C@@H]1Cc1ccccc1]

(S)-4-benzyloxazolidin-2-one (181 mg, 1.021 mmol) was dissolved in THF (20 mL) and cooled to −78° C. BuLi (681 μL, 1.021 mmol) was added and stirring continued for 15 minutes. After this time, a solution of 2-(5-bromo-2-methoxyphenyl)acetyl chloride (538 mg, 2.042 mmol) in a minimal amount of THF was added. Stirring was continued for 48 h as the temperature gradually rose to ambient temperature. The reaction was quenched with saturated NH₄Cl and partially concentrated in vacuo. The crude material was extracted with EtOAc. The organic layer was washed with brine, dried (Na₂SO₄), filtered, and concentrated in vacuo. The crude material was purified by silica gel column chromatography (gradient from 0 to 100% EtOAc in hexanes) to yield Intermediate 17A (0.317 g, 77% yield). 1H NMR (400 MHz, CHLOROFORM-d) δ ppm 7.39 (1 H, dd, J=8.78, 2.51 Hz), 7.31-7.36 (2 H, m), 7.27-7.31 (2 H, m), 7.18-7.24 (2 H, m), 6.79 (1 H, d, J=8.53 Hz), 4.65-4.75 (1H, m), 4.16-4.32 (4 H, m), 3.81 (3 H, s), 3.29 (1 H, dd, J=13.30, 3.26 Hz), 2.82 (1 H, dd, J=13.30, 9.54 Hz).

Intermediate 17B (S)-4-Benzyl-3-((S)-2-(5-bromo-2-methoxyphenyl)propanoyl)oxazolidin-2-one

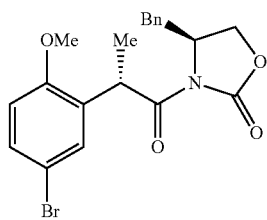 [SMILES: COc1ccc(Br)cc1[C@H](C)C(=O)N1C(=O)OC[C@@H]1Cc1ccccc1]

Intermediate 17A (316.8 mg, 0.784 mmol) was dissolved in THF (4.9 mL) and cooled to −78° C. NaHMDS (862 μL, 0.862 mmol) was added and stirred for 1.5 h. After this time, MeI (1.96 mL, 3.92 mmol) was added and stirring continued for 1.5 hours, then allowed to warm to ambient temperature slowly. The reaction was quenched with saturated NH₄Cl and extracted with EtOAc. The organic layer was further washed with water, saturated Na₂SO₃, and brine, dried (Na₂SO₄), filtered, and concentrated in vacuo. The crude material was purified by column chromatography (ISCO, 40 g silica gel column, 19 minute gradient from 0 to 100% EtOAc in hexanes) to yield Intermediate 17B (0.191 g, 58% yield). MS (ESI) m/z: 418/420 (M+H)⁺. 1H NMR (400 MHz, CHLOROFORM-d) δ ppm 7.31-7.37 (4 H, m), 7.27-7.30 (1 H, m), 7.19-7.25 (2 H, m), 6.71-6.76 (1 H, m), 5.25 (1 H, q, J=7.19 Hz), 4.68 (1 H, ddd, J=9.85, 5.08, 1.63 Hz), 4.18 (2 H, d, J=5.02 Hz), 3.79 (3 H, s), 3.31 (1 H, dd, J=13.43, 3.14 Hz), 2.80 (1 H, dd, J=13.30, 9.54 Hz), 1.51 (3 H, d, J=7.03 Hz).

Intermediate 17C (S)-2-(5-Bromo-2-methoxyphenyl)propanoic acid

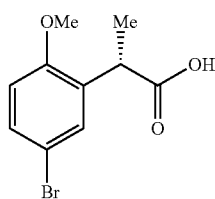 [SMILES: COc1ccc(Br)cc1[C@H](C)C(=O)O]

Intermediate 17B (191.1 mg, 0.457 mmol) was dissolved in THF (2.7 mL) and water (1 mL) and cooled to 0° C. Meanwhile, a solution of Lithium hydroxide monohydrate (28.8 mg, 0.685 mmol) and $H_2O_2$ (40.0 μL, 0.457 mmol) in water (914 μL) was prepared and added slowly to the starting material solution at and allowed to stir for 2.5 h. The reaction was quenched with saturated $Na_2SO_3$ and washed twice with DCM. The aqueous layer was acidified with HCl and extracted twice with EtOAc. The EtOAc layers were combined and washed with brine, dried ($Na_2SO_4$), filtered, and concentrated in vacuo to yield Intermediate 17C (0.109 g, 92% yield). 1H NMR (400 MHz, CHLOROFORM-d) δ ppm 7.30-7.38 (2 H, m), 6.70-6.81 (1 H, m), 4.02 (1 H, q, J=7.19 Hz), 3.81 (3 H, s), 1.47 (3 H, d, J=7.28 Hz).

Intermediate 17D (S)-2-(5-Bromo-2-methoxyphenyl)propan-1-ol

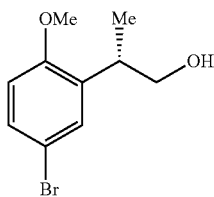 [SMILES: COc1ccc(Br)cc1[C@H](C)CO]

Intermediate 17C (109 mg, 0.421 mmol) was dissolved in THF (1.0 mL) and cooled to 0° C. $BH_3$.THF (841 μL, 0.841 mmol) was added dropwise, and the reaction was allowed to warm slowly to ambient temperature and stir overnight. The reaction was quenched with 50% aqueous AcOH. The reaction was diluted with water and extracted twice with EtOAc. The combined organic layers were washed with water, washed with brine, dried ($Na_2SO_4$), filtered, and concentrated in vacuo to yield Intermediate 17D (100 mg, 97%). 1H NMR (400 MHz, CHLOROFORM-d) δ ppm 7.27-7.33 (2 H, m), 6.75 (1 H, d, J=9.03 Hz), 3.81 (3 H, s), 3.61-3.76 (2 H, m), 3.34-3.46 (1 H, m, J=7.03, 6.90, 6.73, 6.73, 6.73 Hz), 1.45 (1 H, t, J=5.77 Hz), 1.24 (3 H, d, J=7.03 Hz).

Intermediate 17E (S)-2-(5-Bromo-2-methoxyphenyl)propanal

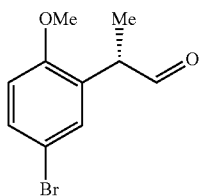 [SMILES: COc1ccc(Br)cc1[C@H](C)C=O]

To a solution of Intermediate 17D (0.176 g, 0.718 mmol) in DCM was added Dess-Martin Periodinane (0.426 g, 1.005 mmol). The reaction was stirred at rt for 45 min. The reaction was quenched by adding sodium thiosulfate doped sodium bicarbcarbonate solution (25 g sodium thiosulfate/ 100 ml sa'td $NaHCO_3$) and stirred for 15 min. The organic layer was collected, dried over $Na_2SO_4$, and filtered to yield Intermediate 17E (0.154 g, 88% yield). 1H NMR (400 MHz, CHLOROFORM-d) δ ppm 9.64 (1 H, s), 7.39 (1 H, dd, J=8.78, 2.51 Hz), 7.22 (1 H, d, J=2.26 Hz), 6.79 (1 H, d, J=8.78 Hz), 3.76-3.90 (4 H, m), 1.39 (3 H, d, J=7.28 Hz).

Intermediate 17

Intermediate 17E (0.25 g, 1.028 mmol) was dissolved in EtOH (6.86 mL). Methylamine solution (0.771 mL, 1.543 mmol) was added and the reaction was stirred for 1 hour at ambient temperature. After this time, the reaction was cooled to 0° C. and sodium borohydride (78 mg, 2.057 mmol) was added. The reaction was warmed to ambient temperature slowly. The reaction was concentrated in vacuo, and the residue was diluted with 1 N HCl (until acidic), then washed twice with DCM. The aqueous layer was basified with 1 N NaOH and extracted thrice with EtOAc. The EtOAc layer was washed with brine, dried ($Na_2SO_4$), filtered, and concentrated in vacuo to yield Intermediate 17 (87 mg, 33% yield). MS (ESI) m/z: 258/260 (M+H)$^+$. $^1$H NMR (400 MHz, CHLOROFORM-d) δ 7.76 (d, J=2.5 Hz, 1H), 7.32-7.23 (m, 2H), 6.73 (d, J=8.8 Hz, 1H), 3.82 (s, 1H), 3.79 (s, 3H), 3.43-3.34 (m, 1H), 2.80-2.63 (m, 2H), 2.40 (s, 3H), 1.20 (d, J=7.0 Hz, 3H).

Intermediate 18

(R)-(4-Methoxy-3-(1-(methyl((2-trimethylsilyl)ethoxy)carbonyl)amino)propan-2-yl)phenyl)boronic acid

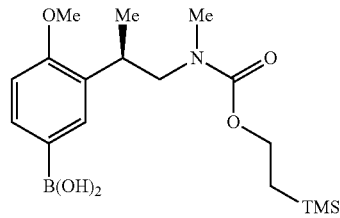 [SMILES: COc1ccc(B(O)O)cc1[C@@H](C)CN(C)C(=O)OCC[Si](C)(C)C]

Intermediate 18A (R)-4-Benzyl-3-(5-bromo-2-methoxyphenyl)acetyl)oxazolidin-2-one

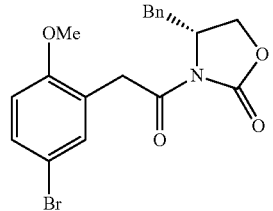 [SMILES: COc1ccc(Br)cc1CC(=O)N1C(=O)OC[C@H]1Cc1ccccc1]

2-(5-bromo-2-methoxyphenyl)acetic acid (1.00 g, 4.08 mmol) was dissolved in THF (16.32 mL). Oxalyl chloride (0.714 mL, 8.16 mmol) followed by DMF (0.016 mL, 0.204 mmol) were added at ambient temperature. After 1 h, the reaction was concentrated in vacuo. The crude material was stored on HIVAC for 3 hours.

(R)-4-benzyloxazolidin-2-one (0.660 g, 3.73 mmol) was dissolved in THF (74.5 mL) and cooled to −78° C. BuLi (2.484 mL, 3.73 mmol) was added and stirring continued for 30 minutes. After this time, a solution of 2-(5-bromo-2-methoxyphenyl)acetyl chloride (1.08 g, 4.10 mmol) in a minimal amount of THF was added. Stirring was continued as the temperature gradually rose to ambient temperature overnight. The reaction was quenched with saturated NH$_4$Cl and partially concentrated in vacuo. The residue was extracted thrice with EtOAc. The combined organic layers were washed with brine, dried (Na$_2$SO$_4$), filtered, and concentrated in vacuo. The crude material was purified by silica gel column chromatography (gradient from 0 to 100% EtOAc in hexanes) to yield Intermediate 18A (1.33 g, 88% yield). MS (ESI) m/z: 402/404 (M+H)$^+$. $^1$H NMR (400 MHz, CHLOROFORM-d) δ 7.37-7.32 (m, 3H), 7.31-7.25 (m, 2H), 7.21-7.16 (m, 3H), 5.51 (br. s., 2H), 4.46 (t, J=8.3 Hz, 2H), 4.19-4.06 (m, 3H), 2.88 (d, J=6.8 Hz, 3H).

Intermediate 18B (R)-4-Benzyl-3-((R)-2-(5-bromo-2-methoxyphenyl)propanoyl)oxazolidin-2-one

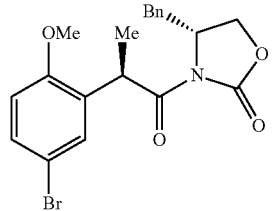 [SMILES: COc1ccc(Br)cc1[C@@H](C)C(=O)N1C(=O)OC[C@H]1Cc1ccccc1]

Prepared analogously to Intermediate 17B, but using Intermediate 18A (1.3 g, 3.22 mmol) to yield Intermediate 18B (0.804 g, 59% yield). MS (ESI) m/z: 418/420 (M+H)$^+$. $^1$H NMR (400 MHz, CHLOROFORM-d) δ 7.33 (d, J=2.3 Hz, 6H), 7.25-7.20 (m, 2H), 5.32-5.18 (m, 1H), 4.68 (dtd, J=9.7, 5.1, 3.3 Hz, 1H), 4.18 (d, J=5.0 Hz, 2H), 3.80 (s, 3H), 3.31 (dd, J=13.3, 3.3 Hz, 1H), 2.80 (dd, J=13.3, 9.8 Hz, 1H), 1.52 (d, J=7.0 Hz, 3H).

Intermediate 18C (R)-2-(5-Bromo-2-methoxyphenyl)propanoic acid

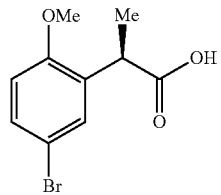 [SMILES: COc1ccc(Br)cc1[C@@H](C)C(=O)O]

Prepared analogously to Intermediate 17C, but using Intermediate 18B (0.800 g, 1.91 mmol) to yield Intermediate 18C (0.289 g, 58% yield). $^1$H NMR (400 MHz, CHLOROFORM-d) δ 11.64-10.42 (m, 1H), 7.40-7.31 (m, 2H), 6.75 (d, J=9.5 Hz, 1H), 4.02 (q, J=7.2 Hz, 1H), 3.81 (s, 3H), 1.47 (d, J=7.3 Hz, 3H).

Intermediate 18D (R)-2-(5-Bromo-2-methoxyphenyl)propan-1-ol

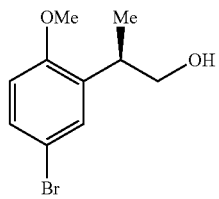 [SMILES: COc1ccc(Br)cc1[C@@H](C)CO]

Prepared analogously to Intermediate 17D, but using Intermediate 18C (0.280 g, 1.08 mmol) to yield Intermediate 18D (0.252 g, 95% yield). $^1$H NMR (400 MHz, CHLOROFORM-d) δ 7.32-7.28 (m, 2H), 6.75 (d, J=8.5 Hz, 1H), 3.81 (s, 3H), 3.74-3.64 (m, 1H), 3.46-3.36 (m, 1H), 2.10 (s, 2H), 1.24 (d, J=7.0 Hz, 3H).

Intermediate 18E (R)-2-(5-Bromo-2-methoxyphenyl)propanal

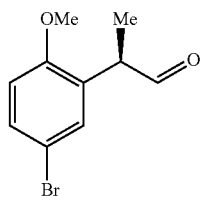 [SMILES: COc1ccc(Br)cc1[C@@H](C)C=O]

Prepared analogously to Intermediate 17E, but using Intermediate 18D (0.250 g, 1.02 mmol) to yield Intermediate 18E (0.273 g, 100% yield). $^1$H NMR (400 MHz, CHLOROFORM-d) δ 9.64 (d, J=0.5 Hz, 1H), 7.40 (d, J=2.5 Hz, 1H), 7.38 (d, J=2.5 Hz, 1H), 7.42-7.35 (m, 1H), 7.23 (d, J=2.5 Hz, 2H), 6.79 (d, J=8.8 Hz, 1H), 3.81 (s, 3H), 1.39 (d, J=7.0 Hz, 3H).

Intermediate 18F: (R)-2-(5-Bromo-2-methoxyphenyl)-N-methylpropan-1-amine

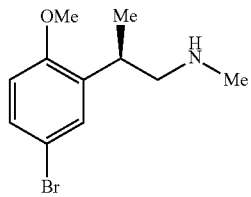 [SMILES: CNC[C@H](C)c1cc(Br)ccc1OC]

Prepared analogously to Intermediate 17, but using Intermediate 18E (0.107 g, 0.414 mmol) to yield Intermediate 18F (107 mg, 37% yield). MS (ESI) m/z: 258/260 (M+H)$^+$. $^1$H NMR (400 MHz, CHLOROFORM-d) δ 7.29-7.26 (m, 2H), 6.73 (d, J=8.5 Hz, 1H), 3.80 (s, 3H), 3.47-3.33 (m, 1H), 2.84-2.64 (m, 2H), 2.40 (s, 3H), 1.20 (d, J=7.0 Hz, 3H).

Intermediate 18G (R)-2-(Trimethylsilyl)ethyl 2-(5-bromo-2-methoxyphenyl)propyl(methyl)carbamate

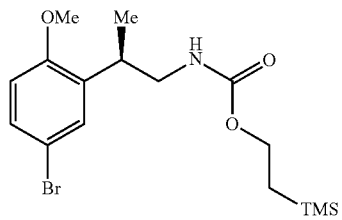 [SMILES: COc1ccc(Br)cc1[C@@H](C)CNC(=O)OCC[Si](C)(C)C]

Intermediate 18F (107 mg, 0.414 mmol) and 2-(trimethylsilyl)ethyl p-nitrophenyl carbonate (117 mg, 0.414 mmol) were dissolved in MeOH (3.3 mL). DIPEA (87 μL, 0.497 mmol) was added and the reaction was allowed to stir overnight. The reaction was concentrated in vacuo and purified by silica gel column chromatography (gradient from 0 to 100% EtOAc in hexanes) to yield Intermediate 18G (0.150 g, 90%).

$^1$H NMR (400 MHz, CHLOROFORM-d) δ 7.35-7.22 (m, 2H), 6.67 (d, J=8.8 Hz, 1H), 4.17-3.93 (m, 2H), 3.75 (s, 3H), 3.49 (dd, J=14.9, 7.7 Hz, 1H), 3.31 (d, J=7.5 Hz, 2H), 2.81-2.69 (m, 3H), 1.15 (d, J=6.5 Hz, 3H), 0.99-0.83 (m, 2H), 0.00 (s, 9H).

Intermediate 18

DMSO (1.55 mL) and dioxane (1.55 mL) were degassed for 15 minutes by bubbling with argon. Meanwhile, Intermediate 18G (150 mg, 0.373 mmol), potassium acetate (91 mg, 0.932 mmol), and bis(neopentyl glycolato)diboron (118 mg, 0.522 mmol) were placed in a microwave tube. To these compounds was added the degassed solvents. The tube was sealed and degassed for an additional 15 minutes. [1,1'-Bis(diphenylphosphino)ferrocene]dichloropalladium(II) (30.7 mg, 0.037 mmol) was subsequently added, and the tube was sealed and heated to 90° C. overnight. The reaction was cooled to ambient temperature, diluted with EtOAc, washed with brine, dried (Na$_2$SO$_4$), filtered, and concentrated in vacuo. The crude material was purified by Prep HPLC (Phenomenex Axia 30×100 mm column, 10 minute gradient from 0 to 100% B in A, A=10:90:0.1 MeCN:H2O:TFA, B=90:10:0.1 MeCN:H2O:TFA) to yield Intermediate Y (0.75 mg, 55%). Used immediately in the next step.

Intermediate 19

2-(Trimethylsilyl)ethyl 5-amino-2-(difluoromethoxy)benzyl(methyl)carbamate

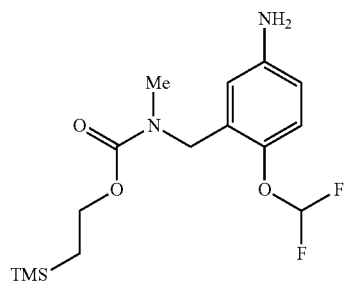 [SMILES: CN(Cc1cc(N)ccc1OC(F)F)C(=O)OCC[Si](C)(C)C]

Intermediate 19A tert-Butyl 2-(difluoromethoxy)-5-nitrobenzyl(methyl)carbamate

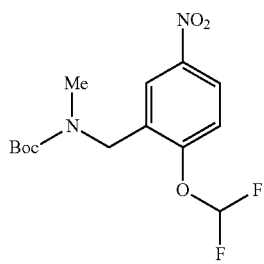 [SMILES: CN(Cc1cc([N+](=O)[O-])ccc1OC(F)F)C(=O)OC(C)(C)C]

tert-Butyl 2-hydroxy-5-nitrobenzyl(methyl)carbamate (1 g, 3.54 mmol), K$_2$CO$_3$ (0.979 g, 7.08 mmol), and sodium chlorodifluoroacetate (1.080 g, 7.08 mmol) were dissolved in DMF (16.10 mL) and water (1.610 mL). The reaction was heated to 130° C. for 20 min. The reaction was diluted with EtOAc and washed with 1 N HCl, washed with brine, dried (Na$_2$SO$_4$), filtered, and concentrated in vacuo to yield Intermediate 19A (1.18 g, 100% yield). 1H NMR (400 MHz, CHLOROFORM-d) δ ppm 8.18 (2 H, d, J=8.53 Hz), 7.24 (1 H, s), 6.41-6.89 (1 H, m), 4.53 (2 H, br. s.), 2.93 (3 H, br. s.), 1.49 (9 H, br. s.).

Intermediate 19B 4-(difluoromethoxy)-3-((methylamino)methyl)aniline dihydrochloride

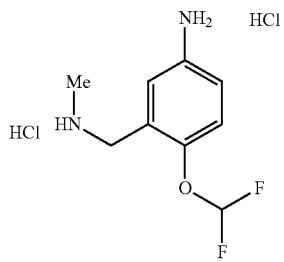 [SMILES: Cl ; CNCc1cc(N)ccc1OC(F)F ; Cl]

Intermediate 19A (5.9 g, 17.76 mmol) was dissolved in MeOH (44.4 mL). Pd/C (1.889 g, 1.776 mmol) was added, and the reaction flushed with hydrogen then sealed with a hydrogen balloon and stirred for 6 h. The reaction was filtered through celite with MeOH and concentrated in vacuo. The crude material was dissolved in DCM (ca 30 mL) and 4 M HCl in dioxanes (15.54 mL, 62.1 mmol) was added and stirred for 2 h. The solid was slurried in DCM and filtered through a buchner funnel. The solid was collected to yield Intermediate 19B (4.69 g, 96% yield). 1H NMR (400 MHz, MeOD) δ ppm 7.70 (1 H, s), 7.51-7.60 (1 H, m), 7.43-7.51 (1 H, m), 7.07 (1 H, t), 4.33 (2 H, s), 2.78 (3 H, s).

Intermediate 19

Intermediate 19B (0.5 g, 1.817 mmol) and 2,5-dioxopyrrolidin-1-yl2-(trimethylsilyl)ethyl carbonate (0.471 g, 1.817 mmol) were dissolved in MeOH (18.17 mL). DIPEA (0.952 mL, 5.45 mmol) was added and the reaction was allowed to stir for 30 min. The reaction was concentrated in vacuo and diluted with EtOAc, washed with brine, dried (Na$_2$SO$_4$), filtered, and concentrated in vacuo. The crude material was purified by silica gel column chromatography (gradient from 0 to 100% EtOAc in hexanes) to yield Intermediate 19 (0.578 g, 92% yield). 1H NMR (400 MHz, CHLOROFORM-d) δ ppm 6.92 (1 H, d, J=8.53 Hz), 6.15-6.67 (3 H, m), 4.47 (2 H, s), 4.18-4.28 (2 H, m), 3.63 (2 H, br. s.), 2.87 (3 H, br. s.), 1.02 (2 H, br. s.), 0.04 (9 H, br. s.).

Example 1

(R)-5-(1-Amino-isoquinolin-6-ylamino)-19-cyclopropanesulfonyl-3-methyl-13-oxa-3,15-diaza-tricyclo[14.3.1.1$^{6,10}$]henicosa-1(19),6(21),7,9,16(20),17-hexaene-4,14-dione trifluoroacetic acid salt+ Enantiomer

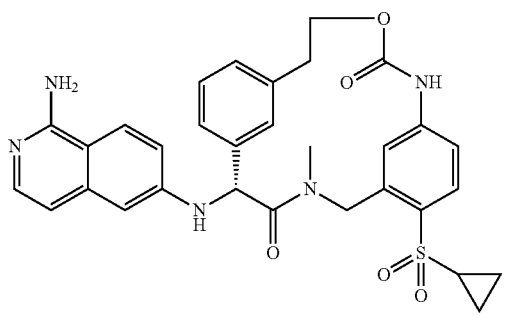 [SMILES: CN1Cc2cc(ccc2S(=O)(=O)C2CC2)NC(=O)OCCc2cccc(c2)[C@@H](Nc2ccc3c(N)nccc3c2)C1=O]

Example 1A

[6-({[(5-Amino-2-cyclopropanesulfonyl-benzyl)-methyl-carbamoyl]-[3-(2-hydroxy-ethyl)-phenyl]-methyl}-amino)-isoquinolin-1-yl]-bis(carbamic acid tert-butyl ester)

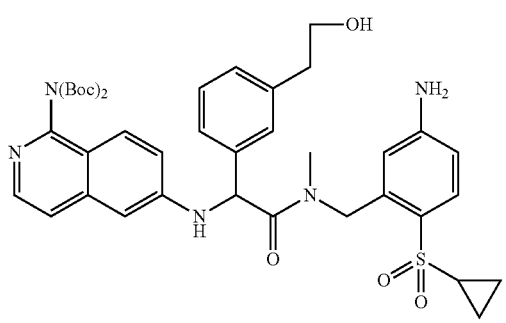

Intermediate 1 (100 mg, 0.602 mmol), imidodicarbonic acid, 2-(6-amino-1-isoquinolinyl)-, 1,3-bis(1,1-dimethylethyl) ester (197 mg, 0.548 mmol), and Glyoxylic acid monohydrate (50.4 mg, 0.548 mmol) were dissolved in DMF (1.71 mL) and MeCN (5.14 mL). The reaction was heated to 80° C. for 2 h then cooled to ambient temperature. To the reaction was added 4-(cyclopropylsulfonyl)-3-((methylamino)methyl)aniline dihydrochloride (223 mg, 0.712 mmol), DIPEA (478 µL, 2.74 mmol), and BOP (242 mg, 0.548 mmol). The reaction was allowed to stir at ambient temperature overnight. The reaction was quenched with water and extracted thrice with EtOAc. The combined organic extracts were washed with brine, dried (Na$_2$SO$_4$), filtered, and concentrated in vacuo. The crude reaction mixture was purified by Prep LC (YMC Sunfire 5µ C18 30×100 mm column, 10 min gradient from 20 to 100% B in A, A=10:90:0.1 MeOH:H$_2$O:TFA, B=90:10:0.1 MeOH:H$_2$O:TFA). The fractions were quenched with saturated NaHCO$_3$ and partially concentrated in vacuo. The aqueous layer was then extracted with EtOAc. The organic layer was washed with brine, dried (Na$_2$SO$_4$), filtered, and concentrated in vacuo to yield Example 1A (78 mg, 19%). MS (ESI) m/z: 760.2 (M+H)$^+$.

Example 1B

[6-(19-Cyclopropanesulfonyl-3-methyl-4,14-dioxo-13-oxa-3,15-diaza-tricyclo[14.3.1.1$^{6,10}$]henicosa-1(19),6(21),7,9,16(20),17-hexaen-5-ylamino)-isoquinolin-1-yl]-bis(carbamic acid tert-butyl ester)

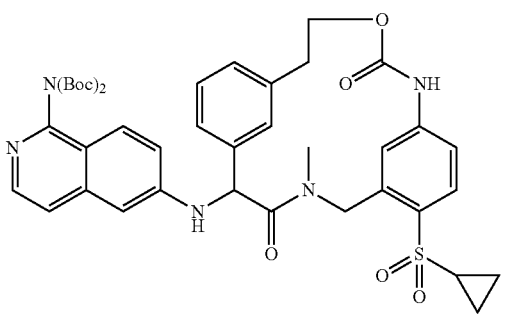

Example 1A (78.2 mg, 0.103 mmol) was dissolved in DCM (1.18 mL) and MeCN (588 µL) and cooled to 0° C. To this solution was added Phosgene solution, 20% in toluene (54.4 µL, 0.103 mmol) and allowed to warm to ambient temperature over 30 min. The reaction was diluted with ca 2 mL DCM and bubbled with Argon for 15 min. Meanwhile, a separate flask was charged with DCM (39.4 mL) and TEA (71.7 µL, 0.515 mmol) at ambient temperature. The starting material solution was transferred via syringe pump addition to the TEA solution over 4 h. The reaction was concentrated in vacuo. The crude reaction mixture was purified by Prep LC (Phenomenex Luna 5µ C18 30×250 mm column, 30 min gradient from 30 to 95% B in A, A=H$_2$O+0.1% TFA, B=MeOH+0.1% TFA). Fractions containing product were diluted with saturated NaHCO$_3$ and partially concentrated in vacuo. The aqueous layer was then extracted with EtOAc. The organic layer was washed with brine, dried (Na$_2$SO$_4$), filtered, and concentrated in vacuo to yield Example 1B (40 mg, 50%). MS (ESI) m/z: 786.3 (M+H)$^+$.

Example 2

5-(1-Amino-4-fluoro-isoquinolin-6-ylamino)-19-cyclopropanesulfonyl-3-methyl-12-oxa-3,15-diazatricyclo[14.3.1.1$^{6,10}$]henicosa-1(19),6(21),7,9,16(20),17-hexaene-4,14-dione

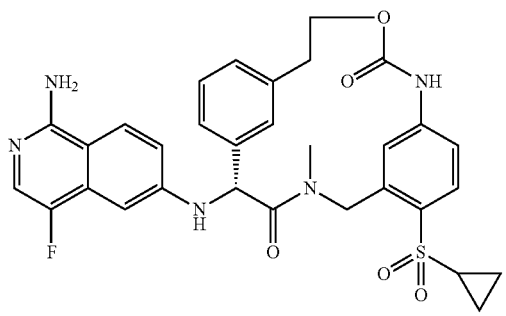 [SMILES: CN1Cc2cc(ccc2S(=O)(=O)C2CC2)NC(=O)OCCc2cccc(c2)[C@@H](Nc2ccc3c(N)ncc(F)c3c2)C1=O]

Example 2A 2-(Trimethylsilyl)ethyl 5-(2-(3-bromobenzyloxy)acetamido)-2-(cyclopropylsulfonyl)benzyl(methyl)carbamate

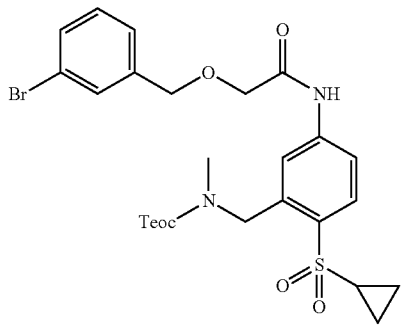

2-(3-Bromobenzyloxy)acetic acid (137 mg, 0.559 mmol) was dissolved in DCM (2.79 mL). oxalyl chloride (307 μL, 0.615 mmol) then DMF (4.33 μL, 0.056 mmol) were added at ambient temperature and stirred for 1 h. The reaction was concentrated in vacuo and azeotroped once with toluene. The crude material was stored on HIVAC for 30 min. DMAP (6.83 mg, 0.056 mmol), TEA (78 μL, 0.559 mmol), and a solution of Intermediate 2 (429.8 mg, 1.118 mmol) in DCM (2.79 mL) was added, and the reaction allowed to stir overnight at ambient temperature. The reaction was diluted with DCM and extracted with 1 N HCl, then brine, dried (Na$_2$SO$_4$), filtered, and concentrated in vacuo. The crude material was purified by silica gel column chromatography (0 to 30% EtOAc in DCM) to yield Example 2A (0.199 g, 58%). 1 H NMR (400 MHz, CHLOROFORM-d) δ ppm 8.45 (1 H, br. s.), 7.73-8.04 (2 H, m), 7.44-7.62 (2 H, m), 7.28-7.37 (2 H, m), 5.00 (2 H, s), 4.67 (2 H, br. s.), 4.25 (2 H, br. s.), 4.10 (2 H, s), 3.02 (3 H, s), 2.62 (1 H, br. s.), 1.33 (2 H, br. s.), 0.86-1.14 (4 H, m), 0.01 (9 H, s). MS (ESI) m/z: 613.0 (M+H)$^+$.

Example 2B 3-((2-(4-(cyclopropylsulfonyl)-3-((methyl((2-(trimethylsilyl)ethoxy)carbonyl)amino)methyl)phenylamino)-2-oxoethoxy)methyl)phenylboronic acid

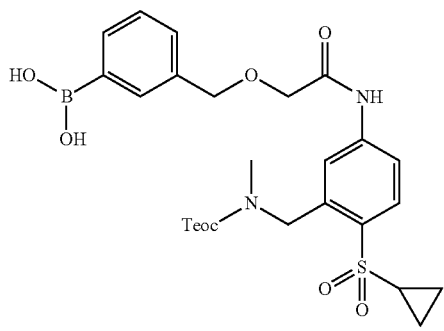

DMSO (763 μL) and dioxane (763 μL) were degassed for 15 min by bubbling with argon. Meanwhile, Example 2A (112 mg, 0.183 mmol), potassium acetate (44.9 mg, 0.458 mmol), and bis(neopentyl glycolato)diboron (57.9 mg, 0.256 mmol) were placed in a microwave tube. To these compounds was added the degassed solvents. The tube was sealed and degassed for an additional 15 min. [1,1'-Bis(diphenylphosphino)ferrocene]dichloropalladium(II) (15.07 mg, 0.018 mmol) was subsequently added, the tube sealed, and heated to 90° C. for 3 h, then cooled to ambient temperature. The reaction was diluted with EtOAc and washed with brine. The organic layer was dried (Na$_2$SO$_4$), filtered, and concentrated in vacuo. The crude material was purified by Prep LC (Phenomenex Luna 5μ. C18 30×250 mm column, 20 min gradient from 20 to 100% B in A, A=10:90:0.1 MeCN:H$_2$O:TFA, B=90:10:0.1 MeCN:H$_2$O:TFA) to yield Example 2B (72 mg, 68%). MS (ESI) m/z: 577.0 (M+H)$^+$.

Example 2C 2-(1-(bis(tert-butoxycarbonyl)amino)-4-fluoroisoquinoline-6-ylamino)-2-(3-((2-(4-(cyclopropylsulfonyl)-3-((methyl((2-(trimethylsilyl)ethoxy)carbonyl)amino)methyl)phenylamino)-2-oxoethoxy)methyl)phenyl)acetic acid

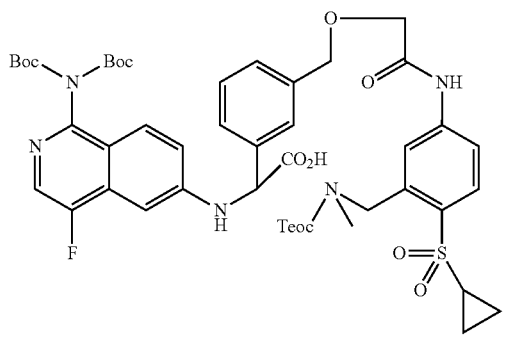

Example 2B (118 mg, 0.205 mmol), Intermediate 3 (77 mg, 0.205 mmol), and glyoxylic acid monohydrate (18.84 mg, 0.205 mmol) were dissolved in DMF (1023 µL) and MeCN (3.07 mL) and heated to 80° C. overnight. The reaction was cooled to rt and diluted with water and extracted thrice with EtOAc. The combined organic layers were washed with brine, dried (Na$_2$SO$_4$), filtered, and concentrated in vacuo. The crude material was purified by Prep LC (Axia Luna 5µ. C18 30×100 mm column, 10 min gradient from 20 to 100% B in A, A=10:90:0.1 MeCN:H$_2$O:TFA, B=90:10:0.1 MeCN:H$_2$O:TFA). The fraction was partially concentrated in vacuo to remove the MeCN. The residue was extracted with EtOAc. The EtOAc layer was washed twice more with water, brine, dried (Na$_2$SO$_4$), filtered, and concentrated in vacuo to yield Example 2C (49 mg, 25%). MS (ESI) m/z: 966.5 (M+H)$^+$.

Example 2D

[6-(19-Cyclopropanesulfonyl-3-methyl-4,14-dioxo-12-oxa-3,15-diaza-tricyclo[14.3.1.1$^{6,10}$]henicosa-1(19),6(21),7,9,16(20),17-hexaen-5-ylamino)-4-fluoro-isoquinolin-1-yl]-bis(carbamic acid tert-butyl ester)

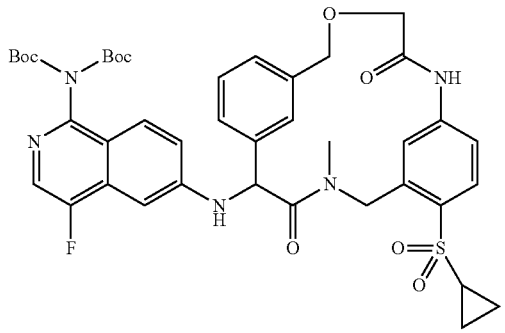 [SMILES: CN1Cc2cc(ccc2S(=O)(=O)C2CC2)NC(=O)COCc2cccc(c2)C(Nc2ccc3c(N(C(=O)OC(C)(C)C)C(=O)OC(C)(C)C)ncc(F)c3c2)C1=O]

Example 2C (49.8 mg, 0.052 mmol) was dissolved in THF (515 µL). TBAF (67.0 µL, 0.067 mmol) was added at ambient temperature. An additional 2 equivalents of TBAF were added and the reaction was allowed to stir for 3 h. The crude material was purified by Prep LC (C18 30×100 mm column, 10 min gradient from 20 to 100% B in A, A=10:90:0.1 MeCN:H$_2$O:TFA, B=90:10:0.1 MeCN:H$_2$O:TFA). To the fractions containing product, TEA (500 µL) was added to obtain 2-(1-(bis(tert-butoxycarbonyl)amino)-4-fluoroisoquinolin-6-ylamino)-2-(3-((2-(4-(cyclopropylsulfonyl)-3-((methylamino)methyl)phenylamino)-2-oxoethoxy)methyl)phenyl)acetic acid, which was used immediately in the next step. BOP (45.6 mg, 0.103 mmol) and DMAP (25.2 mg, 0.206 mmol) were dissolved in DCM (387 µL) and DMF (129 µL) at ambient temperature. 2-(1-(bis(tert-butoxycarbonyl)amino)-4-fluoroisoquinolin-6-ylamino)-2-(3-((2-(4-(cyclopropylsulfonyl)-3-((methylamino)methyl)phenylamino)-2-oxoethoxy)methyl)phenyl)acetic acid (42.4 mg, 0.052 mmol) and DIPEA (90 µL, 0.516 mmol) were dissolved in approximately 2 mL of DMF and added to the coupling reagent solution via syringe pump over 13 h. The reaction was diluted with water and extracted thrice with EtOAc. The combined organic layers were washed with brine, dried (Na$_2$SO$_4$), filtered, and concentrated in vacuo to yield Example 2D (12 mg, 48%). MS (ESI) m/z: 804.1 (M+H)$^+$.

Example 2

Example 2D (12 mg, 0.020 mmol) was dissolved in TFA (ca 1 mL) at ambient temperature and stirred for 1 h. The reaction was concentrated in vacuo, and the residue was purified by Prep LC (YMC-Pack ODS 5 µm 20×100 mm column, 10 min gradient from 20% to 100% B in A, A=10:90:0.1 MeOH:H$_2$O:TFA, B=90:10:0.1 MeOH:H$_2$O:TFA) to yield Example 2 (10 mg, 32%). Analytical HPLC (low pH, 254 nM): Sunfire, RT=8.93 min. MS (ESI) m/z: 604.1 (M+H)$^+$.

Example 3

(R)-11-(1-Amino-isoquinolin-6-ylamino)-16-cyclopropanesulfonyl-13-methyl-4-oxa-2,13-diaza-tricyclo[13.3.1.1$^{6,10}$]icosa-1(19),6,8,10(20),15,17-hexaene-3,12-dione trifluoroacetic acid salt+ Enantiomer

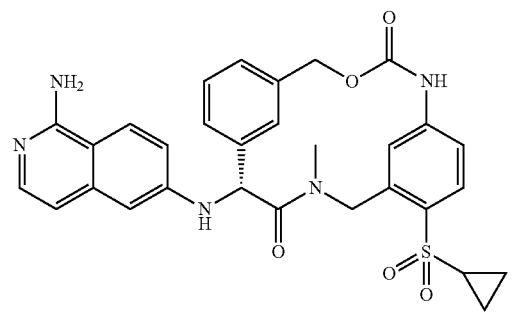 [SMILES: CN1Cc2cc(ccc2S(=O)(=O)C2CC2)NC(=O)OCc2cccc(c2)[C@@H](Nc2ccc3c(N)nccc3c2)C1=O]

Example 3A (3-bromobenzyloxy)(tert-butyl)dimethylsilane

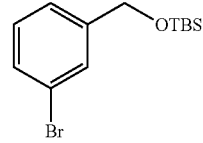 [SMILES: CC(C)(C)[Si](C)(C)OCc1cccc(Br)c1]

(3-Bromophenyl)methanol (0.500 mL, 4.17 mmol) was dissolved in DCM (20.85 mL). Imidazole (1.136 g, 16.68 mmol) and TBS-Cl (1.257 g, 8.34 mmol) were added at ambient temperature. The reaction was stirred for 2 h. The reaction was diluted with DCM, then washed with saturated NaHCO$_3$, water, then brine, dried (Na$_2$SO$_4$), filtered, and concentrated in vacuo to yield Example 3A (1.25 g, 99%). 1H NMR (400 MHz, CHLOROFORM-d) δ ppm 7.48 (1 H, s), 7.38 (1 H, d, J=7.53 Hz), 7.15-7.28 (2 H, m), 4.72 (2 H, s), 0.96 (9 H, s), 0.11 (6 H, s).

Example 3B

3-(Hydroxymethyl)phenylboronic acid

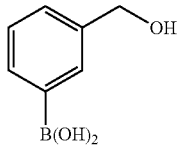

Example 3A (150 mg, 0.498 mmol) was dissolved in THF (2.49 mL) and cooled to −78° C. BuLi (431 μL, 0.647 mmol) was and the reaction was stirred for 30 min. After this time, triisopropyl borate (231 μL, 0.996 mmol) was added and stirring continued for 20 min, then the reaction was warmed to ambient temperature and allowed to stir for 2.5 h. The reaction mixture was diluted with EtOAc and washed with water, then brine, dried ($Na_2SO_4$), filtered, and concentrated in vacuo. The crude material was then dissolved in HPLC solvent B (90:10:0.1 $MeCN:H_2O:TFA$) and allowed to stir at ambient temperature for 1 h. The reaction was concentrated in vacuo and the crude material was purified by Prep LC (Axia Luna 5μ C18 30×100 mm column, 10 min gradient from 20 to 100% B in A, A=10:90:0.1 $MeCN:H_2O:TFA$, B=90:10:0.1 $MeCN:H_2O:TFA$) to yield Example 3B (57 mg, 75%). 1H NMR (400 MHz, ACETONITRILE-$d_3$) δ ppm 7.75 (1 H, s), 7.67 (1 H, d, J=7.28 Hz), 7.40-7.48 (1 H, m), 7.30-7.40 (1 H, m), 4.60 (2 H, s).

Example 3C (6-{[[(5-Amino-2-cyclopropanesulfonyl-benzyl)-methyl-carbamoyl]-(3-hydroxymethyl-phenyl)-methyl]-amino}-isoquinolin-1-yl)-bis(carbamic acid tert-butyl ester)

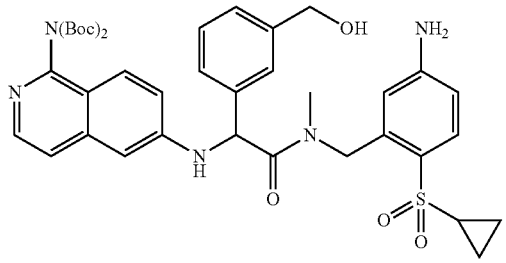

Example 3B (56.7 mg, 0.373 mmol), imidodicarbonic acid, 2-(6-amino-1-isoquinolinyl)-, 1,3-bis(1,1-dimethylethyl) ester (122 mg, 0.339 mmol), and Glyoxylic acid monohydrate (31.2 mg, 0.339 mmol) were dissolved in DMF (1.06 mL) and MeCN (3.18 mL). The reaction was heated at 60° C. overnight. The reaction was cooled to ambient temperature and 4-(cyclopropylsulfonyl)-3-((methylamino)methyl)aniline dihydrochloride (138 mg, 0.441 mmol), DIPEA (296 μL, 1.696 mmol), and BOP (150 mg, 0.339 mmol) were added and stirring continued at ambient temperature for 8 h. The reaction was quenched with water and extracted thrice with EtOAc. The combined organic extracts were washed with brine, dried ($Na_2SO_4$), filtered, and concentrated in vacuo. The crude reaction mixture was purified by Prep LC (Phenomenex Luna 5μ C18 30×100 mm column, 25 min gradient from 40 to 100% B in A, A=$H_2O$ with 0.1% TFA, B=MeOH with 0.1% TFA). The fractions containing product were quenched with saturated $NaHCO_3$, then partially concentrated in vacuo, and extracted thrice with EtOAc. The combined organic layers were washed with brine, dried ($Na_2SO_4$), filtered, and concentrated in vacuo to yield Example 3C (60 mg, 24%). MS (ESI) m/z: 746.2 $(M+H)^+$.

Example 3D

[6-(16-Cyclopropanesulfonyl-13-methyl-3,12-dioxo-4-oxa-2,13-diaza-tricyclo[13.3.1.1$^{6,10}$]icosa-1(19),6,8,10(20),15,17-hexaen-11-ylamino)-isoquinolin-1-yl]-bis(carbamic acid tert-butyl ester)

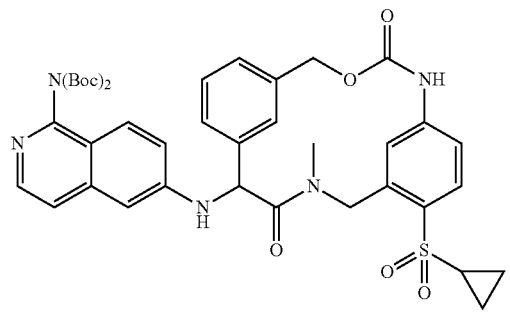

Using a procedure analogous to the one used to prepare Example 1A, Example 3C (59.9 mg, 0.080 mmol) was reacted with phosgene solution, 20% in toluene (42.5 μL, 0.080 mmol) to yield Example 3D (27 mg, 43%). 1H NMR (400 MHz, MeOD) δ ppm 8.07 (1 H, d, J=6.02 Hz), 7.82 (1 H, d, J=8.53 Hz), 7.73 (1 H, s), 7.63-7.69 (2 H, m), 7.60 (1 H, d, J=5.52 Hz), 7.55 (1 H, d, J=2.26 Hz), 7.47 (1 H, t, J=7.65 Hz), 7.37 (1 H, d, J=7.53 Hz), 7.28 (1 H, dd, J=9.29, 2.26 Hz), 7.03 (1 H, dd, J=8.78, 2.26 Hz), 6.96 (1 H, d, J=2.01 Hz), 5.80-5.91 (2 H, m), 5.22-5.35 (2 H, m), 4.71 (1 H, d, J=16.56 Hz), 2.91 (3 H, s), 2.81-2.89 (1 H, m, J=7.75, 7.75, 5.02, 4.83 Hz), 1.29 (18 H, s), 0.95-1.11 (3 H, m), 0.90 (1 H, d, J=6.78 Hz). MS (ESI) m/z: 772.1 $(M+H)^+$.

Example 3

Example 3D (37 mg, 0.034 mmol) was separated by Chiral Prep (Chiralcel OD, 35% MeOH/EtOH (1:1) in heptane). The two enantiomers were separated and Peak 1 was collected. The compound was dissolved in TFA (ca 2 mL) and stirred for 1 h and concentrated in vacuo. The crude reaction mixture was purified by Prep LC (YMC-Pack ODS S-5 μm 20×100 mm column, 10 min gradient from 20 to 100% B in A, A=10:90:0.1 $MeOH:H_2O:TFA$, B=90:10:0.1 $MeOH:H_2O:TFA$) to yield Example 3 (3 mg, 13%) 1H NMR (400 MHz, MeOD) δ ppm 8.11 (1 H, d, J=9.03 Hz), 7.84 (1 H, d, J=8.78 Hz), 7.72 (1 H, s), 7.65 (1 H, d, J=8.03 Hz), 7.55 (1 H, d, J=2.26 Hz), 7.50 (1 H, t, J=7.65 Hz), 7.41 (1 H, d, J=7.78 Hz), 7.36 (1 H, d, J=7.03 Hz), 7.21 (1 H, dd, J=9.16, 2.38 Hz), 7.05 (1 H, dd, J=8.66, 2.13 Hz), 7.01 (1 H, d, J=7.03 Hz), 6.93 (1 H, d, J=2.26 Hz), 5.90 (1 H, s), 5.85 (1 H, d, J=16.56 Hz), 5.25-5.38 (3 H, m), 4.68 (1 H, d, J=16.56 Hz), 2.91 (3 H, s), 2.81-2.89 (1 H, m), 1.23-1.36 (1 H, m), 0.99-1.16 (3 H, m). MS (ESI) m/z: 572.0 (M+H)⁺. Analytical HPLC (low pH, 254 nM): Sunfire, RT=4.94 min.

Example 4

(R)-5-(1-Amino-isoquinolin-6-ylamino)-19-cyclo-propanesulfonyl-3,11,11-trimethyl-13-oxa-3,15-di-aza-tricyclo[14.3.1.1$^{6,10}$]henicosa-1(19),6(21),7,9,16(20),17-hexaene-4,14-dione trifluoroacetic acid salt+Enantiomer

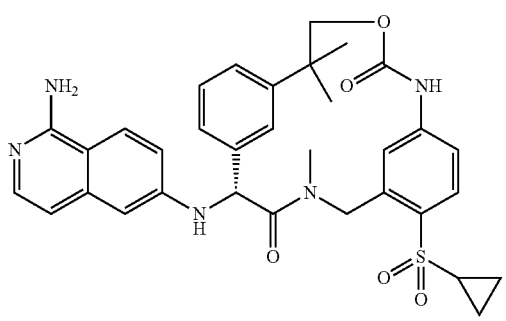 [SMILES: CN1Cc2cc(ccc2S(=O)(=O)C2CC2)NC(=O)OCC(C)(C)c2cccc(c2)[C@@H](Nc2ccc3c(N)nccc3c2)C1=O]

Example 4A methyl 2-(3-bromophenyl)-2-methylpropanoate

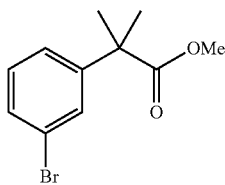

Example 5A (154 mg, 0.672 mmol) was dissolved in THF (2.24 mL). Sodium hydride (46.8 mg, 1.95 mmol) was added and the reaction was stirred for 15 minutes. Methyl iodide (807 μL) was added and the reaction was allowed to stir overnight at ambient temperature. The reaction was quenched with water and extracted twice with EtOAc. The combined organic extracts were washed with brine, dried (Na2SO4), filtered, and concentrated in vacuo. The crude material was purified by silica gel column chromatography (0 to 100% EtOAc in hexanes) to yield Example 4A (87.5 mg, 51%) as a clear oil. 1H NMR (400 MHz, CHLOROFORM-d) δ ppm 7.48 (1 H, t, J=1.88 Hz), 7.37 (1 H, dt, J=7.78, 1.51 Hz), 7.23-7.28 (1 H, m), 7.20 (1 H, d, J=7.78 Hz), 3.65 (3 H, s), 1.56 (6 H, s).

Example 4B 2-(3-bromophenyl)-2-methylpropanoate

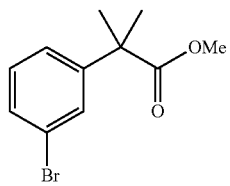

Methyl 2-(3-bromophenyl)-2-methylpropanoate (87.5 mg, 0.34 mmol) was dissolved in toluene (681 μL) and cooled to −78° C. DIBAL-H (3.4 mL, 3.4 mmol, 1 M in toluene) was added and the reaction allowed to slowly warm to ambient temperature and stir overnight. The reaction was quenched with MeOH then 1 N HCl and extracted thrice with EtOAc. The combined organic layers were washed with brine, dried with Na₂SO₄, filtered, and concentrated in vacuo. The crude material was purified by silica gel column chromatography (0 to 100% EtOAc in hexanes) to yield Example 4B (61.8 mg, 79%) as a clear oil. 1H NMR (400 MHz, CHLOROFORM-d) δ ppm 7.52 (1 H, t, J=1.88 Hz), 7.34-7.39 (1 H, m), 7.32 (1 H, ddd, J=8.28, 1.51, 1.25 Hz), 7.21 (1 H, t, J=7.78 Hz), 3.59 (2 H, s), 1.44 (1 H, br. s.), 1.32 (6 H, s).

Example 4C (2-(3-Bromophenyl)-2-methylpropoxy)(tert-butyl)dimethylsilane

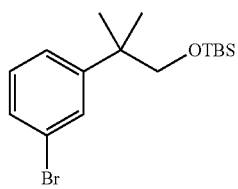 [SMILES: CC(C)(CO[Si](C)(C)C(C)(C)C)c1cccc(Br)c1]

Using a procedure analogous to the one used to prepare Intermediate 1A, Example 4B (61.8 mg, 0.270 mmol) was reacted with TBS-Cl (81 mg, 0.539 mmol) to yield Example 4C (86 mg, 93%). 1H NMR (400 MHz, CHLOROFORM-d) δ ppm 7.53 (1 H, t, J=1.88 Hz), 7.28-7.36 (2 H, m), 7.17 (1 H, t, J=7.78 Hz), 3.51 (2 H, s), 1.29 (6 H, s), 0.85 (9 H, s), −0.06 (6 H, s).

Example 4D 3-(1-Hydroxy-2-methylpropan-2-yl)phenylboronic acid

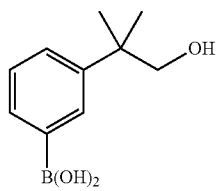

Using a procedure analogous to the one used to prepare Intermediate 1, Example 4C (0.086 g, 0.250 mmol) was reacted with triisopropyl borate (127 μL, 0.549 mmol) to yield Example 4D (45 mg, 94%). The compound was used immediately, after purification.

Example 4E

[6-({[(5-Amino-2-cyclopropanesulfonyl-benzyl)-methyl-carbamoyl]-[3-(2-hydroxy-1,1-dimethyl-ethyl)-phenyl]-methyl}-amino)-isoquinolin-1-yl]-bis(carbamic acid tert-butyl ester)

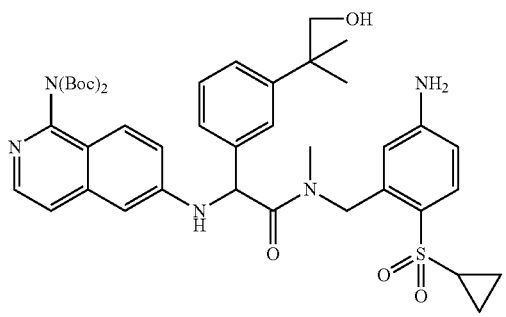

Using a procedure analogous to the one used to prepare Example 1A, Example 4D (45 mg, 0.232 mmol), imidodicarbonic acid, 2-(6-amino-1-isoquinolinyl)-, 1,3-bis(1,1-dimethylethyl) ester (76 mg, 0.211 mmol), and 4-(cyclopropylsulfonyl)-3-((methylamino)methyl)aniline dihydrochloride (86 mg, 0.274 mmol) were reacted to yield Example 4E (48 mg, 29%). MS (ESI) m/z: 788.2 (M+H)+.

Example 4F

[6-(19-Cyclopanesulfonyl-3,11,11-trimethyl-4,14-dioxo-13-oxa-3,15-diaza-tricyclo[14.3.1.1$^{6,10}$]henicosa-1(19),6(21),7,9,16(20),17-hexaen-5-ylamino)-isoquinolin-1-yl]-bis(carbamic acid tert-butyl ester)

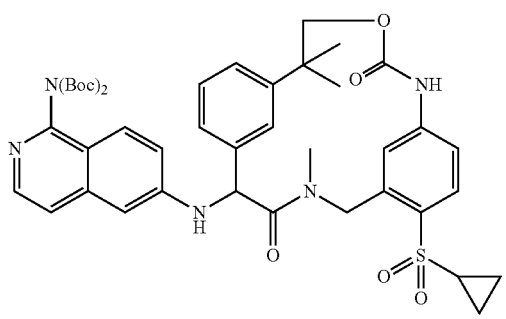

Using a procedure analogous to the one used to prepare Example 1B, Example 4E (45 mg) was reacted with Phosgene solution, 20% in toluene (32.4 μL, 0.061 mmol) to yield Example 4F (19 mg, 38%). MS (ESI) m/z: 814.2 (M+H)+.

Example 4

Example 4F (19 mg, 0.051 mmol) was separated by Chiral Prep LC (Chiralcel OD 25×200 mm column, 25% isocratic MeOH/EtOH (1:1) in heptane). The two enantiomers were separated and Peak 1 was collected. The compound was dissolved in TFA (ca 2 mL) and stirred for 1 h. This mixture was purified by Prep LC (YMC ODS-A S-5 μm 20×100 mm column, 10 min gradient from 10 to 100% B in A, A=10:90:0.1 MeCN:H$_2$O:TFA, B=90:10:0.1 MeCN:H$_2$O:TFA) to yield Example 4 (4 mg, 21%). 1H NMR (400 MHz, MeOD) δ ppm 8.09 (1 H, d, J=9.29 Hz), 7.79 (1 H, d, J=8.78 Hz), 7.68 (1 H, s), 7.56 (1 H, d, J=7.28 Hz), 7.46-7.51 (1 H, m), 7.43 (1 H, d, J=7.53 Hz), 7.35 (1 H, d, J=7.03 Hz), 7.29 (1 H, d, J=1.51 Hz), 7.23 (1 H, dd, J=9.03, 2.26 Hz), 6.95-7.02 (2 H, m), 6.87-6.93 (1 H, m), 5.78 (1 H, s), 5.73 (1 H, d, J=15.56 Hz), 4.78 (1 H, d, J=15.56 Hz), 4.44 (1 H, d, J=11.29 Hz), 2.97 (3 H, s), 2.73-2.87 (2 H, m), 1.38 (3 H, s), 1.30 (3 H, s), 0.96-1.18 (4 H, m). MS (ESI) m/z: 614.1 (M+H)+. Analytical HPLC (low pH, 254 nM): Sunfire, RT=5.15 min.

Example 5

5-(1-Amino-isoquinolin-6-ylamino)-19-cyclopropanesulfonyl-11-cyclopropyl-3-methyl-13-oxa-3,15-diaza-tricyclo[14.3.1.1$^{6,10}$]henicosa-1(19),6(21),7,9,16(20),17-hexaene-4,14-dione trifluoroacetic acid salt

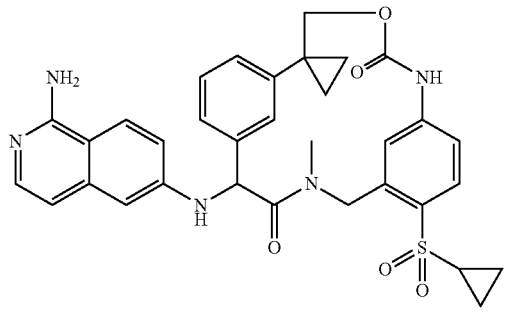 [SMILES: CN1Cc2cc(ccc2S(=O)(=O)C2CC2)NC(=O)OCC2(CC2)c2cccc(c2)C(Nc2ccc3c(N)nccc3c2)C1=O]

Example 5A

Methyl 2-(3-bromophenyl)acetate

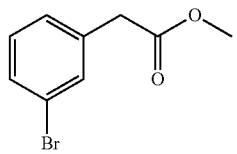

3-Bromophenylacetic acid (2.0 g, 9.30 mmol) was dissolved in MeOH (46.5 mL) and cooled to 0° C. SOCl$_2$ (3.39 mL, 46.5 mmol) was added carefully dropwise. The reaction was then heated to reflux at for 2 h. The reaction was cooled to ambient temperature and concentrated in vacuo. The crude material was purified by silica gel chromatography (0 to 100% EtOAc in hexanes to yield Example 5A (1.97 g, 8.60 mmol). 1H NMR (400 MHz, CHLOROFORM-d) δ ppm 7.44 (1 H, s), 7.36-7.43 (1 H, m), 7.15-7.24 (2 H, m), 3.70 (3 H, s), 3.60 (2 H, s).

Example 5B

Methyl 1-(3-bromophenyl)cyclopropanecarboxylate

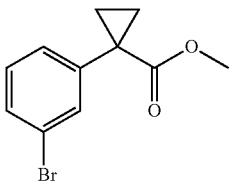

Example 5A (330 mg, 1.441 mmol) was dissolved in DMSO (7.2 mL) at ambient temperature. NaH (104 mg, 4.32 mmol) then 1,2-dibromoethane (374 µL, 4.32 mmol) were added and the reaction was allowed to stir at ambient temperature overnight. The reaction was diluted with saturated NH$_4$Cl and EtOAc. The organic layer was further washed with brine, dried (Na$_2$SO$_4$), filtered, and concentrated in vacuo. The crude material was purified by Prep LC (Phenomenex Axia 30×100 mm 5µ column, 8 min gradient from 0 to 100% B in A, A=10:90:0.1 MeOH:H$_2$O:TFA, B=90:10:0.1 MeOH:H$_2$O:TFA) to yield Example 5B (49 mg, 14%). 1H NMR (400 MHz, CHLOROFORM-d) δ ppm 7.49 (1 H, t, J=1.76 Hz), 7.39 (1 H, dt, J=7.97, 1.54 Hz), 7.24-7.32 (1 H, m), 7.18 (1 H, t, J=7.78 Hz), 3.63 (3 H, s), 1.56-1.66 (2 H, m), 1.14-1.24 (2 H, m). 13C NMR (100 MHz, CHLOROFORM-d) δ ppm 174.4, 141.7, 133.6, 130.3, 129.6, 129.2, 121.9, 52.4, 28.7, 16.6 (2 C). MS (ESI) m/z: 255/257 (M+H)$^+$.

Example 5C (1-(3-Bromophenyl)cyclopropyl)methanol

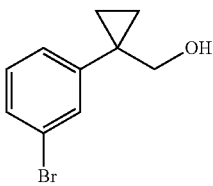 [SMILES: OCC1(c2cccc(Br)c2)CC1]

Example 5B (49 mg, 0.192 mmol) was dissolved in toluene (384 µL) and cooled to −78° C. DIBAL-H in toluene (960 µL, 0.960 mmol) was added, and the reaction was warmed to ambient temperature over 4 h. The reaction was allowed to stir overnight. The reaction was quenched with MeOH. The reaction was then diluted with 1 N HCl and extracted thrice with EtOAc. The combined organic extracts were washed with saturated NaHCO$_3$, then brine, dried (Na$_2$SO$_4$), filtered, and concentrated in vacuo. The crude material was purified by silica gel column chromatography (0 to 100% EtOAc in hexanes) to yield Example 5C (41 mg, 94%). 1H NMR (400 MHz, CHLOROFORM-d) δ ppm 7.50 (1 H, t, J=1.76 Hz), 7.31-7.38 (1 H, m), 7.21-7.32 (1 H, m), 7.17 (1 H, t, J=7.91 Hz), 3.64 (2 H, s), 2.19 (1 H, s), 0.79-0.91 (4 H, m). 13C NMR (100 MHz, CHLOROFORM-d) δ ppm 145.2, 132.0, 129.9, 129.6, 127.6, 122.4, 70.4, 27.8, 11.5 (2 carbons).

Example 5D ((1-(3-Bromophenyl)cyclopropyl)methoxy)(tert-butyl)dimethylsilane

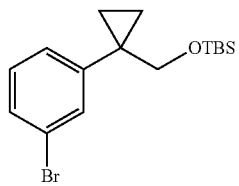 [SMILES: CC(C)(C)[Si](C)(C)OCC1(c2cccc(Br)c2)CC1]

Using a procedure analogous to the one used to prepare Intermediate 1A, Example 5C (61.2 mg, 0.270 mmol) was reacted with TBS-Cl (81 mg, 0.539 mmol) to yield Example 5D (85 mg, 92%). 1H NMR (400 MHz, CHLOROFORM-d) δ ppm 7.52 (1 H, t, J=1.76 Hz), 7.33 (1 H, ddd, J=7.78, 2.01, 1.00 Hz), 7.22-7.30 (1 H, m), 7.14 (1 H, t, J=7.78 Hz), 3.65 (2 H, s), 0.83-0.91 (11 H, m), 0.75-0.81 (2 H, m), −0.07 (6 H, s).

Example 5E 3-(1-(Hydroxymethyl)cyclopropyl)phenylboronic acid

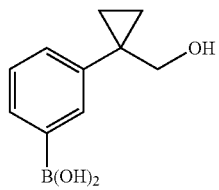 [SMILES: OCC1(c2cccc(B(O)O)c2)CC1]

Using a procedure analogous to the one used to prepare Intermediate 1, Example 5D (85 mg, 0.249 mmol) was reacted with triisopropyl borate (116 µL, 0.498 mmol) to yield Example 5E (36 mg, 75%). Compound used immediately after purification.

Example 5F

[6-({[(5-Amino-2-cyclopropanesulfonyl-benzyl)-methyl-carbamoyl]-[3-(1-hydroxymethyl-cyclopropyl)-phenyl]-methyl}-amino)-isoquinolin-1-yl]-bis (carbamic acid tert-butyl ester)

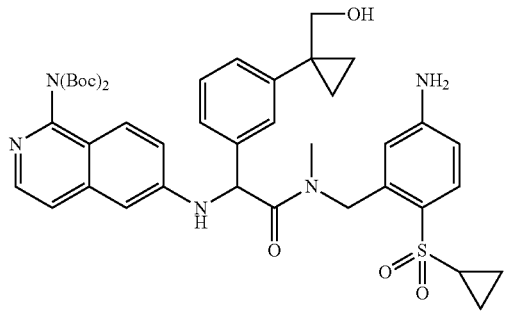

Using a procedure analogous to the one used to prepare Example 1A, Example 5E (35 mg, 0.182 mmol), imidodicarbonic acid, 2-(6-amino-1-isoquinolinyl)-, 1,3-bis(1,1-dimethylethyl) ester (60 mg, 0.166 mmol), and 4-(cyclopropylsulfonyl)-3-((methylamino)methyl)aniline dihydrochloride (68 mg, 0.215 mmol) were reacted to yield Example 5F (45 mg, 34%). MS (ESI) m/z: 786.2 (M+H)+.

Example 5G

[6-(19-Cyclopropanesulfonyl-11-cyclopropyl-3-methyl-4,14-dioxo-13-oxa-3,15-diaza-tricyclo[14.3.1.1$^{6,10}$]henicosa-1(19),6(21),7,9,16(20),17-hexaen-5-ylamino)-isoquinolin-1-yl]-bis(carbamic acid tert-butyl ester)

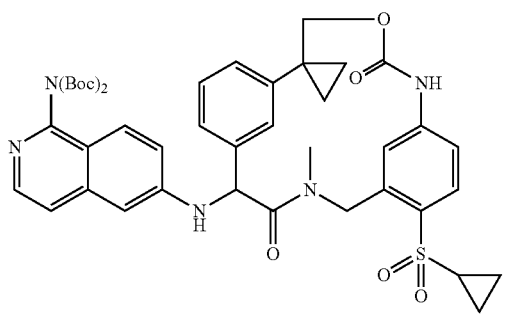

Using a procedure analogous to the one used to prepare Example 1B, Example 5F (45 mg, 0.057 mmol) was reacted with phosgene solution, 20% in toluene (30 µL, 0.057 mmol) to yield Example 5G (5.4 mg, 12%). MS (ESI) m/z: 812.2 (M+H)+.

Example 5

Example 5G (5.4 mg, 0.005 mmol) was dissolved in TFA (ca 2 mL) and stirred for 1 h. This mixture was purified by Prep LC (YMC ODS-A S-5 µm 20×100 mm column, 10 min gradient from 10 to 100% B in A, A=10:90:0.1 MeCN:H$_2$O:TFA, B=90:10:0.1 MeCN:H$_2$O:TFA) to yield Example 5 (4 mg, 82%). 1H NMR (400 MHz, MeOD) δ ppm 8.09 (1 H, d, J=9.29 Hz), 7.75-7.84 (2 H, m), 7.52 (1 H, d, J=7.78 Hz), 7.45 (1 H, s), 7.40 (1 H, t, J=7.78 Hz), 7.35 (1 H, d, J=7.03 Hz), 7.21 (1 H, dd, J=9.29, 2.26 Hz), 7.05 (1 H, d, J=8.03 Hz), 6.96-7.02 (2 H, m), 6.88 (1 H, d, J=2.26 Hz), 5.80 (1 H, s), 5.75 (1 H, d, J=16.06 Hz), 4.79 (1 H, d, J=15.81 Hz), 4.73 (1 H, d, J=12.55 Hz), 4.57 (1 H, d, J=12.05 Hz), 3.00 (3 H, s), 2.77-2.86 (1 H, m), 0.88-1.43 (8 H, m). MS (ESI) m/z: 612.1 (M+H)+. Analytical HPLC (low pH, 254 nM): Sunfire, RT=5.38 min.

Example 6

(R)-5-(1-Amino-isoquinolin-6-ylamino)-19-cyclopropanesulfonyl-9-methoxy-3-methyl-13-oxa-3,15-diaza-tricyclo[14.3.1.1$^{6,10}$]henicosa-1(19),6(21),7,9,16(20),17-hexaene-4,14-dione hydrochloric acid salt+Enantiomer

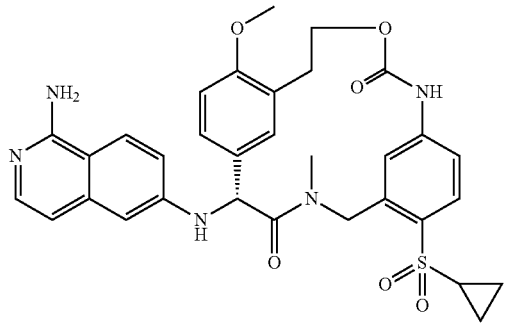

Example 6A 2-(5-Bromo-2-methoxyphenyl)ethanol

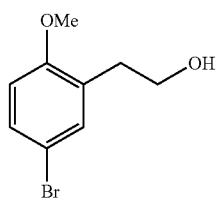 [SMILES: COc1ccc(Br)cc1CCO]

5-Bromo-2-methoxyphenylacetic acid (250 mg, 1.020 mmol) was dissolved in THF (2.55 mL) and cooled to 0° C. BH$_3$.THF (2.04 mL, 2.040 mmol) was added dropwise, and the reaction was warmed to ambient temperature and stirred overnight. The reaction was quenched with 50% AcOH and extracted with EtOAc. The organic layer was further washed with 10% Na$_2$CO$_3$, washed with water, washed with brine, dried (Na$_2$SO$_4$), filtered, and concentrated in vacuo. The crude material was purified by silica gel column chromatography (gradient from 0 to 100% EtOAc in hexanes) to yield Example 6A (0.237 g, 100% yield). MS (ESI) m/z: 231/233 (M+H)+. 1H NMR (400 MHz, CHLOROFORM-d) δ ppm 7.27-7.35 (2 H, m), 6.73 (1 H, d, J=8.59 Hz), 3.79-3.84 (5 H, m), 2.86 (2 H, t, J=6.44 Hz).

Example 6B (5-Bromo-2-methoxyphenethoxy)(tert-burty)dimethylsilane

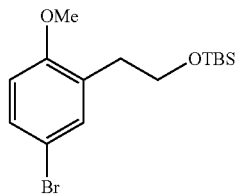 [SMILES: COc1ccc(Br)cc1CCO[Si](C)(C)C(C)(C)C]

Example 6A 235 mg, 1.017 mmol) was dissolved in DCM (5.1 mL Imidazole (277 mg, 4.07 mmol) then TBS-Cl (307 mg, 2.034 mmol) were added at ambient temperature and allowed to stir for 3.5 h. The reaction was diluted with DCM and washed with saturated NaHCO$_3$, washed with water, washed with brine, dried (Na$_2$SO$_4$), filtered, and concentrated in vacuo to yield Example 6B (328 mg, 93% yield). 1H NMR (400 MHz, CHLOROFORM-d) δ ppm 7.26-7.30 (2 H, m), 6.67-6.73 (1 H, m), 3.79 (3 H, s), 3.76 (2 H, t, J=7.03 Hz), 2.80 (2 H, t, J=7.03 Hz), 0.87 (9 H, s), −0.03 (6 H, s).

Example 6C 3-(2-hydroxyethyl)-4-methoxyphenylboronic acid

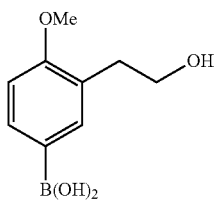 [SMILES: COc1ccc(B(O)O)cc1CCO]

Example 6B (325 mg, 0.941 mmol) was dissolved in THF (4.7 mL) and cooled to −78° C. BuLi (941 µL, 1.223 mmol) was added and the reaction was stirred for 30 minutes. Triisopropyl borate (0.437 mL, 1.882 mmol) was added and stirring continued for 20 minutes, and the reaction was warmed to ambient temperature and allowed to stir for 2 h. The reaction was diluted with EtOAc and washed with water, washed with brine, dried (Na$_2$SO$_4$), filtered, and concentrated in vacuo. The crude material was then dissolved in 90:10:0.1 MeCN:H2O:TFA and allowed to stir at ambient temperature for 1.5 h. The crude material was purified by Prep HPLC (Phenomenex Axia 30×100 mm column, 10 minute gradient from 0 to 100% B in A, A=10:90:0.1 MeCN:H2O:TFA, B=90:10:0.1 MeCN:H2O:TFA) to yield Example 6C (154 mg, 84% yield). $^1$H NMR (400 MHz, METHANOL-d$_4$) δ 7.55-7.32 (m, 2H), 6.82 (dd, J=14.8, 8.3 Hz, 1H), 3.76-3.72 (m, 3H), 3.60 (t, J=7.3 Hz, 2H), 2.75 (t, J=7.3 Hz, 2H).

Example 6D

[6-({[(5-Amino-2-cyclopropanesulfonyl-benzyl)-methyl-carbamoyl]-[3-(2-hydroxy-ethyl)-4-methoxy-phenyl]-methyl}-amino)-isoquinolin-1-yl]-bis(carbamic acid tert-butyl ester)

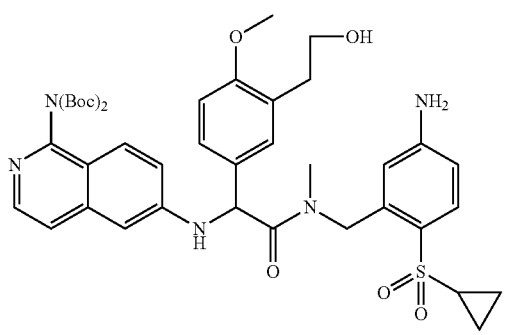

Using a procedure analogous to the one used to prepare 1A, Example 6C (0.150 g, 0.765 mmol), imidodicarbonic acid, 2-(6-amino-1-isoquinolinyl)-, 1,3-bis(1,1-dimethylethyl) ester (0.250 g, 0.696 mmol), and 4-(cyclopropylsulfonyl)-3-((methylamino)methyl)aniline dihydrochloride (0.283 g, 0.904 mmol) were reacted to yield Example 6D (0.446 g, 81%). MS (ESI) m/z: 790.5 (M+H)$^+$.

Example 6E

[6-(19-Cyclopropanesulfonyl-9-methoxy-3-methyl-4,14-dioxo-13-oxa-3,15-diaza-tricyclo[14.3.1.1$^{6,10}$]henicosa-1(19),6(21),7,9,16(20),17-hexaen-5-ylamino)-isoquinolin-1-yl]-bis(carbamic acid tert-butyl ester)

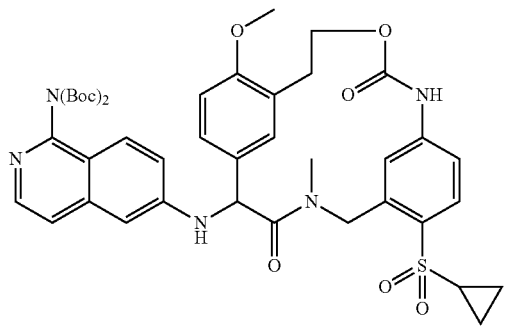

Using a procedure analogous to the one used to prepare Example 1B, Example 6D (0.445 g, 0.563 mmol) was reacted with phosgene solution, 20% in toluene (0.289 mL, 0.563 mmol) to yield Example 6E (0.189 g, 41%). MS (ESI) m/z: 816.4 (M+H)$^+$.

Example 6

Example 6E (0.188 g, 0.230 mmol) was separated by Chiral Prep LC (Chiralcel OD 25×200 mm column, 30% isocratic MeOH/EtOH (1:1) in heptane). The two enantiomers were separated and Peak 1 was collected. The compound was dissolved in TFA (ca 2 mL) and stirred for 1 h. This mixture was purified by Prep LC (YMC ODS-A S-5 µm 20×100 mm column, 10 min gradient from 10 to 100% B in A, A=10:90:0.1 MeCN:H$_2$O:TFA, B=90:10:0.1 MeCN:H$_2$O:TFA) to yield Example 6 (40 mg, 25%). MS (ESI) m/z: 616.2 (M+H)$^+$. Analytical HPLC (low pH, 254 nM): Sunfire, RT=5.66 min.

Example 7

(5R,11S)-5-(1-Amino-isoquinolin-6-ylamino)-19-cyclopropanesulfonyl-3,11-dimethyl-13-oxa-3,15-diaza-tricyclo[14.3.1.1⁶,¹⁰]henicosa-1(19),6(21),7,9,16(20),17-hexaene-4,14-dione hydrochloric acid salt+Diastereomer

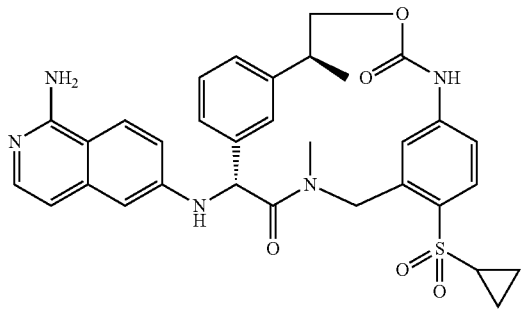 [SMILES: C[C@@H]1COC(=O)Nc2ccc(S(=O)(=O)C3CC3)c(c2)CN(C)C(=O)[C@H](Nc2ccc3c(N)nccc3c2)c2cccc1c2]

Example 7A (S)-4-Benzyl-3-(2-(3-bromophenyl)acetyl)oxazolidin-2-one

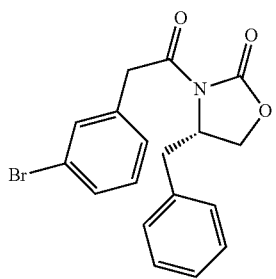 [SMILES: O=C(Cc1cccc(Br)c1)N1C(=O)OC[C@@H]1Cc1ccccc1]

(S)-4-benzyloxazolidin-2-one (206 mg, 1.163 mmol) was dissolved in THF (23.3 mL) and cooled to −78° C. BuLi (775 μL, 1.163 mmol) was added stirring continued for 15 min. After this time, a solution of 2-(3-bromophenyl)acetyl chloride (543 mg, 2.326 mmol) in a minimal amount of THF was added. Stirring was continued at the same temperature for 15 min, and then the reaction was warmed to ambient temperature and allowed to stir overnight. The reaction was quenched with saturated NH₄Cl and partially concentrated in vacuo. The residue was extracted with EtOAc. The organic layer was further washed with brine, dried (Na₂SO₄), filtered, and concentrated in vacuo. The crude material was purified by silica gel column chromatography (30 min of pure DCM, then 10 min at 10% MeOH to flush the column) to yield Example 7A (0.293 g, 67%). 1H NMR (400 MHz, CHLOROFORM-d) δ ppm 7.47-7.53 (1 H, m), 7.43 (1 H, dt, J=7.78, 1.63 Hz), 7.19-7.34 (5 H, m), 7.11-7.17 (2 H, m), 4.63-4.72 (1 H, m), 4.15-4.35 (4 H, m), 3.26 (1 H, dd, J=13.55, 3.26 Hz), 2.77 (1 H, dd, J=13.43, 9.41 Hz). MS (ESI) m/z: 374/376 (M+H)⁺.

Example 7B (S)-4-benzyl-3-((S)-2-(3-bromophenyl)propanoyl)oxazolidin-2-one

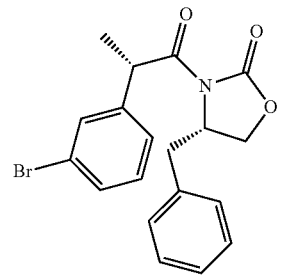 [SMILES: C[C@H](C(=O)N1C(=O)OC[C@@H]1Cc1ccccc1)c1cccc(Br)c1]

Example 7A (240 mg, 0.641 mmol) was dissolved in THF (3.21 mL) and cooled to −78° C. NaHMDS (705 μL, 0.705 mmol) was added and stirring continued for 65 min. After this time, MeI (1.6 mL, 3.21 mmol) was added and stirring continued for 1.5 h, then allowed to warm to ambient temperature slowly (slow warming of the cooling bath) over 6 h. The reaction was quenched with saturated NaHCO₃ and extracted with EtOAc. The organic layer was further washed with water, saturated Na₂SO₃, and brine, dried (Na₂SO₄), filtered, and concentrated in vacuo. The crude material was purified by silica gel column chromatography (0 to 100% EtOAc in hexanes) to yield Example 7B (118 mg, 48%). 1H NMR (400 MHz, CHLOROFORM-d) δ ppm 7.52 (1 H, t, J=1.76 Hz), 7.10-7.43 (8 H, m), 5.09 (1 H, q, J=7.03 Hz), 4.55-4.68 (1 H, m), 4.02-4.25 (2 H, m), 3.34 (1 H, dd, J=13.30, 3.26 Hz), 2.80 (1 H, dd, J=13.30, 9.54 Hz), 1.53 (3 H, d, J=7.03 Hz). MS (ESI) m/z: 388.0 (M+H)⁺.

Example 7C (S)-2-(3-bromophenyl)propanoic acid

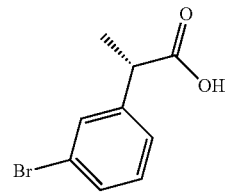

Example 7B (25 mg, 0.064 mmol) was dissolved in THF (386 μL) and Water (129 μL) and cooled to 0° C. Meanwhile, a solution of LiOH (2.313 mg, 0.097 mmol) and H₂O₂ (5.64 μL, 0.064 mmol) in water (129 μL) was prepared and added slowly to the starting material solution. The reaction was stirred for 3 h and then quenched with saturated Na₂SO₃ and washed twice with DCM. The aqueous layer was acidified with HCl and extracted twice with EtOAc. The EtOAc layers were combined and washed with brine, dried (Na₂SO₄), filtered, and concentrated in vacuo to yield Example 7C (12 mg, 81%). 1H NMR (400 MHz, CHLOROFORM-d) δ ppm 7.47 (1 H, s), 7.41 (1 H, d, J=7.78 Hz), 7.13-7.31 (2 H, m), 3.71 (1 H, q, J=6.94 Hz), 1.51 (3 H, d, J=7.28 Hz). MS (ESI) m/z: 229.0 (M+H)⁺.

Example 7D (S)-2-(3-Bromophenyl)propan-1-ol

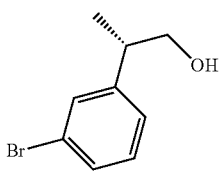

Example 7C (12 mg, 0.052 mmol) was dissolved in THF (131 μL) and cooled to 0° C. BH$_3$·THF (105 μL, 0.105 mmol) was added dropwise, and the reaction was allowed to warm slowly to ambient temperature and stir overnight. The reaction was quenched with 50% aqueous AcOH and diluted with water, then extracted twice with EtOAc. The combined organic extracts were washed with 10% Na$_2$CO$_3$, then brine, dried (Na$_2$SO$_4$), filtered, and concentrated in vacuo. The crude material was purified by silica gel column chromatography (0 to 100% EtOAc in hexanes) to yield Example 7D (3 mg, 30%). 1H NMR (400 MHz, CHLOROFORM-d) δ ppm 7.32-7.44 (2 H, m), 7.13-7.24 (3 H, m), 3.70 (2 H, d, J=6.78 Hz), 2.79-3.02 (1 H, m), 1.27 (3 H, d, J=7.03 Hz).

Example 7E (S)-(2-(3-Bromophenyl)propoxy)(tert-butyl)dimethylsilane

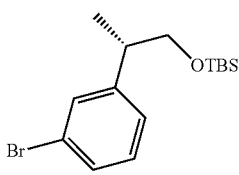

Example 7D 55.8 mg, 0.259 mmol) was dissolved in DCM (1.3 mL Imidazole (70.6 mg, 1.038 mmol) then TBS-Cl (78 mg, 0.519 mmol) were added at ambient temperature and stirred for 1.5 h. The reaction was diluted with DCM and washed with saturated NaHCO$_3$, water, then brine, dried (Na$_2$SO$_4$), filtered, and concentrated in vacuo to yield Example 7E (64 mg, 75%). 1H NMR (400 MHz, CHLOROFORM-d) δ ppm 7.37 (1 H, s), 7.33 (1 H, dt, J=6.09, 2.48 Hz), 7.12-7.19 (2 H, m), 3.61 (2 H, qd, J=9.79, 6.53 Hz), 2.80-2.92 (1 H, m, J=7.03, 6.90, 6.73, 6.73, 6.73 Hz), 1.25 (3 H, d, J=7.03 Hz), 0.85 (9 H, s), −0.04 (3 H, s), −0.06 (3 H, s).

Example 7F (S)-3-(1-Hydroxypropan-2-yl)phenylboronic acid

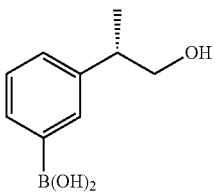

Using a procedure analogous to the one used to prepare Intermediate 1, Example 7E (63 mg, 0.195 mmol) was reacted with triisopropyl borate (91 μL, 0.254 mmol) to yield Example 7F (30 mg, 85%). The compound was used immediately after purification.

Example 7G

[6-({[(5-Amino-2-cyclopropanesulfonyl-benzyl)-methyl-carbamoyl]-[3-((S)-2-hydroxy-1-methyl-ethyl)-phenyl]-methyl}-amino)-isoquinolin-1-yl]-bis(carbamic acid tert-butyl ester)

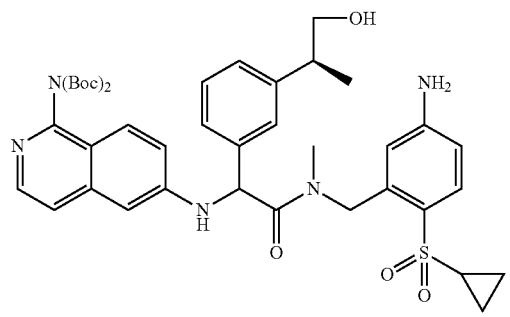

Using a procedure analogous to the one used to prepare Example 1A, Example 7F (30 mg, 0.167 mmol), imidodicarbonic acid, 2-(6-amino-1-isoquinolinyl)-, 1,3-bis(1,1-dimethylethyl) ester (55 mg, 0.152 mmol), and 4-(cyclopropylsulfonyl)-3-((methylamino)methyl)aniline dihydrochloride (62 mg, 0.197 mmol) were reacted to yield Example 7G (26 mg, 22%). MS (ESI) m/z: 774.6 (M+H)$^+$.

Example 7H

[6-((S)-19-Cyclopropanesulfonyl-3,11-dimethyl-4,14-dioxo-13-oxa-3,15-diaza-tricyclo[14.3.1.1$^{6,10}$]henicosa-1(19),6(21),7,9,16(20),17-hexaen-5-ylamino)-isoquinolin-1-yl]-bis(carbamic acid tert-butyl ester)

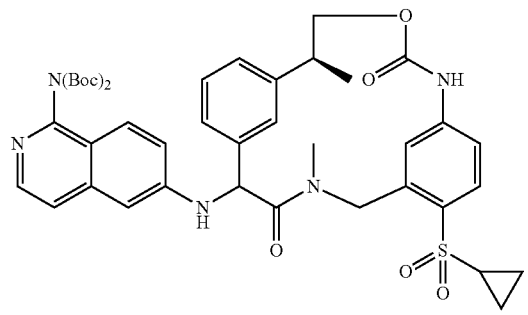

Using a procedure analogous to the one used to prepare Example 1B, Example 7G (25 mg, 0.032 mmol) was reacted with phosgene solution, 20% in toluene (17 μL, 0.032 mmol) to yield Example 7H (18 mg, 71%). MS (ESI) m/z: 800.4 (M+H)$^+$.

Example 7

Example 7H (18 mg, 0.023 mmol) was separated by Chiral Prep LC (Chiralcel OD 25×200 mm column, 25% isocratic MeOH/EtOH (1:1) in heptane). The two enantiomers were separated and Peak 1 was collected. The compound was dissolved in TFA (ca 2 mL) and stirred for 1 h. This mixture was purified by Prep LC (YMC ODS-A S-5 µm 20×100 mm column, 10 min gradient from 10 to 100% B in A, A=10:90:0.1 MeCN:H₂O:TFA, B=90:10:0.1 MeCN:H₂O:TFA) to yield Example 7 (3 mg, 19%). MS (ESI) m/z: 600.2 (M+H)⁺. Analytical HPLC (low pH, 254 nM): Sunfire, RT=5.71 min.

Example 8

(R)-11-(1-Amino-isoquinolin-6-ylamino)-16-cyclopropanesulfonyl-13-methyl-2,13-diaza-tricyclo[13.3.1.1⁶,¹⁰]icosa-1(19),6,8,10(20),15,17-hexaene-3,12-dione trifluoroacetic acid salt+Enantiomer

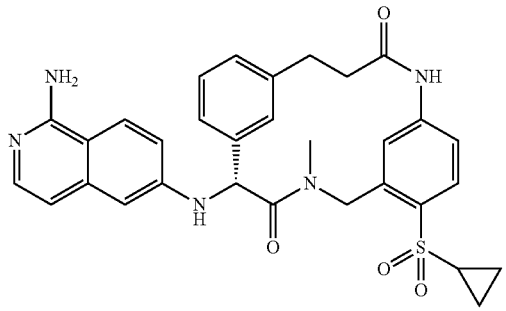

Example 8A 2-(trimethylsilyl)ethyl 5-(3-(3-bromophenyl)propanamido)-2-(cyclopropylsulfonyl)benzyl(methyl)carbamate

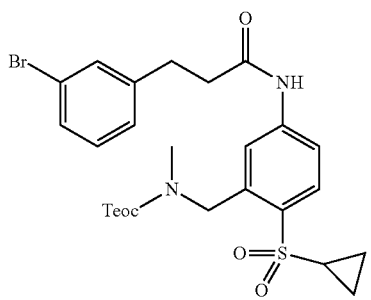

3-(3-Bromophenyl)propionic acid (200 mg, 0.873 mmol) was dissolved in DCM (4.37 mL). Oxalyl chloride (480 µL, 0.960 mmol) then DMF (6.76 µL, 0.087 mmol) (2 drops) were added at ambient temperature and the reaction was allowed to stir for 30 min. The reaction was concentrated in vacuo and stored on HIVAC for 1 h. DMAP (10.67 mg, 0.087 mmol), TEA (122 µL, 0.873 mmol), and a solution of Intermediate 2 (504 mg, 1.310 mmol) in DCM (4365 µL) was added and the reaction allowed to stir for 6 h. The reaction was diluted with DCM and washed with 1 N HCl, brine, dried (Na₂SO₄), filtered, and concentrated in vacuo. The crude mixture was purified by Prep LC (Phenomenex Luna 5µ C18 30×100 mm column, 30 min gradient from 50 to 95% B in A, A=H₂O+0.1% TFA, B=MeOH+0.1% TFA). Fractions containing compound were quenched with saturated NaHCO₃. The material was partially concentrated in vacuo and extracted thrice with EtOAc. The combined organic extracts were washed with brine, dried (Na₂SO₄), filtered, and concentrated in vacuo to yield Example 8A (0.240 g, 46%). MS (ESI) m/z: 595.0 (M+H)⁺.

Example 8B 3-(3-(4-(cyclopropylsulfonyl)-3-((methyl((2-(trimethylsilyl)ethoxy)carbonyl)amino)methyl)phenylamino)-3-oxopropyl)phenylboronic acid

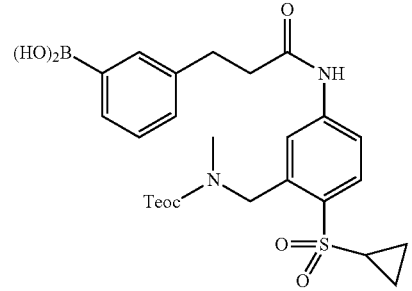

DMSO (1.68 mL) and Dioxane (1.68 mL) were degassed for 15 min by bubbling with argon. Meanwhile, 8A (240 mg, 0.403 mmol), potassium acetate (99 mg, 1.007 mmol), and bis(neopentyl glycolato)diboron (127 mg, 0.564 mmol) were placed in a microwave tube. To these compounds was added the degassed solvents. The tube was sealed and degassed for an additional 15 min. [1,1'-Bis(diphenylphosphino)ferrocene]dichloropalladium(II) (33.1 mg, 0.040 mmol) was subsequently added, the tube sealed, and heated to 90° C. The reaction was allowed to heat for 3 h, then cooled to ambient temperature. The reaction was diluted with EtOAc and washed with brine. The organic layer was dried (Na₂SO₄), filtered, and concentrated in vacuo. The crude material was purified by Prep LC (Axia Luna 5µ C18 30×100 mm column, 10 min gradient from 20 to 100% B in A, A=10:90:0.1 MeCN:H₂O:TFA, B=90:10:0.1 MeCN:H₂O:TFA) to yield Example 8B (0.139 g, 62%). MS (ESI) m/z: 583.2 (M+Na)⁺.

Example 8C 2-(1-(bis(tert-butoxycarbonyl)amino)isoquinolin-6-ylamino)-2-(3-(3-(4-(cyclopropylsulfonyl)-3-((methyl((2-(trimethylsilyl)ethoxy)carbonyl)amino)methyl)phenylamino)-3-oxopropyl)phenyl)acetic acid

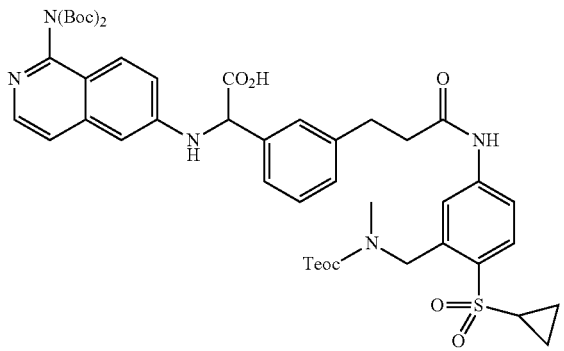

Example 8B (135 mg, 0.241 mmol), imidodicarbonic acid, 2-(6-amino-1-isoquinolinyl)-, 1,3-bis(1,1-dimethylethyl) ester (87 mg, 0.241 mmol), and glyoxylic acid monohydrate (22.17 mg, 0.241 mmol) were dissolved in DMF (1.2 mL) and MeCN (3.6 mL) and heated to 80° C. overnight. The reaction was cooled to ambient temperature and diluted with water and extracted thrice with EtOAc. The combined organic extracts were washed with brine, dried (Na$_2$SO$_4$), filtered, and concentrated in vacuo. The crude reaction mixture was purified by Prep LC (YMC Sunfire 5μ C18 30×100 mm column, 10 min gradient from 30 to 100% B in A, A=10:90:0.1 MeOH:H$_2$O:TFA, B=90:10:0.1 MeOH:H$_2$O:TFA). The fractions containing compound were partially concentrated in vacuo and extracted twice with EtOAc. The combined organic extracts were washed with brine, dried (Na$_2$SO$_4$), filtered, and concentrated in vacuo to yield Example 8C (86 mg, 38%). MS (ESI) m/z: 932.6 (M+H)$^+$.

Example 8D 2-(1-(bis(tert-butoxycarbonyl)amino)isoquinolin-6-ylamino)-2-(3-(3-(4-(cyclopropylsulfonyl)-3-((methylamino)methyl)phenylamino)-3-oxopropyl)phenyl) acetic acid

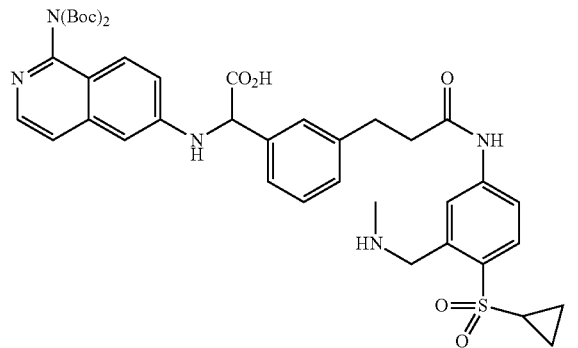

Example 8C (86 mg, 0.092 mmol) was dissolved in THF (923 μL). TBAF (369 μL, 0.369 mmol) was added at ambient temperature and the reaction was allowed to stir for 4 h, and then the reaction was concentrated in vacuo. The crude material was purified by Prep LC (YMC Sunfire 5μ C18 30×100 mm column, 10 min gradient from 30 to 100% B in A, A=10:90:0.1 MeOH:H$_2$O:TFA, B=90:10:0.1 MeOH:H$_2$O:TFA) to yield Example 8D (73 mg, 100%). MS (ESI) m/z: 788.6 (M+H)$^+$.

Example 8E

[6-(16-Cyclopropanesulfonyl-13-methyl-3,12-dioxo-2,13-diaza-tricyclo[13.3.1.1$^{6,10}$]icosa-1(19),6,8,10(20),15,17-hexaen-11-ylamino)-isoquinolin-1-yl]-bis(carbamic acid tert-butyl ester)

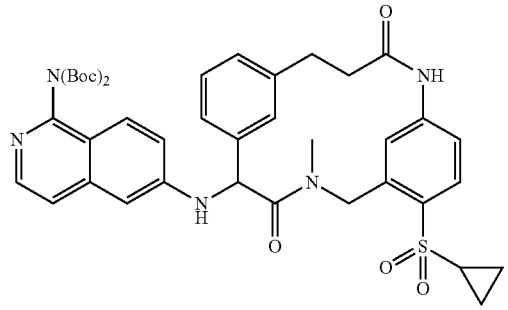

BOP (81 mg, 0.183 mmol) and DMAP (44.7 mg, 0.366 mmol) were dissolved in DCM (685 μL) and DMF (228 μL) at ambient temperature. Example 8D (72 mg, 0.091 mmol) and DIPEA (160 μL, 0.914 mmol) were dissolved in approximately 3 mL of DMF and added to the coupling reagent solution via syringe pump over about 12 h. The reaction was quenched with water and extracted thrice with EtOAc. The combined organic extracts were washed with brine, dried (Na$_2$SO$_4$), filtered, and concentrated in vacuo. The crude reaction mixture was purified by silica gel column chromatography (0 to 100% EtOAc in hexanes) to yield Example 8E (35 mg, 50%). MS (ESI) m/z: 770.4 (M+H)$^+$.

Example 8

Example 8E (35 mg, 0.046 mmol) was separated by Chiral Prep LC (Chiralcel OD 25×200 mm column, 30% isocratic MeOH/EtOH (1:1) in heptane). The two enantiomers were separated and Peak 1 was collected. The compound was dissolved in 4 N HCl in dioxanes (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 8 (2 g, 8%). MS (ESI) m/z: 570.1 (M+H)$^+$. Analytical HPLC (low pH, 254 nM): Sunfire, RT=5.14 min.

Example 9

(R)-5-(1-Amino-isoquinolin-6-ylamino)-19-cyclopropanesulfonyl-9-methoxy-3-methyl-12-oxa-3,15-diaza-tricyclo[14.3.1.1$^{6,10}$]henicosa-1(19),6(21),7,9,16(20),17-hexaene-4,14-dione trifluoroacetic acid salt+Enantiomer

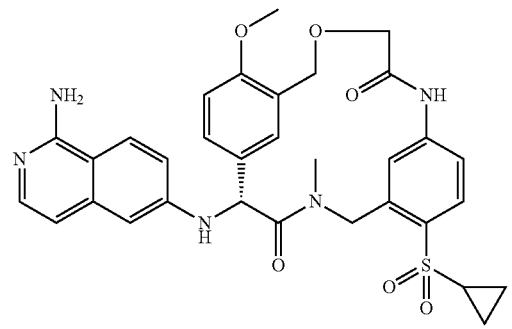 [SMILES: COc1ccc2cc1COCC(=O)Nc1ccc(S(=O)(=O)C3CC3)c(c1)CN(C)C(=O)[C@@H]2Nc1ccc2c(N)nccc2c1]

Example 9A 2-((5-Bromo-2-methoxybenzyl)oxy)acetic acid

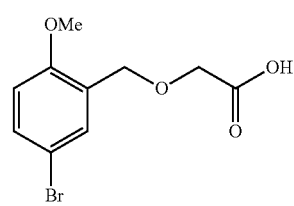 [SMILES: COc1ccc(Br)cc1COCC(=O)O]

(5-Bromo-2-methoxyphenyl)methanol (0.5 g, 2.304 mmol) and bromoacetic acid (0.320 g, 2.304 mmol) were dissolved in THF (11.52 mL). NaH (0.122 g, 5.07 mmol) was added portionwise over the course of 10 minutes. The reaction was then heated to reflux and allowed to stir overnight. The reaction was cooled to ambient temperature, and the reaction was diluted with water and extracted with EtOAc. The aqueous layer was acidified with 1 N HCl and extracted with EtOAc. The combined organic layer was washed with brine, dried ($Na_2SO_4$), filtered, and concentrated in vacuo to yield Example 9A (109 mg, 0.396 mmol, 17% yield). 1H NMR (400 MHz, CHLOROFORM-d) δ ppm 7.40-7.48 (2 H, m), 6.79 (1 H, d, J=8.53 Hz), 4.62 (2 H, s), 4.19 (2 H, s), 3.85 (3 H, s).

Example 9B 2-(trimethylsilyl)ethyl 5-(2-(5-bromo-2-methoxy-benzyloxy)acetamido)-2-(cyclopropylsulfonyl)benzyl(methyl)carbamate

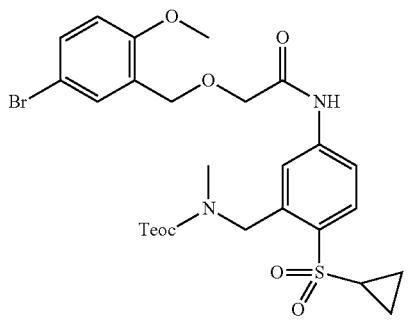

Using a procedure analogous to the one used to prepare Example 8A, Example 9A (0.109 g, 0.396 mmol) was reacted with oxalyl chloride (37 μL, 0.436 mmol) and Intermediate 2 (0.229 g, 0.594 mmol), to yield Example 9B (0.108 g, 43%). MS (ESI) m/z: 664.2 $(M+Na)^+$.

Example 9C 3-((2-(4-(cyclopropylsulfonyl)-3-((methyl((2-(trimethylsilyl)ethoxy)carbonyl)amino)methyl)phenylamino)-2-oxoethoxy)methyl)-4-methoxyphenylboronic acid

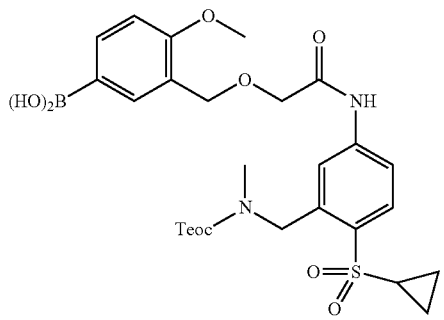

Using a procedure analogous to the one used to prepare Example 8B, Example 9B (108 mg, 0.168 mmol) was reacted with bis(neopentyl glycolato)diboron (53 mg, 0.236 mmol) and [1,1'-Bis(diphenylphospino)ferrocene]dichloropalladium(II) (14 mg, 0.017 mmol), to yield Example 9C (48 mg, 47%). MS (ESI) m/z: 629.2 $(M+Na)^+$.

Example 9D 2-(1-(bis(tert-butoxycarbonyl)amino)isoquinolin-6-ylamino)-2-(3-((2-(4-(cyclopropylsulfonyl)-3-((methyl((2-(trimethylsilyl)ethoxy)carbonyl)amino)methyl)phenylamino)-2-oxoethoxy)methyl)-4-methoxyphenyl)acetic acid

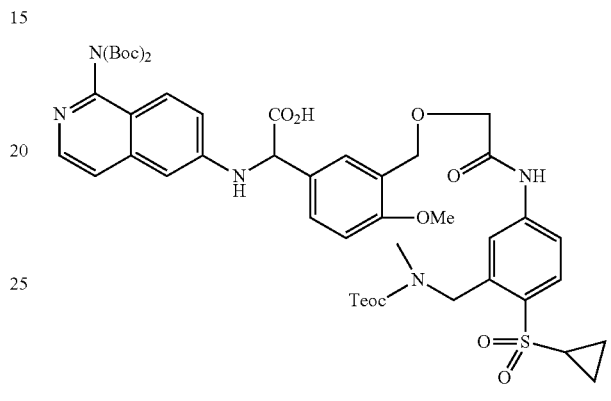

Using a procedure analogous to the one used to prepare Example 8C, Example 9C (48 mg, 0.080 mmol) and imidodicarbonic acid, 2-(6-amino-1-isoquinolinyl)-, 1,3-bis(1,1-dimethylethyl) ester (29 mg, 0.080 mmol) were reacted with glyoxylic acid monohydrate (7.4 mg, 0.080 mmol) to yield Example 9D (69 mg, 88%). MS (ESI) m/z: 978.7 $(M+H)^+$.

Example 9E 2-(1-(bis(tert-butoxycarbonyl)amino)isoquinolin-6-ylamino)-2-(3-((2-(4-(cyclopropylsulfonyl)-3-((methylamino)methyl)phenylamino)-2-oxoethoxy)methyl)-4-methoxyphenyl)acetic acid

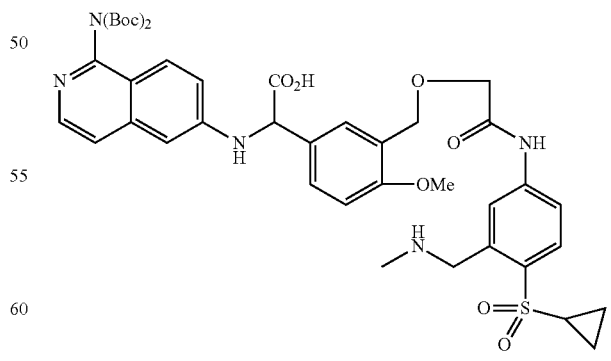

Using a procedure analogous to the one used to prepare Example 8D, Example 9D (69 mg, 0.071 mmol) was reacted with TBAF (705 μL, 0.705 mmol) to yield Example 9E (59 mg, 100%). MS (ESI) m/z: 834.5 $(M+H)^+$.

Example 9F

[6-(19-Cyclopropanesulfonyl-9-methoxy-3-methyl-4,14-dioxo-12-oxa-3,15-diaza-tricyclo[14.3.1.1^{6,10}]henicosa-1(19),6(21),7,9,16(20),17-hexaen-5-ylamino)-isoquinolin-1-yl]-bis(carbamic acid tert-butyl ester)

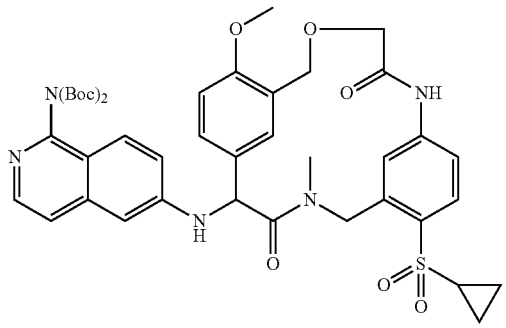

Using a procedure analogous to the one used to prepare Example 8E, Example 9E (59 mg, 0.071 mmol) was reacted with BOP (63 mg, 0.141 mmol) to yield Example 9F (31 mg, 54%). MS (ESI) m/z: 816.5 (M+H)$^+$.

Example 9

Example 9F (31 mg, 0.038 mmol) and was dissolved in TFA (2.92 µL, 0.038 mmol) (ca 1 mL) and stirred for 1 h. The reaction was concentrated in vacuo and the crude reaction mixture was purified by Prep LC (YMC-Pack ODS S-5 µm 20×100 mm column, 10 min gradient from 30 to 100% B in A, A=10:90:0.1 MeOH:H$_2$O:TFA, B=90:10:0.1 MeOH:H$_2$O:TFA) to yield Example 9 (10 mg, 35%). 1H NMR (400 MHz, DMSO-d$_6$) δ ppm 12.20 (1 H, d, J=5.27 Hz), 9.60 (1 H, s), 8.34 (2 H, br. s.), 8.11 (1 H, d, J=9.03 Hz), 7.88 (1 H, dd, J=8.66, 1.88 Hz), 7.82 (1 H, dd, J=8.53, 2.26 Hz), 7.44 (1 H, dd, J=6.65, 5.40 Hz), 7.35 (1 H, d, J=7.78 Hz), 7.17 (1 H, dd, J=9.16, 2.13 Hz), 7.10-7.14 (2 H, m), 6.86-6.92 (2 H, m), 6.70 (1 H, d, J=1.76 Hz), 5.86 (1 H, d, J=7.53 Hz), 5.47 (1 H, d, J=17.07 Hz), 4.94 (1 H, d, J=10.54 Hz), 4.33 (1 H, d, J=9.03 Hz), 4.29 (1 H, d, J=7.78 Hz), 4.00 (1 H, d, J=10.29 Hz), 3.94 (1 H, d, J=15.81 Hz), 3.83 (3 H, s), 3.27 (3 H, s), 2.88-2.97 (1 H, m), 0.96-1.17 (4 H, m). MS (ESI) m/z: 616.3 (M+H)$^+$. Analytical HPLC (low pH, 254 nM): Sunfire, RT=5.43 min.

Example 10

(R)-14-(1-Amino-isoquinolin-6-ylamino)-9-cyclopropanesulfonyl-12-methyl-2-oxa-5,12-diaza-tricyclo[13.3.1.1^{6,10}]icosa-1(18),6(20),7,9,15 (19),16-hexaene-4,13-dione trifluoroacetic acid salt+ Enantiomer

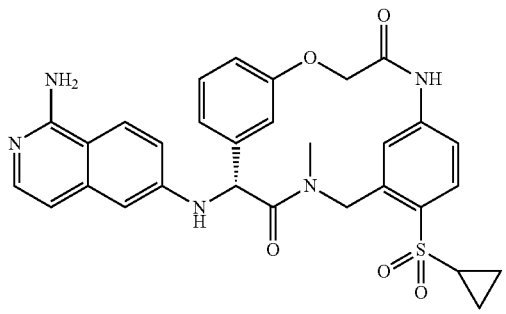 [SMILES: CN1Cc2cc(ccc2S(=O)(=O)C2CC2)NC(=O)COc2cccc(c2)[C@@H](Nc2ccc3c(N)nccc3c2)C1=O]

Example 10A 2-(5-Bromo-2-methoxyphenoxy)acetic acid

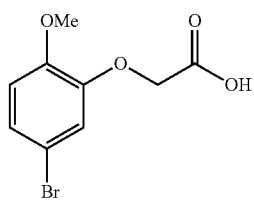 [SMILES: COc1ccc(Br)cc1OCC(=O)O]

3-Bromophenol (1.0 g, 5.78 mmol) and bromoacetic acid (0.803 g, 5.78 mmol) were dissolved in THF (28.9 mL). NaH (0.305 g, 12.72 mmol) was added portionwise over the course of 10 minutes. The reaction was then heated to reflux and allowed to stir overnight. The reaction was cooled to ambient temperature and quenched with water. The THF was concentrated in vacuo and the residue diluted with water and EtOAc. The aqueous layer was acidified with HCl and extracted with EtOAc. The organic layer was further washed with water, washed with brine, dried (Na$_2$SO$_4$), filtered, and concentrated in vacuo to yield Example 10A (869 mg, 65% yield). $^1$H NMR (400 MHz, METHANOL-d$_4$) δ 7.22-7.17 (m, 1H), 7.13-7.10 (m, 2H), 6.91 (ddd, J=8.3, 2.4, 1.1 Hz, 1H), 4.67 (s, 2H)

Example 10B 2-(Trimethylsilyl)ethyl 5-(2-(3-bromophenoxy)acetamido)-2-(cyclopropylsulfonyl)benzyl(methyl)carbamate

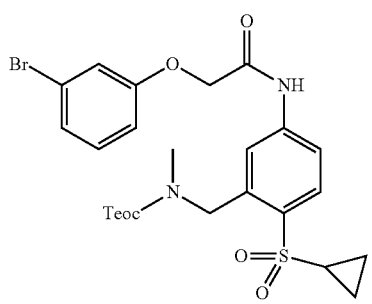

Using a procedure analogous to the one used to prepare Example 8A, Example 10A (456.8 mg, 1.977 mmol) was reacted with oxalyl chloride (184 µL, 2.175 mmol) and Intermediate 2 (836 mg, 2.175 mmol), to yield Example 10B (0.849 g, 72%). MS (ESI) m/z: 621.0 (M+Na)$^+$.

Example 10C 3-(2-(4-(Cyclopropylsulfonyl)-3-((methyl((2-(trimethylsilyl)ethoxy)carbonyl)amino)methyl)phenylamino)-2-oxoethoxy)phenylboronic acid

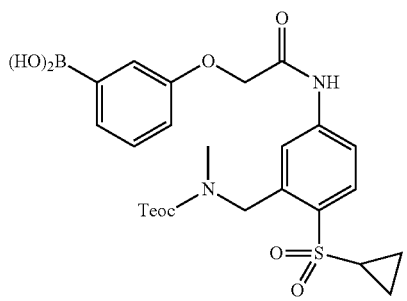

Using a procedure analogous to the one used to prepare Example 8B, Example 10B (848 mg, 1.419 mmol) was reacted with bis(neopentyl glycolato)diboron (0.449 g, 1.99 mmol) and [1,1'-Bis(diphenylphospino)ferrocene]dichloropalladium(II) (0.117 g, 0.142 mmol), to yield Example 10C (0.598 g, 75%). MS (ESI) m/z: 685.2 (M+Na)+.

Example 10D 2-(1-(Bis(tert-butoxycarbonyl)amino)isoquinolin-6-ylamino)-2-(3-(2-(4-(cyclopropylsulfonyl)-3-((methyl((2-(trimethylsilyl)ethoxy)carbonyl)amino)methyl)phenylamino)-2-oxoethoxy)phenyl)acetic acid

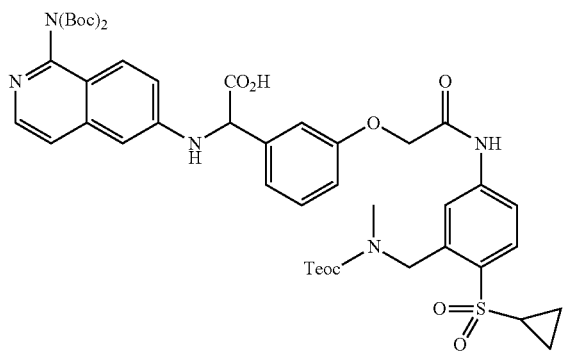

Using a procedure analogous to the one used to prepare Example 8C, Example 10C (0.598 g, 1.06 mmol) and imidodicarbonic acid, 2-(6-amino-1-isoquinolinyl)-, 1,3-bis(1,1-dimethylethyl) ester (0.382 g, 1.06 mmol) were reacted with glyoxylic acid monohydrate (98 mg, 1.06 mmol) to yield Example 10D (0.213 g, 21%). MS (ESI) m/z: 935.6 (M+H)+.

Example 10E 2-(1-(bis(tert-butoxycarbonyl)amino)isoquinolin-6-ylamino)-2-(3-(2-(4-(cyclopropylsulfonyl)-3-((methylamino)methyl)phenylamino)-2-oxoethoxy)phenyl)acetic acid

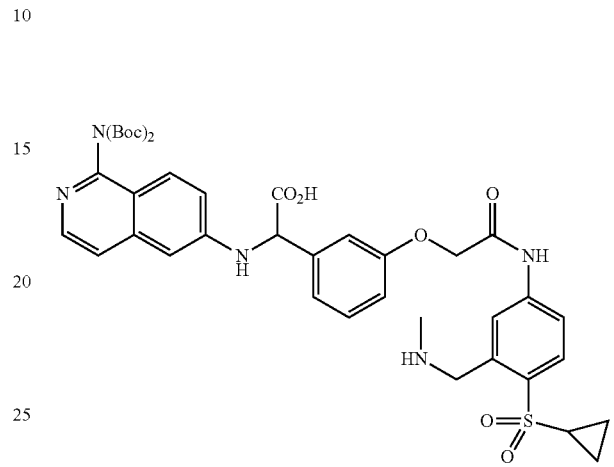

Using a procedure analogous to the one used to prepare Example 8D, Example 10D (0.210 g, 0.225 mmol) was reacted with TBAF (2.2 mL, 2.25 mmol) to yield Example 10E (0.178 g, 100%). MS (ESI) m/z: 790.6 (M+H)+.

Example 10

BOP (199 mg, 0.451 mmol) and DMAP (110 mg, 0.901 mmol) were dissolved in DMF (2253 µL) at ambient temperature. Example 10E (178 mg, 0.225 mmol) and DIPEA (394 µL, 2.253 mmol) were dissolved in approximately 8 mL of DMF and added to the coupling reagent solution via syringe pump over 12 h. The reaction was diluted with water and extracted thrice with EtOAc. The combined organic layers were washed with brine, dried (Na$_2$SO$_4$), filtered, and concentrated in vacuo. The crude reaction mixture was purified by Prep LC (YMC Sunfire 5µ C18 30×100 mm column, 10 min gradient from 40 to 100% B in A, A=10:90:0.1 MeOH:H$_2$O:TFA, B=90:10:0.1 MeOH:H$_2$O:TFA). Fractions containing product were quenched with saturated NaHCO$_3$ then partially concentrated in vacuo and extracted once with EtOAc. The organic layer was washed with brine, dried (Na$_2$SO$_4$), filtered, and concentrated in vacuo. The residue was dissolved in TFA (ca 0.5 mL) and stirred was for 20 min and then the reaction concentrated in vacuo. The crude material was purified by Prep LC (YMC ODS-A 5-5 µm 20×100 mm column, 10 min gradient from 20 to 100% B in A, A=10:90:0.1 MeCN:H$_2$O:TFA, B=90:10:0.1 MeCN:H$_2$O:TFA) to yield Example 10 (4 mg, 2.4%). MS (ESI) m/z: 572.5 (M+H)+. HPLC (low pH, 254 nM): X-Bridge Phenyl, RT=5.42 min.

Example 11

(R)-11-(1-Amino-4-fluoro-isoquinolin-6-ylamino)-16-cyclopropanesulfonyl-7-methoxy-13-methyl-2,13-diaza-tricyclo[13.3.1.1^{6,10}]icosa-1(19),6,8,10(20),15,17-hexaene-3,12-dione trifluoroacetic acid salt+ Enantiomer

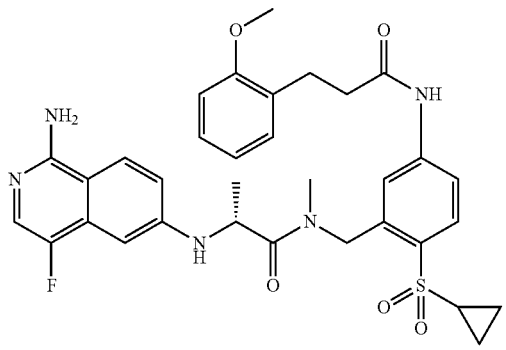 [SMILES: COc1ccccc1CCC(=O)Nc1ccc(S(=O)(=O)C2CC2)c(CN(C)C(=O)[C@@H](C)Nc2ccc3c(N)ncc(F)c3c2)c1]

Example 11A 2-(Trimethylsilyl)ethyl 5-(3-(5-bromo-2-methoxyphenyl)propanamido)-2-(cyclopropylsulfonyl)benzyl(methyl)carbamate

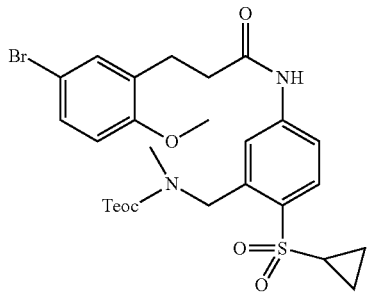

Using a procedure analogous to the one used to prepare Example 8A,
Intermediate 10 (0.324 g, 1.25 mmol) was reacted with oxalyl chloride (116 μL, 1.37 mmol) and Intermediate 2 (0.577 g, 1.50 mmol), to yield Example 11A (0.500 g, 64%). MS (ESI) m/z: 625.0 (M+Na)+.

Example 11B 3-(3-(4-(Cyclopropylsulfonyl)-3-((methyl((2-(trimethylsilyl)ethoxy)carbonyl)amino)methyl)phenylamino)-3-oxopropyl)-4-methoxyphenylboronic acid

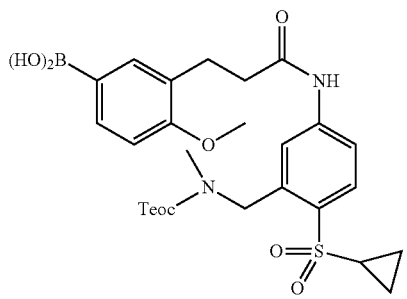

Using a procedure analogous to the one used to prepare Example 8B, Example 11A (0.500 g, 0.799 mmol) was reacted with bis(neopentyl glycolato)diboron (0.253 g, 1.20 mmol) and [1,1'-Bis(diphenylphospino)ferrocene]dichloropalladium(II) (0.066 g, 0.080 mmol), to yield Example 11B (0.300 g, 64%). MS (ESI) m/z: 613.3 (M+Na)+.

Example 11C 2-(1-(bis(tert-butoxycarbonyl)amino)-4-fluoroisoquinolin-6-ylamino)-2-(3-(3-(4-(cyclopropylsulfonyl)-3-((methyl((2-(trimethylsilyl)ethoxy)carbonyl)amino)methyl)phenylamino)-3-oxopropyl)-4-methoxyphenyl)acetic acid

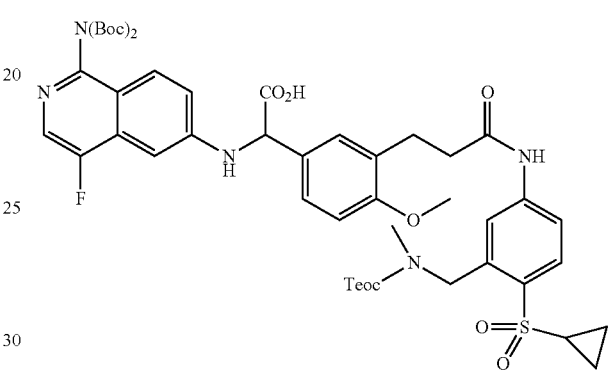

Using a procedure analogous to the one used to prepare Example 8C, Example 11B (300 mg, 0.508 mmol) and Intermediate 3 (192 mg, 0.508 mmol) were reacted with Glyoxylic acid monohydrate (47 mg, 0.508 mmol) to yield Example 11C (0.437 g, 88%). MS (ESI) m/z: 981.7 (M+H)+.

Example 11D 2-(1-(Bis(tert-butoxycarbonyl)amino)-4-fluoroisoquinolin-6-ylamino)-2-(3-(3-(4-(cyclopropylsulfonyl)-3-((methylamino)methyl)phenylamino)-3-oxopropyl)-4-methoxyphenyl)acetic acid

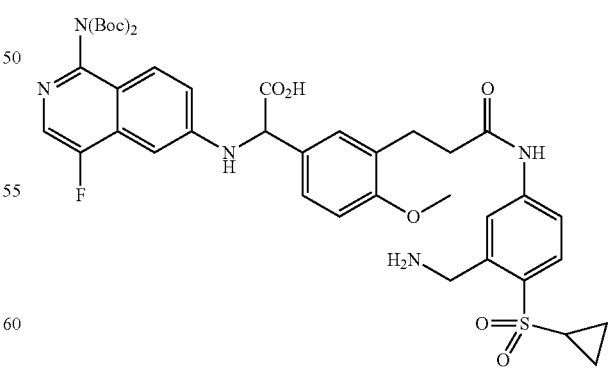

Using a procedure analogous to the one used to prepare Example 8D, Example 11C (437 mg, 0.446 mmol) was reacted with TBAF (4.45 mL, 4.46 mmol) to yield Example 11D (0.373 g, 100%). MS (ESI) m/z: 836.6 (M+H)+.

Example 11E 11-(1-Amino-4-fluoro-isoquinolin-6-ylamino)-16-cyclopropanesulfonyl-7-methoxy-13-methyl-2,13-diaza-tricyclo[13.3.1.1^{6,10}]icosa-1(19),6,8,10(20),15,17-hexaene-3,12-dione

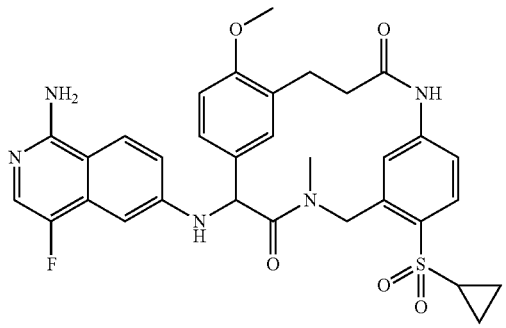 [SMILES: COc1ccc2cc1CCC(=O)Nc1ccc(S(=O)(=O)C3CC3)c(c1)CN(C)C(=O)C2Nc1ccc2c(N)ncc(F)c2c1]

Using a procedure analogous to the one used to prepare Example 8E, Example 11D (0.370 g, 0.443 mmol) was reacted with BOP (392 mg, 0.885 mmol) to yield Example 11E (0.185 g, 51%). MS (ESI) m/z: 818.5 (M+H)$^+$.

Example 11

Example 11E (186 mg, 0.227 mmol) was separated by Chiral Prep LC (Chiralcel OD-H 25×200 mm column, 20% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 11 (25 mg, 14%). 1H NMR (400 MHz, MeOD) δ ppm 8.09 (1 H, dd, J=9.29, 2.01 Hz), 7.80 (1 H, d, J=8.53 Hz), 7.61 (1 H, dd, J=8.53, 2.26 Hz), 7.44 (1 H, d, J=4.77 Hz), 7.23-7.30 (2 H, m), 6.99 (1 H, d, J=8.53 Hz), 6.89-6.97 (3 H, m), 5.77 (1 H, s), 5.64 (1 H, d, J=16.31 Hz), 4.54 (1 H, d, J=16.31 Hz), 3.88 (3 H, s), 3.23 (1 H, ddd, J=12.49, 4.20, 3.89 Hz), 3.14 (3 H, s), 2.73-2.91 (2 H, m), 2.67 (1 H, td, J=11.98, 4.39 Hz), 2.52-2.61 (1 H, m), 1.21-1.29 (1 H, m), 1.00-1.16 (3 H, m). MS (ESI) m/z: 618.4 (M+H)$^+$. Analytical HPLC (low pH, 220 nM): XBridge Phenyl, RT=6.58 min.

Example 12

(S)-5-(1-Amino-isoquinolin-6-ylamino)-19-cyclopropanesulfonyl-9-methoxy-3,11,13-trimethyl-3,13,15-triaza-tricyclo[14.3.1.1^{6,10}]henicosa-1(20),6(21),7,9,16,18-hexaene-4,14-dione trifluoroacetic acid salt

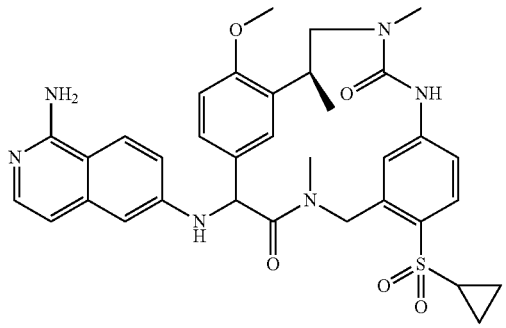 [SMILES: COc1ccc2cc1[C@H](C)CN(C)C(=O)Nc1ccc(S(=O)(=O)C3CC3)c(c1)CN(C)C(=O)C2Nc1ccc2c(N)nccc2c1]

Example 12A

[3-(Benzyloxycarbonylamino-methyl)-4-cyclopropanesulfonyl-phenyl]-carbamic acid phenyl ester

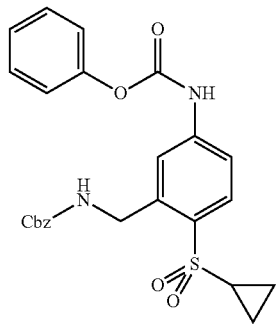 [SMILES: O=C(NCc1cc(NC(=O)Oc2ccccc2)ccc1S(=O)(=O)C1CC1)OCc1ccccc1]

To a solution of Intermediate 16 (0.130 g, 0.347 mmol) in DCM (2 mL) was added pyridine (31 μL, 0.382 mmol) and the solution was then cooled to 0° C. To this solution was added phenyl chloroformate (44 μL, 0.347 mmol) and reaction was allowed to warm to rt. The reaction mixture is then stirred for 1 h at rt. The reaction mixture was diluted with 1N HCl and extracted with ethyl acetate. The combined organic layer was washed with NaHCO$_3$, brine and then dried over Na$_2$SO$_4$. The crude product is then concentrated under reduced pressure to yield Example 12A (0.167 g, 0.338 mmol, 97% yield) as an off-white solid that was carried to the next step without any further purification after vacuum drying. MS (ESI) m/z: 495.2 (M+H)$^+$ RT=1.03.

Example 12B (S)-benzyl 5-(3-(2-(5-bromo-2-methoxyphenyl)propyl)-3-methylureido)-2-(cyclopropylsulfonyl)benzyl(methyl)carbamate

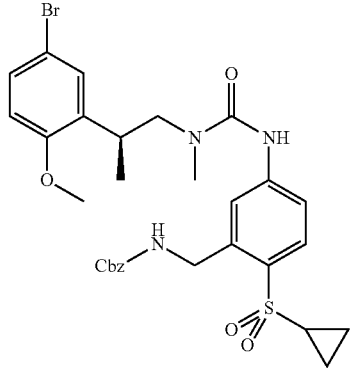 [SMILES: COc1ccc(Br)cc1[C@H](C)CN(C)C(=O)Nc1ccc(S(=O)(=O)C2CC2)c(CNC(=O)OCc2ccccc2)c1]

Example 12A (0.167 g, 0.337 mmol), Intermediate 17 (87 mg, 0.337 mmol), and K$_2$CO$_3$ (47 mg, 0.337 mmol) were dissolved in DMF (3 mL) and stirred at RT for 2 h. Reaction was diluted with water and EtOAc. The layers were separated, and the aqueous layer was extracted with 3×EtOAc. The combined organic layer was washed with brine, dried with Na$_2$SO$_4$, and concentrated under reduced pressure. The crude reaction mixture was purified by silica gel column chromatography (gradient from 0-100% EtOAc in hexanes)

to yield Example 12B (0.215 g, 0.326 mmol, 97% yield) as an off-white solid after concentration. MS (ESI) m/z: 660.2 (M+H)+ RT=1.12.

Example 12C (S)-3-(1-(3-(3-(((benzyloxycarbonyl)(methyl)amino)methyl)-4-(cyclopropylsulfonyl)phenyl)-1-methylureido)propan-2-yl)-4-methoxyphenylboronic acid

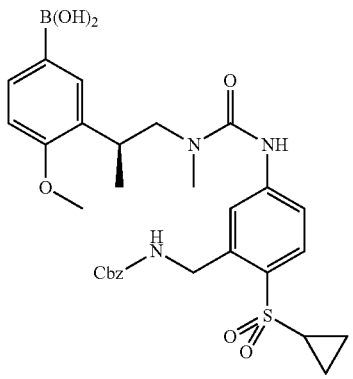 [SMILES: COc1ccc(B(O)O)cc1[C@H](C)CN(C)C(=O)Nc1ccc(S(=O)(=O)C2CC2)c(CNC(=O)OCc2ccccc2)c1]

DMSO (2 mL) and dioxane (2.0 mL) were degassed for 15 min by bubbling with argon. Example 12B (0.214 g, 0.325 mmol), KOAc (0.080 g, 0.812 mmol), and bis(pinacolato)diboron (0.091 g, 0.357 mmol) were placed in a microwave tube. To these compounds was added the degassed solvents. The tube was sealed and degassed for an additional 15 min. $PdCl_2$(dppf) (0.012 g, 0.016 mmol) was subsequently added, the tube sealed, and heated to 90° C. overnight. The reaction was diluted with EtOAc and brine. The layers were separated and the organic layer was filtered through a pad of celite. The filtrate was concentrated under reduced pressure. Purified on Prep HPLC using Solvent A: 10% ACN/90% $H_2O$/0.1% TFA and Solvent B 90% ACN/10% $H_2O$/0.1% TFA on Phenomenex AXIA C18 30×100 mm with a 12 min gradient and 5 min hold time with a flow rate of 40 mL/min to yield Example 12C (87 mg, 0.140 mmol, 42.9% yield). RT=0.88 Compound does not ionize.

Example 12D (S)-3-(1-(3-(3-(((benzyloxycarbonyl)(methyl)amino)methyl)-4-(cyclopropylsulfonyl)phenyl)-1-methylureido)propan-2-yl)-4-methoxyphenylboronic acid

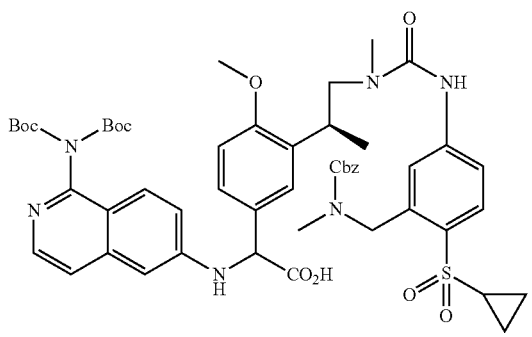 [SMILES: COc1ccc(C(Nc2ccc3c(N(C(=O)OC(C)(C)C)C(=O)OC(C)(C)C)nccc3c2)C(=O)O)cc1[C@H](C)CN(C)C(=O)Nc1ccc(S(=O)(=O)C2CC2)c(CN(C)C(=O)OCc2ccccc2)c1]

A solution of Example 12C (87 mg, 0.140 mmol) in MeCN (2.5 mL) in DMF (1.25 mL) was purged with argon. 2-oxoacetic acid, $H_2O$ (13 mg, 0.140 mmol) and imidodicarbonic acid, 2-(6-amino-1-isoquinolinyl)-, 1,3-bis(1,1-dimethylethyl) ester (50 mg, 0.140 mmol) were added. The reaction was stirred at 80° C. for 2.5 h. The reaction was cooled to rt and diluted with water and EtOAc. The reaction layers were separated, and the aqueous layer was back extracted with EtOAc 3 times. The combined organic layer was washed with brine, dried with $Na_2SO_4$ and concentrated under reduced pressure. Crude reaction mixture purified Prep HPLC using Solvent A: 10% MeOH/90% $H_2O$/0.1% TFA and Solvent B 90% MeOH/10% $H_2O$/0.1% TFA on Phenomenex AXIA C18 30×100 mm with a 10 min gradient and 5 min hold time with a flow rate of 40 mL/min to yield Example 12D (120 mg, 0.121 mmol, 86% yield) as a brown solid.

12E 2-(1-(bis(tert-butoxycarbonyl)amino)isoquinolin-6-ylamino)-2-(3-((S)-1-(3-(4-(cyclopropylsulfonyl)-3-((methylamino)methyl)phenyl)-1-methylureido)propan-2-yl)-4-methoxyphenyl)acetic acid

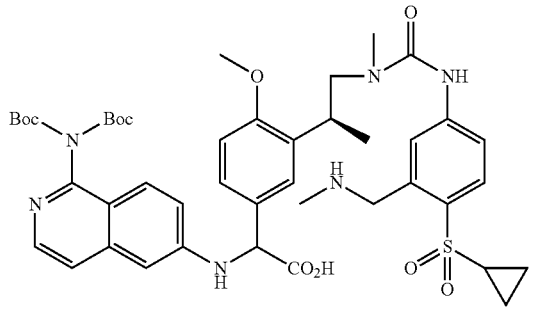 [SMILES: CNCc1cc(NC(=O)N(C)C[C@@H](C)c2cc(C(Nc3ccc4c(N(C(=O)OC(C)(C)C)C(=O)OC(C)(C)C)nccc4c3)C(=O)O)ccc2OC)ccc1S(=O)(=O)C1CC1]

Example 12D (0.120 g, 0.121 mmol) was dissolved in MeOH (1.21 mL) and Pd/C (0.013 g, 0.012 mmol) was added. The reaction vessel was evacuated and back filled with argon 3 times. The reaction was then evacuated and back filled with hydrogen 3 times. The reaction was allowed to stir at RT under a balloon of hydrogen overnight. Reaction filtered through Celite and concentrated to yield Example 12E (0.102 g, 0.118 mmol, 98% yield) as an off-white solid. MS (ESI) m/z: 861.6 (M+H)+.

Example 12F

[6-((S)-19-Cyclopropanesulfonyl-9-methoxy-3,11,13-trimethyl-4,14-dioxo-3,13,15-triaza-tricyclo[14.3.1.1^{6,10}]henicosa-1(20),6(21),7,9,16,18-hexaen-5-ylamino)-isoquinolin-1-yl]-bis(carbamic acid tert-butyl ester)

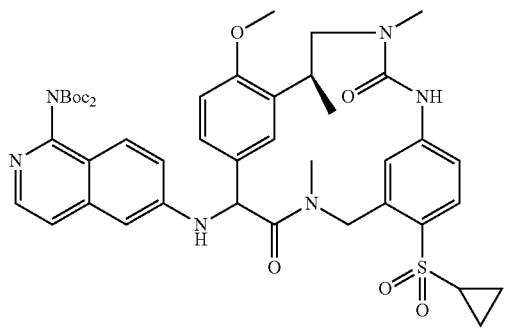

HATU (90 mg, 0.237 mmol) and n-methylmorpholine (78 μL, 0.711 mmol) were dissolved in DMF (100 mL) at RT. Example 12E (102 mg, 0.118 mmol) was dissolved in DMF (6 mL) and added via syringe pump to the HATU solution over the course of 12 h. The reaction was concentrated to remove most of the DMF and then diluted with water and EtOAc, and the layers were separated. The aqueous layer was back-extracted with EtOAc×3. The combined organic layers were washed with brine, dried with Na$_2$SO$_4$, and concentrated under reduced pressure. Crude reaction mixture was purified on Prep HPLC using Solvent A: 10% ACN/90% H$_2$O/0.1% TFA and Solvent B 90% ACN/10% H$_2$O/0.1% TFA on Phenomenex AXIA C18 30×100 mm with a 12 min gradient and 5 min hold time with a flow rate of 40 mL/min. Saturated NaHCO$_3$ was added and the purified compound and concentrated to remove most of the MeCN. The resultant solution was extracted with EtOAc×3. The combined organic layer was washed with brine, dried with Na$_2$SO$_4$, and concentrated under reduced pressure to yield Example 12F (11 mg, 0.013 mmol, 11.01% yield) as a white solid. MS (ESI) m/z: 844.5 (M+H)$^+$.

Example 12

Example 12F (11 mg, 0.013 mmol) was dissolved in TFA (1 mL) and allowed to stir for 20 min. Th reaction was concentrated. The residue was dissolved in DCM and concentrated. The resultant solid was purified on Prep HPLC using Solvent A: 10% MeOH/90% H$_2$O/0.1% TFA and Solvent B 90% MeOH/10% H$_2$O/0.1% TFA on Phenomenex AXIA C18 30×100 mm with a 10 min gradient and 5 min hold time with a flow rate of 40 mL/min to yield Example 12 (3.51 mg, 4.55 μmol) as an off-white solid. Compound submitted as a mixture of diastereomers. Mixture of diastereomers present. MS (ESI) m/z: 643.5 (M+H)$^+$. Analytical HPLC (low pH, 254 nM): Sunfire, RT=5.86 min., 98.5% purity; XBridge, RT=6.71 min, 98.2% purity.

Example 13

5-(1-Amino-isoquinolin-6-ylamino)-19-cyclopropanesulfonyl-9-methoxy-3,13-dimethyl-3,13,15-triaza-tricyclo[14.3.1.1$^{6,10}$]henicosa-1(20),6(21),7,9,16,18-hexaene-4,14-dione trifluoroacetic acid salt

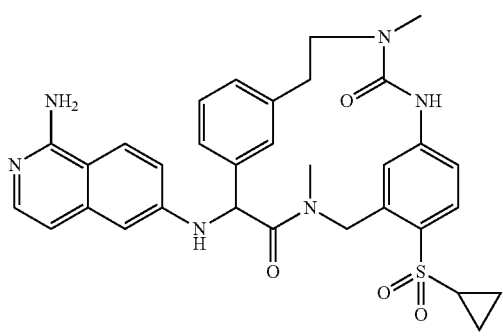 [SMILES: CN1CCc2cccc(c2)C(Nc2ccc3c(N)nccc3c2)C(=O)N(C)Cc2cc(ccc2S(=O)(=O)C2CC2)NC1=O]

Example 13A 2-(3-Bromophenyl)-N-methylethanamine

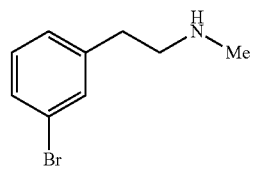 [SMILES: CNCCc1cccc(Br)c1]

2-(3-Bromophenyl)ethanamine (0.500 g, 2.499 mmol) was dissolved in ethyl formate (20.19 mL, 250 mmol) and formic acid (9.58 μL, 0.250 mmol) was added. The reaction was heated to reflux for 45 min. Reaction was concentrated under reduced pressure. The residue was dissolved in THF (10 mL) and cooled to 0° C. BH$_3$.THF (10.00 mL, 10.00 mmol) was added and the reaction was brought to reflux and stirred for 1 h. The material was cooled to 0° C. and diluted with water, then 1 N NaOH. This mixture was allowed to stir for 30 minutes, then extracted thrice with EtOAc. The organic layer was washed with 1N HCl. The combined aqueous layer was then neutalized with 1N NaOH. Upon neutalization, the aqueous layer was washed with 3×EtOAc. The combined organic layer was washed with brine, dried with sodium sulfate, and concentrated to yield Example 13A (98 mg, 0.458 mmol, 18.32% yield) as a colorless oil. MS (ESI) m/z: 216.7 (M+H)$^+$.

Example 13B

Benzyl 5-(3-(3-bromophenethyl)-3-methylureido)-2-(cyclopropylsulfonyl)benzyl(methyl)carbamate

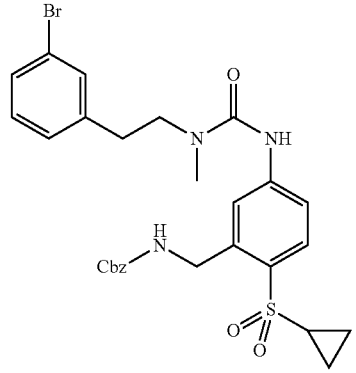 [SMILES: CN(CCc1cccc(Br)c1)C(=O)Nc1ccc(S(=O)(=O)C2CC2)c(CNC(=O)OCc2ccccc2)c1]

Using a procedure analogous to the one used to prepare Example 12B, Example 13A (0.226 g, 0.458 mmol) and Intermediate 16 (0.098 g, 0.458 mmol) were condensed to yield Example 13B (0.191 g, 0.311 mmol, 67.9% yield) as an off-white solid. MS (ESI) m/z: 616.1 (M+H)$^+$.

Example 13C 3-(2-(3-(3-(((benzyloxycarbonyl)(methyl)amino)methyl)-4-(cyclopropylsulfonyl)phenyl)-1-methylureido)ethyl)phenylboronic acid

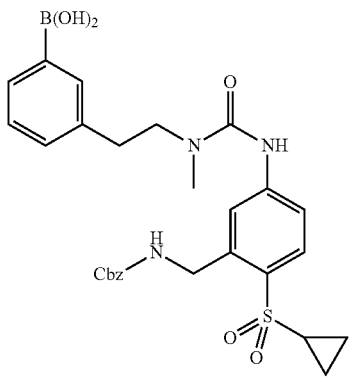 [SMILES: CN(CCc1cccc(B(O)O)c1)C(=O)Nc1ccc(S(=O)(=O)C2CC2)c(CNC(=O)OCc2ccccc2)c1]

Using a procedure analogous to the one used to prepare Example 12C, Example 13B (0.191 g, 0.311 mmol) was reacted with bis(pinacolato)diboron to yield Example 13C (0.109 g, 61%) as a brown solid. LC/MS RT=0.91 MS (ESI) m/z: does not ionize.

Example 13D 2-(3-(2-(3-(3-((Benzyloxycarbonyl)(methyl)amino)methyl)-4-(cyclopropylsulfonyl)phenyl)-1-methylureido)ethyl)phenyl)-2-(1-(bis(tert-butoxycarbonyl)amino)isoquinolin-6-ylamino)acetic acid

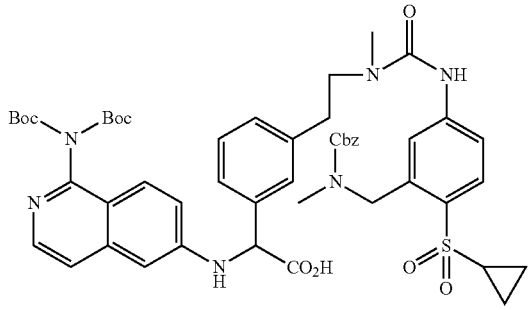 [SMILES: CN(CCc1cccc(C(Nc2ccc3c(N(C(=O)OC(C)(C)C)C(=O)OC(C)(C)C)nccc3c2)C(=O)O)c1)C(=O)Nc1ccc(S(=O)(=O)C2CC2)c(CN(C)C(=O)OCc2ccccc2)c1]

Using a procedure analogous to the one used to prepare Example 12D, 13C (0.109 g, 0.188 mmol) was reacted with imidodicarbonic acid, 2-(6-amino-1-isoquinolinyl)-, 1,3-bis(1,1-dimethylethyl) ester to yield Example 13D (49 mg, 27%) as an off white solid. MS (ESI) m/z: 951.7 (M+H)$^+$.

Example 13E 2-(1-(Bis(tert-butoxycarbonyl)amino)isoquinolin-6-ylamino)-2-(3-(2-(3-(4-(cyclopropylsulfonyl)-3-((methylamino)methyl)phenyl)-1-methylureido)ethyl)phenyl)acetic acid

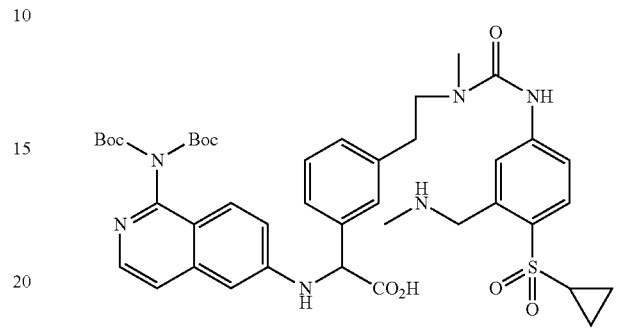

Using a procedure analogous to the one used to prepare Example 12E, Example 13C (49 mg, 0.026 mmol) was treated with palladium on carbon and hydrogen to yield Example 13E (19 mg, 90%) as an off-white solid. MS (ESI) m/z: 817.5 (M+H)$^+$.

Example 13F

[6-(19-Cyclopropanesulfonyl-9-methoxy-3,13-dimethyl-4,14-dioxo-3,13,15-triaza-tricyclo[14.3.1.1$^{6,10}$]henicosa-1(20),6(21),7,9,16,18-hexaen-5-ylamino)-isoquinolin-1-yl]-bis(carbamic acid tert-butyl ester)

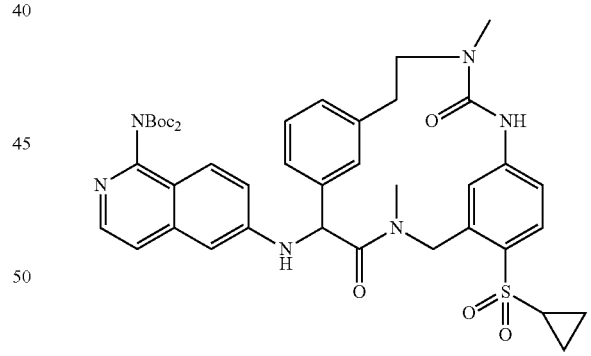

Using a procedure analogous to the one used to prepare Example 12F, Example 13E (25 mg, 0.031 mmol) was reacted with HATU to yield Example 13F (15 mg, 61%) as a white solid. MS (ESI) m/z: 799.5 (M+H)$^+$.

Example 13

Using a procedure analogous to the one used to prepare Example 12, Example 13F (15 mg 0.01 mmol) was treated with trifluoroacetic acid to yield Example 13 (0.3 mg, 2.1%) as a white solid. MS (ESI) m/z: 599.4 (M+H)$^+$. Analytical HPLC (low pH, 254 nM): Sunfire, RT=5.42 min.

Example 14

(R)-11-(1-Amino-4-fluoro-isoquinolin-6-ylamino)-16-cyclopropanesulfonyl-7-fluoro-13-methyl-2,13-diaza-tricyclo[13.3.1.1$^{6,10}$]icosa-1(19),6,8,10(20),15,17-hexaene-3,12-dione trifluoroacetic acid salt+ Enantiomer

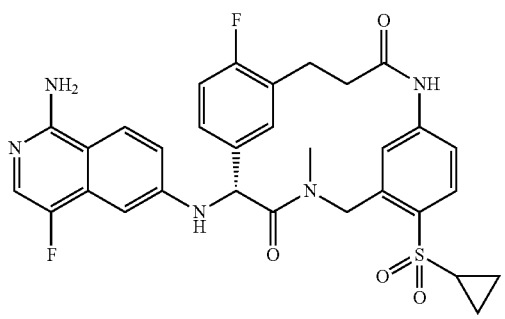 [SMILES: CN1Cc2cc(ccc2S(=O)(=O)C2CC2)NC(=O)CCc2cc(ccc2F)[C@@H](Nc2ccc3c(N)ncc(F)c3c2)C1=O]

Example 14A (E)-methyl 3-(5-bromo-2-fluorophenyl)acrylate

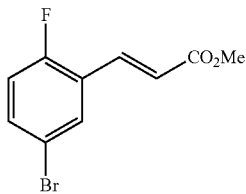 [SMILES: COC(=O)/C=C/c1cc(Br)ccc1F]

5-Bromo-2-fluorobenzaldehyde (0.5 g, 2.463 mmol) was dissolved in toluene (29.3 mL). Methyl (triphenylphosphoranylidine)acetate (0.823 g, 2.463 mmol) was added, and the reaction heated to reflux overnight. The reaction was cooled to ambient temperature and concentrated in vacuo. The crude material was purified by silica gel column chromatography (gradient from 0 to 100% EtOAc in hexanes) to yield Example 14A (0.621 g, 2.397 mmol, 97% yield). MS (ESI) m/z: 259/261 (M+H)$^+$. 1H NMR (400 MHz, CHLOROFORM-d) δ ppm 7.73 (1 H, d, J=16.31 Hz), 7.66 (1 H, dd, J=6.53, 2.51 Hz), 7.45 (1 H, ddd, J=8.78, 4.52, 2.51 Hz), 7.00 (1 H, dd, J=10.04, 8.78 Hz), 6.53 (1 H, d, J=16.31 Hz), 3.82 (3 H, s).

Example 14B

Methyl 3-(5-bromo-2-fluorophenyl)propanoate

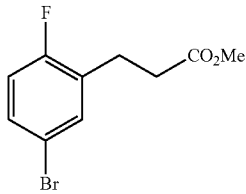 [SMILES: COC(=O)CCc1cc(Br)ccc1F]

Example 14A (570 mg, 2.200 mmol) was dissolved in MeOH (11 mL Magnesium (107 mg, 4.40 mmol) was added at ambient temperature. The reaction was placed in the freezer overnight. The reaction was diluted with saturated NH$_4$Cl and extracted with EtOAc. The organic layer was washed with brine, dried (Na$_2$SO$_4$), filtered, and concentrated in vacuo to yield Example 14B (0.480 g, 83% yield). MS (ESI) m/z: 261/263 (M+H)$^+$. $^1$H NMR (400 MHz, CHLOROFORM-d) δ 7.35 (dd, J=6.8, 2.5 Hz, 1H), 7.30 (ddd, J=8.7, 4.6, 2.5 Hz, 1H), 6.91 (dd, J=9.4, 8.7 Hz, 1H), 3.68 (s, 3H), 2.94 (t, J=7.9 Hz, 2H), 2.65-2.60 (m, 2H).

Example 14C

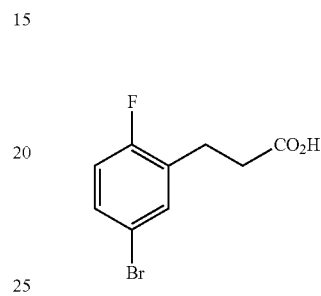

Example 14B (0.48 g, 1.838 mmol) was dissolved in THF (16.71 mL) and MeOH (1.671 mL). NaOH (2.022 mL, 2.022 mmol) was added at ambient temperature, and the reaction was stirred for 3 h. The reaction was concentrated in vacuo, and the residue was diluted with 1 N NaOH and washed twice with DCM. The aqueous layer was acidified with 1 N HCl and extracted twice with EtOAc. The combined EtOAc layers were washed with brine, dried (Na$_2$SO$_4$), filtered, and concentrated in vacuo to yield Example 14C (0.408 g, 1.65 mmol, 90% yield). 1H NMR (400 MHz, CHLOROFORM-d) δ ppm 7.33 (2 H, d, J=17.32 Hz), 6.92 (1 H, t, J=9.16 Hz), 2.90-3.07 (2 H, m), 2.70 (2 H, d, J=6.78 Hz).

Example 14D 2-(Trimethylsilyl)ethyl 5-(3-(5-bromo-2-fluorophenyl)propanamido)-2-(cyclopropylsulfonyl)benzyl(methyl)carbamate

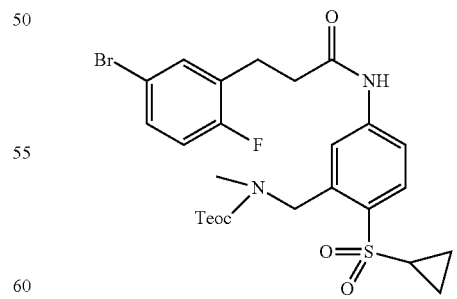

Using a procedure analogous to the one used to prepare Example 8A, Example 14C (0.408 g, 1.65 mmol) was reacted with oxalyl chloride (154 μL, 1.82 mmol) and Intermediate 2 (0.762 g, 1.92 mmol), to yield Example 14D (0.275 g, 27%). MS (ESI) m/z: 636.3 (M+Na)$^+$.

Example 14E 3-(3-(4-(Cyclopropylsulfonyl)-3-((methyl((2-(trimethylsilyl)ethoxy)carbonyl)amino)methyl)phenylamino)-3-oxopropyl)-4-fluorophenylboronic acid

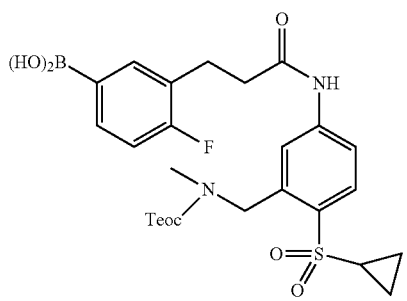

Using a procedure analogous to the one used to prepare Example 8B, Example 14D (0.275 g, 0.477 mmol) was reacted with bis(neopentyl glycolato)diboron (0.141 g, 0.626 mmol) and [1,1'-bis(diphenylphospino)ferrocene]dichloropalladium(II) (37 mg, 0.045 mmol), to yield Example 14E (0.136 g, 53%). MS (ESI) m/z: 601.3 (M+Na)$^+$.

Example 14F 2-(1-(Bis(tert-butoxycarbonyl)amino)-4-fluoroisoquinolin-6-ylamino)-2-(3-(3-(4-(cyclopropylsulfonyl)-3-((methyl((2-(trimethylsilyl)ethoxy)carbonyl)amino)methyl)phenylamino)-3-oxopropyl)-4-fluorophenyl)acetic acid

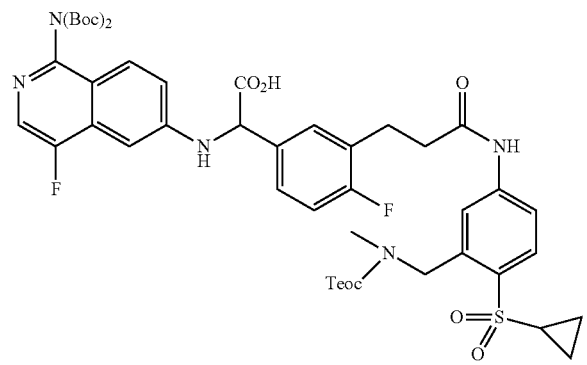

Using a procedure analogous to the one used to prepare Example 8C, Example 14E (136 mg, 0.235 mmol) and Intermediate 3 (89 mg, 0.235 mmol) were reacted with glyoxylic acid monohydrate (22 mg, 0.235 mmol) to yield Example 14F (70 mg, 31%). MS (ESI) m/z: 968.7 (M+H)$^+$.

Example 14G 2-(1-(Bis(tert-butoxycarbonyl)amino)-4-fluoroisoquinolin-6-ylamino)-2-(3-(3-(4-(cyclopropylsulfonyl)-3-((methylamino)methyl)phenylamino)-3-oxopropyl)-4-fluorophenyl)acetic acid

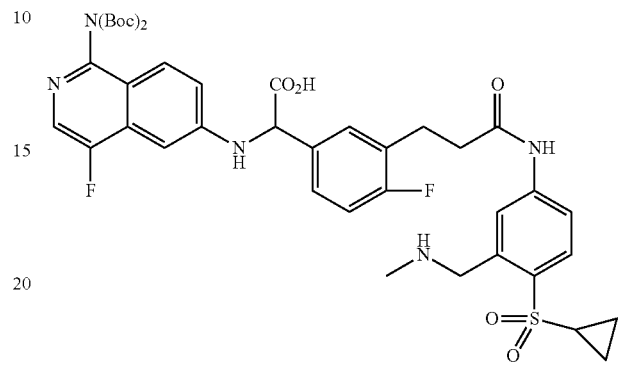

Using a procedure analogous to the one used to prepare Example 8D, Example 14F (70 mg, 0.072 mmol) was reacted with TBAF (0.723 mL, 0.723 mmol) to yield Example 14G (60 mg, 100%). MS (ESI) m/z: 824.6 (M+H)$^+$.

Example 14H

[6-(16-Cyclopropanesulfonyl-7-fluoro-13-methyl-3,12-dioxo-2,13-diaza-tricyclo[13.3.1.1$^{6,10}$]icosa-1(19),6,8,10(20),15,17-hexaen-11-ylamino)-4-fluoro-isoquinolin-1-yl]-bis(carbamic acid tert-butyl ester)

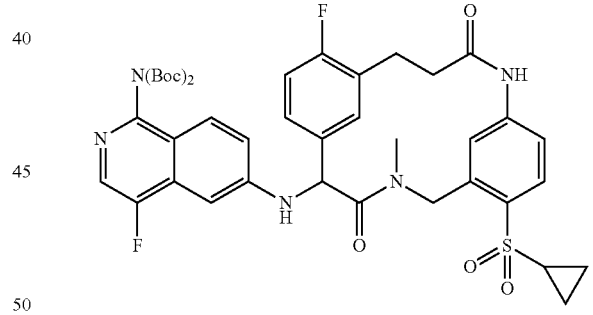

Using a procedure analogous to the one used to prepare Example 8E, Example 14G (60 mg, 0.073 mmol) was reacted with BOP (64 mg, 0.146 mmol) to yield Example 14H (18 mg, 30%). MS (ESI) m/z: 806.5 (M+H)$^+$.

Example 14

Example 14H (18 mg, 0.022 mmol) was separated by Chiral Prep LC (Chiralcel OD-H 25×200 mm column, 20% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 14 (1.7 mg, 11%). 1H NMR (400 MHz, CD3OD) δ ppm 8.11 (1 H, d, J=1.25 Hz), 7.82 (1 H, d, J=8.28 Hz), 7.67 (1 H, br. s.), 7.46 (1 H, d, J=5.02 Hz), 7.39-7.45 (1 H, m), 7.29 (1 H, br. s.), 7.09-7.20 (1 H, m), 6.88-6.99 (3 H, m), 5.88 (1 H, s), 5.66 (1 H, d, J=16.56 Hz), 4.56 (1 H, d, J=16.31 Hz), 3.16 (3 H, s), 3.09-3.14 (1 H, m), 2.89-3.02 (1 H, m), 2.74-2.84 (1 H, m), 2.54-2.72 (2 H, m), 1.22-1.32 (1 H, m), 1.00-1.19 (3 H, m). MS (ESI) m/z: 606.4 (M+H)+. Analytical HPLC (low pH, 220 nM): Sunfire C18, RT=5.63 min.

Example 15

(R)-11-(1-Amino-4-fluoro-isoquinolin-6-ylamino)-16-cyclopropanesulfonyl-8-methoxy-13-methyl-2,13-diaza-tricyclo[13.3.1.1$^{6,10}$]icosa-1(19),6,8,10(20),15,17-hexaene-3,12-dione trifluoroacetic acid salt+ Enantiomer

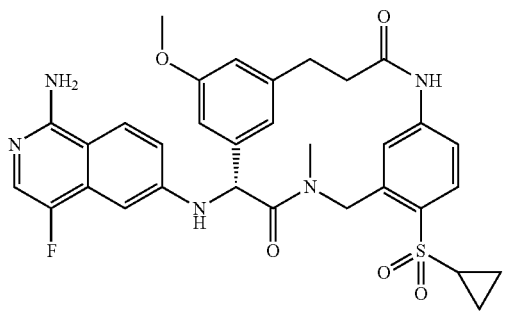 [SMILES: COc1cc2cc(c1)[C@@H](Nc1ccc3c(N)ncc(F)c3c1)C(=O)N(C)Cc1cc(ccc1S(=O)(=O)C1CC1)NC(=O)CC2]

Example 15A

3-Bromo-5-methoxybenzaldehyde

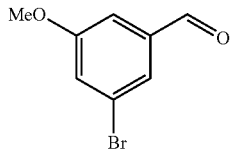 [SMILES: COc1cc(Br)cc(C=O)c1]

3-Bromo-5-hydroxybenzaldehyde (0.5 g, 2.487 mmol) was dissolved in DMF (14.63 mL) and cooled to 0° C. NaH (0.119 g, 4.97 mmol) was added in three portions. The flask was immediately allowed to warm to ambient temperature and MeI (0.933 mL, 14.92 mmol) was added, and the reaction stirred overnight. The reaction was diluted with water and partially concentrated in vacuo. The material was diluted with DCM and washed twice with water, washed with brine, dried (Na$_2$SO$_4$), filtered, and concentrated in vacuo. The crude material was purified by silica gel column chromatography (gradient from 0 to 100% EtOAc in hexanes) to yield Example 15A (0.488 g, 2.27 mmol, 91%).

$^1$H NMR (400 MHz, CHLOROFORM-d) δ ppm 9.91 (1 H, s), 7.58 (1 H, t, J=1.38 Hz), 7.28-7.35 (2 H, m, J=2.38, 2.13, 2.01, 2.01 Hz), 3.86 (3 H, s).

Example 15B 3-(E)-methyl 3-(bromo-5-methoxyphenyl)acrylate

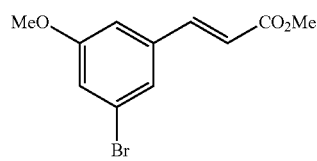 [SMILES: COC(=O)/C=C/c1cc(Br)cc(OC)c1]

Example 15A 0.48 g, 2.232 mmol) was dissolved in toluene (26.6 mL Methyl (triphenylphosphoranylidine)acetate (0.746 g, 2.232 mmol) was added, and the reaction heated to reflux overnight. The reaction was cooled to ambient temperature and concentrated in vacuo. The crude material was purified by silica gel column chromatography (gradient from 0 to 100% EtOAc in hexanes) to yield Example 15B (0.580 g, 2.14 mmol, 96% yield). MS (ESI) m/z: 271/273 (M+H)+. $^1$H NMR (400 MHz, CHLOROFORM-d) δ ppm 7.56 (1 H, d, J=16.06 Hz), 7.26 (1 H, s), 7.07 (1 H, s), 6.95 (1 H, s), 6.41 (1 H, d, J=16.06 Hz), 3.82 (3 H, s), 3.81 (3 H, s).

Example 15C

Methyl 3-(bromo-5-methoxyphenyl)propanoate

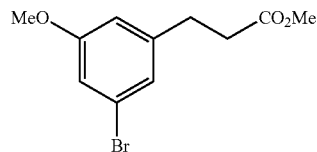 [SMILES: COC(=O)CCc1cc(Br)cc(OC)c1]

Example 15B (530 mg, 1.955 mmol) was dissolved in MeOH (9775 μL Magnesium (95 mg, 3.91 mmol) was added at ambient temperature. The reaction was placed in the freezer overnight. The reaction was diluted with saturated NH$_4$Cl and extracted with EtOAc. The organic layer was washed with brine, dried (Na$_2$SO$_4$), filtered, and concentrated in vacuo to yield Example 15C (0.547 g, 2.00 mmol, 100%). MS (ESI) m/z: 271/273 (M+H)+. $^1$H NMR (400 MHz, CHLOROFORM-d) δ 6.94 (t, J=1.5 Hz, 1H), 6.90 (t, J=2.1 Hz, 1H), 6.67 (dd, J=2.0, 1.5 Hz, 1H), 3.77 (s, 3H), 3.68 (s, 3H), 2.89 (t, J=7.8 Hz, 2H), 2.64-2.58 (m, 2H).

Example 15D

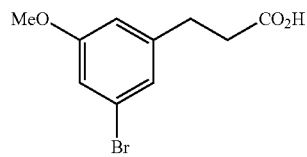 [SMILES: COc1cc(Br)cc(CCC(=O)O)c1]

Example 15C (0.54 g, 1.977 mmol) was dissolved in THF (17.97 mL) and MeOH (1.797 mL). NaOH (2.175 mL, 2.175 mmol) was added at ambient temperature and allowed to stir for 2 h. The reaction was concentrated, and the residue was diluted with 1 N NaOH and washed twice with DCM. The aqueous layer was acidified with 1 N HCl and extracted twice with EtOAc. The combined EtOAc layers were washed with brine, dried (Na₂SO₄), filtered, and concentrated in vacuo to yield Example 15D (0.426 g, 1.644 mmol, 83% yield). $^1$H NMR (400 MHz, CHLOROFORM-d) δ ppm 6.94-6.98 (1 H, m), 6.91 (1 H, t, J=2.01 Hz), 6.65-6.73 (1 H, m), 3.78 (3 H, s), 2.90 (2 H, t, J=7.78 Hz), 2.67 (2 H, t, J=7.78 Hz).

Example 15E 2-(trimethylsilyl)ethyl 5-(3-(3-bromo-5-methoxyphenyl)propanamido)-2-(cyclopropylsulfonyl)benzyl (methyl)carbamate

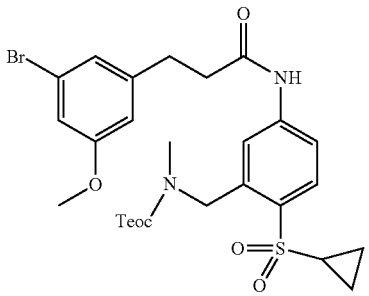

Using a procedure analogous to the one used to prepare Example 8A, Example 15D (0.426 g, 1.64 mmol) was reacted with oxalyl chloride (153 µL, 1.81 mmol) and Intermediate 2 (0.759 g, 1.97 mmol), to yield Example 15E (0.322 g, 31%). MS (ESI) m/z: 649.3 (M+Na)⁺.

Example 15F 3-(3-(4-(Cyclopropylsulfonyl)-3-((methyl((2-(trimethylsilyl)ethoxy)carbonyl)amino)methyl)phenylamino)-3-oxopropyl)-5-methoxyphenylboronic acid

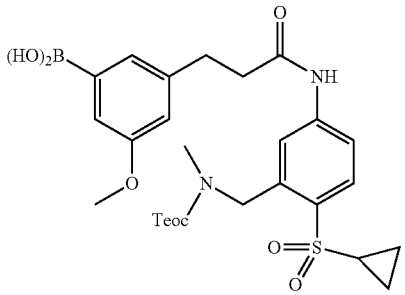

Using a procedure analogous to the one used to prepare Example 8B, Example 15E (0.323 g, 0.515 mmol) was reacted with bis(neopentyl glycolato)diboron (0.163 g, 0.722 mmol) and [1,1'-bis(diphenylphospino)ferrocene]dichloropalladium(II) (42 mg, 0.052 mmol), to yield Example 15F (0.239 g, 78%). MS (ESI) m/z: 613.3 (M+Na)⁺.

Example 15G 2-(1-(Bis(tert-butoxycarbonyl)amino)-4-fluoro isoquinolin-6-ylamino)-2-(3-(3-(4-(cyclopropylsulfonyl)-3-((methyl((2-(trimethylsilyl)ethoxy)carbonyl)amino)methyl)phenylamino)-3-oxopropyl)-5-methoxyphenyl)acetic acid

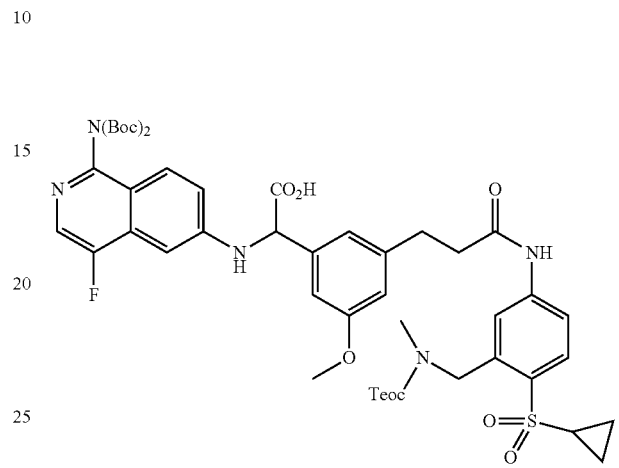

Using a procedure analogous to the one used to prepare Example 8C, 15F (239 mg, 0.405 mmol) and Intermediate 3 (153 mg, 0.405 mmol) were reacted with glyoxylic acid monohydrate (37 mg, 0.405 mmol) to yield Example 15G (0.122 g, 31%). MS (ESI) m/z: 980.7 (M+H)⁺.

Example 15H 2-(1-(Bis(tert-butoxycarbonyl)amino)-4-fluoroisoquinolin-6-ylamino)-2-(3-(3-(4-(cyclopropylsulfonyl)-3-((methylamino)methyl)phenylamino)-3-oxopropyl)-5-methoxyphenyl)acetic acid

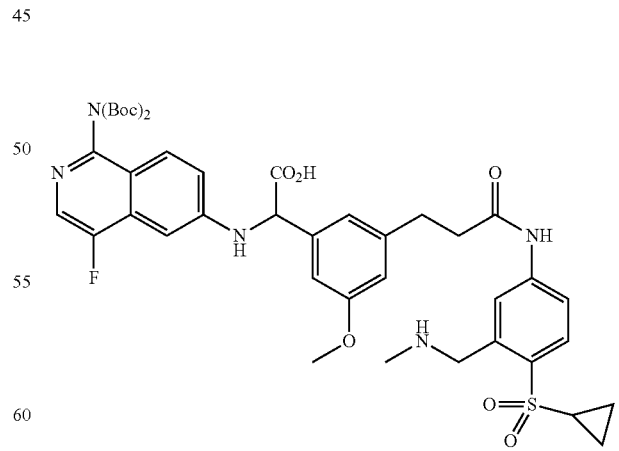

Using a procedure analogous to the one used to prepare Example 8D, Example 15G (122 mg, 0.124 mmol) was reacted with TBAF (1.25 mL, 1.245 mmol) to yield Example 15H (104 mg, 100%). MS (ESI) m/z: 836.6 (M+H)⁺.

Example 15I

[6-(16-Cyclopropanesulfonyl-8-methoxy-13-methyl-3,12-dioxo-2,13-diaza-tricyclo[13.3.1.1$^{6,10}$]icosa-1(19),6,8,10(20),15,17-hexaen-11-ylamino)-4-fluoro-isoquinolin-1-yl]-bis(carbamic acid tert-butyl ester)

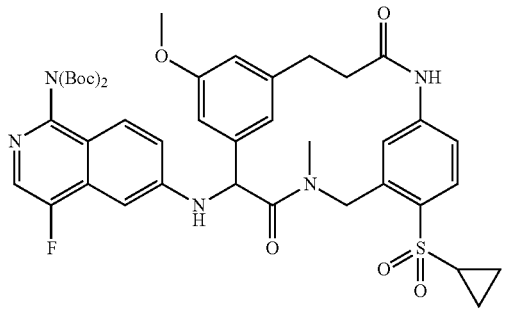

Using a procedure analogous to the one used to prepare Example 8E, Example 15H (104 mg, 0.124 mmol) was reacted with BOP (0.110 g, 0.249 mmol) to yield Example 15I (71 mg, 69%). MS (ESI) m/z: 818.5 (M+H)$^+$.

Example 15

Example 15I (71 mg, 0.022 mmol) was separated by Chiral Prep LC (Chiralcel OD-H 25×200 mm column, 20% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 15 (13 mg, 20%). 1H NMR (400 MHz, CD3OD) δ ppm 8.10 (1 H, d, J=9.29 Hz), 7.81 (1 H, d, J=8.28 Hz), 7.45 (1 H, d, J=4.77 Hz), 7.25-7.32 (1 H, m), 7.22 (1 H, s), 6.86-7.02 (5 H, m), 5.82 (1 H, s), 5.66 (1 H, d, J=16.31 Hz), 4.53 (1 H, d, J=16.31 Hz), 3.82 (1 H, s), 3.20 (3 H, s), 2.93-3.11 (2 H, m), 2.75-2.85 (1 H, m), 2.63-2.71 (1 H, m), 2.46-2.60 (1 H, m), 1.21-1.31 (1 H, m), 1.01-1.17 (3 H, m). MS (ESI) m/z: 618.4 (M+H)$^+$. Analytical HPLC (low pH, 220 nM): Xbridge Phenyl, RT=6.18 min.

Example 16

(R)-11-(1-Amino-4-fluoro-isoquinolin-6-ylamino)-16-cyclopropanesulfonyl-7-hydroxy-13-methyl-2,13-diaza-tricyclo[13.3.1.1$^{6,10}$]icosa-1(19),6,8,10(20),15,17-hexaene-3,12-dione trifluoroacetic acid salt+Enantiomer

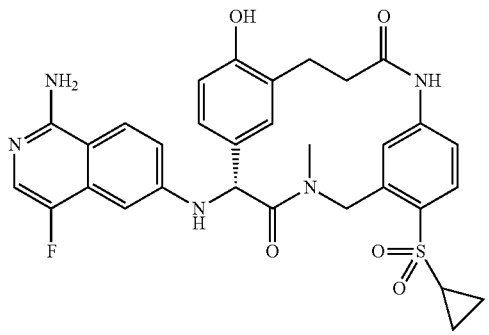 [SMILES: CN1Cc2cc(ccc2S(=O)(=O)C2CC2)NC(=O)CCc2cc(ccc2O)[C@@H](Nc2ccc3c(N)ncc(F)c3c2)C1=O]

Example 16A 2-(Trimethylsilyl)ethyl 5-(3-(2-(benzyloxy)-5-bromophenyl)propanamido)-2-(cyclopropylsulfonyl)benzyl(methyl)carbamate

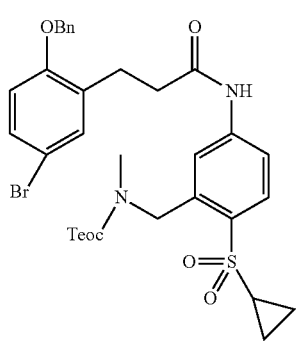

Using a procedure analogous to the one used to prepare Example 8A, Intermediate 8 (0.178 g, 0.531 mmol) was reacted with oxalyl chloride (0.049 mL, 0.584 mmol) and Intermediate 2 (0.245 g, 0.637 mmol), to yield Example 16A (0.181 g, 48%). MS (ESI) m/z: 724.3 (M+Na)$^+$.

Example 16B 4-(Benzyloxy)-3-(3-(4-(cyclopropylsulfonyl)-3-((methyl((2-(trimethylsilyl)ethoxy)carbonyl)amino)methyl)phenylamino)-3-oxopropyl)phenylboronic acid

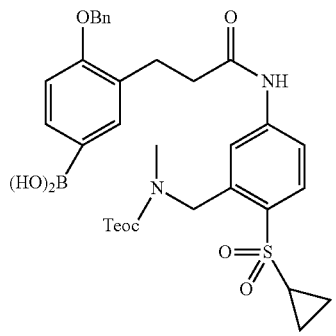

Using a procedure analogous to the one used to prepare Example 8B, Example 16A (0.180 g, 0.257 mmol) was reacted with bis(neopentyl glycolato)diboron (0.081 g, 0.359 mmol) and [1,1'-bis(diphenylphospino)ferrocene]dichloropalladium(II) (0.021 g, 0.026 mmol), to yield Example 16B (50 mg, 29%). MS (ESI) m/z: 689.5 (M+Na)$^+$.

Example 16C 2-(4-(Benzyloxy)-3-(3-(4-(cyclopropylsulfonyl)-3-((methyl((2-(trimethylsilyl)ethoxy)carbonyl)amino)methyl)phenylamino)-3-oxopropyl)phenyl)-2-(1-(bis(tert-butoxycarbonyl)amino)-4-fluoroisoquinolin-6-ylamino)acetic acid

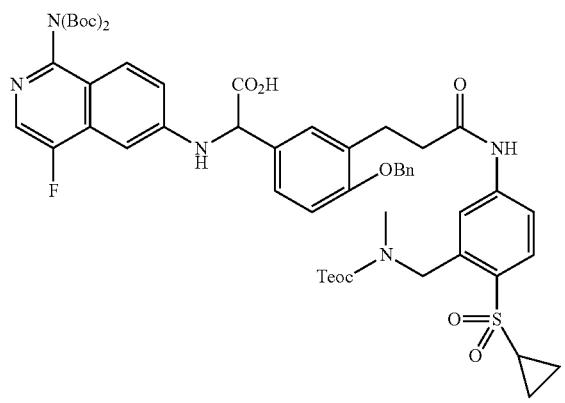

Using a procedure analogous to the one used to prepare Example 8C, Example 16B (50 mg, 0.075 mmol) and Intermediate 3 (0.023 g, 0.075 mmol) were reacted with glyoxylic acid monohydrate (6.9 mg, 0.075 mmol) to yield Example 16C (70 mg, 88%). MS (ESI) m/z: 957.7 (M+H)$^+$-boc.

Example 16D 2-(4-(Benzyloxy)-3-(3-(4-(cyclopropylsulfonyl)-3-((methylamino)methyl)phenylamino)-3-oxopropyl)phenyl)-2-(1-(bis(tert-butoxycarbonyl)amino)-4-fluoroisoquinolin-6-ylamino)acetic acid

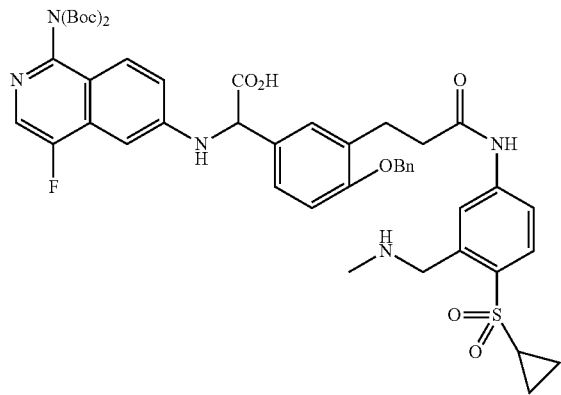

Using a procedure analogous to the one used to prepare Example 8D, Example 16C (47 mg, 0.044 mmol) was reacted with TBAF (0.440 mL, 0.440 mmol) to yield Example 16D (40 mg, 100%). MS (ESI) m/z: 913.0 (M+H)$^+$.

Example 16E

[6-(7-Benzyloxy-16-cyclopropanesulfonyl-13-methyl-3,12-dioxo-2,13-diaza-tricyclo[13.3.1.1$^{6,10}$]icosa-1(19),6,8,10(20),15,17-hexaen-11-ylamino)-4-fluoro-isoquinolin-1-yl]-bis(carbamic acid tert-butyl ester)

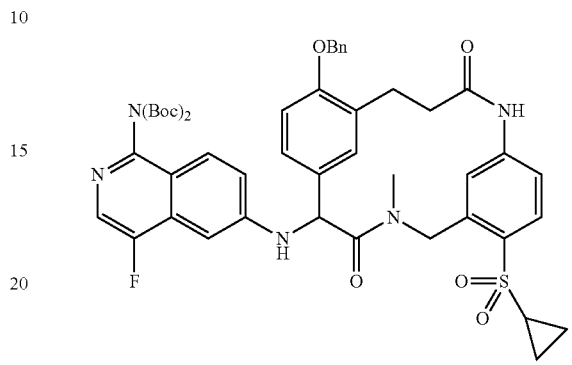

Using a procedure analogous to the one used to prepare Example 8E, Example 16D (40 mg, 0.044 mmol) was reacted with BOP (39 mg, 0.088 mmol) to yield Example 16E (38 mg, 96%). MS (ESI) m/z: 895.7 (M+H)$^+$.

Example 16F

[6-((R)-7-Benzyloxy-16-cyclopropanesulfonyl-13-methyl-3,12-dioxo-2,13-diaza-tricyclo[13.3.1.1$^{6,10}$]icosa-1(19),6,8,10(20),15,17-hexaen-11-ylamino)-4-fluoro-isoquinolin-1-yl]-bis(carbamic acid tert-butyl ester)

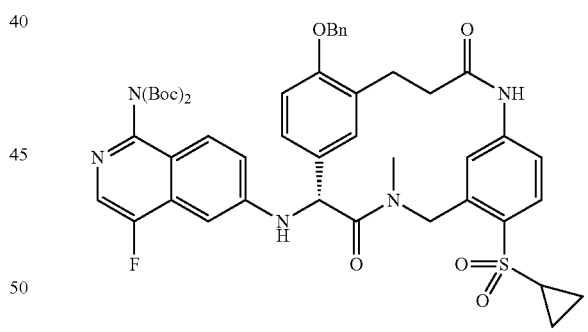

Example 16E (38 mg, 0.042 mmol) was separated by Chiral Prep LC (Chiralcel AD 25×200 mm column, 30% isocratic MeOH/EtOH (1:1) in heptane). The two enantiomers were separated and Peak 2 was collected to yield Example 16F (7.3 mg, 25%). 1H NMR (400 MHz, MeOD) δ ppm 8.09 (1 H, dd, J=9.29, 1.76 Hz), 7.81 (1 H, d, J=8.03 Hz), 7.60 (1 H, dd, J=8.41, 2.38 Hz), 7.49 (2 H, d, J=7.03 Hz), 7.44 (1 H, d, J=5.02 Hz), 7.38 (2 H, t, J=7.28 Hz), 7.28-7.35 (2 H, m), 7.26 (1 H, dd, J=9.16, 2.38 Hz), 7.09 (1 H, d, J=8.28 Hz), 6.89-7.00 (3 H, m), 5.78 (1 H, s), 5.64 (1 H, d, J=16.56 Hz), 5.07-5.22 (2 H, m), 4.54 (1 H, d, J=16.31 Hz), 3.15 (3 H, s), 2.88 (1 H, td, J=12.17, 4.52 Hz), 2.67-2.83 (2 H, m), 2.55-2.64 (1 H, m), 1.21-1.28 (1 H, m), 0.99-1.17 (3 H, m).

Example 16

Example 16F (7.4 mg, 0.002 mmol) was dissolved in MeOH (107 μL). Pd/C (11 mg, 0.001 mmol) was added and the reaction flushed with hydrogen then sealed with a hydrogen balloon and allowed to stir overnight. The reaction was filtered and concentrated to yield Example 16 (0.74 mg, 10%). 1H NMR (400 MHz, MeOD) δ ppm 8.12 (1 H, dd, J=9.41, 1.88 Hz), 7.83 (1 H, d, J=8.03 Hz), 7.39-7.51 (2 H, m), 7.20-7.32 (2 H, m), 6.92-7.02 (3 H, m), 6.83 (1 H, d, J=8.03 Hz), 5.74 (1 H, s), 5.66 (1 H, d, J=16.31 Hz), 4.56 (1 H, d, J=16.31 Hz), 3.12-3.19 (3 H, m), 3.02 (1 H, s), 2.88 (1 H, s), 2.70-2.87 (2 H, m), 2.54-2.65 (1 H, m), 1.23-1.36 (1 H, m), 1.02-1.20 (4 H, m). MS (ESI) m/z: 604.3 (M+H)$^+$. Analytical HPLC (low pH, 254 nM): Sunfire, RT=5.13 min.

Example 17

(R)-11-(1-Amino-4-fluoro-isoquinolin-6-ylamino)-16-cyclopropane sulfonyl-13-methyl-2,13-diaza-tricyclo[13.3.1.1$^{6,10}$]icosa-1(19),6,8,10(20),15,17-hexaene-3,12-dione, trifluoroacetic acid salt+ Enantiomer

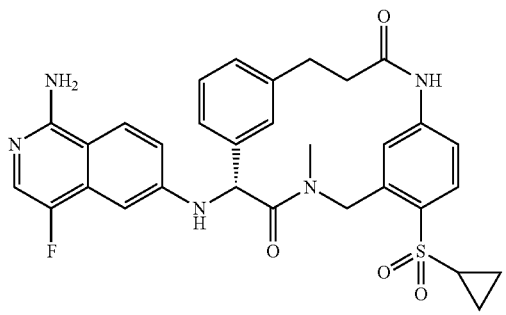 [SMILES: CN1Cc2cc(ccc2S(=O)(=O)C2CC2)NC(=O)CCc2cccc(c2)[C@@H](Nc2ccc3c(N)ncc(F)c3c2)C1=O]

Example 17A 2-(Trimethylsilyl)ethyl 5-(3-(3-bromophenyl)propanamido)-2-(cyclopropylsulfonyl)benzyl(methyl) carbamate

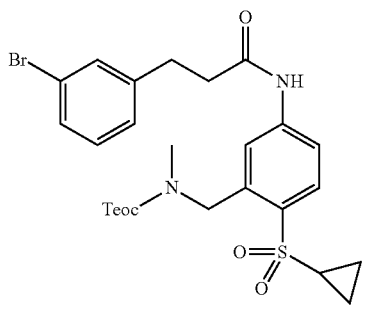

Using a procedure analogous to the one used to prepare Example 8A, 3-(3-bromo)propanoic acid (1.0 g, 4.37 mmol) was reacted with oxalyl chloride (0.406 mL, 4.80 mmol) and Intermediate 2 (2.18 g, 5.68 mmol), to yield Example 17A (0.745 g, 29%). MS (ESI) m/z: 618.3 (M+Na)$^+$.

Example 17B 3-(3-(4-(Cyclopropylsulfonyl)-3-((methyl((2-(trimethylsilyl)ethoxy)carbonyl)amino)methyl)phenylamino)-3-oxopropyl)phenylboronic acid

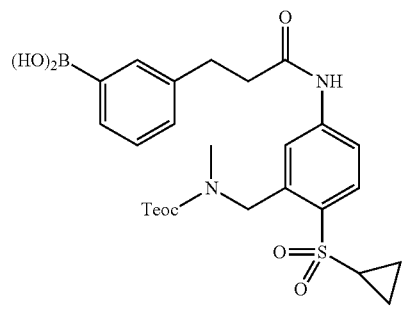

Using a procedure analogous to the one used to prepare Example 8B, Example 17A (0.745 g, 1.25 mmol) was reacted with bis(neopentyl glycolato)diboron (0.307 g, 3.13 mmol) and [1,1'-bis(diphenylphospino)ferrocene]dichloropalladium(II) (0.103 g, 0.125 mmol), to yield Example 17B (0.564 g, 80%). MS (ESI) m/z: 583.4 (M+Na)$^+$.

Example 17C 2-(1-(Bis(tert-butoxycarbonyl)amino)-4-fluoroisoquinolin-6-ylamino)-2-(3-(3-(4-(cyclopropylsulfonyl)-3-((methyl((2-(trimethylsilyl)ethoxy)carbonyl)amino)methyl)phenylamino)-3-oxopropyl)phenyl) acetic acid

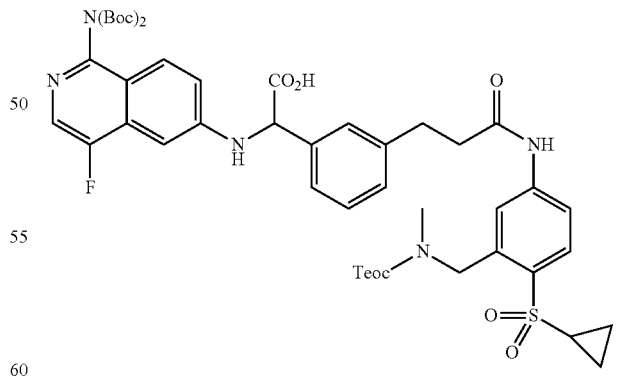

Using a procedure analogous to the one used to prepare Example 8C, Example 17B (564 mg, 1.01 mmol) and Intermediate 3 (380 mg, 1.01 mmol) were reacted with glyoxylic acid monohydrate (93 mg, 1.01 mmol) to yield Example 17C (0.857 g, 85%). MS (ESI) m/z: 951.7 (M+H)$^+$.

Example 17D 2-(1-(Bis(tert-butoxycarbonyl)amino)-4-fluoroiso-quinolin-6-ylamino)-2-(3-(3-(4-(cyclopropylsulfo-nyl)-3-((methylamino)methyl)phenylamino)-3-oxo-propyl)phenyl)acetic acid

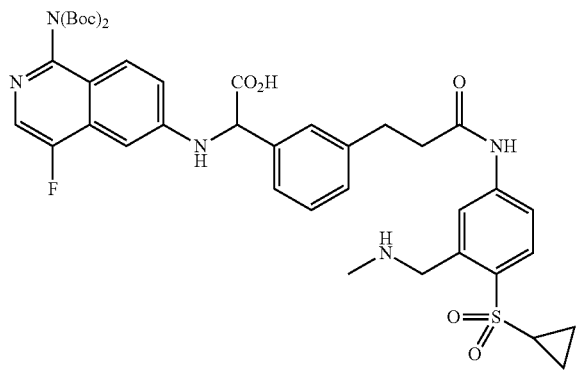

Using a procedure analogous to the one used to prepare Example 8D, Example 17C (800 mg, 0.824 mmol) was reacted with TBAF (8.42 mL, 8.42 mmol) to yield Example 17D (0.679 g, 100%). MS (ESI) m/z: 805.8 (M+H)+.

Example 17E

[6-(16-Cyclopropanesulfonyl-13-methyl-3,12-dioxo-2,13-diaza-tricyclo[13.3.1.1$^{6,10}$]icosa-1(19),6,8,10(20),15,17-hexaen-11-ylamino)-4-fluoro-isoquino-lin-1-yl]-bis(carbamic acid tert-butyl ester)

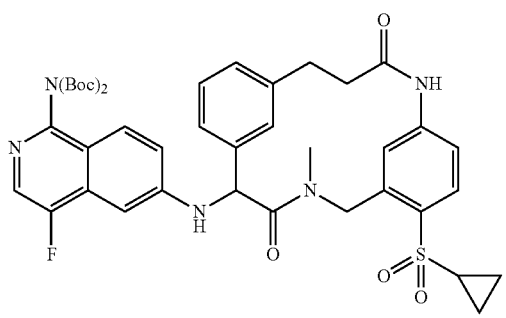

Using a procedure analogous to the one used to prepare Example 8E, Example 17D (0.68 g, 0.844 mmol) was reacted with BOP (0.746 g, 1.69 mmol) to yield Example 17E (0.274 g, 41%). MS (ESI) m/z: 788.6 (M+H)+.

Example 17

Example 17E (274 mg, 0.347 mmol) was separated by Chiral Prep LC (Chiralcel OD-H 25×200 mm column, 20% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 17 (81 mg, 32%). 1H NMR (400 MHz, MeOD) δ ppm 8.10 (1 H, d, J=9.29 Hz), 7.80 (1 H, dd, J=8.28, 2.26 Hz), 7.61 (1 H, d, J=6.02 Hz), 7.33-7.46 (4 H, m), 7.28 (1 H, d, J=9.29 Hz), 6.91-6.98 (2 H, m), 6.87 (1 H, br. s.), 5.85 (1 H, s), 5.66 (1 H, d, J=16.31 Hz), 4.54 (1 H, d, J=16.31 Hz), 3.15 (3 H, s), 2.96-3.13 (2 H, m), 2.74-2.84 (1 H, m), 2.69 (1 H, dd, J=7.78, 4.77 Hz), 2.48-2.59 (1 H, m), 1.21-1.30 (1 H, m), 0.99-1.17 (3 H, m). MS (ESI) m/z: 588.3 (M+H)+. Analytical HPLC (low pH, 220 nM): XBridge Phenyl, RT=6.15 min.

Example 18

(R)-11-(1-Amino-4-fluoro-isoquinolin-6-ylamino)-7-benzyloxy-16-cyclopropanesulfonyl-13-methyl-2,13-diaza-tricyclo[13.3.1.1$^{6,10}$]icosa-1(19),6,8,10(20),15,17-hexaene-3,12-dione trifluoroacetic acid salt+Enantiomer

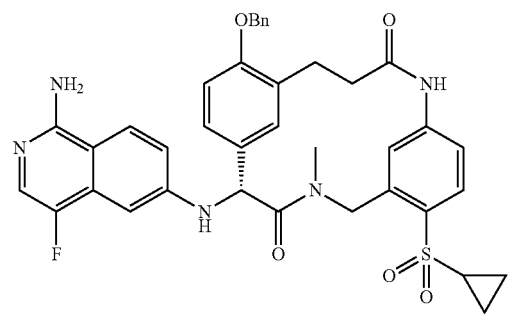

Example 18A 2-(Trimethylsilyl)ethyl 5-(3-(2-(benzyloxy)-5-bro-mophenyl)propanamido)-2-(cyclopropylsulfonyl)benzyl(methyl)carbamate

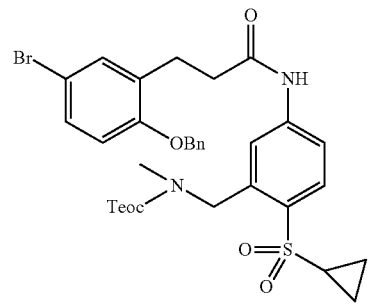

Using a procedure analogous to the one used to prepare Example 8A, Intermediate 8 (3.60 g, 10.73 mmol) was reacted with oxalyl chloride (0.998 mL, 11.80 mmol) and Intermediate 2 (2.18 g, 5.68 mmol), to yield Example 18A (0.745 g, 29%). MS (ESI) m/z: 618.3 (M+Na)+.

Example 18B 4-(Benzyloxy)-3-(3-(4-(cyclopropylsulfonyl)-3-((methyl((2-(trimethylsilyl)ethoxy)carbonyl)amino)methyl)phenylamino)-3-oxopropyl)phenylboronic acid

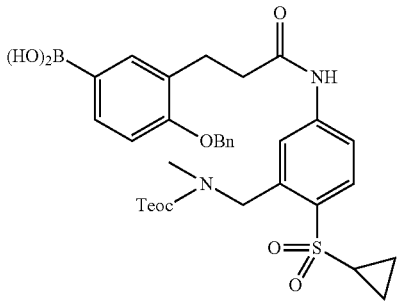

Using a procedure analogous to the one used to prepare Example 8B, Example 18A (2.18 g, 3.11 mmol) was reacted with bis(neopentyl glycolato)diboron (0.982 g, 4.35 mmol) and [1,1'-bis(diphenylphospino)ferrocene]dichloropalladium(II) (0.256 g, 0.311 mmol), to yield Example 18B (1.39 g, 67%). MS (ESI) m/z: 689.2 (M+Na)$^+$.

Example 18C 2-(4-(Benzyloxy)-3-(3-(4-(cyclopropylsulfonyl)-3-((methyl((2-(trimethylsilyl)ethoxy)carbonyl)amino)methyl)phenylamino)-3-oxopropyl)phenyl)-2-(1-(bis(tert-butoxycarbonyl)amino)-4-fluoroisoquinolin-6-ylamino)acetic acid

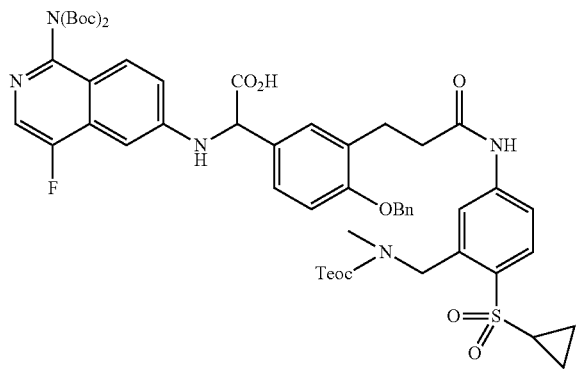

Using a procedure analogous to the one used to prepare Example 8C, Example 18B (1.39 mg, 2.09 mmol) and Intermediate 3 (787 mg, 2.09 mmol) were reacted with glyoxylic acid monohydrate (192 mg, 2.09 mmol) to yield Example 18C (1.51 g, 69%). MS (ESI) m/z: 1057.4 (M+H)$^+$.

Example 18D 2-(4-(Benzyloxy)-3-(3-(4-(cyclopropylsulfonyl)-3-((methylamino)methyl)phenylamino)-3-oxopropyl)phenyl)-2-(1-(bis(tert-butoxycarbonyl)amino)-4-fluoroisoquinolin-6-ylamino)acetic acid

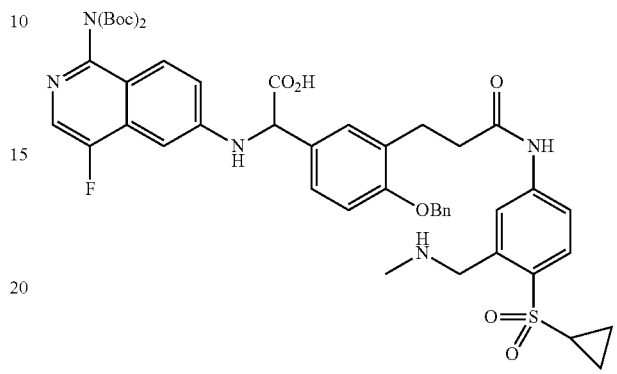

Using a procedure analogous to the one used to prepare Example 8D, Example 18C (1.51 mg, 1.43 mmol) was reacted with TBAF (3.57 mL, 3.57 mmol) to yield Example 18D (1.30 g, 100%). MS (ESI) m/z: 912.8 (M+H)$^+$.

Example 18E

[6-(7-Benzyloxy-16-cyclopropanesulfonyl-13-methyl-3,12-dioxo-2,13-diaza-tricyclo[13.3.1.1$^{6,10}$]icosa-1(19),6,8,10(20),15,17-hexaen-11-ylamino)-4-fluoro-isoquinolin-1-yl]-bis(carbamic acid tert-butyl ester)

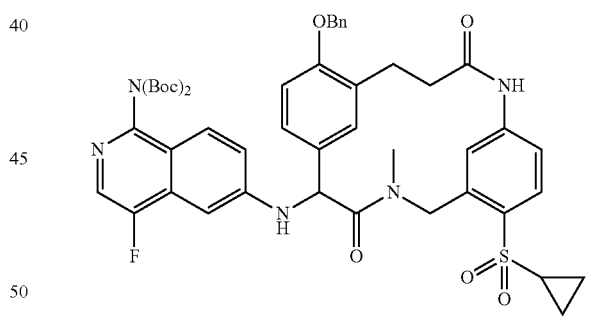

Using a procedure analogous to the one used to prepare Example 8E, Example 18D (1.30 g, 1.43 mmol) was reacted with BOP (1.26 g, 2.85 mmol) to yield Example 18E (0.675 g, 53%). MS (ESI) m/z: 895.4 (M+H)$^+$.

Example 18

Example 18E (675 mg, 0.755 mmol) was separated by Chiral Prep LC (Chiralcel OD-H 25×200 mm column, 25% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:

H₂O:TFA) to yield Example 18 (0.270 g, 40%). 1H NMR (400 MHz, MeOD) δ ppm 8.12 (1 H, dd, J=9.16, 1.88 Hz), 7.83 (1 H, d, J=9.03 Hz), 7.63 (1 H, dd, J=8.53, 2.26 Hz), 7.51 (2 H, d, J=7.28 Hz), 7.46 (1 H, d, J=5.02 Hz), 7.37-7.43 (2 H, m), 7.31-7.36 (2 H, m), 7.28 (1 H, dd, J=9.29, 2.26 Hz), 7.11 (1 H, d, J=8.53 Hz), 6.92-7.02 (2 H, m), 5.79 (1 H, s), 5.66 (1 H, d, J=16.56 Hz), 5.11-5.23 (2 H, m), 4.56 (1 H, d, J=16.31 Hz), 3.18 (3 H, s), 2.91 (1 H, td, J=12.11, 4.39 Hz), 2.76-2.85 (1 H, m), 2.69-2.76 (1 H, m), 2.57-2.66 (1 H, m), 1.24-1.32 (1 H, m), 1.02-1.18 (3 H, m), with one proton buried under the water peak. MS (ESI) m/z: 694.3 (M+H)⁺. Analytical HPLC (low pH, 220 nM): XBridge Phenyl, RT=7.725 min.

Example 19

5-(1-Amino-4-fluoro-isoquinolin-6-ylamino)-9-benzyloxy-19-cyclopropanesulfonyl-3,13-dimethyl-3,13,15-triaza-tricyclo[14.3.1.1⁶,¹⁰]henicosa-1(19),6(21),7,9,16(20),17-hexaene-4,14-dione, trifluoroacetic acid salt

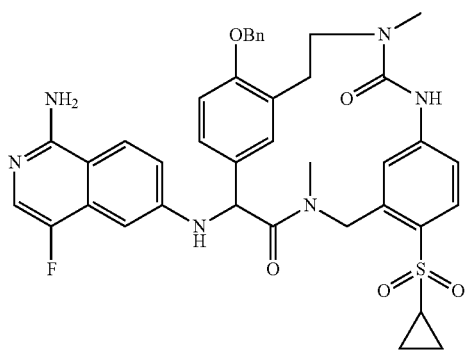

Example 19A 1-(Benzyloxy)-4-bromo-(iodomethyl)benzene

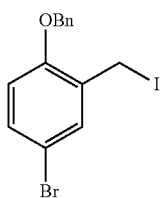

1,1,3,3-Tetramethyldisiloxane (0.304 mL, 1.717 mmol), chlorotrimethylsilane (0.436 mL, 3.43 mmol), and sodium iodide (0.515 g, 3.43 mmol) were dissolved in acetonitrile (17.17 mL) and allowed to stir at RT for 15 min. To the stirred solution, 2-(benzyloxy)-5-bromobenzaldehyde (0.500 g, 1.717 mmol) in 1 mL acetonitrile was added and the reaction was heated to reflux for 1 h. The reaction was diluted with EtOAc and sat'd sodium bicarbonate solution. The layers were separated, and the aqueous layer was back extracted with EtOAc×3. The combined organic layer was washed with brine, dried with sodium sulfate, and concentrated to yield Example 19A (0.117 g, 16.90% yield) as an off-white solid. Used immediately in the next step.

Example 19B 2-(2-(Benzyloxy)-5-bromophenyl)acetonitrile

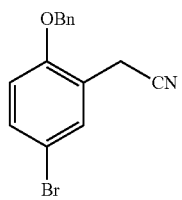 [SMILES: N#CCc1cc(Br)ccc1OCc1ccccc1]

Example 19A (0.505 g, 1.253 mmol) and NaCN (0.123 g, 2.506 mmol) were dissolved in DMSO (5 mL) and allowed to stir at RT for 1 hour. Reaction was diluted with sat'd sodium bicarbonate solution and EtOAc. The layers were separated, and the aqueous layer was back extracted with EtOAc×3. The combined organic layers were washed with brine, dried with sodium sulfate, and concentrated under reduced pressure to yield a yellow oil. The compound was purified by silica gel column chromatography (gradient from 0-20% EtOAc/hexanes) to yield Example 19B (0.353 g, 93% yield) as a yellow oil. MS (ESI) m/z: 302.1 (M+H)⁺. 1H NMR (400 MHz, CHLOROFORM-d) δ ppm 7.49-7.56 (1 H, m), 7.29-7.46 (6 H, m), 6.83 (1 H, d, J=8.78 Hz), 5.10 (2 H, s), 3.69 (2 H, s).

Example 19C 2-(2-(Benzyloxy)-5-bromophenyl)ethanamine, HCl

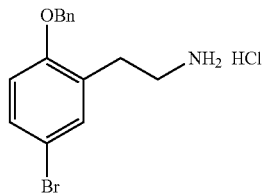 [SMILES: NCCc1cc(Br)ccc1OCc1ccccc1 ; Cl]

Example 19B (0.220 g, 0.728 mmol) was dissolved in THF (10 mL). To this solution was added borane tetrahydrofuran complex (1.456 mL, 1.456 mmol). The solution was allowed to stir at RT for 4 h. The reaction was diluted with 50% aqueous AcOH. The reaction was concentrated, and the residue was redissolved in EtOAc and water. The layers were separated, and the aqueous layer was neutralized with 1 M NaOH. The neutralized aqueous layer was extracted thrice with EtOAc. The combined organic layer was washed with brine, dried with sodium sulfate, and concentrated under reduced pressure to yield Example 19C (105 mg, 42.1% yield) as a white solid. LC/MS MS (ESI) m/z: 306.1 (M+H)⁺. 1H NMR (400 MHz, MeOD) d ppm 7.44 (2 H, s), 7.31-7.42 (5 H, m), 7.03 (1 H, s), 5.13 (2 H, s), 3.09-3.16 (2 H, m), 2.96 (2 H, t, J=7.53 Hz).

Example 19D

2-(Trimethylsilyl)ethyl 2-(benzyloxy)-5-bromophenethylcarbamate

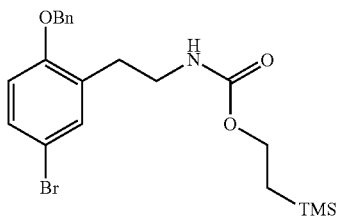 [SMILES: C[Si](C)(C)CCOC(=O)NCCc1cc(Br)ccc1OCc1ccccc1]

Example 19C (105 mg, 0.306 mmol) and 2-(trimethylsilyl)ethyl p-nitrophenyl carbonate (87 mg, 0.306 mmol) were dissolved in MeOH (1 mL) and DIPEA (0.268 mL, 1.532 mmol) was added. The reaction was allowed to stir at RT for 2 h. The reaction mixture was concentrated under reduced pressure. The crude reaction mixture was purified by silica gel column chromatography (gradient from 0-50% EtOAc/Hexane) to yield Example 19D (106 mg, 77% yield) as a colorless oil. MS (ESI) m/z: 450.3 (M+H)$^+$. 1H NMR (400 MHz, CHLOROFORM-d) δ ppm 7.30-7.41 (5 H, m), 7.23-7.28 (2 H, m), 6.76 (1 H, d, J=8.53 Hz), 5.03 (2 H, s), 4.67 (1 H, br. s.), 4.05-4.12 (2 H, m), 3.39 (2 H, q, J=6.11 Hz), 2.81 (2 H, t, J=6.65 Hz), 0.89-0.95 (2 H, m), −0.02-0.03 (9 H, m).

Example 19E

2-(Trimethylsilyl)ethyl 2-(benzyloxy)-5-bromophenethyl(methyl)carbamate

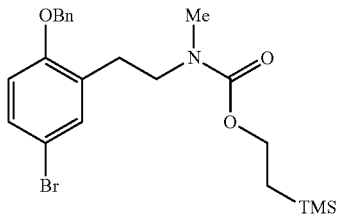 [SMILES: CN(CCc1cc(Br)ccc1OCc1ccccc1)C(=O)OCC[Si](C)(C)C]

Example 19D (106 mg, 0.235 mmol) was dissolved in DMF (3 mL). NaH (19 mg, 0.471 mmol) was added, and the reaction was allowed to stir at RT for 15 min. MeI (29 μL, 0.471 mmol) was added to the solution and the reaction was allowed to stir at RT for 2 h. Reaction diluted with water and EtOAc. The layers were separated, and the aqueous layer was back extracted with EtOAc×3. The combined organic layer was washed with brine, dried with sodium sulfate, and concentrated under reduced pressure to yield Example 19E (106 mg, 97% yield) as a colorless oil. 1H NMR (400 MHz, CHLOROFORM-d) δ ppm 7.21-7.47 (7 H, m), 6.77 (1 H, d, J=8.53 Hz), 5.06 (2 H, br. s.), 4.00-4.23 (2 H, m), 3.45 (2 H, d, J=6.53 Hz), 2.69-2.89 (5 H, m), 0.80-1.03 (2 H, m), −0.02-0.07 (9 H, m).

Example 19F

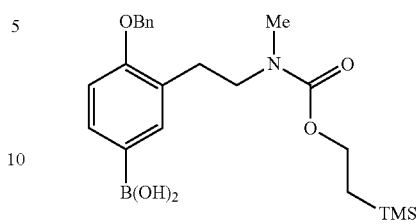

DMSO (2 mL) and Dioxane (2 mL) were degassed for 15 minutes by bubbling with argon. Example 19E (106 mg, 0.228 mmol), potassium acetate (56 mg, 0.571 mmol), and bis(neopentyl glycolato)diboron (52 mg, 0.228 mmol) were placed in a microwave tube. To these compounds was added the degassed solvents. The tube was sealed and degassed for an additional 15 minutes. PdCl$_2$(dppf) (8.35 mg, 0.011 mmol) was subsequently added, the tube sealed, and heated to 90° C. overnight. Reaction diluted with EtOAc and brine. The layers were separated and the organic layer was filtered through a pad of celite. The filtrate was concentrated under reduced pressure. Purified on Prep HPLC using Solvent A: 10% ACN/90% H$_2$O/0.1% TFA and Solvent B 90% ACN/10% H$_2$O/0.1% TFA on Phenomenex AXIA C18 30×100 mm with a 10 min gradient and 5 min hold time with a flow rate of 40 mL/min to yield Example 19F (40 mg, 40.8% yield) as a brown solid. Used immediately in the next step.

Example 19G

4-(benzyloxy)-3-(2-(methyl((2-(trimethylsilyl)ethoxy)carbonyl)amino)ethyl)phenylboronic acid

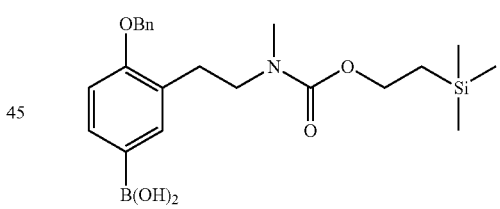

DMSO (2 mL) and dioxane (2 mL) were degassed for 15 min by bubbling with argon. Example 19F (106 mg, 0.228 mmol), KOAc (56 mg, 0.571 mmol), and bis(neopentyl glycolato)diboron (52 mg, 0.228 mmol) were placed in a microwave tube. To these compounds was added the degassed solvents. The tube was sealed and degassed for an additional 15 min. PdCl$_2$(dppf) (8.35 mg, 0.011 mmol) was subsequently added, the tube sealed, and heated to 90° C. overnight. Reaction diluted with EtOAc and brine. The layers were separated and the organic layer was filtered through a pad of celite. The filtrate was concentrated under reduced pressure. Purified on Prep HPLC using Solvent A: 10% ACN/90% H$_2$O/0.1% TFA and Solvent B 90% ACN/10% H$_2$O/0.1% TFA on Phenomenex AXIA C18 30×100 mm with a 10 min gradient and 5 min hold time with a flow rate of 40 mL/min to yield Example 19G (40 mg, 40.8% yield) as a brown solid. MS (ESI) m/z: 429.3 (M+H)$^+$.

Example 19H (6-{[[(5-Amino-2-cyclopropanesulfonyl-benzyl)-methyl-carbamoyl]-(4-benzyloxy-3-{2-[methyl-(2-trimethylsilanyl-ethoxycarbonyl)-amino]-ethyl}-phenyl)-methyl]-amino}-4-fluoro-isoquinolin-1-yl)-bis(carbamic acid tert-butyl ester)

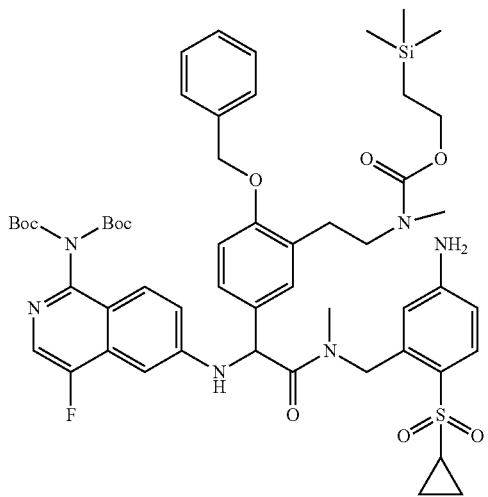 [SMILES: CN(CCc1cc(C(Nc2ccc3c(N(C(=O)OC(C)(C)C)C(=O)OC(C)(C)C)ncc(F)c3c2)C(=O)N(C)Cc2cc(N)ccc2S(=O)(=O)C2CC2)ccc1OCc1ccccc1)C(=O)OCC[Si](C)(C)C]

Example 19G (40 mg, 0.093 mmol), Intermediate 3 (17 mg, 0.093 mmol), and 2-oxoacetic acid, $H_2O$ (6.45 µL, 0.093 mmol) were dissolved in DMF (0.291 mL) and MeCN (0.873 mL). The reaction was heated to 80° C. for 3 h and then cooled to ambient temperature. To the reaction was added 4-(cyclopropylsulfonyl-3-((methylamino)methyl)aniline dihydrochloride (38 mg, 0.121 mmol), DIPEA (81 µL, 0.466 mmol), and BOP (41 mg, 0.093 mmol). The reaction was allowed to stir at ambient temperature overnight. Compound purified by silica gel chromatography (0-100% Hexane/EtOAc) to yield Example 19H (61 mg, 63% yield) as a white solid. MS (ESI) m/z: 1042.8 $(M+H)^+$.

Example 19I

[6-({[(5-Amino-2-cyclopropanesulfonyl-benzyl)-methyl-carbamoyl]-[4-benzyloxy-3-(2-methylamino-ethyl)-phenyl]-methyl}-amino)-4-fluoro-isoquinolin-1-yl]-bis(carbamic acid tert-butyl ester)

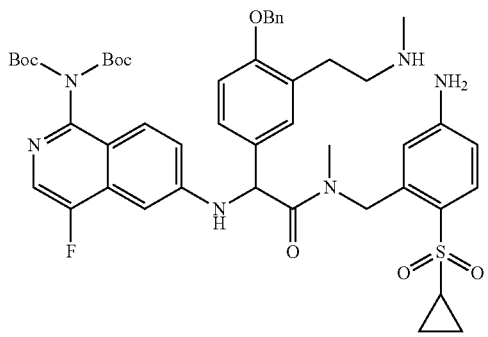 [SMILES: CNCCc1cc(C(Nc2ccc3c(N(C(=O)OC(C)(C)C)C(=O)OC(C)(C)C)ncc(F)c3c2)C(=O)N(C)Cc2cc(N)ccc2S(=O)(=O)C2CC2)ccc1OCc1ccccc1]

Example 19H (0.604 g, 0.580 mmol) was dissolved in THF (6 mL) and TBAF (5.80 mL, 5.80 mmol) was added. The reaction was allowed to stir at rt for 3 h. Reaction was concentrated and Purified on Prep HPLC using Solvent A: 10% MeOH/90% $H_2O$/0.1% TFA and Solvent B 90% MeOH/10% $H_2O$/0.1% TFA on Phenomenex AXIA C18 30×100 mm with a 10 min gradient and 2 min hold time with a flow rate of 40 mL/min. The fractions containing compound were pooled and quenched with the addition of saturated $NaHCO_3$. The solution was concentrated to remove MeOH and extracted with EtOAc×3. The combined organic layer was washed with brine, dried with sodium sulfate, and concentrated under reduced pressure to yield Example 19I (0.370 g, 0.412 mmol, 71.1% yield). MS (ESI) m/z: 898.3 $(M+H)^+$.

Example 19J

[6-(9-Benzyloxy-19-cyclopropanesulfonyl-3,13-dimethyl-4,14-dioxo-3,13,15-triaza-tricyclo[14.3.1.1$^{6,10}$]henicosa-1(19),6(21),7,9,16(20),17-hexaen-5-ylamino)-4-fluoro-isoquinolin-1-yl]-bis(carbamic acid tert-butyl ester)

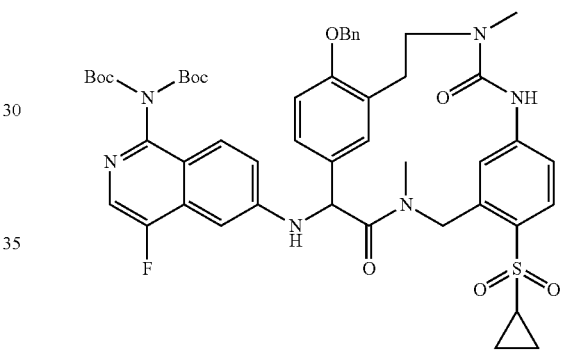

To a solution of Example 19I (25 mg, 0.028 mmol) in DCM (5 mL) was added pyridine (11.26 µL, 0.140 mmol) then cooled to 0° C. To this solution was added p-nitrophenyl chloroformate (56 mg, 0.280 mmol) and reaction was stirred slowly warming to rt over 2.5 h. The reaction was heated to 50° C. and allowed to stir overnight. Reaction diluted with saturated $NaHCO_3$ and DCM. The layers were separated, and the organic layer was washed with saturated aq. $NaHCO_3$, washed with brine, dried with $Na_2SO_4$, and concentrated. The crude reaction mixture was purified on Prep HPLC using Solvent A: 10% MeOH/90% $H_2O$/0.1% TFA and Solvent B 90% MeOH/10% $H_2O$/0.1% TFA on Phenomenex AXIA C18 30×100 mm with a 10 min gradient and 5 min hold time with a flow rate of 40 mL/min. Fractions containing product were diluted with saturated $NaHCO_3$ aq. solution. This solution was concentrated to remove MeOH and the resultant residue was redissolved in EtOAc. The layers were separated and the aqueous layer was back extracted with EtOAc×3. The combined organic layer was washed with brine, dried with sodium sulfate, and concentrated under reduced pressure to yield Example 19J (7 mg, 27% yield) as a white solid. MS (ESI) m/z: 924.5 $(M+H)^+$.

Example 19

Example 19J (7 mg, 7.58 µmol) was dissolved in TFA (1 mL) and allowed to stir for 20 min. The reaction was concentrated. The residue was dissolved in DCM and concentrated. The resultant solid was purified on purified on Prep HPLC using Solvent A: 10% MeOH/90% H₂O/0.1% TFA and Solvent B 90% MeOH/10% H₂O/0.1% TFA on Phenomenex AXIA C18 30×100 mm with a 10 min gradient and 5 min hold time with a flow rate of 40 mL/min to yield Example 19 (4.7 mg, 76% yield) as a white solid. MS (ESI) m/z: 723.2.3 (M+H)⁺. Analytical HPLC (low pH, 254 nM): Sunfire, RT=5.93 min, 100% purity; XBridge, RT=6.81 min, 100% purity. 1H NMR (400 MHz, MeOD) δ ppm 8.07-8.19 (1 H, m), 8.00 (1 H, s), 7.67-7.78 (1 H, m), 7.54-7.66 (1 H, m), 7.19-7.54 (7 H, m), 7.11 (1 H, d, J=8.28 Hz), 6.86-7.08 (1 H, m), 6.75 (1 H, s), 6.28 (1 H, d, J=8.28 Hz), 5.54-5.69 (1 H, m), 4.96-5.08 (2 H, m), 4.77-4.85 (2 H, m), 3.10-3.18 (2 H, m), 3.01 (5 H, s), 2.88 (3 H, s), 1.02-1.33 (5 H, m).

Example 20

5-(1-Amino-4-fluoro-isoquinolin-6-ylamino)-19-cyclopropanesulfonyl-13-cyclopropylmethyl-3-methyl-3,13,15-triaza-tricyclo[14.3.1.1$^{6,10}$]henicosa-1(19),6(21),7,9,16(20),17-hexaene-4,14-dione trifluoroacetic acid salt

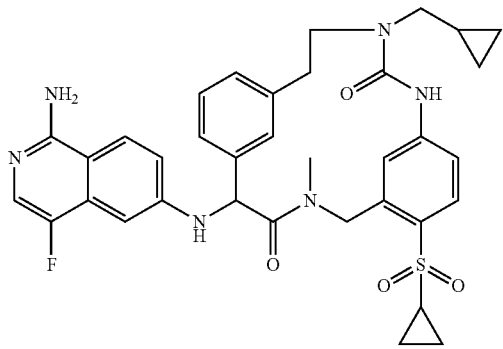 [SMILES: CN1Cc2cc(ccc2S(=O)(=O)C2CC2)NC(=O)N(CC2CC2)CCc2cccc(c2)C(Nc2ccc3c(N)ncc(F)c3c2)C1=O]

Example 20A 2-(trimethylsilyl)ethyl 3-bromophenethylcarbamate

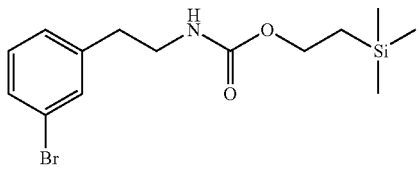 [SMILES: C[Si](C)(C)CCOC(=O)NCCc1cccc(Br)c1]

2-(3-Bromophenyl)ethanamine (1 g, 5.00 mmol) and 2-(trimethylsilyl)ethyl p-nitrophenyl carbonate (1.416 g, 5.00 mmol) were dissolved in MeOH (40.0 mL). DIPEA (1.048 mL, 6.00 mmol) was added, and the reaction was allowed to stir overnight. The reaction was concentrated in vacuo. The crude material was purified by silica gel column chromatography (0 to 100% EtOAc in hexanes) to yield Example 20A (1.61 g, 94%) 1H NMR (400 MHz, CHLOROFORM-d) δ ppm 7.30-7.35 (2 H, m), 7.14 (1 H, t, J=70.53 Hz), 7.06-7.11 (1 H, m), 4.60 (1 H, br. s.), 4.07-4.15 (2 H, m), 3.38 (2 H, q, J=6.61 Hz), 2.75 (2 H, t, J=6.78 Hz), 0.89-0.99 (2 H, m), 0.00 (9 H, s).

Example 20B 2-(Trimethylsilyl)ethyl 3-bromophenethyl(cyclopropylmethyl)carbamate

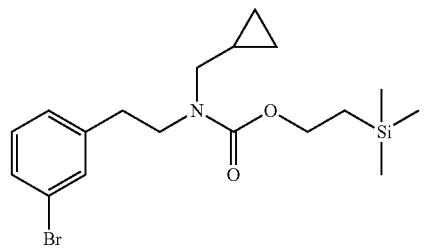 [SMILES: C[Si](C)(C)CCOC(=O)N(CCc1cccc(Br)c1)CC1CC1]

Example 20A (100 mg, 0.290 mmol) was dissolved in DMF (1.45 mL). NaH (13.94 mg, 0.581 mmol) was added at ambient temperature. The reaction was stirred for 15 min, after which time (bromomethyl)cyclopropane (56.3 µL, 0.581 mmol) was added and the reaction allowed to stir overnight. The reaction was quenched with water and extracted thrice with EtOAc. The combined organic layers were washed with brine, dried (Na₂SO₄), filtered, and concentrated in vacuo. The crude material was purified by silica gel column chromatography (0 to 100% EtOAc in hexanes) to yield Example 20B (90 mg, 78%). 1H NMR (400 MHz, CHLOROFORM-d) δ ppm 7.31-7.43 (2 H, m), 7.04-7.23 (2 H, m), 4.16 (2 H, br. s.), 3.41-3.63 (2 H, m), 3.14 (2 H, br. s.), 2.85 (2 H, br. s.), 1.00 (3 H, br. s.), 0.42-0.60 (2 H, m), 0.22 (2 H, br. s.), 0.06 (9 H, s).

Example 20C 3-(2-((cyclopropylmethyl)((2-(trimethylsilyl)ethoxy)carbonyl)amino)ethyl)phenylboronic acid

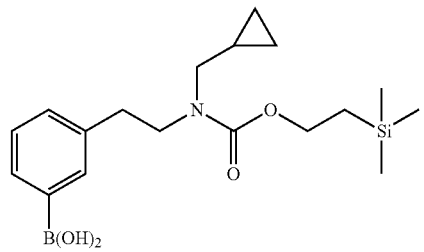 [SMILES: C[Si](C)(C)CCOC(=O)N(CCc1cccc(B(O)O)c1)CC1CC1]

Using a procedure analogous to the one used to prepare Example 19A, Example 20B (0.600 g, 1.506 mmol) was reacted with bis(neopentyl glycolato)diboron (0.370 g, 3.76 mmol) and [1,1'-bis(diphenylphosphino)ferrocene]dichloropalladium(II) (0.124 g, 0.151 mmol) to yield Example 20C (0.388 g, 71%). MS (ESI) m/z: 355.4 (M-28)⁺. M-28 peak typical for Teoc containing compounds.

Example 20D (6-{[[(5-Amino-2-cyclopropanesulfonyl-benzyl)-methyl-carbamoyl]-(3-{2-[cyclopropylmethyl-(2-trimethylsilanyl-ethoxycarbonyl)-amino]-ethyl}-phenyl)-methyl]-amino}-4-fluoro-isoquinolin-1-yl)-bis(carbamic acid tert-butyl ester)

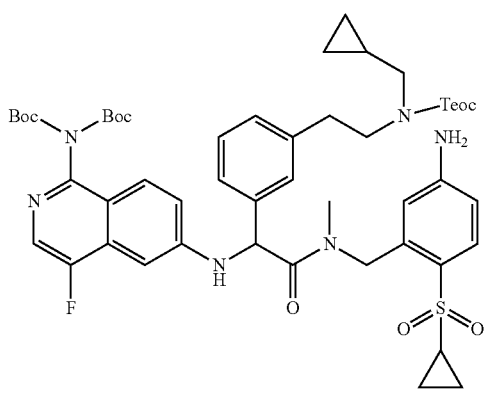

Using a procedure analogous to the one used to prepare Example 19B, Example 20C (0.388 g, 1.068 mmol) was reacted with Intermediate 3 (0.189 g, 1.068 mmol) and 2-oxoacetic acid, H$_2$O (98 mg, 1.068 mmol), 4-(cyclopropylsulfonyl)-3-((methylamino)methyl)aniline dihydrochloride (0.435 g, 1.388 mmol), and BOP (0.472 g, 1.068 mmol) to yield Example 20D (0.404 g, 60%). MS (ESI) m/z: 975.6 (M+H)$^+$.

Example 20E

{6-[([(5-Amino-2-cyclopropanesulfonyl-benzyl)-methyl-carbamoyl]-{3-[2-(cyclopropylmethyl-amino)-ethyl]-phenyl}-methyl)-amino]-4-fluoro-isoquinolin-1-yl}-bis(carbamic acid tert-butyl ester)

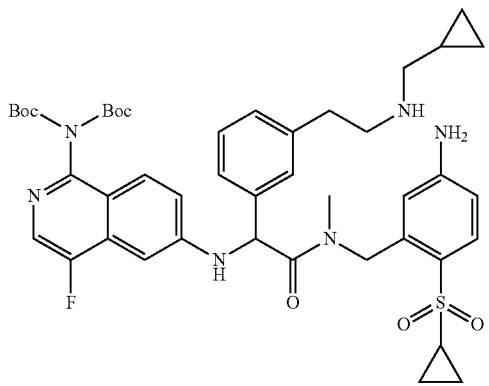 [SMILES: CN(Cc1cc(N)ccc1S(=O)(=O)C1CC1)C(=O)C(Nc1ccc2c(N(C(=O)OC(C)(C)C)C(=O)OC(C)(C)C)ncc(F)c2c1)c1cccc(CCNCC2CC2)c1]

Using a procedure analogous to the one used to prepare Example 19C, Example 20D (0.404 g, 0.249 mmol) was reacted TBAF (2.48 mL, 2.48 mmol) to yield Example 20E (0.133 g, 65%). MS (ESI) m/z: 832.3 (M+H)$^+$.

Example 20F

[6-(19-Cyclopropanesulfonyl-13-cyclopropylmethyl-3-methyl-4,14-dioxo-3,13,15-triaza-tricyclo[14.3.1.1$^{6,10}$]henicosa-1(19),6(21),7,9,16(20),17-hexaen-5-ylamino)-4-fluoro-isoquinolin-1-yl]-bis(carbamic acid tert-butyl ester)

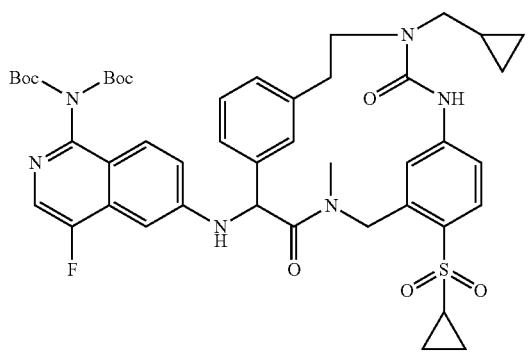 [SMILES: CN1Cc2cc(ccc2S(=O)(=O)C2CC2)NC(=O)N(CC2CC2)CCc2cccc(c2)C(Nc2ccc3c(N(C(=O)OC(C)(C)C)C(=O)OC(C)(C)C)ncc(F)c3c2)C1=O]

Using a procedure analogous to the one used to prepare Example 19D, Example 20D (38 mg, 0.046 mmol) was reacted with pyridine (37 μL, 4.57 mmol) and p-nitrophenyl chloroformate (46 mg, 0.229 mmol) to yield Example 20F (38 mg, 86%). MS (ESI) m/z: 857.4 (M+H)$^+$.

Example 20

Using a procedure analogous to the one used to prepare Example 19, Example 20F (48 mg, 0.049 mmol) was reacted TFA (1 mL) to yield Example 20 (37 mg, 92%). MS (ESI) m/z: 657.4 (M+H)$^+$. Analytical HPLC (low pH, 254 nM): Sunfire, RT=6.17 min.

Example 21

(R)-11-(1-Amino-4-fluoro-isoquinolin-6-ylamino)-16-cyclopropane sulfonyl-7-(2,2-difluoro-ethoxy)-13-methyl-2,13-diaza-tricyclo[13.3.1.1$^{6,10}$]icosa-1(19),6,8,10(20),15,17-hexaene-3,12-dione trifluroracetic acid salt

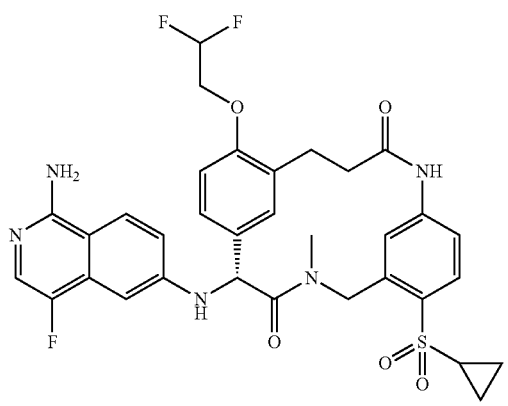 [SMILES: CN1Cc2cc(ccc2S(=O)(=O)C2CC2)NC(=O)CCc2cc(ccc2OCC(F)F)[C@@H](Nc2ccc3c(N)ncc(F)c3c2)C1=O]

Example 21A (R)-11-(1-Amino-4-fluoro-isoquinolin-6-ylamino)-16-cyclopropanesulfonyl-7-hydroxy-13-methyl-2,13-diaza-tricyclo[13.3.1.1^{6,10}]icosa-1(19),6,8,10(20),15,17-hexaene-3,12-dione

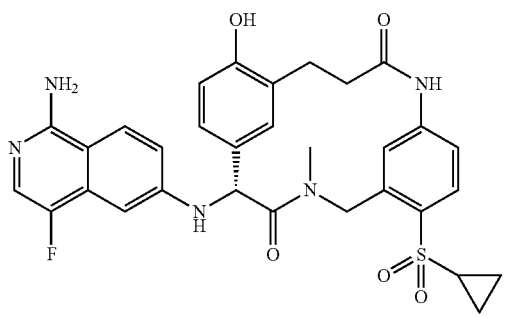 [SMILES: CN1Cc2cc(ccc2S(=O)(=O)C2CC2)NC(=O)CCc2cc(ccc2O)[C@@H](Nc2ccc3c(N)ncc(F)c3c2)C1=O]

Example 18 (250 mg, 0.280 mmol) was dissolved in MeOH (2.8 mL). Pd/C (29.8 mg, 0.280 mmol) was added and the reaction flushed with hydrogen then sealed with a hydrogen balloon and allowed to stir overnight. The reaction was filtered and concentrated to yield Example 21A (0.207 g, 92%). MS (ESI) m/z: 804.3 (M+H)$^+$.

Example 21

Example 21A (20 mg, 0.025 mmol) and 2-Bromo-1,1-difluoroethane (2.092 µL, 0.026 mmol) were dissolved in DMF (498 µL). Cs$_2$CO$_3$ (16.21 mg, 0.050 mmol) was added and the reaction was heated to 50° C. and allowed to stir overnight. The reaction was diluted with MeOH and purified by Prep LC (YMC-Pack ODS S-5 µm 20×100 mm column, 10 min gradient from 40 to 100% B in A, A=10:90:0.1 MeOH:H$_2$O:TFA, B=90:10:0.1 MeOH:H$_2$O:TFA). The fractions containing product were combined and this material was dissolved in approximately 1 mL of TFA and stirred for 1 h. The reaction was concentrated in vacuo. The crude material was purified by Prep LC (YMC-Pack ODS S-5 µm 20×100 mm column, 10 min gradient from 40 to 100% B in A, A=10:90:0.1 MeOH:H$_2$O:TFA, B=90:10:0.1 MeOH:H$_2$O:TFA) to yield Example 21 (4.3 mg, 22%). 1H NMR (400 MHz, MeOD) δ ppm 8.10 (1 H, dd, J=9.16, 1.88 Hz), 7.81 (1 H, d, J=8.03 Hz), 7.63 (1 H, dd, J=8.41, 2.38 Hz), 7.45 (1 H, d, J=5.02 Hz), 7.31 (1 H, d, J=2.26 Hz), 7.27 (1 H, dd, J=9.29, 2.51 Hz), 7.03 (1 H, d, J=8.28 Hz), 6.91-6.99 (3 H, m), 6.06-6.41 (1 H, m), 5.80 (1 H, s), 5.64 (1 H, d, J=16.31 Hz), 4.53 (1 H, d, J=16.31 Hz), 4.24-4.38 (2 H, m, J=13.68, 13.68, 5.77, 3.76 Hz), 3.16 (3 H, s), 2.88 (1 H, td, J=12.11, 4.89 Hz), 2.74-2.83 (1 H, m), 2.56-2.73 (2 H, m), 1.21-1.32 (2 H, m), 1.00-1.17 (3 H, m). MS (ESI) m/z: 668.2 (M+H)$^+$. Analytical HPLC (low pH, 220 nM): Sunfire C18, RT=5.958 min.

Example 22

(R)-11-(1-Amino-4-fluoro-isoquinolin-6-ylamino)-16-cyclopropane sulfonyl-7-cyclopropylmethoxy-13-methyl-2,13-diaza-tricyclo[13.3.1.1^{6,10}]icosa-1(19),6,8,10(20),15,17-hexaene-3,12-dione trifluroracetic acid salt

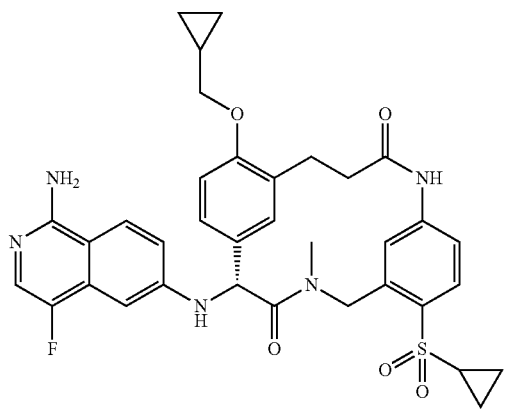 [SMILES: CN1Cc2cc(ccc2S(=O)(=O)C2CC2)NC(=O)CCc2cc(ccc2OCC2CC2)[C@@H](Nc2ccc3c(N)ncc(F)c3c2)C1=O]

Using a procedure analogous to the one used to prepare Example 21, Example 21A (20 mg, 0.025 mmol) was reacted with (bromomethyl)cyclopropane (3.53 mg, 0.026 mmol) to yield Example 22 (5.1 mg, 26%). 1H NMR (400 MHz, MeOD) δ ppm 8.10 (1 H, dd, J=9.29, 2.01 Hz), 7.81 (1 H, d, J=8.53 Hz), 7.56 (1 H, dd, J=8.41, 2.38 Hz), 7.44 (1 H, d, J=4.77 Hz), 7.24-7.29 (2 H, m), 6.90-7.00 (4 H, m), 5.75 (1 H, s), 5.64 (1 H, d, J=16.31 Hz), 4.53 (1 H, d, J=16.56 Hz), 3.90 (2 H, d, J=6.78 Hz), 3.14 (3 H, s), 2.81-2.90 (1 H, m), 2.69-2.81 (2 H, m), 2.55-2.66 (1 H, m), 1.20-1.36 (3 H, m), 1.00-1.17 (3 H, m), 0.58-0.68 (2 H, m), 0.34-0.46 (2 H, m). MS (ESI) m/z: 658.3 (M+H)$^+$. Analytical HPLC (low pH, 220 nM): Sunfire C18, RT=6.316.

Example 23

(R)-11-(1-Amino-4-fluoro-isoquinolin-6-ylamino)-7-butoxy-16-cyclopropanesulfonyl-13-methyl-2,13-diaza-tricyclo[13.3.1.1^{6,10}]icosa-1(19),6,8,10(20),15,17-hexaene-3,12-dione trifluroracetic acid salt

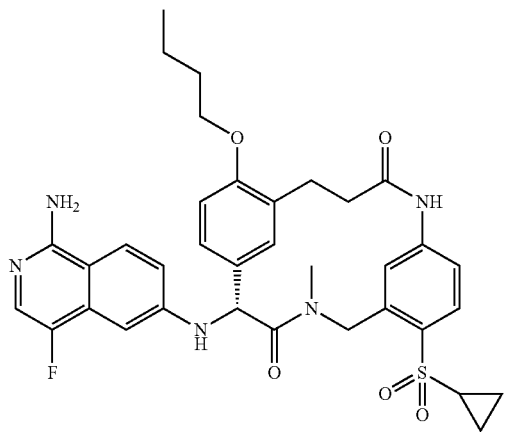 [SMILES: CCCCOc1ccc2cc1CCC(=O)Nc1ccc(S(=O)(=O)C3CC3)c(c1)CN(C)C(=O)[C@@H]2Nc1ccc2c(N)ncc(F)c2c1]

Using a procedure analogous to the one used to prepare Example 21, Example 21A (20 mg, 0.025 mmol) was reacted with 1-bromobutane (3.6 mg, 0.026 mmol) to yield Example 23 (6.2 mg, 31%). 1H NMR (400 MHz, MeOD) δ ppm 8.09 (1 H, d, J=9.03 Hz), 7.81 (1 H, d, J=8.03 Hz), 7.57 (1 H, dd, J=8.28, 1.76 Hz), 7.44 (1 H, d, J=4.77 Hz), 7.22-7.29 (2 H, m), 6.90-7.01 (4 H, m), 5.75 (1 H, s), 5.64 (1 H, d, J=16.56 Hz), 4.53 (1 H, d, J=16.31 Hz), 3.96-4.13 (2 H, m), 3.21-3.28 (1 H, m), 2.74-2.90 (2 H, m), 2.69 (1 H, td, J=11.92, 4.02 Hz), 2.54-2.63 (1 H, m), 1.77-1.88 (2 H, m), 1.56 (2 H, sxt, J=7.43 Hz), 1.22-1.31 (1 H, m), 1.04-1.17 (3 H, m), 1.01 (3 H, t, J=7.40 Hz). MS (ESI) m/z: 660.4 (M+H)+. Analytical HPLC (low pH, 220 nM): Sunfire C18, RT=6.676 min.

Example 24

(R)-11-(1-Amino-4-fluoro-isoquinolin-6-ylamino)-16-cyclopropanesulfonyl-7-isobutoxy-13-methyl-2,13-diaza-tricyclo[13.3.1.1$^{6,10}$]icosa-1(19),6,8,10(20),15,17-hexaene-3,12-dione trifluroracetic acid salt

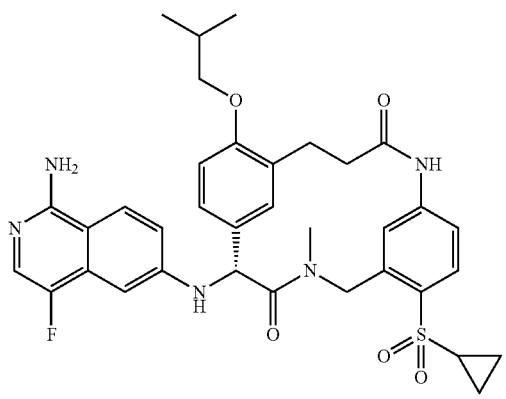 [SMILES: CC(C)COc1ccc2cc1CCC(=O)Nc1ccc(S(=O)(=O)C3CC3)c(c1)CN(C)C(=O)[C@@H]2Nc1ccc2c(N)ncc(F)c2c1]

Using a procedure analogous to the one used to prepare Example 21, Example 21A (20 mg, 0.025 mmol) was reacted with 1-bromo-2-methylpropane (3.6 mg, 0.026 mmol) to yield Example 24 (6.7 mg, 34%). 1H NMR (400 MHz, MeOD) δ ppm 8.06-8.16 (1 H, m), 7.77-7.86 (1 H, m), 7.58 (1 H, dd, J=8.28, 2.26 Hz), 7.44 (1 H, t, J=4.27 Hz), 7.21-7.30 (2 H, m), 6.89-7.03 (4 H, m), 5.73-5.80 (1 H, m), 5.59-5.69 (1 H, m), 4.49-4.60 (1 H, m), 3.84-3.91 (1 H, m), 3.74-3.83 (1 H, m), 3.23-3.28 (1 H, m), 3.13-3.19 (3 H, m), 2.75-2.92 (2 H, m), 2.70 (1 H, td, J=11.86, 4.14 Hz), 2.56-2.65 (1 H, m), 2.08-2.21 (1 H, m), 1.21-1.33 (1 H, m), 1.01-1.18 (9 H, m). MS (ESI) m/z: 660.4 (M+H)+. Analytical HPLC (low pH, 220 nM): Sunfire C18, RT=6.660 min.

Example 25

(R)-11-(1-Amino-4-fluoro-isoquinolin-6-ylamino)-7-cyclobutylmethoxy-16-cyclopropanesulfonyl-13-methyl-2,13-diaza-tricyclo[13.3.1.1$^{6,10}$]icosa-1(19),6,8,10(20),15,17-hexaene-3,12-dione trifluroracetic acid salt

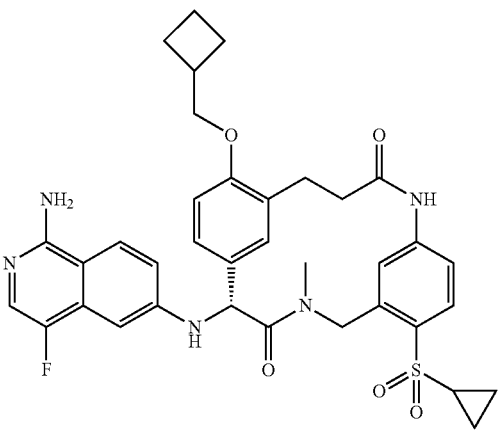 [SMILES: CN1Cc2cc(ccc2S(=O)(=O)C2CC2)NC(=O)CCc2cc(ccc2OCC2CCC2)[C@@H](Nc2ccc3c(N)ncc(F)c3c2)C1=O]

Using a procedure analogous to the one used to prepare Example 21, Example 21A (20 mg, 0.025 mmol) was reacted with (bromomethyl)cyclobutane (3.9 mg, 0.026 mmol) to yield Example 25 (5.8 mg, 28%). 1H NMR (400 MHz, MeOD) δ ppm 8.07-8.16 (1 H, m), 7.77-7.86 (1 H, m), 7.55-7.63 (1 H, m), 7.45 (1 H, t, J=4.89 Hz), 7.23-7.30 (2 H, m), 6.91-7.04 (4 H, m), 5.73-5.79 (1 H, m), 5.59-5.70 (1 H, m), 4.49-4.58 (1 H, m), 4.01-4.09 (1 H, m), 3.94-4.01 (1 H, m), 3.22-3.29 (1 H, m), 2.76-2.91 (3 H, m), 2.65-2.75 (1 H, m), 2.56-2.64 (1 H, m), 2.18 (2 H, d, J=3.76 Hz), 1.99 (4 H, br. s.), 1.21-1.32 (1 H, m), 1.00-1.18 (3 H, m). MS (ESI) m/z: 672.4 (M+H)+. Analytical HPLC (low pH, 220 nM): Sunfire C18, RT=6.798 min.

Example 26

(R)-11-(1-Amino-4-fluoro-isoquinolin-6-ylamino)-16-cyclopropanesulfonyl-7-isopropoxy-13-methyl-2,13-diaza-tricyclo[13.3.1.1$^{6,10}$]icosa-1(19),6,8,10(20),15,17-hexaene-3,12-dione trifluroracetic acid salt

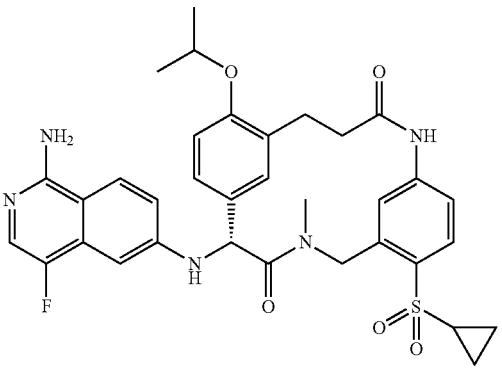 [SMILES: CC(C)Oc1ccc2cc1CCC(=O)Nc1ccc(S(=O)(=O)C3CC3)c(c1)CN(C)C(=O)[C@@H]2Nc1ccc2c(N)ncc(F)c2c1]

Using a procedure analogous to the one used to prepare Example 21, Example 21A (20 mg, 0.025 mmol) was reacted with 2-bromopropane (3.2 mg, 0.026 mmol) to yield Example 26 (5.0 mg, 26%). 1H NMR (400 MHz, MeOD) δ ppm 8.10 (1 H, dd, J=9.29, 1.76 Hz), 7.81 (1 H, d, J=8.53 Hz), 7.56 (1 H, dd, J=8.28, 2.26 Hz), 7.44 (1 H, d, J=4.77 Hz), 7.22-7.29 (2 H, m), 6.90-7.03 (4 H, m), 5.75 (1 H, s), 5.63 (1 H, d, J=16.56 Hz), 4.69 (1 H, quin, J=5.96 Hz), 4.53 (1 H, d, J=16.31 Hz), 3.24 (1 H, ddd, J=12.42, 4.27, 4.14 Hz), 3.16 (3 H, s), 2.74-2.88 (2 H, m), 2.69 (1 H, td, J=11.86, 4.14 Hz), 2.54-2.62 (1 H, m), 1.41 (3 H, d, J=6.02 Hz), 1.32 (3 H, d, J=6.02 Hz), 1.21-1.29 (1 H, m), 1.00-1.18 (3 H, m). MS (ESI) m/z: 646.3 (M+H)⁺. Analytical HPLC (low pH, 220 nM): Column, RT=6.163 min.

Example 27

5-(1-Amino-4-fluoro-isoquinolin-6-ylamino)-13-cyclobutylmethyl-19-cyclopropanesulfonyl-3-methyl-3,13,15-triaza-tricyclo[14.3.1.1$^{6,10}$]henicosa-1(19),6(21),7,9,16(20),17-hexaene-4,14-dione trifluoroacetic acid salt

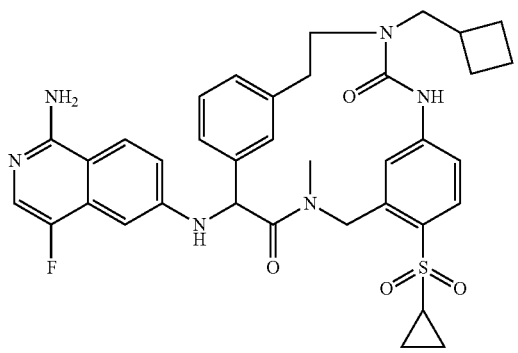 [SMILES: CN1Cc2cc(ccc2S(=O)(=O)C2CC2)NC(=O)N(CC2CCC2)CCc2cccc(c2)C(Nc2ccc3c(N)ncc(F)c3c2)C1=O]

Example 27A 2-(Trimethylsilyl)ethyl 3-bromophenethyl(cyclobutylmethyl)carbamate

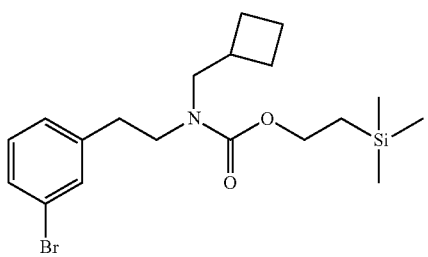 [SMILES: C[Si](C)(C)CCOC(=O)N(CCc1cccc(Br)c1)CC1CCC1]

Using a procedure analogous to the one used to prepare Example 20B, Example 20A (0.470 g, 1.365 mmol) was reacted with NaH (65 mg, 0.273 mmol) and (bromomethyl)cyclobutane (307 µL, 2.73 mmol) to yield 27A (99 mg, 18%). 1H NMR (400 MHz, CHLOROFORM-d) δ ppm 7.35 (2 H, d, J=6.27 Hz), 7.03-7.23 (2 H, m), 4.02-4.31 (2 H, m), 3.39 (2 H, t, J=7.40 Hz), 3.21 (2 H, br. s.), 2.79 (2 H, br. s.), 2.54 (1 H, br. s.), 2.02 (2 H, br. s.), 1.79-1.96 (2 H, m), 1.71 (2 H, br. s.), 1.00 (2 H, br. s.), 0.06 (9 H, s).

Example 27B 3-(2-((cyclopropylmethyl)((2-(trimethylsilyl)ethoxy)carbonyl)amino)ethyl)phenylboronic acid

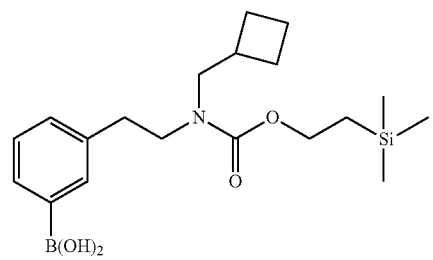 [SMILES: C[Si](C)(C)CCOC(=O)N(CCc1cccc(B(O)O)c1)CC1CCC1]

Using a procedure analogous to the one used to prepare Example 19A, Example 27A (99 mg, 0.240 mmol) was reacted with bis(neopentyl glycolato)diboron (76 mg, 0.599 mmol) and [1,1'bis(diphenylphosphino)ferrocene]dichloropalladium(II) (20 mg, 0.024 mmol) to yield Example 27B (52 mg, 57%). MS (ESI) m/z: 350.2 (M-28)⁺. M-28 peak typical for Teoc containing compounds.

Example 27C (6-{[[(5-Amino-2-cyclopropanesulfonyl-benzyl)-methyl-carbamoyl]-(3-{2-[cyclobutylmethyl-(2-trimethylsilanyl-ethoxycarbonyl)-amino]-ethyl}-phenyl)-methyl]-amino}-4-fluoro-isoquinolin-1-yl)-bis (carbamic acid tert-butyl ester)

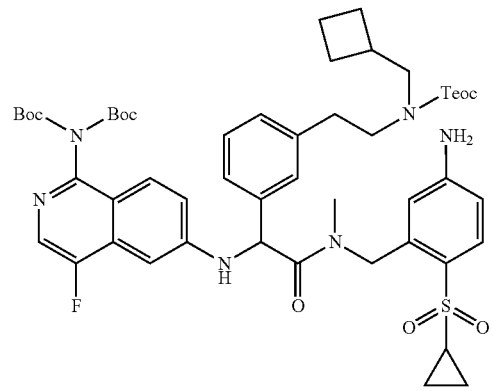

Using a procedure analogous to the one used to prepare Example 19B, Example 27B 52 mg, 0.138 mmol) was reacted with Intermediate 3 (52 mg, 0.138 mmol and 2-oxoacetic acid, H₂O (12 mg, 0.138 mmol), 4-(cyclopropylsulfonyl)-3-((methylamino)methyl)aniline dihydrochloride (56 mg, 0.179 mmol), and BOP (61 mg, 0.138 mmol) to yield Example 27C (79 mg, 58%). MS (ESI) m/z: 990.7 (M+H)⁺.

Example 27D

{6-[[[(5-Amino-2-cyclopropanesulfonyl-benzyl)-methyl-carbamoyl]-{3-[2-(cyclobutylmethyl-amino)-ethyl]-phenyl}-methyl)-amino]-4-fluoro-isoquinolin-1-yl}-bis(carbamic acid tert-butyl ester)

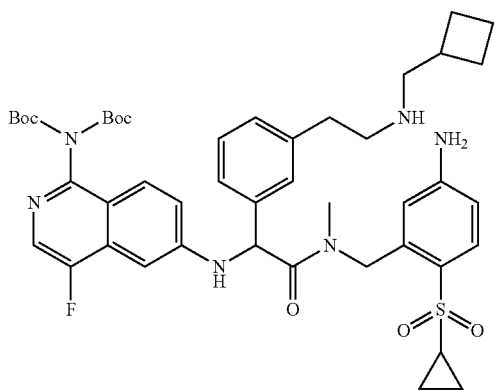 [SMILES: CN(Cc1cc(N)ccc1S(=O)(=O)C1CC1)C(=O)C(Nc1ccc2c(N(C(=O)OC(C)(C)C)C(=O)OC(C)(C)C)ncc(F)c2c1)c1cccc(CCNCC2CCC2)c1]

Using a procedure analogous to the one used to prepare Example 19C, Example 27C (79 mg, 0.079 mmol) was reacted TBAF (0.795 mL, 0.795 mmol) to yield Example 27D (32 mg, 47%). MS (ESI) m/z: 846.3 (M+H)⁺.

Example 27E

[6-(13-Cyclobutylmethyl-19-cyclopropanesulfonyl-3-methyl-4,14-dioxo-3,13,15-triaza-tricyclo[14.3.1.1⁶,¹⁰]henicosa-1(19),6(21),7,9,16(20),17-hexaen-5-ylamino)-4-fluoro-isoquinolin-1-yl]-carbamic acid tert-butyl ester

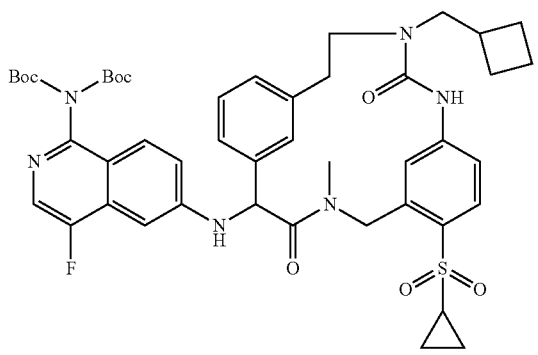 [SMILES: CN1Cc2cc(ccc2S(=O)(=O)C2CC2)NC(=O)N(CC2CCC2)CCc2cccc(c2)C(Nc2ccc3c(N(C(=O)OC(C)(C)C)C(=O)OC(C)(C)C)ncc(F)c3c2)C1=O]

Using a procedure analogous to the one used to prepare Example 19D, Example 27D (32 mg, 0.038 mmol) was reacted with pyridine (31 μL, 0.379 mmol) and p-nitrophenyl chloroformate (38 mg, 0.189 mmol) to yield Example 27E (35 mg, 94%). MS (ESI) m/z: 872.5 (M+H)⁺.

Example 27

Using a procedure analogous to the one used to prepare Example 19, Example 27E (35 mg, 0.036 mmol) was reacted TFA (1 mL) to yield Example 27 (23 mg, 77%). MS (ESI) m/z: 657.4 (M+H)⁺. MS (ESI) m/z: 671.4 (M+H)⁺. Analytical HPLC (low pH, 254 nM): Sunfire, RT=6.17 min.

Example 28

(R)-5-(1-Amino-4-fluoro-isoquinolin-6-ylamino)-19-cyclopropanesulfonyl-3,13-dimethyl-3,13,15-triaza-tricyclo[14.3.1.1⁶,¹⁰]henicosa-1(19),6(21),7,9,16(20),17-hexaene-4,14-dione trifluoroacetic acid salt+Enantiomer

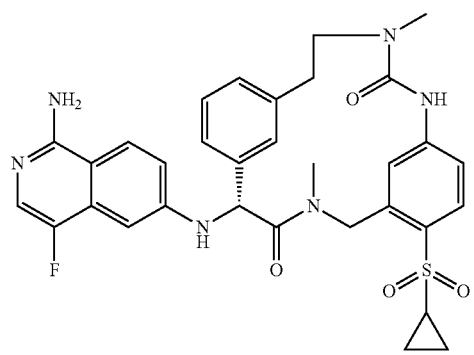 [SMILES: CN1CCc2cccc(c2)[C@@H](Nc2ccc3c(N)ncc(F)c3c2)C(=O)N(C)Cc2cc(ccc2S(=O)(=O)C2CC2)NC1=O]

Example 28A 2-(Trimethylsilyl)ethyl 3-bromophenethylcarbamate

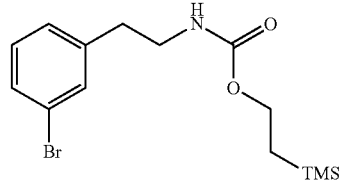 [SMILES: C[Si](C)(C)CCOC(=O)NCCc1cccc(Br)c1]

2-(3-Bromophenyl)ethanamine (1 g, 5.00 mmol) and 2-(trimethylsilyl)ethyl p-nitrophenyl carbonate (1.416 g, 5.00 mmol) were dissolved in MeOH (40.0 mL). DIPEA (1.048 mL, 6.00 mmol) was added, and the reaction was allowed to stir overnight. The reaction was concentrated in vacuo. The crude material was purified by silica gel column chromatography (gradient from 0 to 100% EtOAc in hexanes) to yield Example 28A (1.61 g, 4.68 mmol, 94% yield). 1H NMR (400 MHz, CHLOROFORM-d) δ ppm 7.30-7.35 (2 H, m), 7.14 (1 H, t, J=7.53 Hz), 7.06-7.11 (1 H, m), 4.60 (1 H, br. s.), 4.07-4.15 (2 H, m), 3.38 (2 H, q, J=6.61 Hz), 2.75 (2 H, t, J=6.78 Hz), 0.89-0.99 (2 H, m), 0.00 (9 H, s).

Example 28B 2-(Trimethylsilyl)ethyl 3-bromophenethy(methyl)carbamate

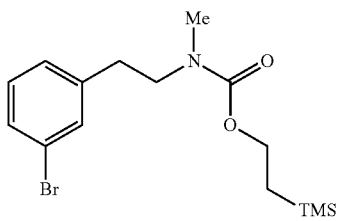 [SMILES: CN(CCc1cccc(Br)c1)C(=O)OCC[Si](C)(C)C]

Example 28A (300 mg, 0.871 mmol) was dissolved in DMF (4.36 mL). NaH (69.7 mg, 1.743 mmol) was added at ambient temperature, and the reaction was stirred for 0.5 h. Iodomethane (109 μL, 1.743 mmol) was added, and the reaction was stirred for 2 h. The reaction was quenched with water and extracted with EtOAc. The organic layer was washed with brine, dried (Na$_2$SO$_4$), filtered, and concentrated in vacuo. The crude material was purified by silica gel column chromatography (gradient from 0 to 100% EtOAc in hexanes) to yield Example 28B (0.273 g, 0.762 mmol, 87% yield). 1H NMR (400 MHz, CHLOROFORM-d) δ ppm 7.25-7.39 (2 H, m), 6.96-7.16 (2 H, m), 4.08 (2 H, dd, J=14.43, 7.15 Hz), 3.33-3.52 (2 H, m), 2.80 (5 H, d, J=16.06 Hz), 0.91 (2 H, br. s.), 0.00 (9 H, s).

Example 28C

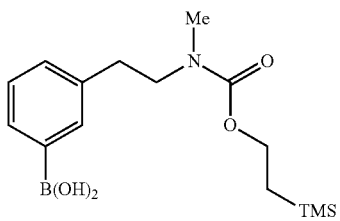 [SMILES: CN(CCc1cccc(B(O)O)c1)C(=O)OCC[Si](C)(C)C]

DMSO (3.17 mL) and Dioxane (3.17 mL) were degassed for 15 minutes by bubbling with argon. Meanwhile, Example 28B (273 mg, 0.762 mmol), Potassium acetate (187 mg, 1.905 mmol), and bis(neopentyl glycolato)diboron (241 mg, 1.067 mmol) were placed in a flask. To these compounds was added the degassed solvents. The tube was sealed and degassed for an additional 15 minutes. [1,1'-Bis(diphenylphosphino)ferrocene]dichloropalladium(II) (62.7 mg, 0.076 mmol) was subsequently added, the tube sealed, and heated to 90° C. overnight. The reaction was diluted with EtOAc, washed twice with brine, dried (Na$_2$SO$_4$), filtered, and concentrated in vacuo. The crude material was purified by Prep LC (Axia Luna 5u C18 30×100 mm column, 10 minute gradient from 40 to 100% B in A, A=10:90:0.1 MeCN:H2O:TFA, B=90:10:0.1 MeCN:H2O:TFA) to yield Example 28C (0.194 g, 0.602 mmol, 79% yield).

Example 28D (6-{[[(5-Amino-2-cyclopropanesulfonyl-benzyl)-methyl-carbamoyl]-(3-{2-[methyl-(2-trimethylsilanyl-ethoxycarbonyl)-amino]-ethyl}-phenyl)-methyl]-amino}-4-fluoro-isoquinolin-1-yl)-bis(carbamic acid tert-butyl ester)

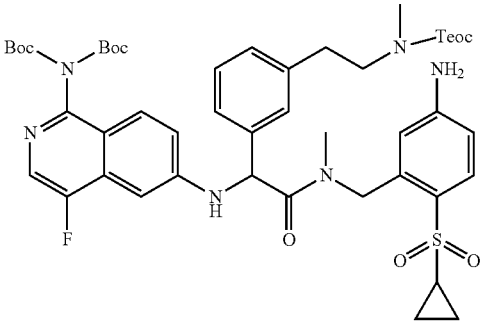

Using a procedure analogous to the one used to prepare Example 19B, Example 28C (0.196 g, 0.602 mmol) was reacted with Intermediate 3 (0.227 g, 0.602 mmol) and 2-oxoacetic acid, monohydrate (0.055 g, 0.602 mmol), 4-(cyclopropylsulfonyl)-3-((methylamino)methyl)aniline dihydrochloride (0.245 g, 0.783 mmol), and BOP (0.266 g, 0.602 mmol) to yield Example 28D (0.428 g, 76%). MS (ESI) m/z: 936.6 (M+H)$^+$.

Example 28E

[6-({[(5-Amino-2-cyclopropanesulfonyl-benzyl)-methyl-carbamoyl]-[3-(2-methylamino-ethyl)-phenyl]-methyl}-amino)-4-fluoro-isoquinolin-1-yl]-bis(carbamic acid tert-butyl ester)

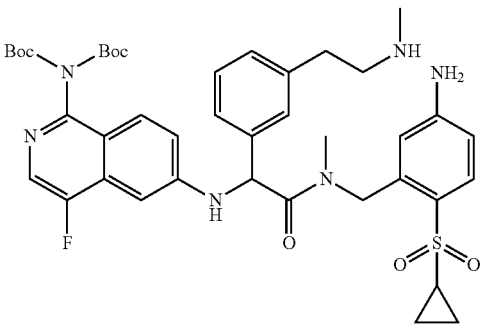 [SMILES: CNCCc1cccc(C(Nc2ccc3c(N(C(=O)OC(C)(C)C)C(=O)OC(C)(C)C)ncc(F)c3c2)C(=O)N(C)Cc2cc(N)ccc2S(=O)(=O)C2CC2)c1]

Using a procedure analogous to the one used to prepare Example 19C, Example 28D (0.428 g, 0.458 mmol) was reacted TBAF (2.23 mL, 2.23 mmol) to yield Example 28E (0.197 g, 43%). MS (ESI) m/z: 791.3 (M+H)$^+$.

Example 28F

[6-(19-Cyclopropanesulfonyl-3,13-dimethyl-4,14-dioxo-3,13,15-triaza-tricyclo[14.3.1.1^{6,10}]henicosa-1(19),6(21),7,9,16(20),17-hexaen-5-ylamino)-4-fluoro-isoquinolin-1-yl]-bis(carbamic acid tert-butyl ester)

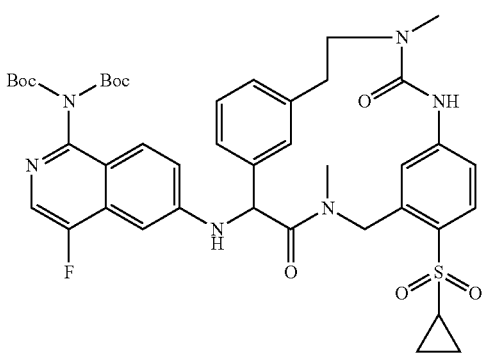

Using a procedure analogous to the one used to prepare Example 19D, Example 28E (0.156 g, 0.197 mmol) was reacted with pyridine (0.160 mL, 1.972 mmol and p-nitrophenyl chloroformate (0.199 g, 0.986 mmol) to yield Example 28F (86 mg, 53%). MS (ESI) m/z: 817.4 (M+H)$^+$.

Example 28

Example 28F (87 mg, 0.106 mmol) was separated by Chiral Prep LC (Chiralcel AD 20×200 mm column, 40% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 28 (21 mg, 26%). MS (ESI) m/z: 617.3 (M+H)$^+$. Analytical HPLC (low pH, 254 nM): Sunfire, RT=5.23 min.

Example 29

(R)-5-(1-Amino-4-fluoro-isoquinolin-6-ylamino)-13-benzyl-19-cyclopropanesulfonyl-3-methyl-3,13,15-triaza-tricyclo[14.3.1.1$^{6,10}$]henicosa-1(19),6(21),7,9,16(20),17-hexaene-4,14-dione trifluoroacetic acid salt+Enantiomer

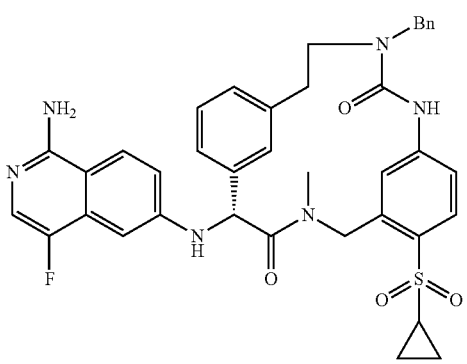 [SMILES: CN1Cc2cc(ccc2S(=O)(=O)C2CC2)NC(=O)N(Cc2ccccc2)CCc2cccc(c2)[C@@H](Nc2ccc3c(N)ncc(F)c3c2)C1=O]

Example 29A 2-(Trimethylsilyl)ethyl benzyl(3-bromophenethyl)carbamate

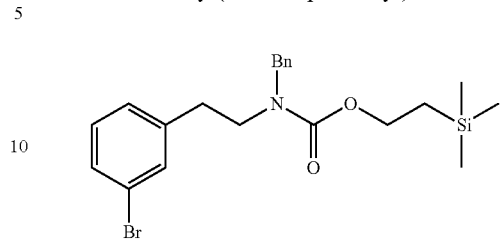

Using a procedure analogous to the one used to prepare Example 20B, Example 20A (0.500 g, 1.452 mmol) was reacted with NaH (0.116 g, 2.90 mmol) and benzyl bromide (0.173 mL, 1.452 mmol) to yield Example 29A (0.507 g, 80%). MS (ESI) m/z: 406.0 (M-28)$^+$. M-28 peak typical for Teoc containing compounds.

Example 29B 3-(2-(Benzyl((2-(trimethylsilyl)ethoxy)carbonyl)amino)ethyl)phenylboronic acid

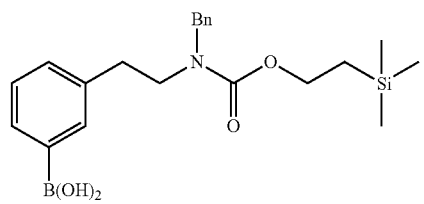 [SMILES: C[Si](C)(C)CCOC(=O)N(CCc1cccc(B(O)O)c1)Cc1ccccc1]

Using a procedure analogous to the one used to prepare Example 19A, Example 29A (0.507 g, 1.167 mmol) was reacted with bis(neopentyl glycolato)diboron (0.264 g, 1.167 mmol) and [1,1'bis(diphenylphosphino)ferrocene]dichloropalladium(II) (0.043 g, 0.058 mmol) to yield Example 29B (0.180 g, 38%). MS (ESI) m/z: 372.2 (M-28)$^+$. M-28 peak typical for Teoc containing compounds.

Example 29C (6-{[[(5-Amino-2-cyclopropanesulfonyl-benzyl)-methyl-carbamoyl]-(3-{2-[benzyl-(2-trimethylsilanyl-ethoxycarbonyl)-amino]-ethyl}-phenyl)-methyl]-amino}-4-fluoro-isoquinolin-1-yl)-bis(carbamic acid tert-butyl ester)

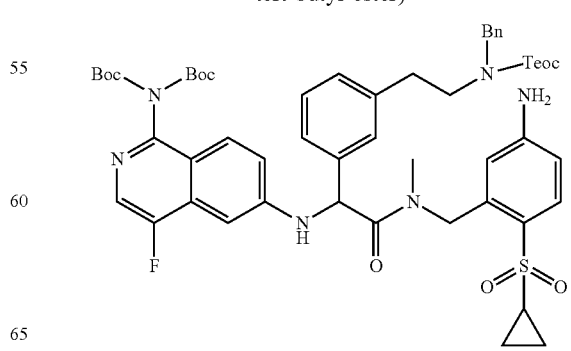

Using a procedure analogous to the one used to prepare Example 19B, Example 29B (0.180 g, 0.451 mmol) was reacted with Intermediate 3 (0.170 g, 0.451 mmol) and 2-oxoacetic acid, monohydrate (0.041 g, 0.451 mmol), 4-(cyclopropylsulfonyl)-3-((methylamino)methyl)aniline dihydrochloride (0.184 g, 0.586 mmol), and BOP (0.199 g, 0.451 mmol) to yield Example 29C (0.292 g, 64%). MS (ESI) m/z: 911.5 (M-boc)+.

Example 29D

[6-({[(5-Amino-2-cyclopropanesulfonyl-benzyl)-methyl-carbamoyl]-[3-(2-benzylamino-ethyl)-phenyl]-methyl}-amino)-4-fluoro-isoquinolin-1-yl]-bis(carbamic acid tert-butyl ester)

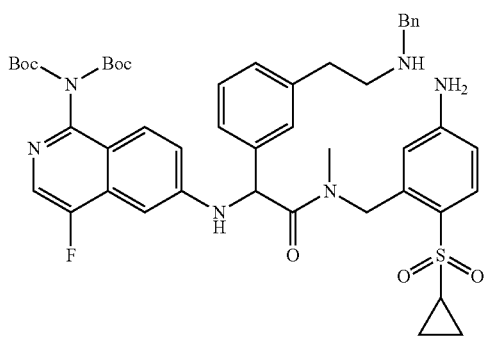 [SMILES: CN(Cc1cc(N)ccc1S(=O)(=O)C1CC1)C(=O)C(Nc1ccc2c(N(C(=O)OC(C)(C)C)C(=O)OC(C)(C)C)ncc(F)c2c1)c1cccc(CCNCc2ccccc2)c1]

Using a procedure analogous to the one used to prepare Example 19C, Example 29C (0.292 g, 0.289 mmol) was reacted TBAF (2.89 mL, 2.89 mmol) to yield Example 29D (0.153 g, 61%). MS (ESI) m/z: 868.6 (M+H)+.

Example 29E

[6-(13-Benzyl-19-cyclopropanesulfonyl-3-methyl-4,14-dioxo-3,13,15-triaza-tricyclo[14.3.1.1$^{6,10}$]henicosa-1(19),6(21),7,9,16(20),17-hexaen-5-ylamino)-4-fluoro-isoquinolin-1-yl]-bis(carbamic acid tert-butyl ester)

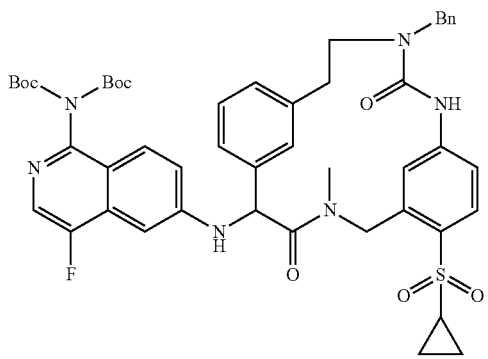 [SMILES: CN1Cc2cc(ccc2S(=O)(=O)C2CC2)NC(=O)N(Cc2ccccc2)CCc2cccc(c2)C(Nc2ccc3c(N(C(=O)OC(C)(C)C)C(=O)OC(C)(C)C)ncc(F)c3c2)C1=O]

Using a procedure analogous to the one used to prepare Example 19D, Example 29D 0.153 g, 0.176 mmol) was reacted with pyridine (0.140 mL, 1.765 mmol and p-nitrophenyl chloroformate (0.178 g, 0.882 mmol) to yield Example 29E (88 mg, 56%). MS (ESI) m/z: 794.4 (M-boc)+.

Example 29

Example 29E (88 mg, 0.111 mmol) was separated by Chiral Prep LC (Chiralcel AD 20×200 mm column, 60% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 29 (32 mg, 34%). MS (ESI) m/z: 693.4 (M+H)+. Analytical HPLC (low pH, 254 nM): Sunfire, RT=6.63 min.

Example 30

(R)-11-(1-Amino-4-fluoro-isoquinolin-6-ylamino)-16-cyclopropane sulfonyl-8-fluoro-7-methoxy-13-methyl-2,13-diaza-tricyclo[13.3.1.1$^{6,10}$]icosa-1(19), 6,8,10(20),15,17-hexaene-3,12-dione trifluoroacetic acid salt+Enantiomer

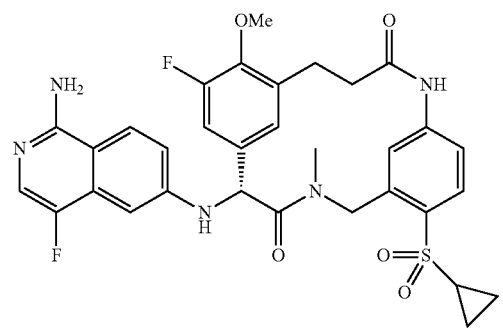 [SMILES: COc1c(F)cc2cc1CCC(=O)Nc1ccc(S(=O)(=O)C3CC3)c(c1)CN(C)C(=O)[C@@H]2Nc1ccc2c(N)ncc(F)c2c1]

Example 30A 2-(Trimethylsilyl)ethyl 5-(3-(5-bromo-3-fluoro-2-methoxyphenyl)propanamido)-2-(cyclopropylsulfonyl)benzyl(methyl)carbamate

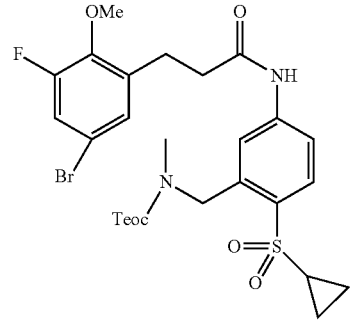

Using a procedure analogous to the one used to prepare Example 8A, Intermediate 9 (0.557 g, 2.01 mmol) was reacted with oxalyl chloride (1.11 mL, 2.42 mmol) and Intermediate 2 (0.928 g, 2.42 mmol), to yield Example 30A (0.207 g, 16%). MS (ESI) m/z: 646.1 (M+Na)+.

Example 30B 3-(3-(4-(Cyclopropylsulfonyl)-3-((methyl((2-(trimethylsilyl)ethoxy)carbonyl)amino)methyl)phenylamino)-3-oxopropyl)-5-fluoro-4-methoxyphenylboronic acid

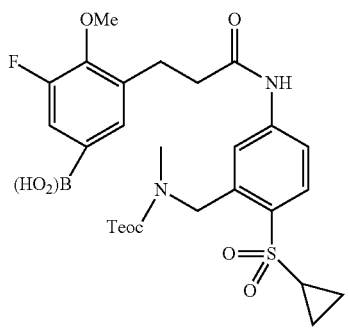

Using a procedure analogous to the one used to prepare Example 8B, Example 30A (0.200 g, 0.311 mmol) was reacted with bis(neopentyl glycolato)diboron (98 mg, 0.435 mmol) and [1,1'-bis(diphenylphospino)ferrocene]dichloropalladium(II) (26 mg, 0.031 mmol), to yield Example 30B (0.148 g, 78%). MS (ESI) m/z: 631.3 (M+Na)$^+$.

Example 30C 2-(1-(Bis(tert-butoxycarbonyl)amino)-4-fluoroisoquinolin-6-ylamino)-2-(3-(3-(4-(cyclopropylsulfonyl)-3-((methyl((2-(trimethylsilyl)ethoxy)carbonyl)amino)methyl)phenylamino)-3-oxopropyl)-5-fluoro-4-methoxyphenyl)acetic acid

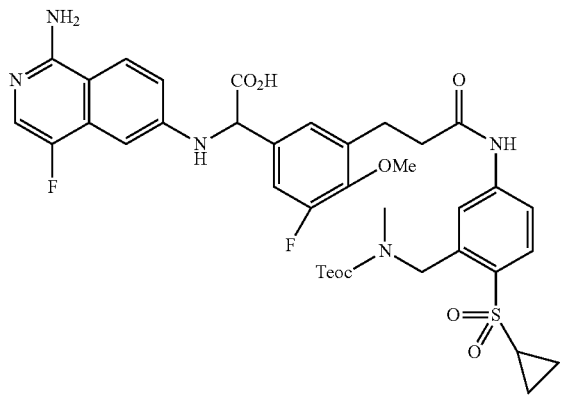

Using a procedure analogous to the one used to prepare Example 8C, Example 30B (0.148 g, 0.243 mmol) and Intermediate 3 (0.092 g, 0.243 mmol) were reacted with glyoxylic acid monohydrate (22 mg, 0.243 mmol) to yield Example 30C (0.223 g, 92%). MS (ESI) m/z: 899.5 (M+H)$^+$-boc.

Example 30D 2-(1-(Bis(tert-butoxycarbonyl)amino)-4-fluoroisoquinolin-6-ylamino)-2-(3-(3-(4-(cyclopropylsulfonyl)-3-((methylamino)methyl)phenylamino)-3-oxopropyl)-5-fluoro-4-methoxyphenyl)acetic acid

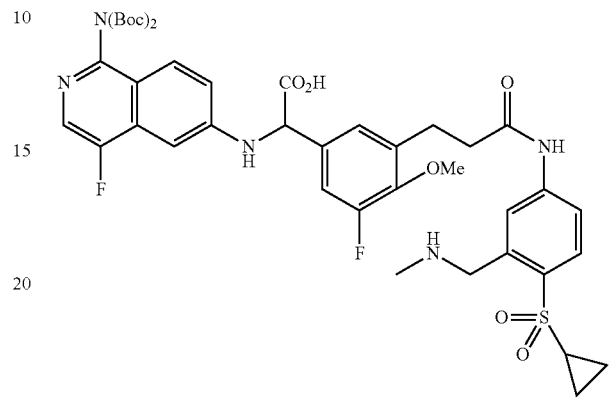

Using a procedure analogous to the one used to prepare Example 8D, Example 30C (0.223 g, 0.223 mmol) was reacted with TBAF (2.23 mL, 2.23 mmol) to yield Example 30D (0.189 g, 99%). MS (ESI) m/z: 854.5 (M+H)$^+$.

Example 30E

[6-(16-Cyclopropanesulfonyl-8-fluoro-7-methoxy-13-methyl-3,12-dioxo-2,13-diaza-tricyclo[13.3.1.1$^{6,10}$]icosa-1(19),6,8,10(20),15,17-hexaen-11-ylamino)-4-fluoro-isoquinolin-1-yl]-bis(carbamic acid tert-butyl ester)

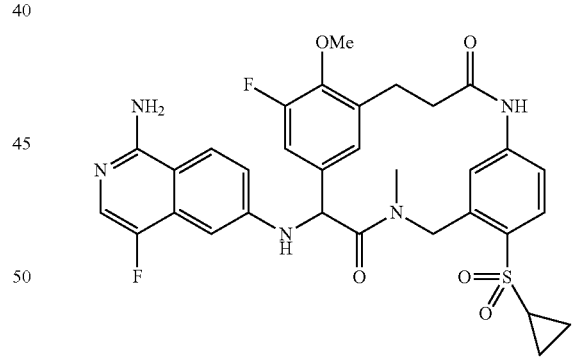

Using a procedure analogous to the one used to prepare Example 8E, Example 30D (0.150 g, 0.176 mmol) was reacted with BOP (0.155 g, 0.351 mmol) to yield Example 30E (27 mg, 18%). MS (ESI) m/z: 836.3 (M+H)$^+$.

Example 30

Example 30E (26 mg, 0.031 mmol) was separated by Chiral Prep LC (Chiral OD 25×200 mm column, 25% isocratic MeOH/EtOH (1:1) in heptane). The two enantiomers were separated and Peak 1 was collected to yield Example 30 (2.8 mg, 11%). 1H NMR (400 MHz, MeOD) δ ppm 8.13 (1 H, dd, J=9.29, 1.76 Hz), 7.76-7.95 (1 H, m), 7.40-7.58 (2 H, m), 7.29 (1 H, dd, J=9.29, 2.26 Hz), 7.15 (1 H, s), 6.86-7.02 (3 H, m), 5.84 (1 H, s), 5.65 (1 H, d, J=16.56 Hz), 4.54 (1 H, d, J=16.31 Hz), 4.01 (3 H, d, J=2.51 Hz), 3.14-3.27 (4 H, m), 2.92 (1 H, m), 2.70-2.85 (1 H, m), 2.63 (2 H, m), 1.20-1.36 (1 H, m), 0.97-1.21 (4 H, m). MS (ESI) m/z: 636.2 (M+H)⁺. Analytical HPLC (low pH, 254 nM): Sunfire, RT=5.65 min.

Example 31

(5R,11R)-5-(1-Amino-4-fluoro-isoquinolin-6-ylamino)-19-cyclopropanesulfonyl-9-methoxy-3,11,13-trimethyl-3,13,15-triaza-tricyclo[14.3.1.1$^{6,10}$]henicosa-1(19),6(21),7,9,16(20),17-hexaene-4,14-dione trifluoroacetic acid salt+Diasteromer

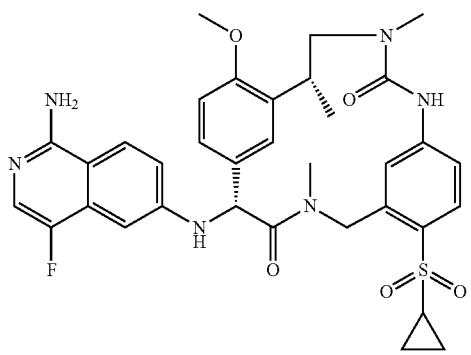 [SMILES: COc1ccc2cc1[C@@H](C)CN(C)C(=O)Nc1ccc(S(=O)(=O)C3CC3)c(c1)CN(C)C(=O)[C@@H]2Nc1ccc2c(N)ncc(F)c2c1]

Example 31A (6-{[[(5-Amino-2-cyclopropanesulfonyl-benzyl)-methyl-carbamoyl]-(4-methoxy-3-{(R)-1-methyl-2-[methyl-(2-trimethylsilanyl-ethoxycarbonyl)-amino]-ethyl}-phenyl)-methyl]-amino}-4-fluoro-isoquinolin-1-yl)-bis(carbamic acid tert-butyl ester)

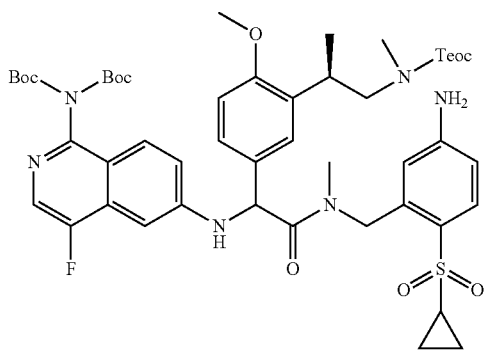

Using a procedure analogous to the one used to prepare Example 19B, Intermediate 18 (75 mg, 0.205 mmol) was reacted with Intermediate 3 (0.077 g, 0.205 mmol) and 2-oxoacetic acid, monohydrate (0.019 g, 0.205 mmol), 4-(cyclopropylsulfonyl)-3-((methylamino)methyl)aniline dihydrochloride (0.083 g, 0.266 mmol), and BOP (0.091 g, 0.205 mmol) to yield Example 31A (0.198 g, 98%). MS (ESI) m/z: 980.5 (M+H)⁺.

Example 31B

[6-({[(5-Amino-2-cyclopropanesulfonyl-benzyl)-methyl-carbamoyl]-[4-methoxy-3-((R)-1-methyl-2-methylamino-ethyl)-phenyl]-methyl}-amino)-4-fluoro-isoquinolin-1-yl]-bis(carbamic acid tert-butyl ester)

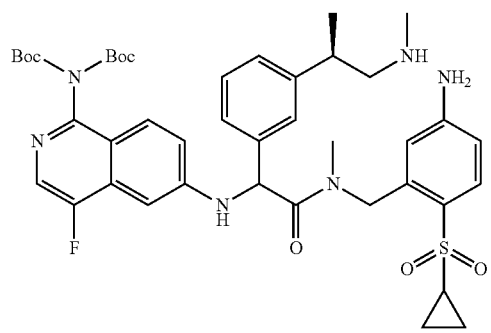 [SMILES: CNC[C@H](C)c1cccc(C(Nc2ccc3c(N(C(=O)OC(C)(C)C)C(=O)OC(C)(C)C)ncc(F)c3c2)C(=O)N(C)Cc2cc(N)ccc2S(=O)(=O)C2CC2)c1]

Using a procedure analogous to the one used to prepare Example 19C, Example 31A (0.187 g, 0.191 mmol) was reacted TBAF (1.91 mL, 1.91 mmol) to yield Example 31B (102 mg, 64%). MS (ESI) m/z: 836.3 (M+H)⁺.

Example 31C

[6-((R)-19-Cyclopropanesulfonyl-9-methoxy-3,11,13-trimethyl-4,14-dioxo-3,13,15-triaza-tricyclo[14.3.1.1$^{6,10}$]henicosa-1(19),6(21),7,9,16(20),17-hexaen-5-ylamino)-4-fluoro-isoquinolin-1-yl]-bis(carbamic acid tert-butyl ester)

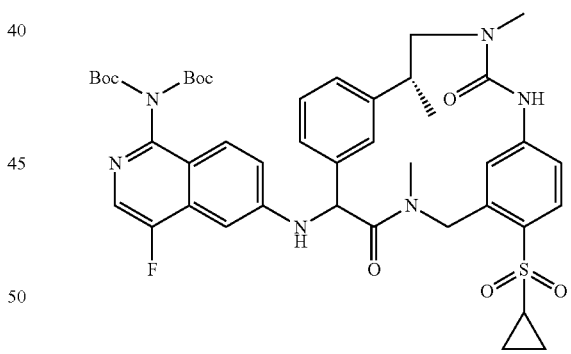

Using a procedure analogous to the one used to prepare Example 19D, Example 31B (48 mg, 0.057 mmol) was reacted with pyridine (16 μL, 0.201 mmol) and p-nitrophenyl chloroformate (35 mg, 0.172 mmol) to yield Example 31C (18 mg, 36%). MS (ESI) m/z: 861.4 (M+H)⁺.

Example 31

Example 31C (18 mg, 0.021 mmol) was separated by Chiral Prep LC (Chiralcel AD 20×200 mm column, 40% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H₂O:TFA, B=90:10:0.1 MeCN:H₂O:TFA) to yield Example 31 (6 mg, 35%). MS (ESI) m/z: 661.3 (M+H)⁺. Analytical HPLC (low pH, 254 nM): Sunfire, RT=5.67 min. 1H NMR (400 MHz, MeOD) δ ppm 7.98-8.11 (1 H, m), 7.69 (1 H, br. s.), 7.54 (1 H, d, J=8.53 Hz), 7.40 (1 H, dd, J=16.69, 4.89 Hz), 7.10-7.26 (1 H, m), 6.80-7.03 (3 H, m), 6.65 (1 H, br. s.), 6.50 (1 H, dd, J=8.41, 2.38 Hz), 5.97-6.13 (1 H, m), 5.58 (1 H, s), 4.85-4.96 (1 H, m), 3.77-3.87 (1 H, m), 3.61 (2 H, s), 2.96-3.08 (3 H, m), 2.85-2.96 (3 H, m), 0.94-1.34 (8 H, m).

Example 32

(5S,11R)-11-(1-Amino-4-fluoro-isoquinolin-6-ylamino)-16-cyclopropane sulfonyl-7-(2,2-difluoro-ethoxy)-5,13-dimethyl-2,13-diaza-tricyclo[13.3.1.1⁶,¹⁰]icosa-1(18),6,8,10(20),15(19),16-hexaene-3,12-dione, trifluoroacetic acid salt+Diastereomer

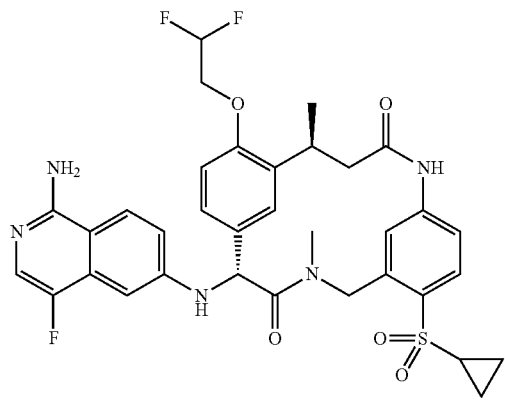 [SMILES: C[C@H]1CC(=O)Nc2ccc(S(=O)(=O)C3CC3)c(c2)CN(C)C(=O)[C@H](Nc2ccc3c(N)ncc(F)c3c2)c2ccc(OCC(F)F)c1c2]

Example 32A (S)-2-(Trimethylsilyl)ethyl 5-(3-(2-(benzyloxy)-5-bromophenyl)butanamido)-2-(cyclopropylsulfonyl)benzyl(methyl)carbamate

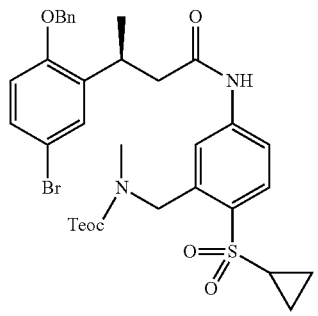

Using a procedure analogous to the one used to prepare 8A, Intermediate 4 (0.622 g, 1.78 mmol) was reacted with oxalyl chloride (0.980 mL, 1.96 mmol) and Intermediate 2 (0.822 g, 2.14 mmol), to yield Example 32A (0.502 g, 39%). MS (ESI) m/z: 738.2 (M+Na)⁺.

Example 32B (S)-4-(benzyloxy)-3-(4-(4-(cyclopropylsulfonyl)-3-((methyl((2-(trimethylsilyl)ethoxy)carbonyl)amino)methyl)phenylamino)-4-oxobutan-2-yl)phenylboronic acid

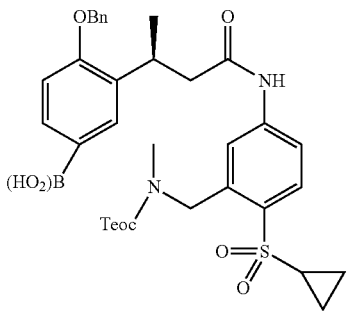

Using a procedure analogous to the one used to prepare Example 8B, Example 32A (0.410 g, 0.573 mmol) was reacted with bis(neopentyl glycolato)diboron (0.141 g, 1.43 mmol) and [1,1'-bis(diphenylphospino)ferrocene]dichloropalladium(II) (47 mg, 0.057 mmol), to yield Example 32B (0.323 g, 83%). MS (ESI) m/z: 703.3 (M+Na)⁺.

Example 32C 2-(4-(Benzyloxy)-3-((S)-4-(4-(cyclopropylsulfonyl)-3-((methyl((2-(trimethylsilyl)ethoxy)carbonyl)amino)methyl)phenylamino)-4-oxobutan-2-yl)phenyl)-2-(1-(bis(tert-butoxycarbonyl)amino)-4-fluoroisoquinolin-6-ylamino)acetic acid

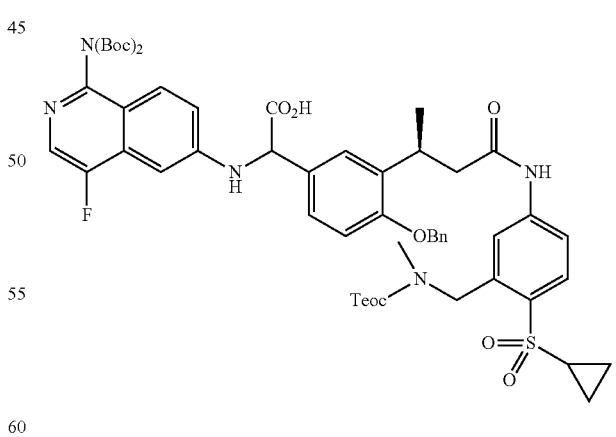

Using a procedure analogous to the one used to prepare Example 8C, Example 32B (0.323 g, 0.475 mmol) and Intermediate 3 (0.179 g, 0.475 mmol) were reacted with glyoxylic acid monohydrate (44 m g, 0.475 mmol) to yield Example 32C (0.180 g, 35%). MS (ESI) m/z: 970.6 (M+H)⁺-boc.

Example 32D 2-(4-(Benzyloxy)-3-((S)-4-(4-(cyclopropylsulfonyl)-3-((methylamino)methyl)phenylamino)-4-oxobutan-2-yl)phenyl)-2-(1-(bis(tert-butoxycarbonyl)amino)-4-fluoroisoquinolin-6-ylamino)acetic acid

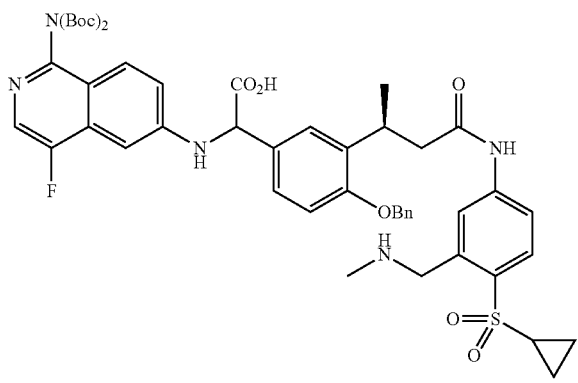

Using a procedure analogous to the one used to prepare Example 8D, Example 32C (0.180 g, 0.168 mmol) was reacted with TBAF (1.68 mL, 1.68 mmol) to yield Example 32D (0.156 g, 100%). MS (ESI) m/z: 927.9 (M+H)$^+$.

Example 32E

[6-((S)-7-Benzyloxy-16-cyclopropanesulfonyl-5,13-dimethyl-3,12-dioxo-2,13-diaza-tricyclo[13.3.1.1$^{6,10}$]icosa-1(18),6,8,10(20),15 (19),16-hexaen-11-ylamino)-4-fluoro-isoquinolin-1-yl]-bis(carbamic acid tert-butyl ester)

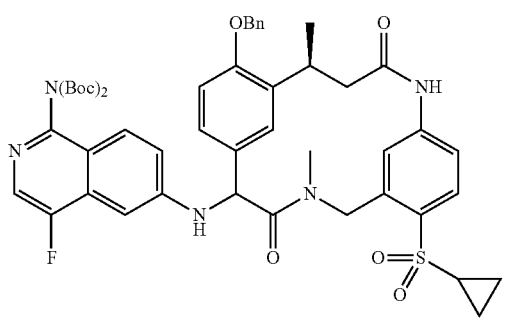

Using a procedure analogous to the one used to prepare Example 8E, Example 32D (0.156 g, 0.168 mmol) was reacted with BOP (0.139 g, 0.337 mmol) to yield Example 32E (37 mg, 24%). MS (ESI) m/z: 909.4 (M+H)$^+$.

Example 32F

[6-((5S,11R)-7-Benzyloxy-16-cyclopropanesulfonyl-5,13-dimethyl-3,12-dioxo-2,13-diaza-tricyclo[13.3.1.1$^{6,10}$]icosa-1(18),6,8,10(20),15(19),16-hexaen-11-ylamino)-4-fluoro-isoquinolin-1-yl]-bis(carbamic acid tert-butyl ester)

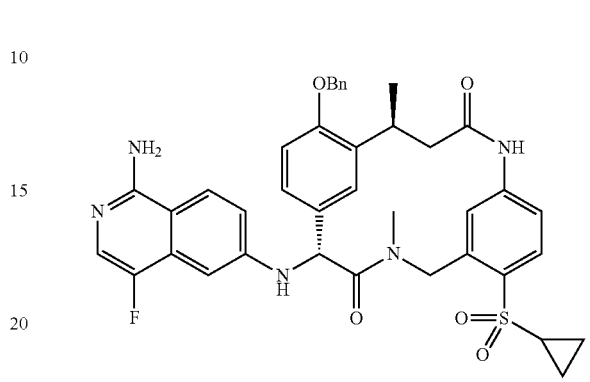

Example 32E (37 mg, 0.041 mmol) was separated by Chiral Prep LC (Chiralcel OD 25×200 mm column, 25% isocratic MeOH/EtOH (1:1) in heptane). The two enantiomers were separated and Peak 1 was collected to yield Example 32F (20 mg, 53%). 1H NMR (400 MHz, CHLOROFORM-d) δ ppm 8.04 (1 H, d, J=2.01 Hz), 7.80 (1 H, d, J=8.53 Hz), 7.64 (1 H, dd, J=9.16, 1.63 Hz), 7.56 (1 H, d, J=7.53 Hz), 7.36-7.49 (5 H, m), 7.22 (1 H, br. s.), 7.03-7.13 (3 H, m), 6.78 (1 H, d, J=1.51 Hz), 6.66 (1 H, br. s.), 6.40-6.53 (1 H, m), 6.37 (1 H, s), 5.61 (1 H, d, J=16.31 Hz), 5.40 (1 H, d, J=1.25 Hz), 5.09-5.24 (2 H, m), 4.53 (1 H, d, J=16.06 Hz), 3.12 (3 H, br. s.), 2.96-3.07 (1 H, m), 2.47-2.56 (1 H, m), 2.36-2.47 (1 H, m), 1.39-1.52 (4 H, m), 1.33 (18 H, s), 0.98-1.21 (3 H, m).

Example 32G

[6-((5S,11R)-16-Cyclopropanesulfonyl-7-hydroxy-5,13-dimethyl-3,12-dioxo-2,13-diaza-tricyclo[13.3.1.1$^{6,10}$]icosa-1(18),6,8,10(20),15(19),16-hexaen-11-ylamino)-4-fluoro-isoquinolin-1-yl]-bis(carbamic acid tert-butyl ester)

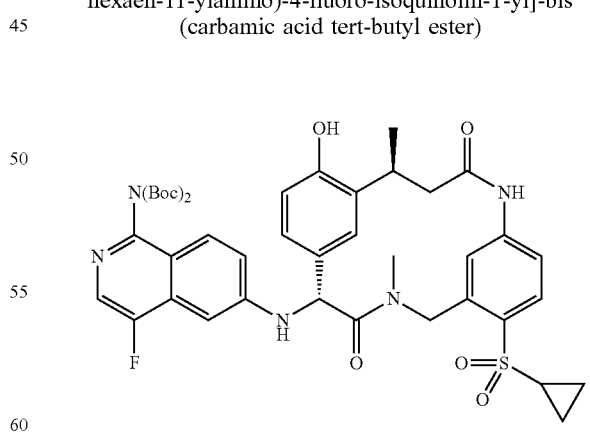

Example 32F (20 mg, 0.022 mmol) was dissolved in MeOH (2.8 mL). Pd/C (29.8 mg, 0.280 mmol) was added and the reaction flushed with hydrogen then sealed with a hydrogen balloon and allowed to stir overnight. The reaction was filtered and concentrated to yield Example 32G (17 mg, 93%). MS (ESI) m/z: 818.4 (M+H)$^+$.

Example 32

Example 32G (16.6 mg, 0.020 mmol) and 2-Bromo-1,1-difluoroethane (1.707 μL, 0.021 mmol) were dissolved in DMF (406 μL). Cs$_2$CO$_3$ (13.23 mg, 0.041 mmol) was added and the reaction was heated to 50° C. and allowed to stir overnight. The reaction was diluted with MeOH and purified by Prep LC (YMC Sunfire 5μ C18 30×100 mm column, 10 min gradient from 40 to 100% B in A, A=10:90:0.1 MeOH:H$_2$O:TFA, B=90:10:0.1 MeOH:H$_2$O:TFA). The isolated product was dissolved in approximately 1 mL of TFA for 30 min then concentrated in vacuo and purified by Prep LC (YMC Sunfire 5μ C18 30×100 mm column, 10 min gradient from 40 to 100% B in A, A=10:90:0.1 MeOH:H$_2$O:TFA, B=90:10:0.1 MeOH:H$_2$O:TFA) to yield Example 32 (6 mg, 36%). 1H NMR (400 MHz, MeOD) δ ppm 8.11 (1 H, dd, J=9.29, 2.01 Hz), 7.81 (1 H, d, J=8.28 Hz), 7.66 (1 H, d, J=7.53 Hz), 7.45 (1 H, d, J=5.02 Hz), 7.27 (1 H, dd, J=9.29, 2.26 Hz), 7.19 (1 H, br. s.), 7.04 (1 H, d, J=8.28 Hz), 6.97 (2 H, dd, J=8.78, 7.28 Hz), 6.82 (1 H, br. s.), 6.11-6.47 (1 H, m), 5.76 (1 H, s), 5.60 (1 H, d, J=16.56 Hz), 4.51 (1 H, d, J=16.56 Hz), 4.20-4.41 (2 H, m), 3.19-3.28 (1 H, m), 3.10 (3 H, br. s.), 2.87-2.95 (1 H, m), 2.74-2.83 (1 H, m), 2.55 (1 H, d, J=8.28 Hz), 1.51 (3 H, d, J=6.78 Hz), 1.20-1.33 (1 H, m), 0.98-1.17 (3 H, m). MS (ESI) m/z: 682.2 (M+H)$^+$. Analytical HPLC (low pH, 220 nM): Sunfire C18, RT=6.105 min.

Example 33

(R)-11-(1-Amino-4-fluoro-isoquinolin-6-ylamino)-16-cyclopropane sulfonyl-7-(2,2-difluoro-ethoxy)-13-methyl-2,13-diaza-tricyclo[13.3.1.1$^{6,10}$]icosa-1(18),6,8,10(20),15(19),16-hexaene-3,12-dione trifluoroacetic acid salt+Enantiomer

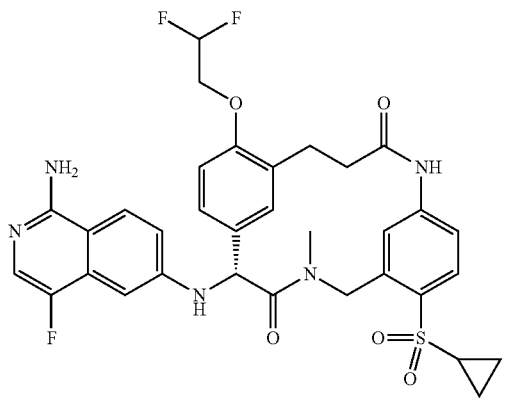 [SMILES: CN1Cc2cc(ccc2S(=O)(=O)C2CC2)NC(=O)CCc2cc(ccc2OCC(F)F)[C@@H](Nc2ccc3c(N)ncc(F)c3c2)C1=O]

Example 33A 2-(Trimethylsilyl)ethyl 5-(3-(5-bromo-2-(2,2-difluoroethoxy)phenyl)propanamido)-2-(trifluoromethylsulfonyl)benzyl(methyl)carbamate

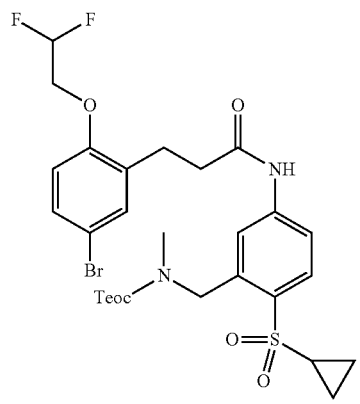

Using a procedure analogous to the one used to prepare Example 8A, Intermediate 6 (0.120 g, 0.388 mmol) was reacted with oxalyl chloride (0.214 mL, 0.427 mmol) and Intermediate 2 (0.240 g, 0.582 mmol), to yield 33A (0.187 g, 68%). MS (ESI) m/z: 726.1 (M+Na)$^+$.

Example 33B 4-(2,2-Difluoroethoxy)-3-(3-(3-((methyl((2-(trimethylsilyl)ethoxy)carbonyl)amino)methyl)-4-(trifluoromethylsulfonyl)phenylamino)-3-oxopropyl)phenylboronic acid

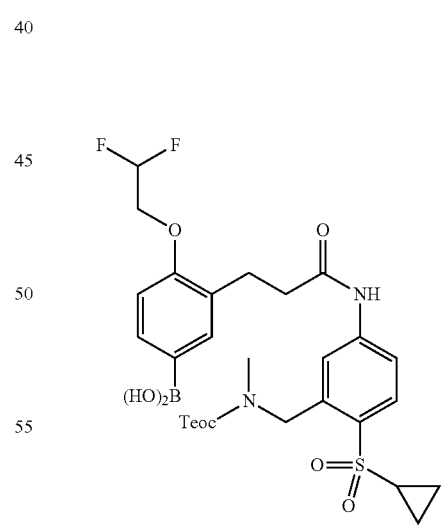

Using a procedure analogous to the one used to prepare Example 8B, Example 33A (0.187 g, 0.265 mmol) was reacted with bis(neopentyl glycolato)diboron (84 mg, 0.372 mmol) and [1,1'-bis(diphenylphospino)ferrocene]dichloropalladium(II) (22 mg, 0.027 mmol), to yield Example 33B (63 mg, 35%). MS (ESI) m/z: 640.3 (M-28)$^+$.

Example 33C 2-(1-(Bis(tert-butoxycarbonyl)amino)-4-fluoroiso-quinolin-6-ylamino)-2-(4-(2,2-difluoroethoxy)-3-(3-(3-((methyl((2-(trimethylsilyl)ethoxy)carbonyl)amino)methyl)-4-(trifluoromethylsulfonyl)phenylamino)-3-oxopropyl)phenyl)acetic acid

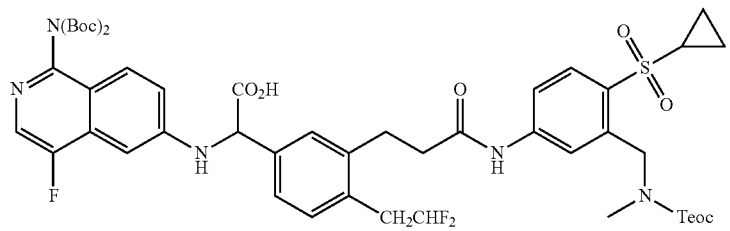

Using a procedure analogous to the one used to prepare Example 8C, Example 33B (63 mg, 0.094 mmol) and Intermediate 3 (35 mg, 0.094 mmol) were reacted with glyoxylic acid monohydrate (8.7 mg, 0.094 mmol) to yield Example 33C (53 mg, 53%). MS (ESI) m/z: 959.4 (M+H)$^+$-boc.

Example 33D 2-(1-(Bis(tert-butoxycarbonyl)amino)-4-fluoroiso-quinolin-6-ylamino)-2-(4-(2,2-difluoroethoxy)-3-(3-(3-((methylamino)methyl)-4-(trifluoromethylsulfonyl)phenylamino)-3-oxopropyl)phenyl)acetic acid

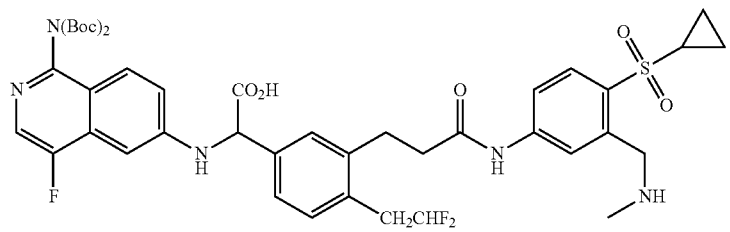

Using a procedure analogous to the one used to prepare Example 8D, Example 33C (53 mg, 0.050 mmol) was reacted with TBAF (0.496 mL, 0.496 mmol) to yield Example 33D (45 mg, 100%). MS (ESI) m/z: 914.8 (M+H)$^+$.

Example 33E

{6-[16-Cyclopropanesulfonyl-7-(2,2-difluoro-ethoxy)-13-methyl-3,12-dioxo-2,13-diaza-tricyclo[13.3.1.1$^{6,10}$]icosa-1(18),6,8,10(20),15(19),16-hexaen-11-ylamino]-4-fluoro-isoquinolin-1-yl}-bis(carbamic acid tert-butyl ester)

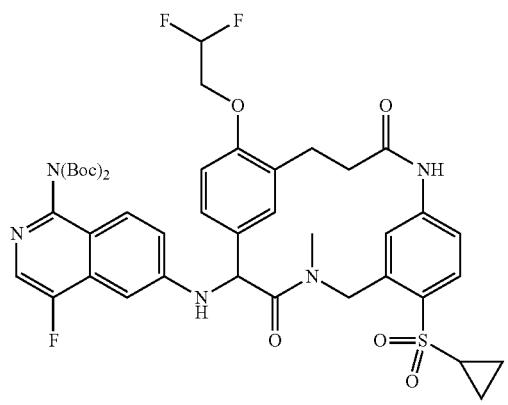

Using a procedure analogous to the one used to prepare Example 8E, Example 33D (45 mg, 0.050 mmol) was reacted with BOP (44 mg, 0.099 mmol) to yield Example 33E (44 mg, 45%). MS (ESI) m/z: 896.3 (M+H)$^+$.

Example 33

Example 33E (35 mg, 0.039 mmol) was separated by Chiral Prep LC (Chiralcel OD-H 25×200 mm column, 30% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 33 (10 mg, 32%). 1H NMR (400 MHz, METHANOL-d$_3$) δ ppm 8.10 (1 H, d, J=10.99 Hz), 8.02 (1 H, d, J=8.24 Hz), 7.63 (1 H, dd, J=8.25, 2.20 Hz), 7.44 (1 H, d, J=4.95 Hz), 7.22-7.29 (2 H, m), 7.13 (1 H, s), 7.08 (1 H, dd, J=8.25, 2.20 Hz), 7.03 (1 H, d, J=8.24 Hz), 6.93 (1 H, s), 6.24 (1 H, tt, J=54.97, 3.57 Hz), 5.80 (1 H, s), 5.59 (1 H, d, J=17.04 Hz), 4.42 (1 H, d, J=17.04 Hz), 4.31 (2 H, tt, J=13.95, 4.26, 4.12 Hz), 3.26-3.30 (1 H, m), 3.16 (3 H, s), 2.81-2.92 (1 H, m), 2.62-2.76 (2 H, m). MS (ESI) m/z: 696.2 (M+H)$^+$. Analytical HPLC (low pH, 220 nM): XBridge Phenyl, RT=7.969 min.

Example 34

(R)-11-(1-Amino-isoquinolin-6-ylamino)-7-methoxy-13-methyl-16-trifluoromethanesulfonyl-2,13-diaza-tricyclo[13.3.1.1$^{6,10}$]icosa-1(19),6,8,10(20),15,17-hexaene-3,12-dione trifluoroacetic acid salt+ Enantiomer

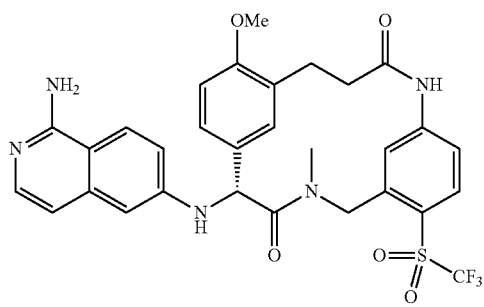 [SMILES: COc1ccc2cc1CCC(=O)Nc1ccc(S(=O)(=O)C(F)(F)F)c(c1)CN(C)C(=O)[C@@H]2Nc1ccc2c(N)nccc2c1]

Example 34A 2-(Trimethylsilyl)ethyl 5-(3-(5-bromo-2-methoxy-phenyl)propanamido)-2-(trifluoromethylsulfonyl)benzyl(methyl)carbamate

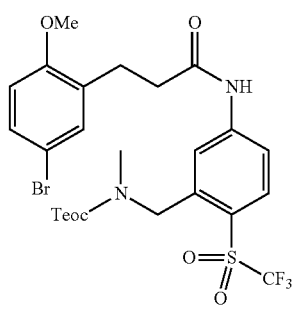

Using a procedure analogous to the one used to prepare Example 8A, Intermediate 10 (0.300 g, 1.16 mmol) was reacted with oxalyl chloride (0.637 mL, 1.27 mmol) and Intermediate 11 (0.584 g, 1.27 mmol), to yield Example 34A (0.300 g, 40%). MS (ESI) m/z: 627.1 (M+H)$^+$-28. M-28 peak is typical for Teoc containing compounds

Example 34B

4-Methoxy-3-(3-(3-((methyl((2-(trimethylsilyl)ethoxy)carbonyl)amino)methyl)-4-(trifluoromethylsulfonyl)phenylamino)-3-oxopropyl)phenylboronic acid

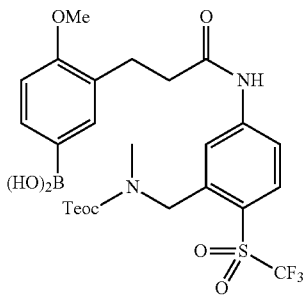

Using a procedure analogous to the one used to prepare Example 8B, Example 34A (0.300 g, 0.459 mmol) was reacted with bis(neopentyl glycolato)diboron (0.104 g, 0.459 mmol) and [1,1'-bis(diphenylphospino)ferrocene]dichloropalladium(II) (17 mg, 0.023 mmol), to yield Example 34B (0.167 g, 59%). MS (ESI) m/z: 595.2 (M-28)$^+$. M-28 peak typical with Teoc containing compounds.

Example 34C 2-(1-(Bis(tert-butoxycarbonyl)amino)isoquinolin-6-ylamino)-2-(4-methoxy-3-(3-(3-((methyl((2-(trimethylsilyl)ethoxy)carbonyl)amino)methyl)-4-(trifluoromethylsulfonyl)phenylamino)-3-oxopropyl)phenyl)acetic acid

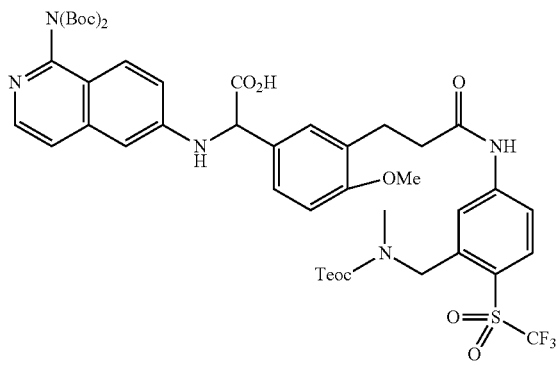

Using a procedure analogous to the one used to prepare Example 8C, Example 34B (0.167 g, 0.270 mmol) and imidodicarbonic acid, 2-(6-amino-1-isoquinolinyl)-, 1,3-bis(1,1-dimethylethyl) ester (97 mg, 0.270 mmol) were reacted with Glyoxylic acid monohydrate (25 mg, 0.270 mmol) to yield Example 34C (0.254 g, 95%). MS (ESI) m/z: 991.4 (M+H)$^+$.

Example 34D 2-(1-(Bis(tert-butoxycarbonyl)amino)isoquinolin-6-ylamino)-2-(4-methoxy-3-(3-(3-((methylamino)methyl)-4-(trifluoromethylsulfonyl)phenylamino)-3-oxopropyl)phenyl)acetic acid

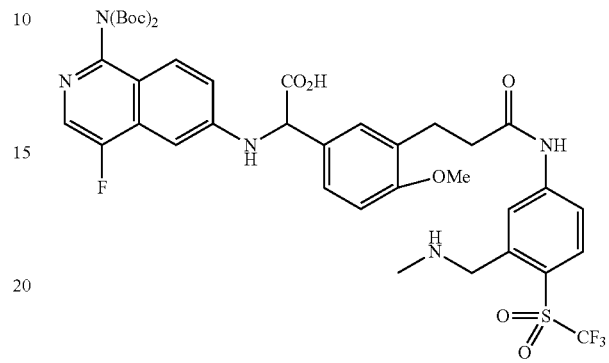

Using a procedure analogous to the one used to prepare Example 8D, Example 34C (0.254 g, 0.257 mmol) was reacted with TBAF (2.57 mL, 2.57 mmol) to yield Example 34D (0.217 g, 100%). MS (ESI) m/z: 846.2 (M+H)$^+$.

Example 34E 11-(1-Amino-isoquinolin-6-ylamino)-16-trifluoromethylsulfonyl-7-methoxy-13-methyl-2,13-diaza-tricyclo[13.3.1.1$^{6,10}$]icosa-1(19),6,8,10(20),15,17-hexaene-3,12-dione

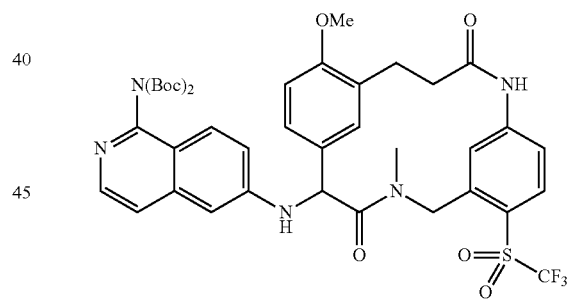

Using a procedure analogous to the one used to prepare Example 8E, Example 34D (0.107 g, 0.126 mmol) was reacted with BOP (0.112 g, 0.253 mmol) to yield Example 34E (42 mg, 40%). MS (ESI) m/z: 828.3 (M+H)$^+$.

Example 34

Example 34E (78 mg, 0.094 mmol) was separated by Chiral Prep LC (Whelco-01 25×200 mm column, 30% isocratic MeOH/EtOH (1:1) in heptane). The two enantiomers were separated and Peak 2 was collected to yield Example 34 (26 mg, 36%). 1H NMR (400 MHz, MeOD) δ ppm 8.01 (2 H, dd, J=8.66, 5.14 Hz), 7.58 (1 H, dd, J=8.53, 2.26 Hz), 7.34 (1 H, d, J=7.03 Hz), 7.23 (1 H, d, J=2.01 Hz), 7.11-7.19 (2 H, m), 7.06 (1 H, dd, J=8.66, 1.88 Hz), 6.99 (1 H, d, J=8.53 Hz), 6.89 (1 H, d, J=7.03 Hz), 6.77 (1 H, d, J=2.01 Hz), 5.53-5.73 (2 H, m), 4.33-4.61 (2 H, m), 3.88 (3

H, s), 3.16 (3 H, s), 2.78-2.94 (1 H, m), 2.57-2.72 (2 H, m). MS (ESI) m/z: 628.1 (M+H)⁺. Analytical HPLC (low pH, 254 nM): Sunfire, RT=6.31 min.

Example 35

4-((R)-19-Difluoromethoxy-18-fluoro-3,13-dimethyl-4,14-dioxo-3,13,15-triaza-tricyclo[14.3.1.1$^{6,10}$] henicosa-1(19),6(21),7,9,16(20),17-hexaen-5-ylamino)-benzamidine trifluoroacetic acid salt+ Enantiomer

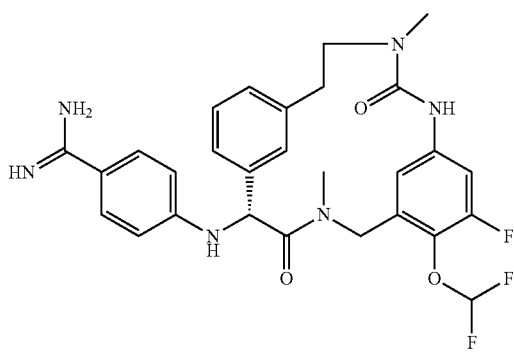 [SMILES: CN1CCc2cccc(c2)[C@@H](Nc2ccc(C(=N)N)cc2)C(=O)N(C)Cc2cc(cc(F)c2OC(F)F)NC1=O]

Example 35A 2-(trimethylsilyl)ethyl 3-(2-((5-amino-2-(difluoromethoxy)-3-fluorobenzyl)(methyl)amino)-1-(4-cyanophenylamino)-2-oxoethyl)phenethyl(methyl) carbamate

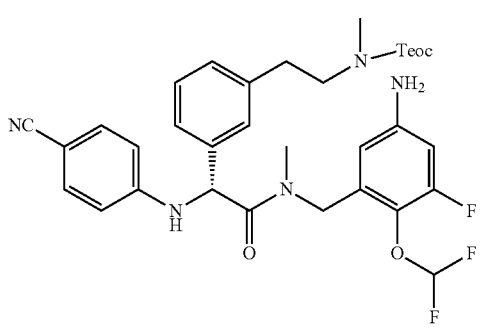

Using a procedure analogous to the one used to prepare Example 19B, Example 28C (0.136 g, 0.421 mmol) was reacted with 4-aminobenzonitrile (50 mg, 0.421 mmol) and 2-oxoacetic acid, monohydrate (39 mg, 0.421 mmol), Intermediate 7 (0.160 g, 0.547 mmol), and BOP (0.186 g, 0.421 mmol) to yield Example 35A (0.276 g, 100%). MS (ESI) m/z: 656.3 (M+H)⁺.

Example 35B

N-(5-amino-2-(difluoromethoxy)-3-fluorobenzyl)-2-(4-cyanophenylamino)-N-methyl-2-(3-(2-(methylamino)ethyl)phenyl)acetamide

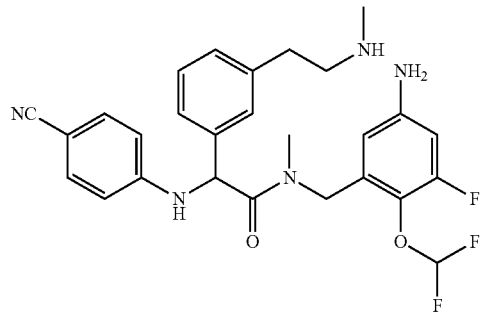 [SMILES: CNCCc1cccc(C(Nc2ccc(C#N)cc2)C(=O)N(C)Cc2cc(N)cc(F)c2OC(F)F)c1]

Using a procedure analogous to the one used to prepare Example 19C, Example 35A (0.276 g, 0.421 mmol) was reacted TBAF (4.21 mL, 4.21 mmol) to yield Example 35B (0.114 g, 53%). MS (ESI) m/z: 512.2 (M+H)⁺.

Example 35C 4-((R)-19-Difluoromethoxy-18-fluoro-3,13-dimethyl-4,14-dioxo-3,13,15-triaza-tricyclo[14.3.1.1$^{6,10}$] henicosa-1(19),6(21),7,9,16(20),17-hexaen-5-ylamino)-benzonitrile

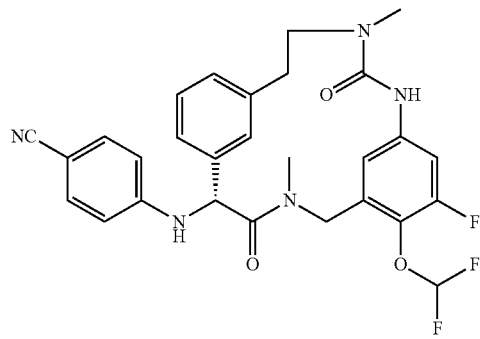 [SMILES: CN1CCc2cccc(c2)[C@@H](Nc2ccc(C#N)cc2)C(=O)N(C)Cc2cc(cc(F)c2OC(F)F)NC1=O]

Using a procedure analogous to the one used to prepare Example 19D, Example 35B 0.116 g, 0.227 mmol) was reacted with pyridine (0.183 mL, 2.268 mmol and p-nitrophenyl chloroformate (0.229 g, 1.134 mmol) which was separated by Chiral Prep LC (Whelco-01 25×200 mm column, 30% isocratic MeOH/EtOH (1:1) in heptane). Peak 1 was collected to yield Example 35C (19 mg, 39%). MS (ESI) m/z: 538.2 (M+H)⁺.

Example 35

Using a procedure analogous to the one used to prepare Example 40, Example 35C was reacted with hydroxylamine hydrochloride (73 mg, 1.055 mmol). The resultant product was reduced with H₂ using Pd/C (10%) catalyst to yield Example 35 (6.4 mg, 26% yield). MS (ESI) m/z: 555.2 (M+H)⁺. Analytical HPLC (low pH, 254 nM): Sunfire, RT=5.56 min.

Example 36

(R)-11-(5-Amino-8-fluoro-naphthalen-2-ylamino)-16-cyclopropanesulfonyl-7-cyclopropyl-13-methyl-2,13-diaza-tricyclo[13.3.1.1^{6,10}]icosa-1(18),6,8,10(20),15(19),16-hexaene-3,12-dione trifluoroacetic acid salt+Enantiomer

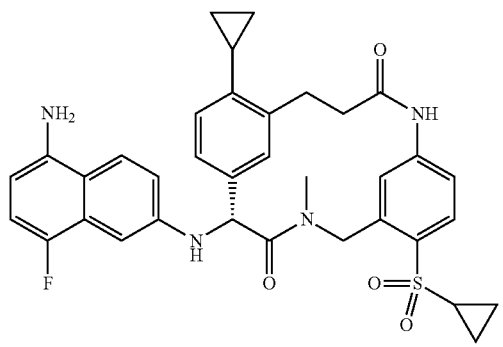 [SMILES: CN1Cc2cc(ccc2S(=O)(=O)C2CC2)NC(=O)CCc2cc(ccc2C2CC2)[C@@H](Nc2ccc3c(N)ccc(F)c3c2)C1=O]

Example 36A

2-Cyclopropyl-5-nitrobenzaldehyde

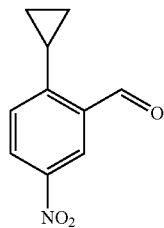 [SMILES: O=Cc1cc([N+](=O)[O-])ccc1C1CC1]

2-Bromo-5-nitrobenzaldehyde (100 mg, 0.435 mmol), cyclopropylboronic acid (48.5 mg, 0.565 mmol), palladium (II) acetate (4.88 mg, 0.022 mmol), tricyclohexylphosphine (12.19 mg, 0.043 mmol), and Potassium orthophosphate (323 mg, 1.522 mmol) were degassed by HIVAC/$N_2$ backfill thrice. Toluene (1.76 mL) and water (138 µL) were added and the reaction degassed by bubbling 15 min with Ar. The reaction was heated to 100° C. overnight. The reaction was diluted with EtOAc and washed twice with water, brine, dried ($Na_2SO_4$), filtered, and concentrated in vacuo. The crude material was purified by silica gel column chromatography (0 to 100% EtOAc in hexanes) to yield 36A (43 mg, 52%). 1H NMR (400 MHz, CHLOROFORM-d) δ ppm 10.59 (1 H, s), 8.63 (1 H, d, J=2.51 Hz), 8.30 (1 H, dd, J=8.41, 2.38 Hz), 7.24 (1 H, d, J=8.53 Hz), 2.83 (1 H, tt, J=8.41, 5.27 Hz), 1.21-1.36 (2 H, m), 0.87-1.03 (2 H, m).

Example 36B (E)-methyl 3-(2-cyclopropyl-5-nitrophenyl)acrylate

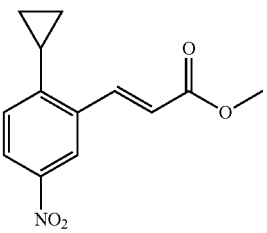 [SMILES: COC(=O)/C=C/c1cc([N+](=O)[O-])ccc1C1CC1]

Example 36A 0.2 g, 1.046 mmol) was dissolved in toluene (12.45 mL Methyl (triphenylphosphoranylidine)acetate (0.350 g, 1.046 mmol) was added, and the reaction heated to reflux overnight. The reaction was concentrated in vacuo. The crude material was purified by silica gel column chromatography (0 to 100% EtOAc in hexanes) to yield Example 36B (0.252 g, 97%). 1H NMR (400 MHz, CHLOROFORM-d) δ ppm 8.37 (1 H, d, J=2.51 Hz), 8.25 (1 H, d, J=16.06 Hz), 8.12 (1 H, dd, J=8.53, 2.51 Hz), 7.17 (1 H, d, J=8.53 Hz), 6.52 (1 H, d, J=15.81 Hz), 3.85 (3 H, s), 2.13 (1 H, tt, J=8.44, 5.36 Hz), 1.14-1.23 (2 H, m), 0.78-0.87 (2 H, m).

Example 36C

Methyl 3-(5-amino-2-cyclopropylphenyl)propanoate

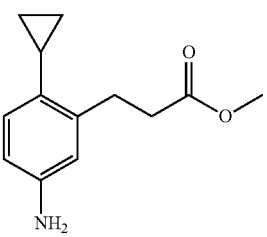 [SMILES: COC(=O)CCc1cc(N)ccc1C1CC1]

Example 36B (50 mg, 0.202 mmol) was dissolved in MeOH (2.02 mL). Pd/C (21.52 mg, 0.020 mmol) was added and the reaction sealed under an atmosphere of hydrogen. The reaction was allowed to stir for 3 h. The reaction was filtered through a syringe filter and concentrated in vacuo to yield Example 36C (42 mg, 94%). 1H NMR (400 MHz, CHLOROFORM-d) δ ppm 6.82 (1 H, d, J=8.28 Hz), 6.44-6.65 (2 H, m), 4.01 (2 H, br. s.), 3.69 (3 H, s), 2.99-3.12 (2 H, m), 2.58-2.68 (2 H, m), 1.72-1.90 (1 H, m, J=8.34, 8.34, 5.52, 5.40 Hz), 0.79-0.94 (2 H, m), 0.48-0.66 (2 H, m).

Example 36D methyl 3-(2-cyclopropyl-5-iodophenyl)propanoate

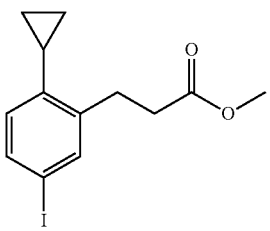 [SMILES: COC(=O)CCc1cc(I)ccc1C1CC1]

Nitrosonium tetrafluoroborate (19.52 mg, 0.167 mmol) was dissolved in MeCN (570 μL) and cooled to −40° C. A solution of Example 36C (33 mg, 0.152 mmol) in MeCN (190 μL) was added, and the reaction was warmed to 0° C. then cooled back to −40° C. over the ensuing 30 min. A mixture of sodium iodide (45.5 mg, 0.304 mmol) and iodine (38.6 mg, 0.152 mmol) was added portionwise, and the reaction was allowed to warm to −10° C. and quenched with saturated $Na_2SO_3$ then DCM. The organic layer was washed with water, brine, dried ($Na_2SO_4$), filtered, and concentrated in vacuo. The crude reaction mixture was purified by Prep LC (YMC Sunfire 5μ C18 30×100 mm column, 16 min gradient from 60 to 100% B in A, A=10:90:0.1 MeOH:$H_2O$:TFA, B=90:10:0.1 MeOH:$H_2O$:TFA) to yield Example 36D (5.7 mg, 11%) 1H NMR (400 MHz, CHLOROFORM-d) δ ppm 7.41-7.50 (2 H, m), 6.70 (1 H, d, J=8.28 Hz), 3.70 (3 H, s), 3.03-3.13 (2 H, m), 2.60-2.69 (2 H, m), 1.81-1.92 (1 H, m, J=8.34, 8.34, 5.52, 5.40 Hz), 0.93-1.01 (2 H, m), 0.60-0.68 (2 H, m).

Example 36E 3-(2-Cyclopropyl-5-iodophenyl)propanoic acid

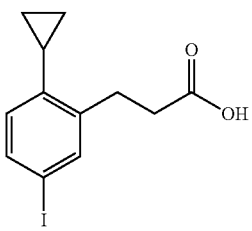 [SMILES: O=C(O)CCc1cc(I)ccc1C1CC1]

Example 36D (222 mg, 0.672 mmol) was dissolved in THF (6.11 mL) and MeOH (611 μL). NaOH (1 mL, 1.009 mmol) was added at ambient temperature, and the reaction was allowed to stir overnight. The reaction was diluted with 1N NaOH and washed with DCM. The aqueous layer was acidified with HCl and extracted twice with EtOAc. The combined EtOAc layers were washed with brine, dried ($Na_2SO_4$), filtered, and concentrated in vacuo as to yield Example 36E (0.206 g, 97%). 1H NMR (400 MHz, CHLOROFORM-d) δ ppm 7.49 (1 H, s), 7.46 (1 H, d, J=7.70 Hz), 6.71 (1 H, d, J=8.25 Hz), 3.05-3.14 (2 H, m), 2.66-2.74 (2 H, m), 1.81-1.92 (1 H, m), 0.94-1.01 (2 H, m), 0.61-0.67 (2 H, m).

Example 36F 2-(trimethylsilyl)ethyl 5-(3-(2-cyclopropyl-5-iodophenyl)propanamido)-2-(cyclopropylsulfonyl)benzyl (methyl)carbamate

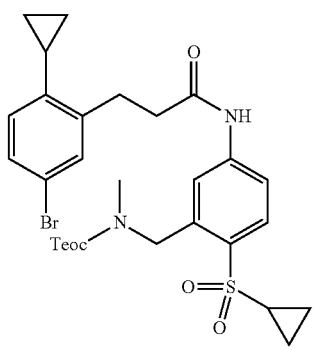

Using a procedure analogous to the one used to prepare Example 8A, Example 36E (0.206 g, 0.652 mmol) was reacted with oxalyl chloride (0.358 mL, 0.717 mmol) and Intermediate 2 (0.240 g, 0.582 mmol), to yield Example 36F (0.412 g, 93%). MS (ESI) m/z: 655.2 (M-28)$^+$.

Example 36G 4-cyclopropyl-3-(3-(4-(cyclopropylsulfonyl)-3-((methyl((2-(trimethylsilyl)ethoxy)carbonyl)amino) methyl)phenylamino)-3-oxopropyl)phenylboronic acid

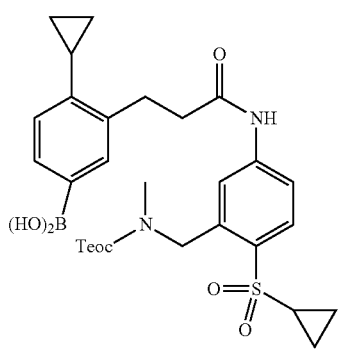

Using a procedure analogous to the one used to prepare Exanoke 8B, Exanoke 36F (0.412 g, 0.627 mmol) was reacted with bis(neopentyl glycolato)diboron (0.198 g, 0.878 mmol) and [1,1'-bis(diphenylphospino)ferrocene]dichloropalladium(II) (52 mg, 0.063 mmol), to yield Example 36G (0.207 g, 55%) which was used immediately after purification.

Example 36H 2-(1-(bis(tert-butoxycarbonyl)amino)-4-fluoroisoquinolin-6-ylamino)-2-(4-cyclopropyl-3-(3-(4-(cyclopropylsulfonyl)-3-((methyl((2-(trimethylsilyl)ethoxy)carbonyl)amino)methyl)phenylamino)-3-oxopropyl)phenyl)acetic acid

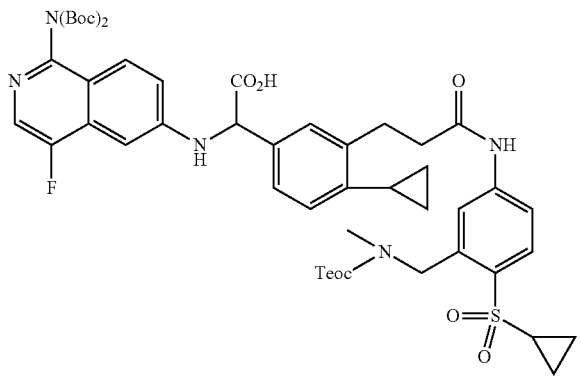

Using a procedure analogous to the one used to prepare Example 8C, Example 36G (0.207 g, 0.345 mmol) and Intermediate 3 (0.130 g, 0.345 mmol) were reacted with glyoxylic acid monohydrate (32 mg, 0.345 mmol) to yield Example 36H (0.163 g, 48%). MS (ESI) m/z: 991.4 (M+H)$^+$.

Example 36I 2-(1-(bis(tert-butoxycarbonyl)amino)-4-fluoroisoquinolin-6-ylamino)-2-(4-cyclopropyl-3-(3-(4-(cyclopropylsulfonyl)-3-((methylamino)methyl)phenylamino)-3-oxopropyl)phenyl)acetic acid

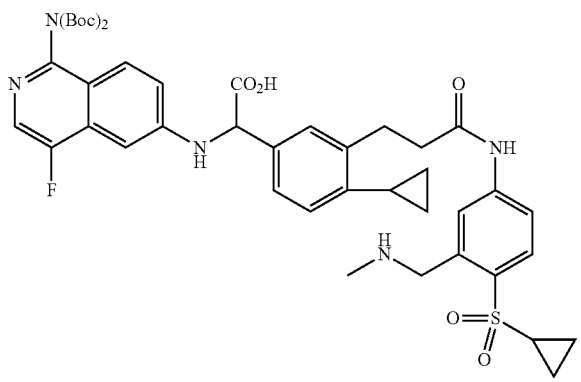

Using a procedure analogous to the one used to prepare Example 8D, Example 36H (163 mg, 0.165 mmol) was reacted with TBAF (1.65 mL, 1.65 mmol) to yield Example 36I (0.139 g, 100%). MS (ESI) m/z: 846.5 (M+H)$^+$.

Example 36J

[6-(16-Cyclopropanesulfonyl-7-cyclopropyl-13-methyl-3,12-dioxo-2,13-diaza-tricyclo[13.3.1.1$^{6,10}$]icosa-1(18),6,8,10(20),15(19),16-hexaen-11-ylamino)-4-fluoro-isoquinolin-1-yl]-bis(carbamic acid tert-butyl ester)

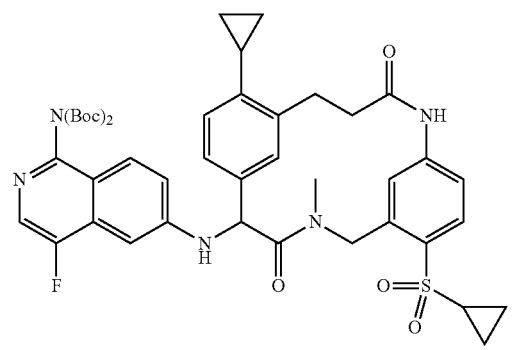

Using a procedure analogous to the one used to prepare Example 8E, Example 36I (0.139 g, 0.164 mmol) was reacted with BOP (0.145 g, 0.329 mmol) to yield Example 36J (0.111 g, 82%). MS (ESI) m/z: 828.2 (M+H)$^+$.

Example 36

Example 36J (111 mg, 0.134 mmol) was separated by Chiral Prep LC (Chiralcel AD 25×200 mm column, 60% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 36 (30 mg, 30%). 1H NMR (400 MHz, MeOD) δ ppm 8.08 (1 H, dd, J=9.29, 1.51 Hz), 7.80 (1 H, d, J=8.28 Hz), 7.51 (1 H, dd, J=7.91, 1.88 Hz), 7.42 (1 H, d, J=4.77 Hz), 7.31 (1 H, d, J=2.01 Hz), 7.24 (1 H, dd, J=9.29, 2.01 Hz), 7.03 (1 H, s), 7.01 (1 H, d, J=7.78 Hz), 6.95 (1 H, dd, J=8.53, 2.01 Hz), 6.91 (1 H, s), 5.77 (1 H, s), 5.64 (1 H, d, J=16.31 Hz), 4.55 (1 H, d, J=16.31 Hz), 3.46 (1 H, ddd, J=13.36, 4.58, 4.39 Hz), 3.13 (3 H, s), 3.04-3.12 (1 H, m), 2.64-2.82 (3 H, m), 2.02-2.13 (1 H, m), 1.20-1.28 (1 H, m), 0.96-1.17 (5 H, m), 0.76-0.84 (1 H, m), 0.58-0.67 (1 H, m). MS (ESI) m/z: 628.1 (M+H)$^+$. Analytical HPLC (low pH, 220 nM): Sunfire C18, RT=5.943.

Example 37

4-((R)-16-Difluoromethoxy-17-fluoro-3,12-dioxo-2,13-diaza-tricyclo[13.3.1.1$^{6,10}$]icosa-1(19),6,8,10(20),15,17-hexaen-11-ylamino)-benzamidine trifluoroacetic acid salt+Enantiomer

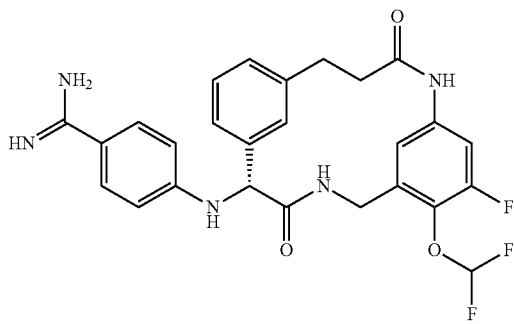 [SMILES: N=C(N)c1ccc(N[C@H]2C(=O)NCc3cc(cc(F)c3OC(F)F)NC(=O)CCc3cccc2c3)cc1]

Example 37A methyl 3-(3-bromophenyl)propanoate

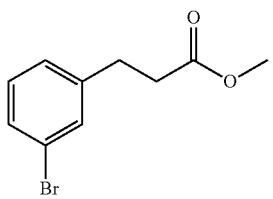

3-(3-bromophenyl)propanoic acid (1 g, 4.37 mmol) was dissolved in MeOH (17.46 mL). SOCl$_2$ (1.593 mL, 21.83 mmol) was added dropwise, and the reaction heated to reflux for 3 h. The reaction was concentrated in vacuo to yield Example 37A (1.08 g, 100%). 1H NMR (400 MHz, CHLOROFORM-d) δ ppm 7.30-7.42 (2 H, m), 7.06-7.21 (2 H, m), 3.67 (3 H, s), 2.92 (2 H, t, J=7.78 Hz), 2.62 (2 H, t, J=7.65 Hz).

Example 37B 3-(3-methoxy-3-oxopropyl)phenylboronic acid

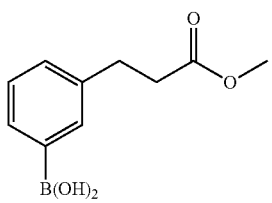

DMSO (6.86 mL) and dioxane (6.86 mL) were degassed for 15 min by bubbling with argon. Meanwhile, Example 37A (400 mg, 1.645 mmol), KOAc (404 mg, 4.11 mmol), and bis(neopentyl glycolato)diboron (520 mg, 2.304 mmol) were placed in a microwave tube. To these compounds was added the degassed solvents. The tube was sealed and degassed for an additional 15 min. [1,1'-bis(diphenylphosphino)ferrocene]dichloropalladium(II) (135 mg, 0.165 mmol) was subsequently added, the tube sealed, and heated to 90° C. and allowed to stir overnight. The reaction was diluted with EtOAc and washed twice with brine, dried (Na$_2$SO$_4$), filtered, and concentrated in vacuo. The crude reaction mixture was purified by Prep LC (Axia Luna 5μ C18 30×100 mm column, 10 min gradient from 40 to 100% B in A, A=10:90:0.1 MeCN:H$_2$O:TFA, B=90:10:0.1 MeCN:H$_2$O:TFA) to yield Example 37B (0.224 g, 64%) which was used immediately after purification.

Example 37C

Methyl 3-(3-(2-((5-amino-2-(difluoromethoxy)-3-fluorobenzyl)(methyl)amino)-1-(4-cyanophenylamino)-2-oxoethyl)phenyl)propanoate

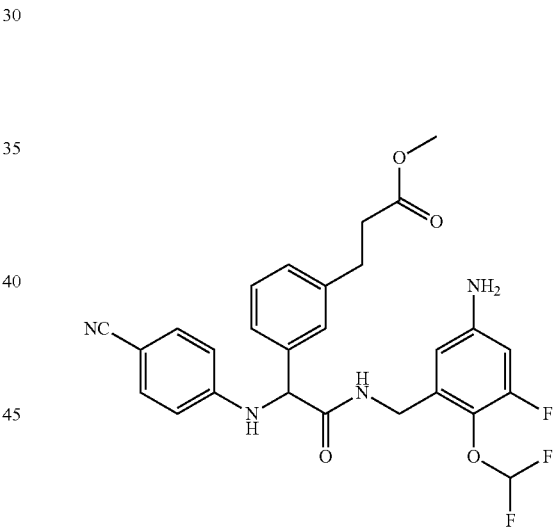

Example 37B (224 mg, 1.077 mmol), p-aminobenzonitrile (127 mg, 1.077 mmol), and glyoxylic acid monohydrate (99 mg, 1.077 mmol) were dissolved in DMF (2.99 mL) and MeCN (8.97 mL) and heated to 80° C. and stirred for 3 h. The reaction was cooled to ambient temperature. Intermediate 7 (379 mg, 1.292 mmol), DIPEA (940 μL, 5.38 mmol), and BOP (476 mg, 1.077 mmol) were added and allowed to stir overnight. The reaction was diluted with water and extracted thrice with EtOAc. The combined organic layers were washed with brine, dried (Na$_2$SO$_4$), filtered, and concentrated in vacuo. The crude material was purified by silica gel column chromatography (0 to 100% EtOAc in hexanes) to yield Example 37C (0.347 g, 60%). MS (ESI) m/z: 541.2 (M+H)$^+$.

Example 37D 3-(3-(2-((5-Amino-2-(difluoromethoxy)-3-fluorobenzyl)(methyl)amino)-1-(4-cyanophenylamino)-2-oxoethyl)phenyl)propanoic acid

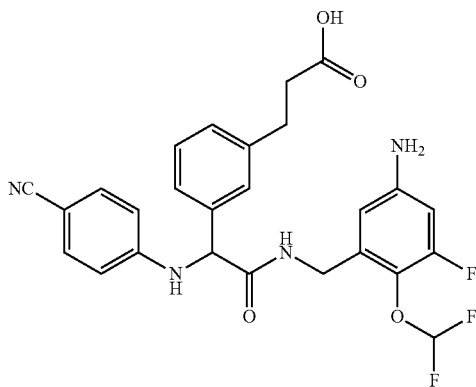 [SMILES: N#Cc1ccc(NC(C(=O)NCc2cc(N)cc(F)c2OC(F)F)c2cccc(CCC(=O)O)c2)cc1]

Example 37C (347 mg, 0.642 mmol) was dissolved in THF (5.84 mL) and MeOH (584 µL). 1 N NaOH (706 µL, 0.706 mmol) was added and the reaction was allowed to stir overnight. The reaction was diluted with 1 N NaOH and water, then washed with DCM. The aqueous layer was acidified with HCl and extracted twice with EtOAc. The combined EtOAc layers were washed with brine, dried (Na$_2$SO$_4$), filtered, and concentrated in vacuo to yield Example 37D (0.327 g, 97%). MS (ESI) m/z: 527.1 (M+H)$^+$.

37E

4-[16 difluoromethoxy-17-fluoro-13-methyl-3,12-dioxo-2,13-diazatricyclo[13.3.1.1$^{6,10}$]icosa-1(19),6,8,10(20),15,17-hexaene-11-ylamino]-benzonitrile

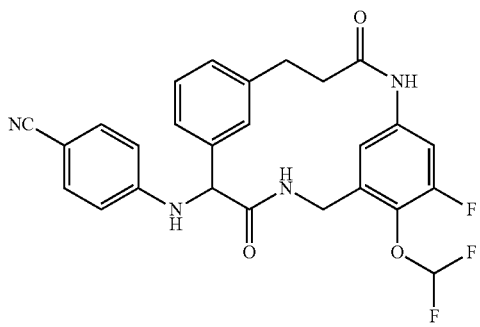 [SMILES: N#Cc1ccc(NC2C(=O)NCc3cc(cc(F)c3OC(F)F)NC(=O)CCc3cccc2c3)cc1]

BOP (0.462 g, 1.045 mmol) and DMAP (0.255 g, 2.089 mmol) were dissolved in DCM (95 mL) and DMF (9.50 mL) and heated to 40° C. A solution of Example 37D (0.275 g, 0.522 mmol) and DIPEA (0.274 mL, 1.567 mmol) in DMF (ca 5 mL) was added by syringe pump over the course of 5 hours. The reaction was allowed to stir overnight. The reaction was heated to 50° C. and blown with Argon to remove the DCM. The reaction was then diluted with EtOAc, washed with 1 N HCl, saturated NaHCO$_3$, then brine, dried (Na$_2$SO$_4$), filtered, and concentrated in vacuo. The crude reaction mixture was purified by silica gel column chromatography (0 to 100% EtOAc in hexanes) to yield Example 37E (0.214 g, 80%). MS (ESI) m/z: 509.0 (M+H)$^+$.

Example 37

Example 37E (214 mg, 0.421 mmol) was separated by Chiral Prep LC (Welco-01 25×200 mm column, 35% isocratic MeOH/EtOH (1:1) in heptane). The two enantiomers were separated and Peak 1 was collected. Hydroxylamine hydrochloride (387 mg, 5.58 mmol) was suspended in DMSO (6.2 mL) and TEA (777 µL, 5.58 mmol) and stirred for 5 min at ambient temperature. The material was diluted with THF (6.2 mL), filtered and concentrated in vacuo. This material was added to the chirally resolved 37F (94.5 mg, 0.186 mmol) and heated to 70° C. for 5 h. The reaction was diluted with EtOAc and washed twice with water, then brine, dried (Na$_2$SO$_4$), filtered, diluted with Ac$_2$O (52.6 µL, 0.558 mmol), and concentrated in vacuo. The crude material was dissolved in MeOH (6195 µL). Pd/C (19.78 mg, 0.019 mmol) was added and the reaction sealed under a hydrogen balloon overnight. The reaction was purified by Prep LC (YMC Sunfire 5µ C18 30×100 mm column, 10 min gradient from 20 to 100% B in A, A=10:90:0.1 MeOH:H$_2$O:TFA, B=90:10:0.1 MeOH:H$_2$O:TFA) to yield Example 37 (56 mg, 45%). 1H NMR (400 MHz, MeOD) δ ppm 7.52-7.64 (3 H, m), 7.28-7.41 (3 H, m), 6.54-7.01 (4 H, m), 5.70 (1 H, s), 5.36 (1 H, d, J=16.31 Hz), 3.92-4.02 (1 H, m), 3.33-3.37 (1 H, m), 3.06-3.11 (3 H, m), 2.92-3.06 (2 H, m), 2.58-2.68 (1 H, m), 2.44-2.56 (1 H, m). MS (ESI) m/z: 526.1 (M+H)$^+$. Analytical HPLC (low pH, 254 nM): Sunfire C18, RT=5.513 min.

Example 38

(5R,11R)-11-(1-Amino-4-fluoro-isoquinolin-6-ylamino)-16-cyclopropanesulfonyl-7-(2,2-difluoro-ethoxy)-5,13-dimethyl-2,13-diaza-tricyclo[13.3.1.1$^{6,10}$]icosa-1(19),6,8,10(20),15,17-hexaene-3,12-dione trifluoroacetic acid salt+Enantiomer

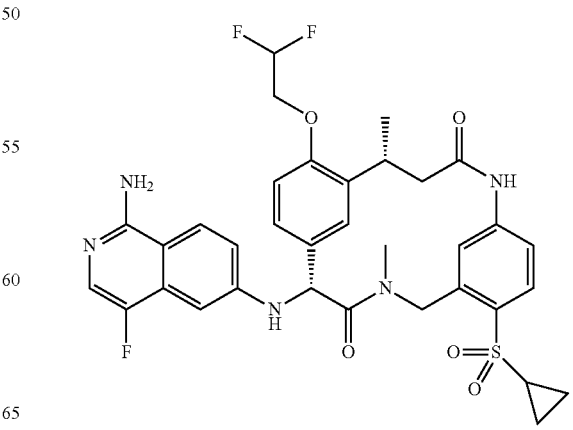

Example 38A (R)-2-(trimethylsilyl)ethyl 5-(3-(2-(benzyloxy)-5-bromophenyl)butanamido)-2-(cyclopropylsulfonyl)benzyl(methyl)carbamate

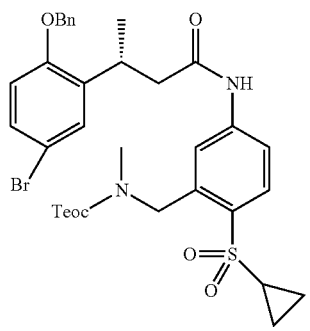

Using a procedure analogous to the one used to prepare Example 8A, Intermediate 5 (0.490 g, 1.40 mmol) was reacted with oxalyl chloride (0.772 mL, 1.54 mmol) and Intermediate 2 (0.648 g, 1.68 mmol), to yield Example 38A (0.972 g, 97%). MS (ESI) m/z: 738.2 (M+Na)$^+$.

Example 38B (R)-4-(benzyloxy)-3-(4-(4-(cyclopropylsulfonyl)-3-((methyl((2-(trimethylsilyl)ethoxy)carbonyl)amino)methyl)phenylamino)-4-oxobutan-2-yl)phenylboronic acid

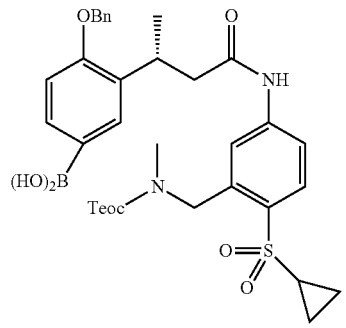

Using a procedure analogous to the one used to prepare Example 8B, Example 38A (0.942 g, 1.32 mmol) was reacted with bis(neopentyl glycolato)diboron (0.416 g, 1.84 mmol) and [1,1'-bis(diphenylphospino)ferrocene]dichloropalladium(II) (0.108 g, 0.132 mmol), to yield Example 38B (0.700 g, 78%). MS (ESI) m/z: 652.2 (M-28)$^+$.

Example 38C 2-(4-(Benzyloxy)-3-((R)-4-(4-(cyclopropylsulfonyl)-3-((methyl((2-(trimethylsilyl)ethoxy)carbonyl)amino)methyl)phenylamino)-4-oxobutan-2-yl)phenyl)-2-(1-(bis(tert-butoxycarbonyl)amino)-4-fluoroisoquinolin-6-ylamino)acetic acid

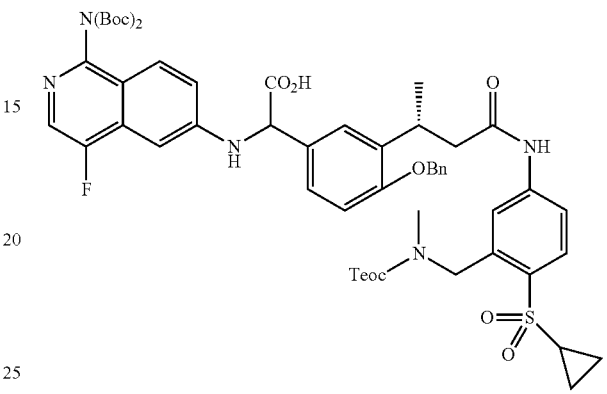

Using a procedure analogous to the one used to prepare Example 8C, Example 38B (0.700 g, 1.03 mmol) and Intermediate 3 (0.388 g, 1.03 mmol) were reacted with glyoxylic acid monohydrate (95 mg, 1.03 mmol) to yield Example 38C (1.07 g, 97%). MS (ESI) m/z: 971.3 (M+H)$^+$-boc.

Example 38D 2-(4-(Benzyloxy)-3-((R)-4-(4-(cyclopropylsulfonyl)-3-((methylamino)methyl)phenylamino)-4-oxobutan-2-yl)phenyl)-2-(1-(bis(tert-butoxycarbonyl)amino)-4-fluoroisoquinolin-6-ylamino)acetic acid

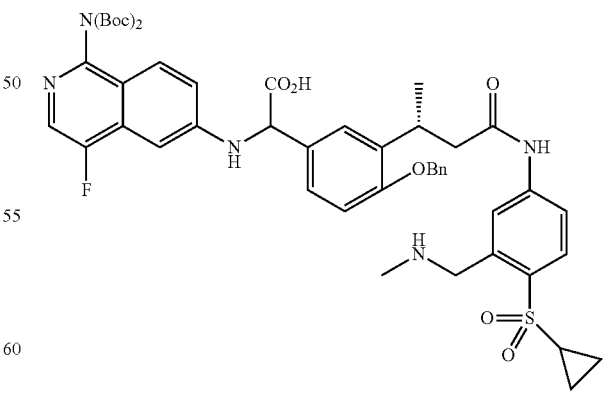

Using a procedure analogous to the one used to prepare Example 8D, Example 38C (1.07 g, 1.00 mmol) was reacted with TBAF (10 mL, 10 mmol) to yield Example 38D (0.926 g, 100%). MS (ESI) m/z: 927.2 (M+H)$^+$.

Example 38E

[6-((R)-7-Benzyloxy-16-cyclopropanesulfonyl-5,13-dimethyl-3,12-dioxo-2,13-diaza-tricyclo[13.3.1.1[6,10]]icosa-1(19),6,8,10(20),15,17-hexaen-11-ylamino)-4-fluoro-isoquinolin-1-yl]-bis(carbamic acid tert-butyl ester)

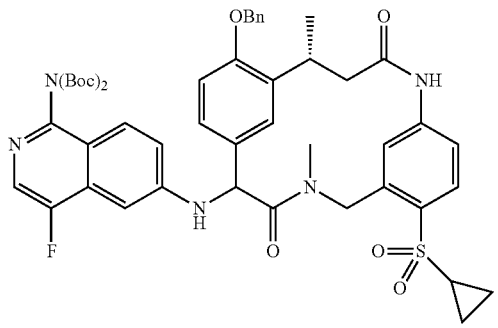

Using a procedure analogous to the one used to prepare Example 8E, Example 38D (0.926 g, 1.00 mmol) was reacted with BOP (0.885 g, 2.00 mmol) to yield Example 38E (0.174 g, 19%). MS (ESI) m/z: 909.3 (M+H)$^+$.

Example 38F

[6-((5R,11R)-7-Benzyloxy-16-cyclopropanesulfonyl-5,13-dimethyl-3,12-dioxo-2,13-diaza-tricyclo[13.3.1.1[6,10]]icosa-1(19),6,8,10(20),15,17-hexaen-11-ylamino)-4-fluoro-isoquinolin-1-yl]-bis(carbamic acid tert-butyl ester)

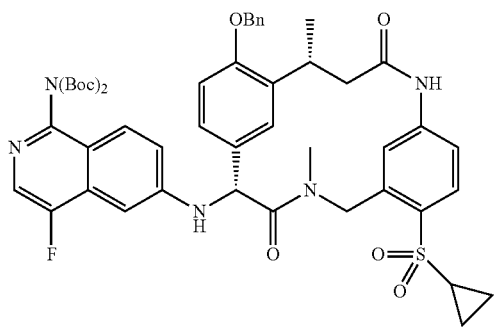

Example 38E (174 mg, 0.192 mmol) was separated by Chiral Prep LC (Chiralcel AD 25×200 mm column, 50% isocratic MeOH/EtOH (1:1) in heptane). The two enantiomers were separated and Peak 1 was collected to yield Example 38F (89 mg, 51%). MS (ESI) m/z: 909.3 (M+H)$^+$.

Example 38G

[6-((5R,11R)-16-Cyclopropanesulfonyl-7-hydroxy-5,13-dimethyl-3,12-dioxo-2,13-diaza-tricyclo[13.3.1.1[6,10]]icosa-1(19),6,8,10(20),15,17-hexaen-11-ylamino)-4-fluoro-isoquinolin-1-yl]-bis(carbamic acid tert-butyl ester)

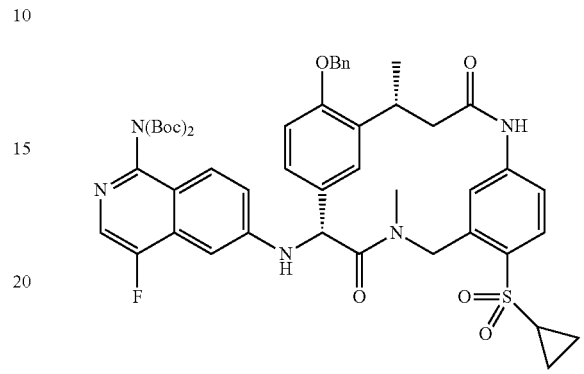

Example 38F (89 mg, 0.098 mmol) was dissolved in MeOH (9.77 mL). Pd/C (10.4 mg, 0.001 mmol) was added and the reaction flushed with hydrogen then sealed with a hydrogen balloon and allowed to stir overnight. The reaction was filtered and concentrated to yield Example 38G (76 mg, 95%). MS (ESI) m/z: 818.3 (M+H)$^+$.

Example 38

Example 38G (76 mg, 0.093 mmol) and 2-bromo-1,1-difluoroethane (7.79 µL, 0.097 mmol) were dissolved in DMF (1.85 mL). Cs$_2$CO$_3$ (60 mg, 0.185 mmol) was added and the reaction was heated to 50° C. and allowed to stir overnight. The reaction was diluted with MeOH and purified by Prep LC (YMC Sunfire 5µ C18 30×100 mm column, 10 min gradient from 40 to 100% B in A, A=10:90:0.1 MeOH:H$_2$O:TFA, B=90:10:0.1 MeOH:H$_2$O:TFA). The isolated product was dissolved in approximately 1 mL of TFA for 30 min then concentrated in vacuo and purified by Prep LC (YMC Sunfire 5µ C18 30×100 mm column, 10 min gradient from 40 to 100% B in A, A=10:90:0.1 MeOH:H$_2$O:TFA, B=90:10:0.1 MeOH:H$_2$O:TFA) to yield Example 38 (32 mg, 43%). 1H NMR (400 MHz, MeOD) δ ppm 8.09 (1 H, dd, J=9.29, 2.01 Hz), 7.80 (1 H, d, J=8.28 Hz), 7.66 (1 H, d, J=7.53 Hz), 7.43 (1 H, d, J=5.02 Hz), 7.26 (1 H, dd, J=9.29, 2.26 Hz), 7.20 (1 H, br. s.), 7.04 (1 H, d, J=8.53 Hz), 6.98 (1 H, dd, J=8.28, 1.76 Hz), 6.93 (1 H, d, J=2.01 Hz), 6.82 (1 H, br. s.), 6.28 (1 H, tt, J=54.87, 3.61 Hz), 5.75 (1 H, s), 5.61 (1 H, d, J=16.31 Hz), 4.50 (1 H, d, J=16.56 Hz), 4.25-4.39 (2 H, m), 3.20-3.28 (1 H, m), 3.10 (3 H, br. s.), 2.88 (1 H, t, J=11.67 Hz), 2.73-2.82 (1 H, m), 2.55 (1 H, d, J=10.54 Hz), 1.51 (3 H, d, J=6.78 Hz), 1.20-1.28 (1 H, m), 0.99-1.16 (3 H, m). MS (ESI) m/z: 682.1 (M+H)$^+$. Analytical HPLC (low pH, 220 nM): Sunfire C18, RT=6.041 min.

Example 39

(R)-5-(1-Amino-4-fluoro-isoquinolin-6-ylamino)-9-(2,2-difluoro-ethoxy)-19-(difluoro-methanesulfonyl)-3,13-dimethyl-3,13,15-triaza-tricyclo[14.3.1.1^{6,10}]henicosa-1(19),6(21),7,9,16(20),17-hexaene-4,14-dione trifluoroacetic acid salt+Enantiomer

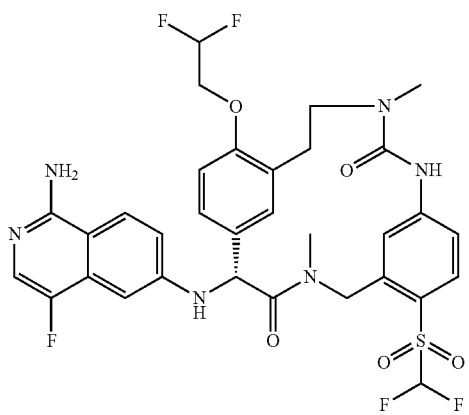 [SMILES: CN1CCc2cc(ccc2OCC(F)F)[C@@H](Nc2ccc3c(N)ncc(F)c3c2)C(=O)N(C)Cc2cc(ccc2S(=O)(=O)C(F)F)NC1=O]

Example 39A

5-Bromo-2-(2,2-difluoroethoxy)benzaldehyde

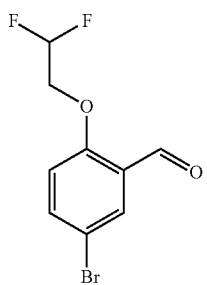 [SMILES: O=Cc1cc(Br)ccc1OCC(F)F]

5-Bromo-2-hydroxybenzaldehyde (1.00 g, 4.97 mmol) and 2-Bromo-1,1-difluoroethane (0.478 mL, 5.97 mmol) were dissolved in DMF (49.7 mL). Cs$_2$CO$_3$ (2.431 g, 7.46 mmol) was added, and the reaction allowed to stir at 55° C. overnight. The reaction was quenched with 1 N HCl and extracted thrice with EtOAc. The combined organic extracts were washed with water, then brine, dried (Na$_2$SO$_4$), filtered, and concentrated in vacuo. The crude material was purified by silica gel column chromatography (0 to 100% EtOAc in hexanes) to yield Example 39A (1.19 g, 4.49 mmol, 90% yield) as a brown solid. MS (ESI) m/z: 265.0 (M+H)$^+$.

Example 39B

2-[5-Bromo-2-(2,2-difluoro-ethoxy)-phenyl]-ethyl-amine

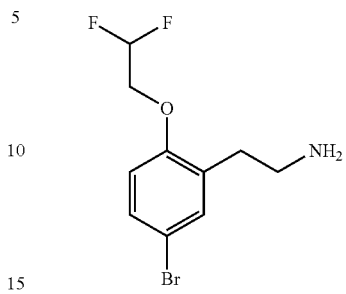

1,1,3,3-Tetramethyldisiloxane (0.794 mL, 4.49 mmol), chlorotrimethylsilane (1.140 mL, 8.98 mmol), and sodium iodide (1.346 g, 8.98 mmol) were dissolved in acetonitrile (44.9 mL) and allowed to stir at RT for 15 min. To the stirred solution, 39A (1.19 g, 4.49 mmol) in 1 mL MeCN was added and the reaction was heated to reflux for 1 h. The reaction was diluted with EtOAc and saturated NaHCO$_3$ solution. The layers were separated, and the aqueous layer was back extracted with EtOAc×3. The combined organic layer was washed with brine, dried with Na$_2$SO$_4$ and concentrated to yield 4-bromo-1-(2,2-difluoroethoxy)-2-(iodomethyl)benzene (1.608 g, 4.27 mmol, 95% yield).

The residue was suspended in DMSO (10 mL) and NaCN (0.374 g, 7.64 mmol) was added. The reaction was allowed to stir at RT overnight. Reaction was diluted with saturated NaHCO$_3$ solution and EtOAc. The layers were separated, and the aqueous layer was back extracted with EtOAc×3. The combined organic layers were washed with brine, dried with Na$_2$SO$_4$, and concentrated under reduced pressure to yield 2-(5-bromo-2-(2,2-difluoroethoxy)phenyl)acetonitrile (1.12 g, 3.65 mmol, 86% yield) as a tan solid.

The residue was dissolved in THF (50 mL) and borane tetrahydrofuran complex (8.11 mL, 8.11 mmol) was added, and the reaction was allowed to stir overnight. The reaction was diluted with 50% aqueous AcOH. The reaction was concentrated, and the residue was redissolved in EtOAc and water. The layers were separated, and the aqueous layer was neutralized with 1 N NaOH. The neutralized aqueous layer was extracted 3× with EtOAc. The combined organic layer was washed with brine, dried with Na$_2$SO$_4$ and concentrated under reduced pressure to yield Example 39B (0.486 g, 42.8% yield) as a yellow oil. MS (ESI) m/z: 280.0 (M+H)$^+$.

Example 39C 2-(Trimethylsilyl)ethyl 5-bromo-2-(2,2-difluoroethoxy)phenethyl(methyl)carbamate

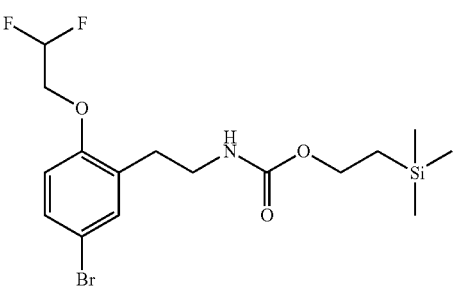 [SMILES: C[Si](C)(C)CCOC(=O)NCCc1cc(Br)ccc1OCC(F)F]

Example 39B (0.486 g, 1.735 mmol) and 2-(trimethylsilyl)ethyl p-nitrophenyl carbonate (0.492 g, 1.735 mmol) were dissolved in MeOH (10.0 mL). DIPEA (0.909 mL, 5.21 mmol) was added, and the reaction was allowed to stir overnight. The reaction was concentrated in vacuo. The crude material was purified by silica gel column chromatography (0 to 100% EtOAc in hexanes) to yield Example 39C (0.650 g, 75%) MS (ESI) m/z: 398.0 (M-28)+ (M-28 is consistent with Teoc containing compounds). 1H NMR (400 MHz, CHLOROFORM-d) δ ppm 7.17-7.35 (2 H, m), 6.66 (1 H, d, J=8.53 Hz), 6.07 (1 H, tt, J=55.09, 4.02 Hz), 4.00-4.28 (4 H, m), 3.36 (2 H, q, J=6.53 Hz), 2.77 (2 H, t, J=6.78 Hz), 0.87-0.98 (2 H, m), −0.11-0.11 (9 H, m).

Example 39D 4-(2,2-difluoroethoxy)-3-(2-(methyl((2-(trimethylsilyl)ethoxy)carbonyl)amino)ethyl)phenylboronic acid

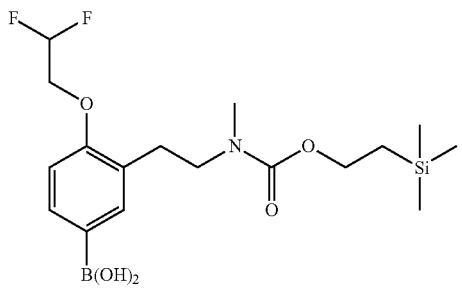 [SMILES: CN(CCc1cc(B(O)O)ccc1OCC(F)F)C(=O)OCC[Si](C)(C)C]

Using a procedure analogous to the one used to prepare Example 19A, Example 39C (0.325 g, 0.741 mmol) was reacted with bis(neopentyl glycolato)diboron (0.167 g, 1.853 mmol) and [1,1'bis(diphenylphosphino)ferrocene]dichloropalladium(II) (27 mg, 0.037 mmol) to yield Example 39D (0.135 g, 45%). MS (ESI) m/z: 376.1 (M-28)+. M-28 peak is typical for Teoc containing compounds.

Example 39E (6-{[{[5-Amino-2-(difluoro-methanesulfonyl)-benzyl]-methyl-carbamoyl}-(4-(2,2-difluoro-ethoxy)-3-{2-[methyl-(2-trimethylsilanyl-ethoxycarbonyl)-amino]-ethyl}-phenyl)-methyl]-amino}-4-fluoro-isoquinolin-1-yl)-bis(carbamic acid tert-butyl ester)

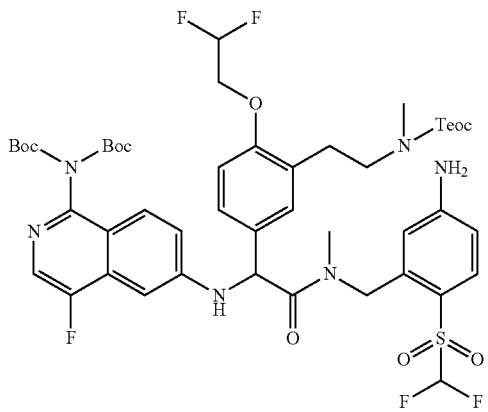

Using a procedure analogous to the one used to prepare Example 19B, Example 39D (0.135 g, 0.335 mmol) was reacted with Intermediate 3 (59 mg, 0.335 mmol) and 2-oxoacetic acid, monohydrate (0.031 g, 0.335 mmol), Intermediate 12 (0.141 g, 0.435 mmol), and BOP (0.148 g, 0.335 mmol) to yield Example 39E (97 mg, 28%). MS (ESI) m/z: 925.3 (M-boc)+.

Example 39F

[6-({{[5-Amino-2-(difluoro-methanesulfonyl)-benzyl]-methyl-carbamoyl}-[4-(2,2-difluoro-ethoxy)-3-(2-methylamino-ethyl)-phenyl]-methyl}-amino)-4-fluoro-isoquinolin-1-yl]-bis(carbamic acid tert-butyl ester)

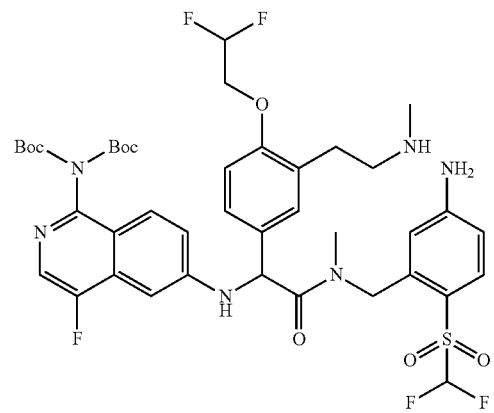 [SMILES: CNCCc1cc(C(Nc2ccc3c(N(C(=O)OC(C)(C)C)C(=O)OC(C)(C)C)ncc(F)c3c2)C(=O)N(C)Cc2cc(N)ccc2S(=O)(=O)C(F)F)ccc1OCC(F)F]

Using a procedure analogous to the one used to prepare Example 19C, Example 39E (97 mg, 0.095 mmol) was reacted TBAF (0.946 mL, 0.946 mmol) to yield Example 39F (48 mg, 58%). MS (ESI) m/z: 881.2 (M+H)+.

Example 39G

{6-[9-(2,2-Difluoro-ethoxy)-19-(difluoro-methanesulfonyl)-3,13-dimethyl-4,14-dioxo-3,13,15-triazatricyclo[14.3.1.1⁶,¹⁰]henicosa-1(19),6(21),7,9,16(20),17-hexaen-5-ylamino]-4-fluoro-isoquinolin-1-yl}-bis(carbamic acid tert-butyl ester)

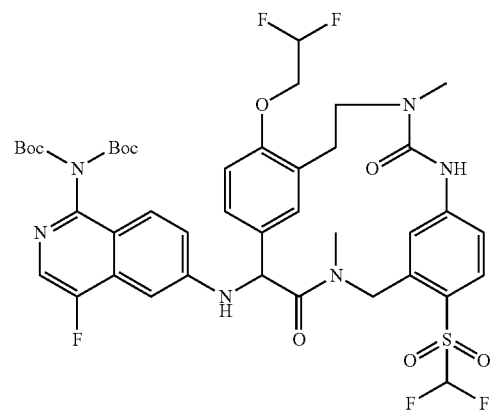 [SMILES: CN1CCc2cc(ccc2OCC(F)F)C(Nc2ccc3c(N(C(=O)OC(C)(C)C)C(=O)OC(C)(C)C)ncc(F)c3c2)C(=O)N(C)Cc2cc(ccc2S(=O)(=O)C(F)F)NC1=O]

Using a procedure analogous to the one used to prepare Example 19D, Example 39F (51 mg, 0.058 mmol) was reacted with pyridine (47 μL, 0.579 mmol) and p-nitrophenyl chloroformate (58 mg, 0.289 mmol) to yield Example 39G (31 mg, 59%). MS (ESI) m/z: 907.2 (M+H)+.

Example 39

Example 39G (31 mg, 0.034 mmol) was separated by Chiral Prep LC (Chiralcel AD 20×200 mm column, 40% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 nm 30×100 mm column, 10 min gradient from 10 to 100% B in A, A=10:90:0.1 MeCN:H$_2$O:TFA, B=90:10:0.1 MeCN: H$_2$O:TFA) to yield Example 39 (2 mg, 7%). MS (ESI) m/z: 707.2 (M+H)+. Analytical HPLC (low pH, 254 nM): Sunfire, RT=5.23 min.

Example 40

4-[(R)-7,16-Bis-(2,2-difluoro-ethoxy)-17-fluoro-13-methyl-3,12-dioxo-2,13-diaza-tricyclo[13.3.1.1$^{6,10}$]icosa-1(19),6,8,10(20),15,17-hexaen-11-ylamino]-benzamidine trifluoroacetic acid salt+Enantiomer

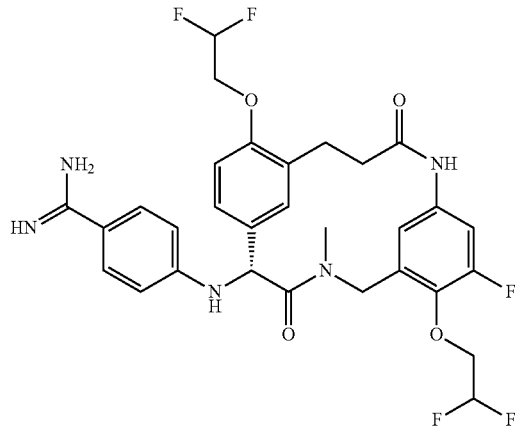 [SMILES: CN1Cc2cc(cc(F)c2OCC(F)F)NC(=O)CCc2cc(ccc2OCC(F)F)[C@@H](Nc2ccc(C(=N)N)cc2)C1=O]

Example 40A 2-(trimethylsilyl)ethyl 5-(3-(5-bromo-2-(2,2-difluoroethoxy)phenyl)propanamido)-2-(2,2-difluoroethoxy)-3-fluorobenzyl(methyl)carbamate

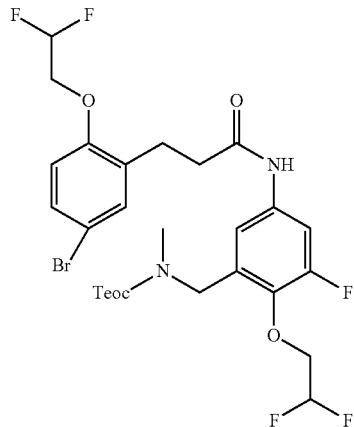

Using a procedure analogous to the one used to prepare Example 8A, Intermediate 6 (0.150 g, 0.485 mmol) was reacted with oxalyl chloride (0.267 mL, 0.534 mmol) and Intermediate 13 (0.220 g, 0.582 mmol), to yield Example 40A (0.315 g, 97%). MS (ESI) m/z: 643.0 (M+H)+-28. M-28 peak is typical for Teoc containing compounds Example 40B 4-(2,2-difluoroethoxy)-3-(3-(4-(2,2-difluoroethoxy)-3-fluoro-5-((methyl((2-(trimethylsilyl)ethoxy)carbonyl)amino)methyl)phenylamino)-3-oxopropyl)phenylboronic acid

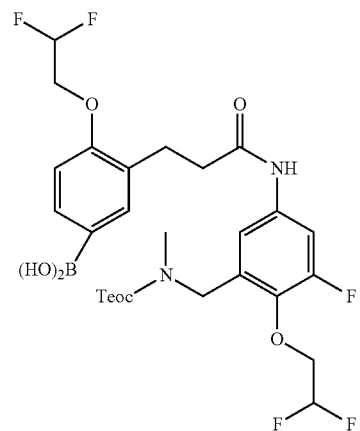

Using a procedure analogous to the one used to prepare Example 8B, Example 40A (0.315 g, 0.470 mmol) was reacted with bis(neopentyl glycolato)diboron (0.106 g, 0.470 mmol) and [1,1'-bis(diphenylphospino)ferrocene]dichloropalladium(II) (17 mg, 0.023 mmol), to yield Example 40B (94 mg, 32%). MS (ESI) m/z: 607.2 (M-28)+. M-28 peak typical with Teoc containing compounds.

Example 40C 2-(4-cyanophenylamino)-2-(4-(2,2-difluoroethoxy)-3-(3-(4-(2,2-difluoroethoxy)-3-fluoro-5-((methyl((2-(trimethylsilyl)ethoxy)carbonyl)amino)methyl)phenylamino)-3-oxopropyl)phenyl)acetic acid

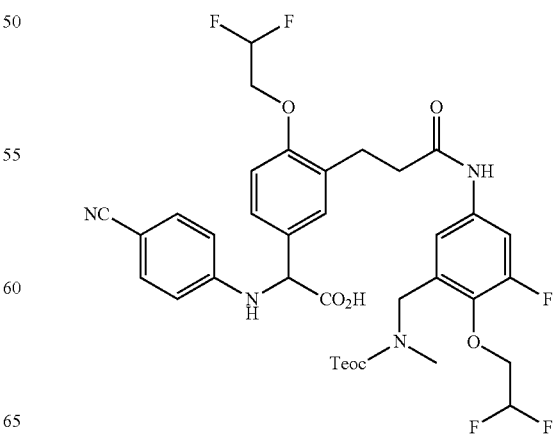

Using a procedure analogous to the one used to prepare Example 8C, Example 40B (94 mg, 0.148 mmol) and 4-aminobenzonitrile (18 mg, 0.148 mmol) were reacted with glyoxylic acid monohydrate (14 mg, 0.148 mmol) to yield Example 40C (99 mg, 87%). MS (ESI) m/z: 737.1 (M-28)⁺. M-28 peak typical with Teoc containing compounds.

Example 40D 2-(4-cyanophenylamino)-2-(4-(2,2-difluoroethoxy)-3-(3-(4-(2,2-difluoroethoxy)-3-fluoro-5-((methylamino)methyl)phenylamino)-3-oxopropyl)phenyl) acetic acid

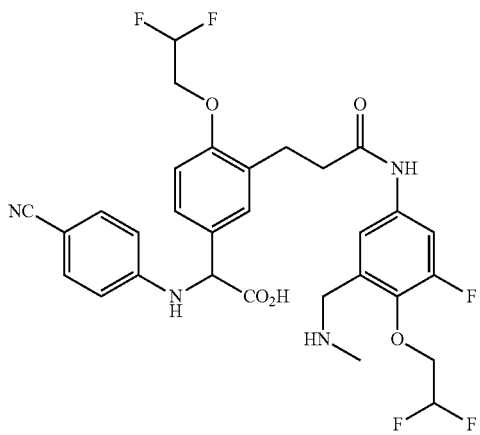 [SMILES: CNCc1cc(NC(=O)CCc2cc(C(Nc3ccc(C#N)cc3)C(=O)O)ccc2OCC(F)F)cc(F)c1OCC(F)F]

Using a procedure analogous to the one used to prepare Example 8D, Example 40C (83 mg, 0.109 mmol) was reacted with TBAF (1.09 mL, 1.085 mmol) to yield Example 40D (67 mg, 99%). MS (ESI) m/z: 621.1 (M+H)⁺.

Example 40E

4-[7,16-Bis-(2,2-difluoro-ethoxy)-17-fluoro-13-methyl-3,12-dioxo-2,13-diaza-tricyclo[13.3.1.1⁶,¹⁰] icosa-1(19),6,8,10(20),15,17-hexaen-11-ylamino]-benzonitrile

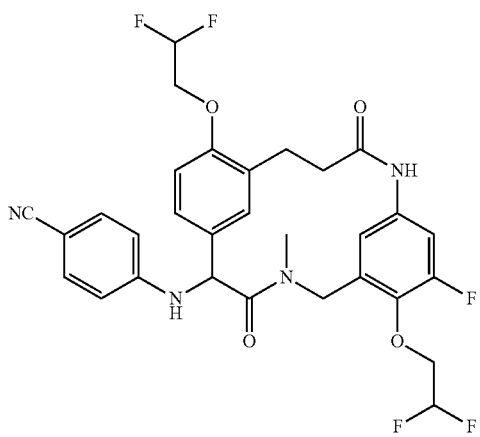 [SMILES: CN1Cc2cc(cc(F)c2OCC(F)F)NC(=O)CCc2cc(ccc2OCC(F)F)C(Nc2ccc(C#N)cc2)C1=O]

Using a procedure analogous to the one used to prepare Example 8E, Example 40D (67 mg, 0.108 mmol) was reacted with BOP (96 mg, 0.216 mmol) to yield Example 40E (40 mg, 62%) which separated by Chiral Prep LC (Welco-01 25×200 mm column, 40% isocratic MeOH/EtOH (1:1) in heptane). Peak 2 was collected (20 mg, 50%).

Example 40

To a partial solution hydroxylamine hydrochloride (69 mg, 0.986 mmol) in DMSO (1 mL), was added TEA (0.137 mL, 0.986 mmol). The resultant suspension was stirred at rt for 5 min. The mixture was diluted with THF (3 mL) and was filtered. The filtrate was concentrated to remove the THF, then was added to chirally resolved Example 40E (20 mg, 0.033 mmol). The mixture was stirred at 60° C. for 3 h, then 70° C. for 2 h. The reaction mixture was diluted with EtOAc. The organic phase was washed with H₂O (2×) and brine, dried (Na₂SO₄), filtered, treated with Ac₂O (0.027 mL, 0.289 mmol), then concentrated. The resultant white solid was dissolved in MeOH (5 mL), then was treated with Pd—C (10%) (10.49 mg, 9.86 μmol). The mixture was evacuated and flushed with H₂ (3×), then was stirred under an atmosphere of H₂ for 1.5 h. The reaction mixture was filtered, then concentrated. The crude product was purified on Prep HPLC using Solvent A: 10% MeOH/90% H₂O/0.1% TFA and Solvent B 90% MeOH/10% H₂O/0.1% TFA on Phenomenex AXIA C18 30×100 mm with a 10 min gradient and 5 min hold time with a flow rate of 40 mL/min to yield Example 40 (14.9 mg, 58.7% yield). MS (ESI) m/z: 620.1 (M+H)⁺. 1H NMR (400 MHz, MeOD) δ ppm 7.98 (1 H, s), 7.48-7.66 (3 H, m), 7.27 (1 H, d, J=2.26 Hz), 6.99 (1 H, d, J=8.28 Hz), 6.77-6.85 (2 H, m), 6.69 (1 H, dd, J=11.92, 2.38 Hz), 5.92-6.42 (3 H, m), 5.65 (1 H, s), 5.28 (1 H, d, J=16.56 Hz), 4.19-4.38 (4 H, m), 4.00 (1 H, d, J=16.31 Hz), 3.06-3.16 (3 H, m), 2.95-3.03 (2 H, m), 2.81-2.90 (3 H, m), 2.70 (2 H, s), 2.47-2.58 (1 H, m). Analytical HPLC (low pH, 254 nM): Sunfire, RT=5.98 min.

Example 41

(R)-5-(1-Amino-4-fluoro-isoquinolin-6-ylamino)-19-cyclopropanesulfonyl-3-methyl-3,13,15-triaza-tricyclo[14.3.1.1⁶,¹⁰]henicosa-1(19),6(21),7,9,16(20),17-hexaene-4,14-dione trifluoroacetic acid salt+ Enantiomer

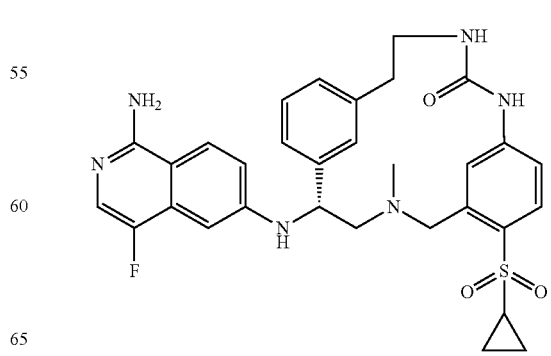

Example 41A 2-(Trimethylsilyl)ethyl 3-bromophenethylcarbamate

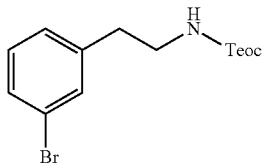

2-(3-Bromophenyl)ethanamine (1 g, 5.00 mmol) and 2-(trimethylsilyl)ethyl p-nitrophenyl carbonate (1.416 g, 5.00 mmol) were dissolved in MeOH (40.0 mL). DIPEA (1.048 mL, 6.00 mmol) was added and the reaction was allowed to stir for 2 h. The reaction was concentrated under reduced pressure. The residue was re-dissolved in EtOAc and washed with 1 N NaOH (until yellow color is removed), washed with brine, dried with $Na_2SO_4$, and concentrated under reduced pressure to yield Example 41A (0.830 g, 48.2% yield) as a colorless oil. 1H NMR (400 MHz, CHLOROFORM-d) δ ppm 7.28-7.39 (2 H, m), 7.02-7.17 (2 H, m), 4.04-4.17 (2 H, m), 3.38 (2 H, q, J=6.78 Hz), 2.75 (2 H, t, J=6.90 Hz), 0.88-0.97 (2 H, m), −0.01 (9 H, s).

Example 41B 2-(Trimethylsilyl)ethyl 3-bromophenethyl(4-methoxybenzyl)carbamate

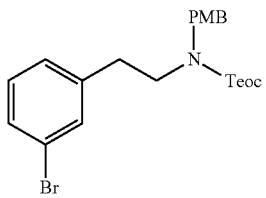

Example 41A (0.830 g, 2.411 mmol) was dissolved in DMF (24.11 mL) and NaH (0.145 g, 3.62 mmol) was added. The reaction was allowed to stir for 15 min at rt followed by the addition of 4-methoxybenzyl chloride (0.490 mL, 3.62 mmol). The reaction was allowed to stir at RT overnight. Reaction diluted with water and EtOAc. Layers were separated and the aqueous layer was back extracted with EtOAc× 3. The combined organic layer was washed with saturated aqueous $NaHCO_3$ solution, brine, dried with $Na_2SO_4$, and concentrated under reduced pressure to yield Example 41B (0.760 g, 68%). MS (ESI) m/z: 436.9 (M-28)$^+$. M-28 typical for Teoc containing compounds.

Example 41C 3-(2-((4-methoxybenzyl)((2-(trimethylsilyl)ethoxy)carbonyl)amino)ethyl)phenylboronic acid

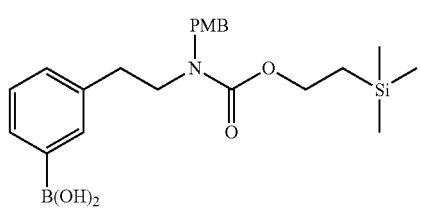

Using a procedure analogous to the one used to prepare Example 19A, Example 41B (0.760 g, 1.636 mmol) was reacted with bis(neopentyl glycolato)diboron (0.370 g, 1.636 mmol) and [1,1'bis(diphenylphosphino)ferrocene]dichloropalladium(II) (0.060 g, 0.082 mmol) to yield Example 41C (0.363 g, 52%). MS (ESI) m/z: 402.1 (M-28)$^+$. M-28 peak is typical for Teoc containing compounds.

Example 41D (6-{[[(5-Amino-2-cyclopropanesulfonyl-benzyl)-methyl-carbamoyl]-(3-{2-[(4-methoxy-benzyl)-(2-trimethylsilanyl-ethoxycarbonyl)-amino]-ethyl}-phenyl)-methyl]-amino}-4-fluoro-isoquinolin-1-yl)-bis(carbamic acid tert-butyl ester)

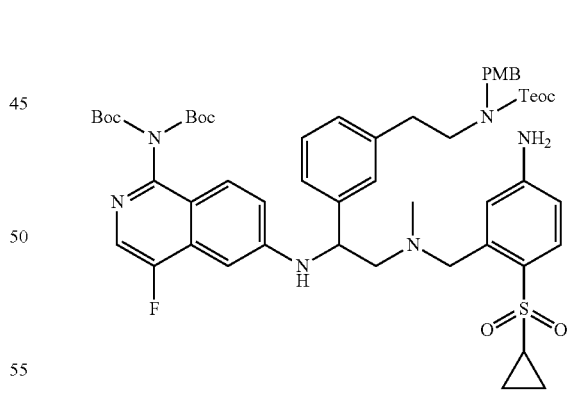

Using a procedure analogous to the one used to prepare Example 19B, Example 41C (0.363 g, 0.845 mmol) was reacted with Intermediate 3 (0.319 g, 0.845 mmol) and 2-oxoacetic acid, monohydrate (0.078 g, 0.845 mmol), 4-(cyclopropylsulfonyl)-3-((methylamino)methyl)aniline dihydrochloride (0.344 g, 1.099 mmol), and BOP (0.374 g, 4.23 mmol) to yield Example 41D (0.803 g, 91%). MS (ESI) m/z: 941.3 (M-boc)$^+$.

Example 41E

{6-[([(5-Amino-2-cyclopropanesulfonyl-benzyl)-methyl-carbamoyl]-{3-[2-(4-methoxy-benzylamino)-ethyl]-phenyl}-methyl)-amino]-4-fluoro-isoquinolin-1-yl}-bis(carbamic acid tert-butyl ester)

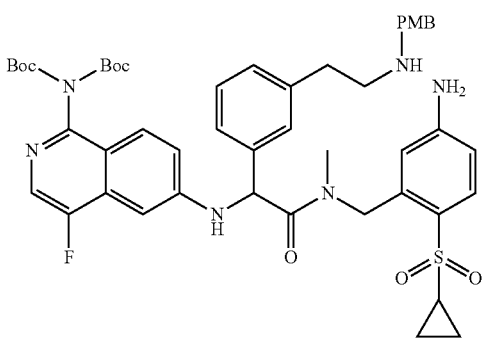

Using a procedure analogous to the one used to prepare Example 19C, Example 41D (0.802 g, 0.770 mmol) was reacted TBAF (7.70 mL, 7.70 mmol) to yield Example 41E (0.365 g, 53%). MS (ESI) m/z: 887.3 (M+H)$^+$.

Example 41F

{6-[19-Cyclopropanesulfonyl-13-(4-methoxy-benzyl)-3-methyl-4,14-dioxo-3,13,15-triaza-tricyclo[14.3.1.1$^{6,10}$]henicosa-1(19),6(21),7,9,16(20),17-hexaen-5-ylamino]-4-fluoro-isoquinolin-1-yl}-bis(carbamic acid tert-butyl ester)

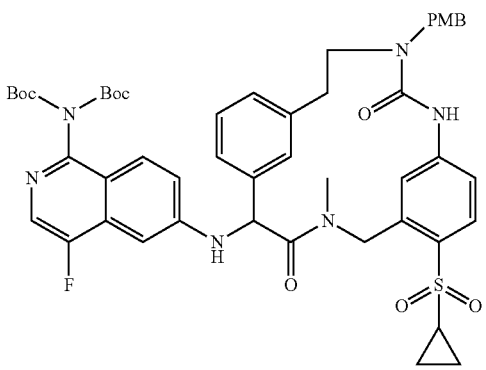

Using a procedure analogous to the one used to prepare Example 19D, Example 41E (0.150 g, 0.167 mmol) was reacted with pyridine (0.135 mL, 0.1.672 mmol) and p-nitrophenyl chloroformate (0.169 g, 0.836 mmol) to yield Example 41F (49 mg, 32%). MS (ESI) m/z: 924.3 (M+H)$^+$.

Example 41

Example 41F (0.049 g, 0.053 mmol) was separated by Chiral Prep LC (Chiralcel AD 20×200 mm column, 40% isocratic MeOH/EtOH (1:1) in heptane). The two enantiomers were separated and Peak 1 was collected. The compound was dissolved in TFA (ca 2 mL) and stirred for 2 h. This mixture was purified by Prep LC (YMC Sunfire 5 μm 30×100 mm column, 10 min gradient from 10 to 100% B in A, A=10:90:0.1 MeCN:H$_2$O:TFA, B=90:10:0.1 MeCN:H$_2$O:TFA) to yield Example 41 (10 mg, 50%). MS (ESI) m/z: 603.1 (M+H)$^+$. Analytical HPLC (low pH, 254 nM): Sunfire, RT=5.00 min. 1H NMR (400 MHz, MeOD) δ ppm 8.00-8.17 (1 H, m), 7.81 (1 H, d, J=8.28 Hz), 7.60 (1 H, d, J=7.53 Hz), 7.34-7.52 (3 H, m), 7.21-7.32 (2 H, m), 6.96 (2 H, d, J=2.26 Hz), 6.81 (1 H, s), 5.82 (1 H, s), 3.47-3.63 (3 H, m), 2.98-3.21 (5 H, m), 2.82 (2 H, d, J=7.78 Hz), 1.19-1.34 (2 H, m), 0.99-1.17 (2 H, m).

Example 42

4-[(R)-7-(2,2-Difluoro-ethoxy)-17-fluoro-16-(2-fluoro-1-fluoromethyl-ethoxy)-13-methyl-3,12-dioxo-2,13-diaza-tricyclo[13.3.1.1$^{6,10}$]icosa-1(19),6,8,10(20),15,17-hexaen-11-ylamino]-benzamidine trifluoroacetic acid salt+Enantiomer

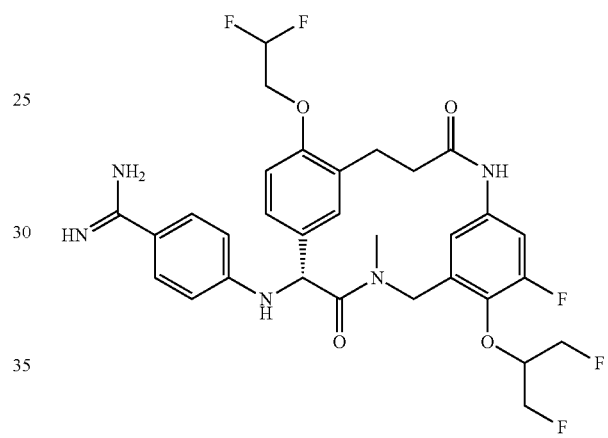

Example 42A 2-(trimethylsilyl)ethyl 5-(3-(5-bromo-2-(2,2-difluoroethoxy)phenyl)propanamido)-2-(1,3-difluoropropan-2-yloxy)-3-fluorobenzyl(methyl)carbamate

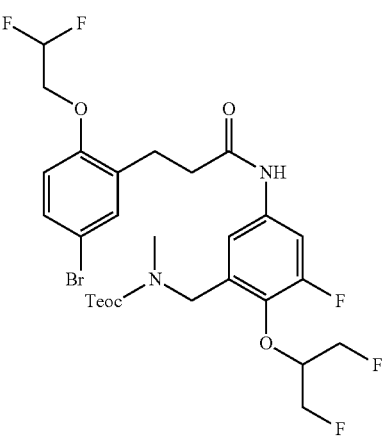

Using a procedure analogous to the one used to prepare Example 8A, Intermediate 6 (0.150 g, 0.485 mmol) was reacted with oxalyl chloride (0.267 mL, 0.534 mmol) and Intermediate 14 (0.229 g, 0.582 mmol), to yield Example 42A (0.264 g, 80%). MS (ESI) m/z: 655.1 (M+H)⁺-28. M-28 peak is typical for Teoc containing compounds.

Example 42B 4-(2,2-difluoroethoxy)-3-(3-(4-(1,3-difluoropropan-2-yloxy)-3-fluoro-5-((methyl((2-(trimethylsilyl)ethoxy)carbonyl)amino)methyl)phenylamino)-3-oxopropyl)phenylboronic acid

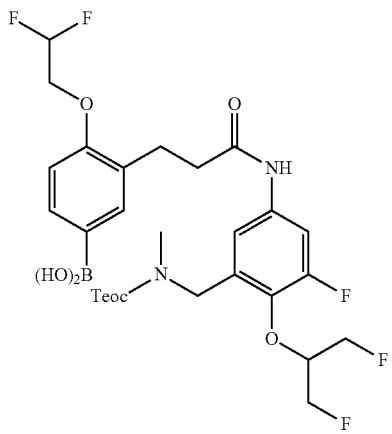

Using a procedure analogous to the one used to prepare Example 8B, Example 42A (0.263 g, 0.385 mmol) was reacted with bis(neopentyl glycolato)diboron (87 mg, 0.385 mmol) and [1,1'-bis(diphenylphospino)ferrocene]dichloropalladium(II) (14 mg, 0.019 mmol), to yield Example 42B (89 mg, 36%). MS (ESI) m/z: 621.1 (M-28)⁺. M-28 peak typical with Teoc containing compounds.

Example 42C 2-(4-cyanophenylamino)-2-(4-(2,2-difluoroethoxy)-3-(3-(4-(1,3-difluoropropan-2-yloxy)-3-fluoro-5-((methyl((2-(trimethylsilyl)ethoxy)carbonyl)amino)methyl)phenylamino)-3-oxopropyl)phenyl)acetic acid

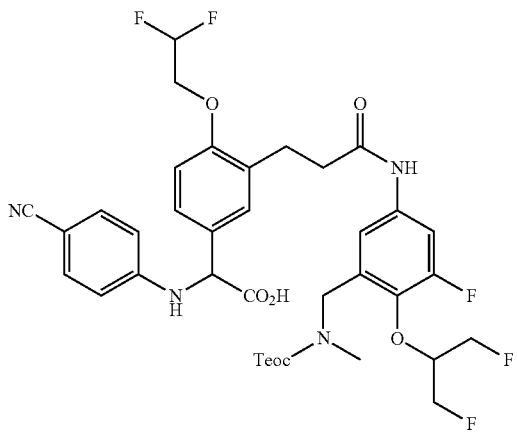

Using a procedure analogous to the one used to prepare Example 8C, Example 42B (89 mg, 0.137 mmol) and 4-aminobenzonitrile (16 mg, 0.137 mmol) were reacted with glyoxylic acid monohydrate (13 mg, 0.137 mmol) to yield Example 42C (83 mg, 78%). MS (ESI) m/z: 751.1 (M-28)⁺. M-28 peak typical with Teoc containing compounds.

Example 42D 2-(4-cyanophenylamino)-2-(4-(2,2-difluoroethoxy)-3-(3-(4-(1,3-difluoropropan-2-yloxy)-3-fluoro-5-((methylamino)methyl)phenylamino)-3-oxopropyl)phenyl)acetic acid

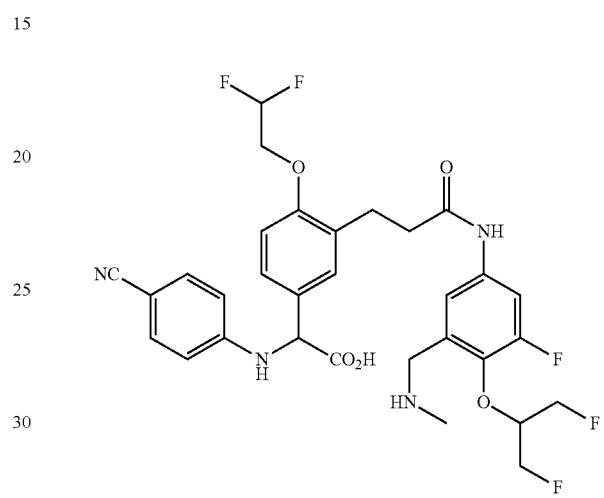

Using a procedure analogous to the one used to prepare Example 8D, Example 42C (83 mg, 0.107 mmol) was reacted with TBAF (1.09 mL, 1.085 mmol) to yield Example 42D (68 mg, 99%). MS (ESI) m/z: 635.1 (M+H)⁺.

Example 42E

4-[7-(2,2-Difluoro-ethoxy)-17-fluoro-16-(2-fluoro-1-fluoromethyl-ethoxy)-13-methyl-3,12-dioxo-2,13-diaza-tricyclo[13.3.1.1⁶,¹⁰]icosa-1(19),6,8,10(20),15,17-hexaen-11-ylamino]-benzonitrile

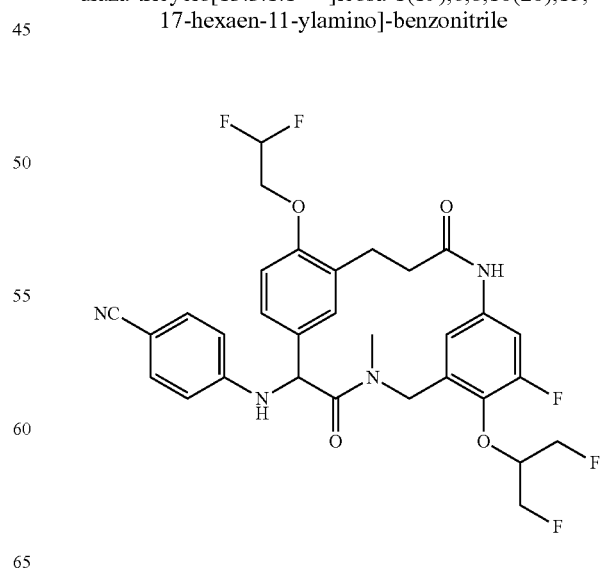

Using a procedure analogous to the one used to prepare Example 8E, Example 42D (68 mg, 0.107 mmol) was reacted with BOP (95 mg, 0.214 mmol) to yield Example 42E (29 mg, 44%) which separated by Chiral Prep LC (IA 25×100 mm column, 50% isocratic IPA in heptane). Peak 2 was collected (13 mg, 33%).

Example 42

Using a procedure analogous to the one used to prepare Example 40, chirally resolved Example 42E was reacted with hydroxylamine hydrochloride (0.045 g, 0.642 mmol). The resultant product was reduced with $H_2$ using Pd/C (10%) catalyst to yield Example 42 (9.1 mg, 58.7% yield). MS (ESI) m/z: 634.1 (M+H)$^+$. 1H NMR (400 MHz, CHLOROFORM-d) δ ppm 7.53-7.63 (3 H, m), 7.29 (1 H, d, J=2.51 Hz), 6.99 (1 H, d, J=8.53 Hz), 6.78-6.86 (2 H, m), 6.62-6.77 (1 H, m), 6.06-6.41 (2 H, m), 5.65 (1 H, s), 5.28 (1 H, s), 4.72-4.77 (2 H, m), 4.60-4.68 (2 H, m), 4.20-4.37 (1 H, m), 3.48 (1 H, dt, J=3.26, 1.63 Hz), 3.13 (1 H, dt, J=3.26, 1.63 Hz), 3.08 (3 H, s), 3.01-3.04 (1 H, m), 2.97 (2 H, s), 2.81-2.91 (1 H, m), 2.55 (1 H, s). Analytical HPLC (low pH, 254 nM): Sunfire, RT=5.93 min.

Example 43

4-[(5R,11R)-7-(2,2-Difluoro-ethoxy)-16-difluoromethoxy-5,13-dimethyl-3,12-dioxo-2,13-diazatricyclo[13.3.1.1$^{6,10}$]icosa-1(19),6,8,10(20),15,17-hexaen-11-ylamino]-benzamidine trifluoroacetic acid salt+Diastereomer

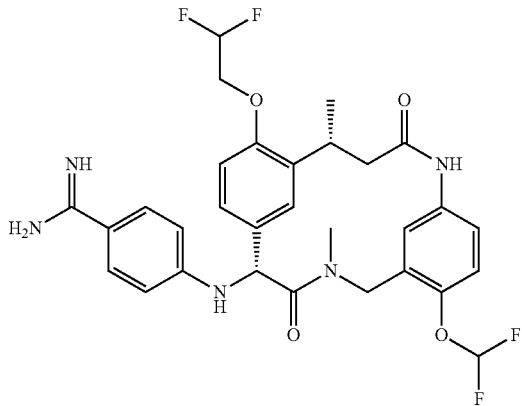 [SMILES: C[C@@H]1CC(=O)Nc2ccc(OC(F)F)c(c2)CN(C)C(=O)[C@H](Nc2ccc(C(=N)N)cc2)c2ccc(OCC(F)F)c1c2]

Example 43A (R)-2-(trimethylsilyl)ethyl 5-(3-(2-(benzyloxy)-5-bromophenyl)butanamido)-2-(difluoromethoxy)benzyl(methyl)carbamate

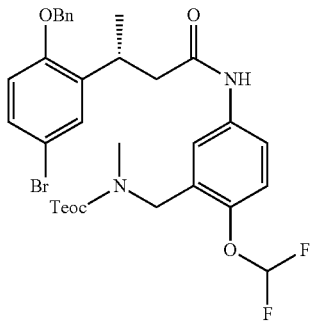

Using a procedure analogous to the one used to prepare Example 8A, Intermediate 5 (0.225 g, 0.644 mmol) was reacted with oxalyl chloride (0.354 mL, 0.709 mmol) and Intermediate 19 (0.268 g, 0.773 mmol), to yield Example 43A (0.395 g, 90%). MS (ESI) m/z: 700.1 (M+Na)$^+$.

Example 43B (R)-4-(benzyloxy)-3-(4-(4-(difluoromethoxy)-3-((methyl((2-(trimethylsilyl)ethoxy)carbonyl)amino) methyl)phenylamino)-4-oxobutan-2-yl)phenylboronic acid

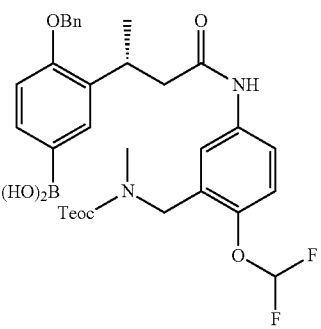

Using a procedure analogous to the one used to prepare Example 8B, Example 43A (0.395 g, 0.583 mmol) was reacted with bis(neopentyl glycolato)diboron (0.184 g, 0.816 mmol) and [1,1'-bis(diphenylphospino)ferrocene]dichloropalladium(II) (48 mg, 0.058 mmol), to yield Example 43B (0.256 g, 68%). MS (ESI) m/z: 615.02 (M-28)$^+$.

Example 43C 2-(4-(benzyloxy)-3-((R)-4-(4-(difluoromethoxy)-3-((methyl((2-(trimethylsilyl)ethoxy)carbonyl)amino) methyl)phenylamino)-4-oxobutan-2-yl)phenyl)-2-(4-cyanophenylamino)acetic acid

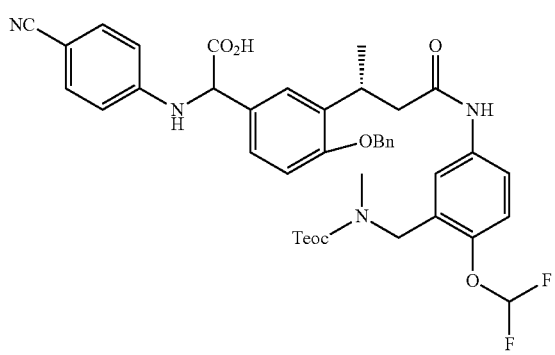

Using a procedure analogous to the one used to prepare Example 8C, Example 43B (0.256 g, 0.398 mmol) and 4-aminobenzonitrile (47 mg, 0.398 mmol) were reacted with glyoxylic acid monohydrate (37 mg, 0.398 mmol) to yield Example 43C (0.308 g, 100%). MS (ESI) m/z: 795.1 (M+Na)+.

Example 43D 2-(4-(Benzyloxy)-3-((R)-4-(4-(difluoromethoxy)-3-((methylamino)methyl)phenylamino)-4-oxobutan-2-yl)phenyl)-2-(4-cyanophenylamino)acetic acid

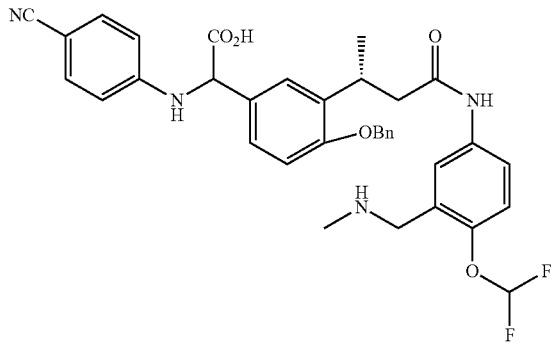 [SMILES: CNCc1cc(NC(=O)C[C@@H](C)c2cc(C(Nc3ccc(C#N)cc3)C(=O)O)ccc2OCc2ccccc2)ccc1OC(F)F]

Using a procedure analogous to the one used to prepare Example 8D, Example 43C (0.307 g, 0.397 mmol) was reacted with TBAF (3.97 mL, 3.97 mmol) to yield Example 43D (0.250 g, 100%). MS (ESI) m/z: 628.1 (M+H)+.

Example 43E 4-((R)-7-Benzyloxy-16-difluoromethoxy-5,13-dimethyl-3,12-dioxo-2,13-diaza-tricyclo[13.3.1.1^{6,10}]icosa-1(19),6,8,10(20),15,17-hexaen-11-ylamino)-benzonitrile

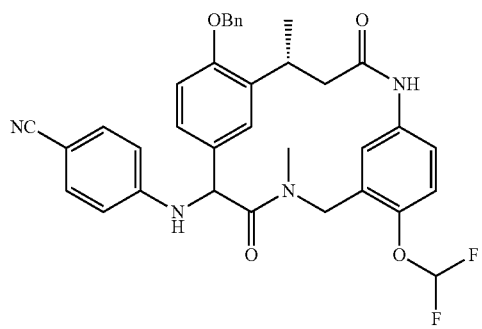 [SMILES: C[C@@H]1CC(=O)Nc2ccc(OC(F)F)c(c2)CN(C)C(=O)C(Nc2ccc(C#N)cc2)c2ccc(OCc3ccccc3)c1c2]

Using a procedure analogous to the one used to prepare Example 8E, Example 43D (0.250 g, 0.398 mmol) was reacted with BOP (0.352 g, 0.795 mmol) to yield Example 43E (0.157 g, 64%). The compound was used immediately upon isolation.

Example 43F 4-((5R,11R)-7-Benzyloxy-16-difluoromethoxy-5,13-dimethyl-3,12-dioxo-2,13-diaza-tricyclo[13.3.1.1^{6,10}]icosa-1(19),6,8,10(20),15,17-hexaen-11-ylamino)-benzonitrile

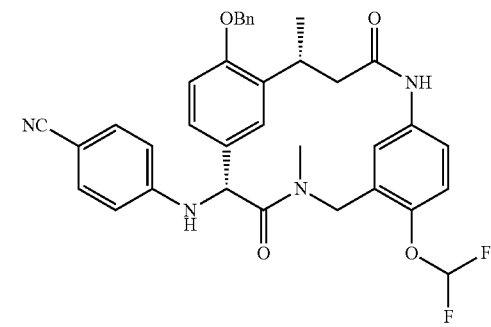 [SMILES: C[C@@H]1CC(=O)Nc2ccc(OC(F)F)c(c2)CN(C)C(=O)[C@H](Nc2ccc(C#N)cc2)c2ccc(OCc3ccccc3)c1c2]

Example 43E (157 mg, 0.257 mmol) was separated by Chiral Prep LC (Welco-01 25×200 mm column, 50% isocratic MeOH/EtOH (1:1) in heptane). The two enantiomers were separated and Peak 1 was collected to yield Example 43F (68 mg, 44%). The compound was used immediately upon isolation.

Example 43G 4-((5R,11R)-16-Difluoromethoxy-7-hydroxy-5,13-dimethyl-3,12-dioxo-2,13-diaza-tricyclo[13.3.1.1^{6,10}]icosa-1(19),6,8,10(20),15,17-hexaen-11-ylamino)-benzonitrile

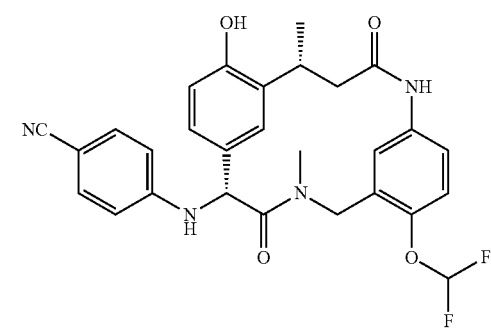 [SMILES: C[C@@H]1CC(=O)Nc2ccc(OC(F)F)c(c2)CN(C)C(=O)[C@H](Nc2ccc(C#N)cc2)c2ccc(O)c1c2]

43F (36 mg, 0.059 mmol) was dissolved in EtOAc (2.95 mL). Pd/C (13 mg, 0.012 mmol) was added and the reaction flushed with hydrogen then sealed with a hydrogen balloon and allowed to stir overnight. The reaction was filtered and concentrated to yield Example 43G (17 mg, 55%). MS (ESI) m/z: 543.1 (M+H)+.

Example 43

Example 43G (17 mg, 0.033 mmol) and 2-Bromo-1,1-difluoroethane (2.75 µL, 0.033 mmol) were dissolved in DMF (653 µL). Cs2CO3 (21 mg, 0.065 mmol) was added and the reaction was heated to 50° C. and allowed to stir overnight. The reaction was diluted with MeOH and purified by Prep LC (YMC Sunfire 5µ C18 30×100 mm column, 10 min gradient from 40 to 100% B in A, A=10:90:0.1 MeOH:H$_2$O:TFA, B=90:10:0.1 MeOH:H$_2$O:TFA). The product was isolated. Hydroxylamine hydrochloride (42 mg, 0.600 mmol) was suspended in DMSO (667 µL) and TEA (84 µL, 0.600 mmol) and stirred for 5 min at ambient temperature. The material was diluted with THF (667 µL), filtered and concentrated in vacuo. This material was added to the alkylation product (12 mg, 0.020 mmol) and heated to 70° C. for 5 h. The reaction was diluted with EtOAc and washed twice with water, then brine, dried (Na$_2$SO$_4$), filtered, diluted with Ac$_2$O (5.7 µL, 0.060 mmol), and concentrated in vacuo. The crude material was dissolved in MeOH (667 µL). Pd/C (2.1 mg, 0.002 mmol) was added and the reaction sealed under a hydrogen balloon overnight. The reaction was purified by Prep LC (YMC Sunfire 5µ C18 30×100 mm column, 10 min gradient from 20 to 100% B in A, A=10:90:0.1 MeOH:H$_2$O:TFA, B=90:10:0.1 MeOH:H$_2$O:TFA) to yield Example 43 (5.1 mg, 33%). MS (ESI) m/z: 602.0 (M+H)$^+$. The 1H NMR was complicated. Analytical HPLC (low pH, 254 nM): Sunfire C18, RT=5.928 min.

Example 44

[(5R,11R,14R)-11-(4-Carbamimidoyl-phenylamino)-7-(2,2-difluoro-ethoxy)-5,13-dimethyl-3,12-dioxo-2,13-diaza-tricyclo[13.3.1.1$^{6,10}$]icosa-1(19),6,8,10(20),15,17-hexaen-14-yl]-acetic acid, trifluoroacetic acid salt+Diasteromer

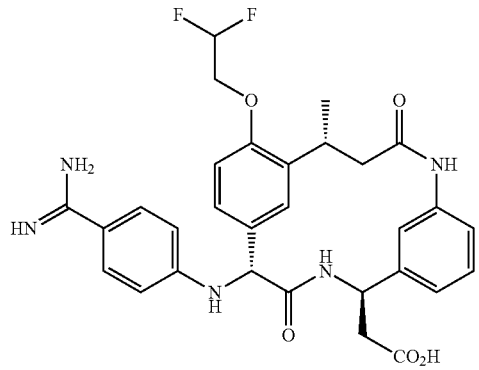 [SMILES: C[C@@H]1CC(=O)Nc2cccc(c2)[C@@H](CC(=O)O)NC(=O)[C@H](Nc2ccc(C(=N)N)cc2)c2ccc(OCC(F)F)c1c2]

Example 44A 2-(trimethylsilyl)ethyl 5-(3-(5-bromo-2-(2,2-difluoroethoxy)phenyl)propanamido)-2-(1,3-difluoropropan-2-yloxy)-3-fluorobenzyl(methyl)carbamate

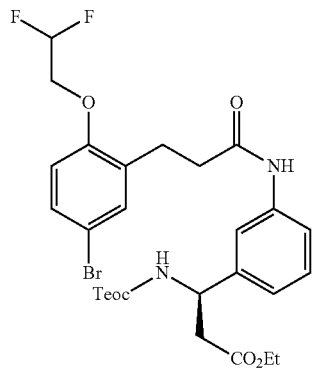

Using a procedure analogous to the one used to prepare Example 8A, Intermediate 6 (0.134 g, 0.415 mmol) was reacted with oxalyl chloride (0.228 mL, 0.456 mmol) and Intermediate 15 (0.249 g, 0.582 mmol), to yield Example 44A (0.264 g, 98%). MS (ESI) m/z: 636.9 (M+Na)$^+$.

Example 44B 3-((R)-4-(3-((R)-1-(tert-butoxycarbonylamino)-3-ethoxy-3-oxopropyl)phenylamino)-4-oxobutan-2-yl)-4-(2,2-difluoroethoxy)phenylboronic acid

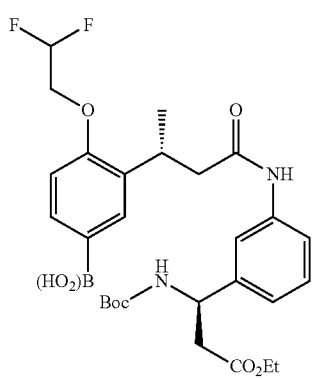

Using a procedure analogous to the one used to prepare Example 8B, Example 44A (0.249 g, 0.406 mmol) was reacted with bis(neopentyl glycolato)diboron (92 mg, 0.406 mmol) and [1,1'-bis(diphenylphospino)ferrocene]dichloropalladium(II) (15 mg, 0.020 mmol), to yield Example 44B (0.127 g, 54%). MS (ESI) m/z: 478.1.1 (M-boc)$^+$.

Example 44C 2-(3-((R)-4-(3-((R)-1-(tert-butoxycarbonylamino)-3-ethoxy-3-oxopropyl)phenylamino)-4-oxobutan-2-yl)-4-(2,2-difluoroethoxy)phenyl)-2-(4-cyanophenylamino)acetic acid

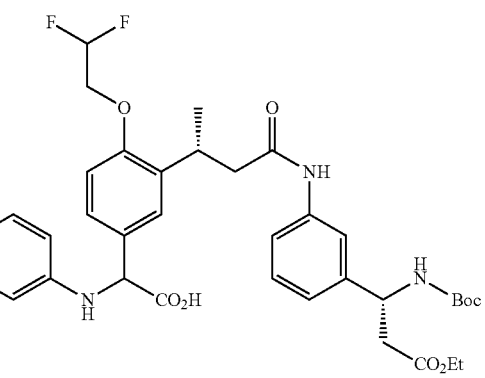

Using a procedure analogous to the one used to prepare Example 8C, Example 44B (0.127 g, 0.220 mmol) and 4-aminobenzonitrile (26 mg, 0.220 mmol) were reacted with glyoxylic acid monohydrate (13 mg, 0.137 mmol) to yield Example 44C (0.125 g, 80%). MS (ESI) m/z: 609.1 (M-boc)+.

Example 44D 2-(3-((R)-4-(3-((R)-1-amino-3-ethoxy-3-oxopropyl) phenylamino)-4-oxobutan-2-yl)-4-(2,2-difluoroethoxy)phenyl)-2-(4-cyanophenylamino)acetic acid

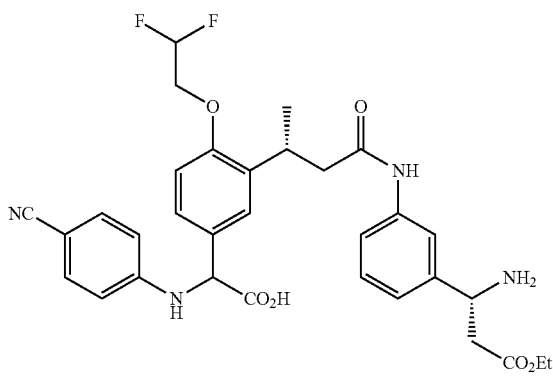 [SMILES: CCOC(=O)C[C@@H](N)c1cccc(NC(=O)C[C@@H](C)c2cc(C(Nc3ccc(C#N)cc3)C(=O)O)ccc2OCC(F)F)c1]

Example 44C (0.125 g, 0.176 mmol) was reacted with 4 M HCl in dioxane (5 mL, 20 mmol) to yield Example 44D (0.102 g, 95%). MS (ESI) m/z: 609.1 (M+H)+.

Example 44E

[(R)-11-(4-Cyano-phenylamino)-7-(2,2-difluoro-ethoxy)-3,12-dioxo-2,13-diaza-tricyclo[13.3.1.1$^{6,10}$] icosa-1(19),6,8,10(20),15,17-hexaen-14-yl]-acetic acid ethyl ester

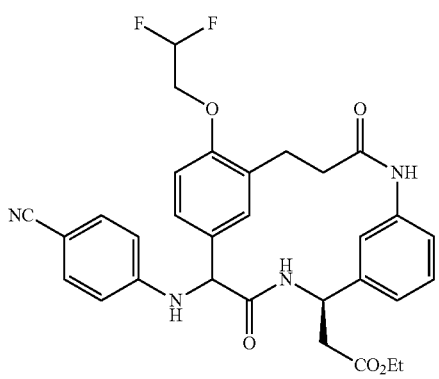 [SMILES: CCOC(=O)C[C@H]1NC(=O)C(Nc2ccc(C#N)cc2)c2ccc(OCC(F)F)c(c2)CCC(=O)Nc2cccc1c2]

Using a procedure analogous to the one used to prepare Example 8E, Example 44D (90 mg, 0.148 mmol) was reacted with HATU (0.112 g, 0.296 mmol) to yield Example 44E 20 mg, 21%).

Example 44F

[(R)-11-(4-Carbamimidoyl-phenylamino)-7-(2,2-difluoro-ethoxy)-3,12-dioxo-2,13-diaza-tricyclo [13.3.1.1$^{6,10}$]icosa-1(19),6,8,10(20),15,17-hexaen-14-yl]-acetic acid ethyl ester

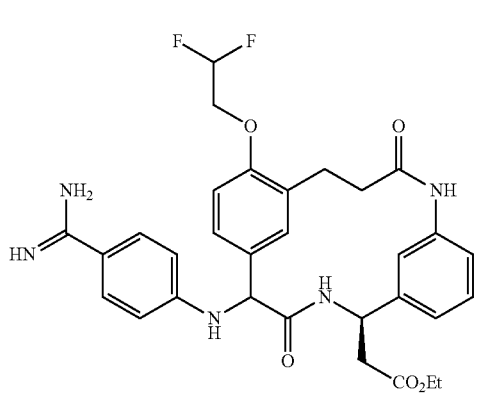

Using a procedure analogous to the one used to prepare Example 40, Example 44E (0.020 g, 0.034 mmol) was reacted with hydroxylamine hydrochloride (45 mg, 0.642 mmol). The resultant product was reduced with $H_2$ using Pd/C (10%) catalyst to yield Example 44F 20 mg, 97% yield).

Example 44

Example 44F (20 mg, 0.041 mmol) was dissolved in THF (1 mL) and LiOH (3 mg, 0.123 mmol) was added. The reaction was allowed to stir overnight. The reaction was diluted with 1 N HCl and EtOAc. The layers were separated and the combined organic layer was washed with brine, dried with $Na_2SO_4$, and concentrated under reduced pressure. The diasteromers were separated by Prep HPLC using Solvent A: 10% MeOH/90% $H_2O$/0.1% TFA and Solvent B 90% MeOH/10% $H_2O$/0.1% TFA on Phenomenex AXIA C18 30×100 mm with a 12 min gradient and 5 min hold time with a flow rate of 40 mL/min to yield Example 44 (4.1 mg, 13%). MS (ESI) m/z: 580.2 (M+H)+. 1H NMR (400 MHz, MeOD) δ ppm 7.51-7.66 (2 H, m), 7.43-7.52 (1 H, m), 7.28-7.40 (1 H, m), 7.11-7.23 (1 H, m), 6.98-7.09 (1 H, m), 6.82-6.92 (1 H, m), 6.78 (3 H, d, J=8.53 Hz), 6.02-6.49 (1 H, m), 5.24-5.38 (1 H, m), 5.10 (1 H, s), 4.82-4.92 (1 H, m), 4.08-4.39 (2 H, m), 3.34-3.53 (1 H, m), 2.81-3.03 (2 H, m), 2.73 (2 H, s), 2.29-2.52 (1 H, m), 1.58 (2 H, d, J=6.78 Hz). Analytical HPLC (low pH, 254 nM): Sunfire, RT=5.26 min.

What is claimed is:
1. A compound of Formula (I):

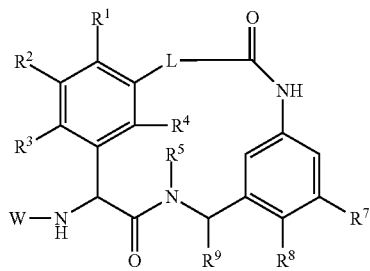

or a stereoisomer, a tautomer, a pharmaceutically acceptable salt, or a solvate thereof, wherein:
W is independently selected from:

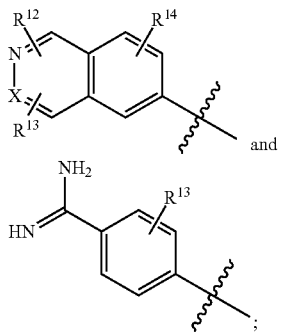
and

W is independently selected from:
X is independently selected from: $CR^{13}$ and N;
L is independently $C_{1-5}$ alkylene substituted with 0-2 $R^9$ or $C_{2-5}$ alkenylene substituted with 0-2 $R^9$; optionally one of the carbon atoms of said alkylene and alkenylene may be replaced by O, S, $SO_2$, NH, $N(C_{1-4}$ alkyl), $N(C_{1-4}$ fluoroalkyl), and N(—$CH_2$—$C_{3-6}$ carbocycle);
$R^9$ is independently selected from: halogen, $C_{1-4}$ alkyl, $C_{1-4}$ haloalkyl, hydroxy, $C_{1-4}$ alkoxy, and $C_{1-4}$ haloalkoxy; optionally when two $R^9$ groups are substituted on the same carbon atom of L, they may combine, with the carbon atom to which they are attached, to form a $C_{3-6}$ cycloalkyl ring;
$R^1$ and $R^2$ are independently selected from: H, OH, halogen, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, —$(CH_2)_{0-1}$—$C_{3-6}$ carbocycle and —O—$(CH_2)_{0-1}$—$C_{3-6}$ carbocycle;
$R^3$, $R^4$ and $R^7$ are independently selected from H, halogen, $C_{1-2}$ alkyl, $C_{1-2}$ alkoxy, and $C_{1-2}$ haloalkoxy;
$R^5$ is independently selected from: H $C_{1-2}$ alkyl, and $C_{1-2}$ haloalkyl;
$R^6$ is independently selected from: H, CN, $C_{1-4}$ alkyl, —$CO_2H$, $CO_2(C_{1-4}$ alkyl), —$CH_2CO_2H$, and —$CH_2CO_2(C_{1-4}$ alkyl);
$R^8$ is independently selected from: H, halogen, CN, OH, SH, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, —$SO_2$ ($C_{1-4}$ alkyl), —$SO_2(C_{1-4}$ haloalkyl), —$SO_2(C_{3-6}$ cycloalkyl), —$SO_2NH_2$, —$SO_2NH(C_{1-4}$ alkyl), —$SO_2N(C_{1-4}$ alkyl)$_2$, and —$SO_2(C_{3-6}$ cycloalkyl);
$R^{12}$ is independently selected from H, halogen, CN, —C(=NH)$NH_2$, $NH_2$, $NH(C_{1-4}$ alkyl), $N(C_{1-4}$ alkyl)$_2$, $CH_2NH_2$, $CH_2NH(C_{1-4}$ alkyl), $CH_2N(C_{1-4}$ alkyl)$_2$, C(O)$NH_2$, C(O)NH($C_{1-4}$ alkyl), and C(O)N($C_{1-4}$ alkyl)$_2$; and
$R^{13}$ and $R^{14}$ are independently selected from: H, F, Cl, $C_{1-2}$ alkyl, and $C_{1-2}$ alkoxy.

2. A compound according to claim 1, wherein:
W is independently selected from:

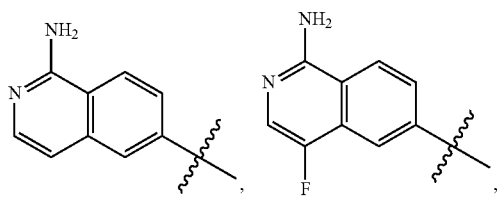

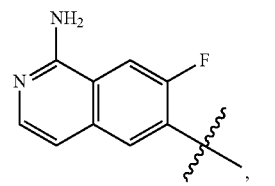,

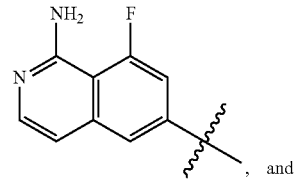, and

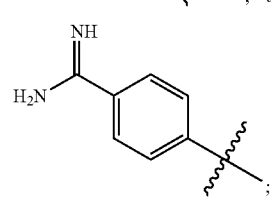;

L is independently selected from: —$CH_2CH_2$—, —CH($C_{1-2}$ alkyl)$CH_2$—, —$CH_2O$—, —$OCH_2$—, —$CH_2CH_2O$—, —$CH_2OCH_2$—, —$C(C_{1-2}$ alkyl)$_2CH_2O$—, —$CH_2CH_2N(C_{1-2}$ alkyl)-, —$CH(C_{1-2}$ alkyl)$CH_2N(C_{1-2}$ alkyl)-, —$CH_2CH_2N(Bn)$-,

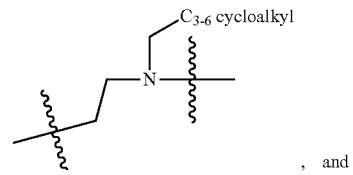, and

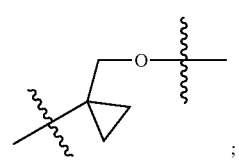;

$R^1$ is independently selected from: H, F, Cl, OH, $C_{1-4}$ alkoxy, $C_{1-4}$ fluoroalkoxy, OBn, $C_{3-6}$ cycloalkyl, and —O—$C_{3-6}$ cycloalkyl;
$R^2$ is independently selected from: H, F, Cl and $C_{1-4}$ alkoxy;
$R^3$, $R^4$ and $R^9$ are independently selected from: H and F;
$R^5$ is independently selected from: H and $CH_3$;
$R^6$ is independently selected from: H and —$CH_2CO_2H$; and
$R^8$ is independently selected from: H, $C_{1-4}$ fluoroalkoxy, —$SO_2(C_{1-4}$ fluoroalkyl), and —$SO_2(C_{3-6}$ cycloalkyl).

3. A compound according to claim 1, wherein:
L is independently selected from: —$CH_2CH_2$—, —CH($CH_3$)$CH_2$—, —$CH_2O$—, —$OCH_2$—, —$CH_2CH_2O$—, —$CH_2OCH_2$—, —$C(CH_3)_2CH_2O$—, —$CH_2CH_2N(CH_3)$—, —$CH(CH_3)CH_2N(CH_3)$—, —$CH_2CH_2N$(cyclopropylmethyl)-, —$CH_2CH_2N$(cyclobutylmethyl)-, —$CH_2CH_2N(Bn)$-, and

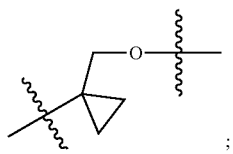 [SMILES: *OCC1(*)CC1]

W is independently selected from:

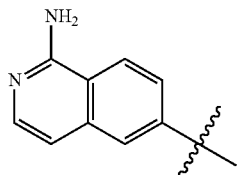

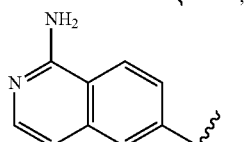
, and

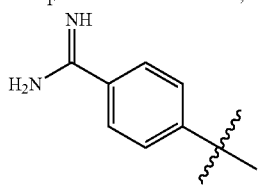
;

R⁶ is independently selected from: H and —CH₂CO₂H; and

R⁸ is independently selected from: H, —OCHF₂, —OCH₂CHF₂, —OCH(CH₂F)₂, —SO₂CHF₂, —SO₂CF₃, and —SO₂(cyclopropyl).

4. A compound according to claim 1, wherein:

L is independently selected from: —CH₂CH₂—, —CH(CH₃)CH₂—, —CH₂CH₂O—, —CH₂OCH₂—, —CH₂CH₂N(CH₃)—, —CH(CH₃)CH₂N(CH₃)—, —CH₂CH₂N(cyclopropylmethyl)-, and —CH₂CH₂N(Bn)-;

R¹ is independently selected from: H, F, OH, OCH₃, —OCH(CH₃)₂, —O(CH₂)₃CH₃, —OCH₂CH(CH₃)₂, —OCH₂CHF₂, OBn, cyclopropyl,

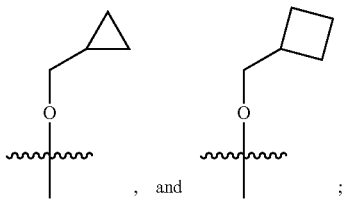 [SMILES: *OCC1CC1 ; *OCC1CCC1]
, and ;

R² is independently selected from: H, F, and OCH₃;

R⁵ is CH₃;

R⁶ is H; and

R⁸ is independently selected from: —OCHF₂, —OCH₂CHF₂, —OCH(CH₂F)₂, —SO₂CF₃, and —SO₂(cyclopropyl).

5. A compound according to claim 1, wherein the compound is selected from the exemplified examples 1 to 44 or a stereoisomer, a tautomer, a pharmaceutically acceptable salt, or a solvate thereof.

6. A pharmaceutical composition, comprising: a pharmaceutically acceptable carrier and a compound of claim 1.

7. A method of treating a thromboembolic disorder, comprising administering to a patient in need thereof a therapeutically effective amount of a compound of claim 1.

* * * * *

UNITED STATES PATENT AND TRADEMARK OFFICE
CERTIFICATE OF CORRECTION

PATENT NO. : 9,657,006 B2
APPLICATION NO. : 14/897764
DATED : May 23, 2017
INVENTOR(S) : Richter et al.

Page 1 of 2

It is certified that error appears in the above-identified patent and that said Letters Patent is hereby corrected as shown below:

In the Claims

Claim 1, Column 204, Lines 55-65 delete " 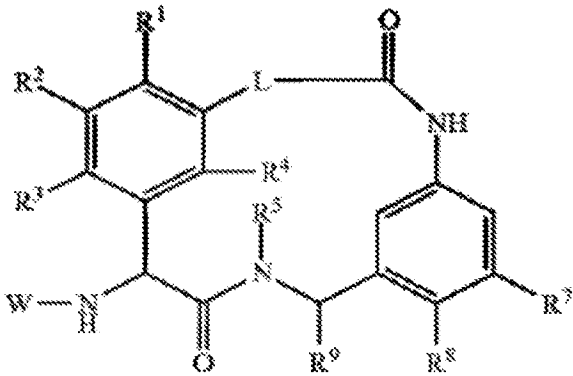 " and insert -- 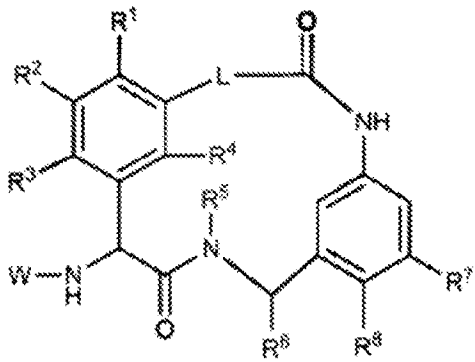 --.

Signed and Sealed this
Twentieth Day of November, 2018

Andrei Iancu
*Director of the United States Patent and Trademark Office*

CERTIFICATE OF CORRECTION (continued)
U.S. Pat. No. 9,657,006 B2

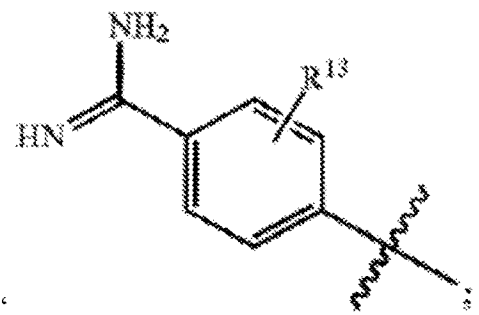

Claim 1, Column 205, Line 19 below " 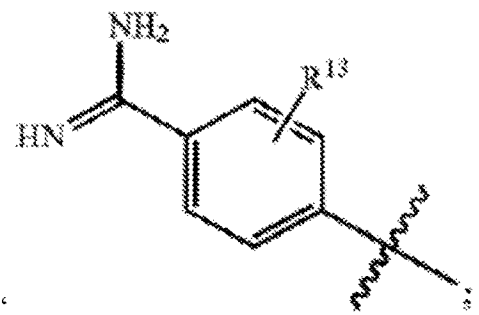 " delete "W is independently selected from:".

Claim 1, Column 205, Lines 25-26 delete "carboycle);" and insert -- carbocycle); --.